US006845328B2

(12) United States Patent
Wimberly et al.

(10) Patent No.: US 6,845,328 B2
(45) Date of Patent: Jan. 18, 2005

(54) SCREENING METHODS USING THE CRYSTAL STRUCTURE OF RIBOSOMAL PROTEIN L11/GTPASE ACTIVATING REGION RRNA COMPLEX

(75) Inventors: Brian T. Wimberly, Guilford, CT (US); Venkatraman Ramakrishnan, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/998,805

(22) Filed: Nov. 1, 2001

(65) Prior Publication Data

US 2003/0099955 A1 May 29, 2003

Related U.S. Application Data

(63) Continuation of application No. PCT/US00/12019, filed on May 3, 2002.
(60) Provisional application No. 60/134,171, filed on May 13, 1999.

(51) Int. Cl.[7] .............................................. G06F 19/00
(52) U.S. Cl. ............................ 702/27; 435/7.1; 702/19
(58) Field of Search ....................... 702/19, 27; 435/7.1

(56) References Cited

U.S. PATENT DOCUMENTS 6,160,092 A  * 12/2000  Chen et al. .................. 530/350

OTHER PUBLICATIONS

Rodnina, et al.(1997). Hydrolysis of GTP by elongation factor G drives tRNA movement on the ribosome. Nature 385, 37–41.

Moazed, D., Robertson, J. M., and Noller, H. F. (1988). Interaction of elongation factors EF–G and EF–Tu with a conserved loop in 23S RNA. Nature 334, 362–4.

Rosendahl, G., and Douthwaite, S. (1993). Ribosomal proteins L11 and L10.(L12)4 and the antibiotic thiostrepton interact with overlapping regions of the 23 S rRNA backbone in the ribosomal GTPase centre. J Mol Biol 234, 1013–20.

Hinck, et al. (1997). The RNA binding domain of ribosomal protein L11: three–dimensional structure of the RNA–bound form of the protein and its interaction with 23 S rRNA. J Mol Biol 274, 101–13.

Xing, Y., and Draper, D. E. (1996). Cooperative interactions of RNA and thiostrepton antibiotic with two domains of ribosomal protein L11. Biochemistry 35, 1581–8.

Conn, et al.(1998). A functional ribosomal RNA tertiary structure involves a base triple interaction. Biochemistry 37, 11980–8.

Rosendahl, G., and Douthwaite, S. (1994). The antibiotics micrococcin and thiostrepton interact directly with 23S rRNA nucleotides 1067A and 1095A. Nucleic Acids Res 22, 357–63.

Noller, et al. (1981). Secondary structure model for 23S ribosomal RNA. Nucleic Acids Res 9, 6167–89.

(List continued on next page.)

*Primary Examiner*—Ardin H. Marschel
*Assistant Examiner*—Carolyn L. Smith
(74) *Attorney, Agent, or Firm*—Kathleen M. Williams; Palmer & Dodge, LLP

(57) ABSTRACT

The present invention is broadly directed to methods of screening ribosomal protein L11/GTPase activating region (GAR) RNA-modulating compounds by using information from the high-resolution structure of the L11/GAR complex. The methods are useful in identifying compounds useful for anti-bacterial treatments.

6 Claims, 7 Drawing Sheets

OTHER PUBLICATIONS

Briones, et al. (1998). The GTPase center protein L12 is required for correct ribosomal stalk assembly but not for *Saccharomyces cerevisiae* viability. J Biol Chem 273, 31956–61.

Schmidt, et al.(1981). The binding site for ribosomal protein L11 within 23 S ribosomal RNA of *Escherichia coli*. J Biol Chem 256, 12301–5.

Glotz, et al. (1981). Secondary structure of the large subunit ribosomal RNA from *Escherichia coli, Zea mays* chloroplast, and human and mouse mitochondrial ribosomes. Nucleic Acids Res 9, 3287–306.

Thompson, et al., 1993, EMBO J. 12: 1499–1504.

Thompson, et al.(1979). Binding of thiostrepton to a complex of 23–S rRNA with ribosomal protein L11. Eur J Biochem 98, 261–5.

Markus, et al. (1997). High resolution solution structure of ribosomal protein L11–C76, a helical protein with a flexible loop that becomes structured upon binding to RNA. Nat Struct Biol 4, 70–7.

Donner, et al. (1978). Guanosinetriphosphatase activity dependent on elongation factor Tu and ribosomal protein L7/L12. Proc Natl Acad Sci U S A 75l, 3192–5.

Cundliffe, E., and Thompson, J. (1981). Concerning the mode of action of micrococcin upon bacterial protein synthesis. Eur J Biochem 118, 47–52.

Pestka, S. (1970). Thiostrepton: a ribosomal inhibitor of translocation. Biochem Biophys Res Commun 40, 667–74.

Sopori, M. L., and Lengyel, P. (1972). Components of the 50S ribosomal subunit involved in GTP cleavage. Biochem Biophys Res Commun 46, 238–44.

Tate, et al. (1975), J. Mol. Biol. 93:375–389.

* cited by examiner

SEQUENCE LISTING

<160> NUMBER OF SEQ ID NOS: 5

<210> SEQ ID NO 1
<211> LENGTH: 142
<212> TYPE: PRT
<213> ORGANISM: Escherichia coli

<400> SEQUENCE: 1

```
Met Ala Lys Lys Val Gln Ala Tyr Val Lys Leu Gln Val Ala Ala Gly
1               5                   10                  15

Met Ala Asn Pro Ser Pro Val Gly Pro Ala Leu Gly Gln Gln Gly
            20                  25                  30

Val Asn Ile Met Glu Phe Cys Lys Ala Phe Asn Ala Lys Thr Asp Ser
            35                  40                  45

Ile Glu Lys Gly Leu Pro Ile Pro Val Val Ile Thr Val Thr Ala Asp
        50                  55                  60

Arg Ser Phe Thr Phe Val Ile Lys Thr Pro Pro Ala Ala Val Leu Leu
65                  70                  75                  80

Lys Lys Ala Ala Gly Ile Lys Ser Gly Ser Gly Lys Pro Asn Lys Asp
                85                  90                  95

Lys Val Gly Lys Ile Ser Arg Ala Gln Leu Gln Glu Leu Ala Gln Thr
            100                 105                 110

Lys Ala Ala Asp His Thr Gly Ala Asp Ile Glu Ala Met Thr Arg Ser
            115                 120                 125

Ile Glu Gly Thr Ala Arg Ser Met Gly Leu Val Val Glu Asp
        130                 135                 140
```

<210> SEQ ID NO 2
<211> LENGTH: 141
<212> TYPE: PRT
<213> ORGANISM: Thermotoga maritima

<400> SEQUENCE: 2

```
Met Ala Lys Lys Val Ala Ala Gln Ile Lys Leu Gln Leu Pro Ala Gly
1               5                   10                  15

Lys Ala Thr Pro Ala Pro Pro Val Gly Pro Ala Leu Gly Gln His Gly
            20                  25                  30

Val Asn Ile Met Glu Phe Cys Lys Arg Phe Asn Ala Glu Thr Ala Asp
            35                  40                  45
```

```
Lys Ala Gly Met Ile Leu Pro Val Val Thr Val Tyr Glu Asp Lys
         50                  55                  60

Ser Phe Thr Phe Ile Ile Lys Thr Pro Pro Ala Ser Phe Leu Leu Lys
 65                  70                  75                  80

Lys Ala Ala Gly Ile Glu Lys Gly Ser Ser Glu Pro Lys Arg Lys Ile
                 85                  90                  95

Val Gly Lys Val Thr Arg Lys Gln Ile Glu Ile Ala Lys Thr Lys
                100                 105                 110

Met Pro Asp Leu Asn Ala Asn Ser Leu Glu Ala Ala Met Lys Ile Ile
            115                 120                 125

Glu Gly Thr Ala Lys Ser Met Gly Ile Glu Val Val Asp
        130                 135                 140

<210> SEQ ID NO 3
<211> LENGTH: 139
<212> TYPE: PRT
<213> ORGANISM: Sulfolobus acidocaldarius

<400> SEQUENCE: 3

Met Pro Thr Lys Thr Ile Lys Ile Met Val Glu Gly Gly Ser Ala Lys
  1               5                  10                  15

Pro Gly Pro Pro Leu Gly Pro Thr Leu Ser Gln Leu Gly Leu Asn Val
                 20                  25                  30

Gln Glu Val Val Lys Lys Ile Asn Asp Val Thr Ala Gln Phe Lys Gly
             35                  40                  45

Met Ser Val Pro Val Thr Ile Lys Ile Asp Ser Ser Thr Lys Lys Tyr
         50                  55                  60

Asp Ile Lys Val Gly Val Pro Thr Thr Thr Ser Leu Leu Leu Lys Ala
 65                  70                  75                  80

Ile Asn Ala Gln Glu Pro Ser Gly Asp Pro Ala Lys Lys Ile Gly
                 85                  90                  95

Asn Leu Asp Leu Glu Gln Leu Ala Asp Leu Ala Ile Lys Lys Lys Pro
            100                 105                 110

Gln Leu Ser Ala Lys Thr Leu Thr Ala Ala Ile Lys Ser Leu Leu Gly
            115                 120                 125

Thr Ala Arg Ser Ile Gly Ile Thr Val Glu Gly
        130                 135

<210> SEQ ID NO 4
<211> LENGTH: 146
<212> TYPE: PRT
<213> ORGANISM: Saccharomyces cerevisiae

<400> SEQUENCE: 4

Met Pro Pro Lys Phe Asp Pro Asn Glu Val Lys Tyr Leu Tyr Leu Arg
  1               5                  10                  15

Ala Val Gly Gly Glu Val Gly Ala Ser Ala Ala Leu Ala Pro Lys Ile
                 20                  25                  30

Gly Pro Leu Gly Leu Ser Pro Lys Lys Val Gly Glu Asp Ile Ala Lys
             35                  40                  45

Ala Thr Lys Glu Phe Lys Gly Ile Lys Val Thr Val Gln Leu Leu Ile
         50                  55                  60

Gln Met Arg Gln Ala Ala Ala Ser Val Val Pro Ser Ala Ser Ser Leu
 65                  70                  75                  80

Val Ile Thr Ala Leu Lys Glu Pro Pro Arg Asp Arg Lys Lys Asp Lys
                 85                  90                  95
```

```
-continued

Asn Val Lys His Ser Gly Asn Ile Gln Leu Asp Glu Ile Ile Glu Ile
            100                 105                 110

Ala Lys Gln Met Arg Asp Lys Ser Phe Gly Arg Thr Leu Ala Ser Val
            115                 120                 125

Thr Lys Thr Ile Leu Gly Thr Ala Gln Ser Val Gly Cys Arg Val Asp
    130                 135                 140

Phe Lys
145

<210> SEQ ID NO 5
<211> LENGTH: 58
<212> TYPE: RNA
<213> ORGANISM: Thermotoga maritima

<400> SEQUENCE: 5
gcugggaugu uggcuuagaa gcagccauca uuuaaaaggu gcguaacagc ucaccagc        58
```

SCREENING METHODS USING THE CRYSTAL STRUCTURE OF RIBOSOMAL PROTEIN L11/GTPASE ACTIVATING REGION RRNA COMPLEX

TECHNICAL FIELD OF THE INVENTION

The present invention relates to methods of screening for compounds that inhibit or activate bacterial growth by binding to the complex formed between ribosomal protein L11 and the 23S ribosomal RNA region that interacts with it in vivo.

BACKGROUND

The elongation cycle of protein synthesis is driven by two elongation factors that bind to nearly identical sites on the large (50S) ribosomal subunit (Spahn and Nierhaus, 1998; Wilson and Noller, 1998). EF-Tu delivers aminoacyl tRNAs to the ribosome, whereas EF-G catalyzes the translocation of the ribosome by one codon relative to the mRNA and the concomitant movement of the A and P site tRNAs. Both elongation factors are G proteins, and their interactions with the ribosome are coupled to the binding and hydrolysis of GTP. Like most G proteins, EF-Tu and EF-G are molecular switches that have limited inherent GTPase activity, and they rely on an accessory factor to stimulate activity at the appropriate time. This accessory factor is an integral part of the 50S ribosomal subunit and has usually been referred to as the "GTPase center," but by analogy with the functionally equivalent GAP proteins that stimulate GTPase activity in G-proteins, it seems more appropriate to refer to it as the "GTPase activating region" (hereafter abbreviated as the GAR). Early work on the identification of the molecular components of the GAR implicated a complex between ribosomal protein L11 and a highly conserved 58-nucleotide stretch of 23S ribosomal RNA (rRNA), nucleotides 1051–1108 in *Escherichia coli* (Schmidt et al., 1981; Thompson et al., 1979). The L11-RNA complex is the target for a family of thiazole antibiotics that includes thiostrepton and micrococcin. Thiostrepton binds essentially irreversibly to 50S subunits (Sopori and Lengyel, 1972) and inhibits hydrolysis of GTP by EF-G (Pestka, 1970; Rodnina et al., 1997), while micrococcin binds to the same complex and stimulates GTP hydrolysis by EF-G (Cundliffe and Thompson, 1981).

Other components of the ribosome have also been implicated in stimulation of GTP hydrolysis by elongation factors. Classical work suggested that protein L7/L12, which together with L10 forms the "stalk" of the 50S subunit that lies adjacent to L11, is involved in stimulation of GTPase activity in EF-Tu (Donner et al., 1978). However, recently it has been shown that protein L7/L12, although essential for stalk formation, is not required for viability in yeast (Briones et al., 1998). The sarcin/ricin loop, a small, highly conserved stem-loop in the 23S rRNA that is known to be essential for ribosome function, has been footprinted by the elongation factors (Moazed et al., 1988), and is also considered a candidate for being part of the GAR. Therefore, it is not yet clear whether the L11-RNA complex per se should be considered the GAR, or whether the GAR should be defined as a more extensive region of the 50S subunit. In any event, it appears that the L11-RNA complex is at the heart of the GAR; the complex of L11 with its cognate RNA will be referred to herein as the GAR.

The GAR is one of the most thoroughly characterized RNA-protein complexes. The secondary structure of the RNA was first inferred from biochemical and genetic studies (Glotz et al., 1981; Noller et al., 1981). It consists of a junction of four double-helical stems (FIG. 1A). Approximately one-third of the residues in the GAR RNA are very highly conserved. The structure, thermodynamic stability, and ion-binding affinities of the RNA component have been extensively probed by a variety of biophysical and biochemical techniques; these data suggest that the 1067 and 1095 stem-loops are folded into a compact tertiary structure (Conn et al., 1998; Rosendahl and Douthwaite, 1994). Protein L11 consists of two domains: the C-terminal domain binds tightly to the RNA tertiary structure, while the N-terminal domain is required for the cooperative interaction with thiostrepton (Xing and Draper, 1996). The structure of the C-terminal domain has been determined by NMR techniques (Hinck et al., 1997; Markus et al., 1997). Footprinting studies (Rosendahl and Douthwaite, 1993) have identified regions of RNA involved in the interaction with L11, while NMR chemical shift measurements (Hinck et al., 1997) have identified an RNA-binding surface on the C-terminal domain of the protein.

It is an object of the invention to provide a detailed view of a functionally important protein-RNA complex in the ribosome.

It is also an object of the invention to provide a high-resolution structure of a ribosomal protein-RNA complex.

Yet another object of the invention is to provide new principles of RNA folding, of RNA-protein recognition, and of indirect RNA tertiary structure stabilization.

Yet another object of the invention is to solve the three dimensional structure of L11 complexed with GAR RNA and to determine its structure coordinates.

SUMMARY OF THE INVENTION

The present invention is broadly directed to methods of screening ribosomal protein L11/GTPase activating region (GAR) RNA-modulating compounds by using information from the high-resolution structure of the L11/GAR complex.

The invention encompasses use of the structure coordinates of an L11/GAR crystal to define the atomic details of regions of the L11/GAR complex, such as the GTPase activating region and one or more binding sites of accessory factors, which are target sites for inhibitors or activators.

The invention also encompasses use of the structure coordinates and atomic details of the L11/GAR RNA complex or its co-complexes to design, evaluate computationally, synthesize and use inhibitors or activators of the L11/GAR.

Structure coordinates for L11/GAR RNA complex according to Table II may be modified from this original set by mathematical manipulation. Such manipulations include, but are not limited to, crystallographic permutations, fractionalizations, or inversion of the raw structure coordinates, integer additions or subtractions to sets of the raw structure coordinates, and any combination of the above.

The crystal structure of the GAR allows the screening and design of novel classes of GAR inhibitory or activating compounds with great medical potential, for example, to prevent or stimulate growth of certain bacteria.

The invention encompasses a method for identifying a potential modulator of ribosomal protein L11/GAR activity, comprising the steps of: a) using a three-dimensional structure of the L11/GAR complex as defined by atomic coordinates of the L11/GAR according to FIG. 7; b) employing the three-dimensional structure to design or select the potential modulator; c) providing the potential modulator; and d) contacting the potential modulator with L11/GAR in the presence of an activity to determine the ability of the potential modulator to modulate the activity, for example, L11/GAR activity.

In one embodiment of the invention, the potential modulator is designed de novo.

In another embodiment of the invention, the potential modulator is designed from a known modulator.

In another embodiment of the invention, the step of employing the three-dimensional structure to design or select the compound comprises the steps of: a) identifying chemical entities or fragments capable of associating with the L11/GAR; and b) assembling the identified chemical entities or fragments into a single molecule to provide the structure of the potential modulator. Relative to this embodiment, the potential modulator may be designed de novo or designed from a known modulator.

The invention further encompasses a method for screening L11/GAR-binding compounds comprising the steps of: 1) incubating in vitro one or more compounds, a known L11/GAR binding activity and labeled RNA comprising GAR RNA; 2) separating that fraction of the labeled RNA bound to the known L11/GAR binding activity from that fraction of the labeled RNA not bound to the known L11/GAR binding activity; and 3) detecting labeled RNA, wherein a decrease in the level of the labeled RNA bound to the known L11/GAR binding activity in the presence of one or more compounds indicates the binding of one or more of the compounds to L11/GAR.

The invention further encompasses a method for screening L11/GAR-binding compounds comprising the steps of: 1) incubating in vitro one or more compounds, a labeled known L11/GAR binding activity and an RNA comprising GAR RNA; 2) separating that fraction of the labeled known L11/GAR binding activity bound to the RNA from that fraction of the labeled known L11/GAR binding activity not bound to the RNA; and 3) detecting labeled known L11/GAR binding activity wherein a decrease in the level of the labeled known L11/GAR binding activity bound to the RNA in the presence of one or more compounds indicates that one or more of the compounds binds L11/GAR.

In one embodiment of the the method of screening L11/GAR-binding compounds, the known L11/GAR binding activity is an antibiotic. In another embodiment the antibiotic is micrococcin. In a preferred embodiment the antibiotic is thiostrepton.

In another embodiment of the method of screening L11/GAR-binding compounds, the RNA comprising GAR RNA is contained within a ribosome.

In another embodiment of the method of screening L11/GAR-binding compounds, a plurality of compounds is screened for L11/GAR binding in a plurality of separate, simultaneous assays.

The invention further encompasses a method for screening L11/GAR-binding compounds comprising the steps of: 1) incubating in vitro one or more compounds with a translationally competent cell extract and a translatable RNA; and 2) detecting translation, wherein a decrease in the level of translation indicates binding of one or more of the compounds to L11/GAR.

In one embodiment, the translatable RNA encodes an enzyme and the step of detecting translation comprises detecting the activity of the enzyme.

In a preferred embodiment, the enzyme is luciferase.

In another embodiment, the translatable RNA is poly-U, and the step of detecting translation detects the incorporation of labeled phenylalanine into polyphenylalanine.

In another embodiment, the translationally competent cell extract comprises isolated ribosomes.

The invention further encompasses a method for screening L11/GAR-binding compounds comprising the steps of: 1) incubating in vitro one or more compounds, isolated 70S ribosomes, isolated EF-G and gamma-labeled GTP; and 2) detecting GTP hydrolysis wherein a decrease in GTP hydrolysis indicates one or more of the compounds binds L11/GAR.

The invention further encompasses a method for screening anti-bacterial compounds comprising the steps of: 1) incubating in vitro one or more compounds, a known L11/GAR binding activity and labeled RNA comprising GAR RNA; 2) separating that fraction of the labeled RNA bound to the known L11/GAR binding activity from that fraction of the labeled RNA not bound to the known L11/GAR binding activity; and 3) detecting labeled RNA, wherein a decrease in the level of the labeled RNA bound to the known L11/GAR binding activity in the presence of one or more compounds indicates that one or more of the compounds has anti-bacterial properties.

The invention further encompasses a method for screening anti-bacterial compounds comprising the steps of: 1) incubating in vitro one or more compounds, a labeled known L11/GAR binding activity and an RNA comprising GAR RNA; 2) separating that fraction of the labeled known L11/GAR binding activity bound to the RNA from that fraction of the labeled known L11/GAR binding activity not bound to the RNA; and 3) detecting labeled known L11/GAR binding activity wherein a decrease in the level of the labeled known L11/GAR binding activity bound to the RNA in the presence of one or more compounds indicates that one or more of the compounds has anti-bacterial properties.

In one embodiment of the the method of screening anti-bacterial compounds, the known L11/GAR binding activity is an antibiotic. In another embodiment the antibiotic is micrococcin. In a preferred embodiment the antibiotic is thiostrepton.

In another embodiment of the method of screening anti-bacterial compounds, the RNA comprising GAR RNA is contained within a ribosome.

In another embodiment of the method of screening anti-bacterial compounds, a plurality of compounds is screened for L11/GAR binding in a plurality of separate, simultaneous assays.

The invention further encompasses a method for screening anti-bacterial compounds comprising the steps of: 1) incubating in vitro one or more compounds with a translationally competent cell extract and a translatable RNA; and 2) detecting translation, wherein a decrease in the level of translation indicates that one or more of the compounds has anti-bacterial properties.

In one embodiment, the translatable RNA encodes an enzyme and the step of detecting translation comprises detecting the activity of the enzyme.

In a preferred embodiment, the enzyme is luciferase.

In another embodiment, the translatable RNA is poly-U, and the step of detecting translation detects the incorporation of labeled phenylalanine into polyphenylalanine.

In another embodiment, the translationally competent cell extract comprises isolated ribosomes.

The invention further encompasses a method for screening anti-bacterial compounds comprising the steps of: 1) incubating in vitro one or more compounds, isolated 70S ribosomes, isolated EF-G and gamma-labeled GTP; and 2) detecting GTP hydrolysis wherein a decrease in GTP hydrolysis indicates that one or more of the compounds has anti-bacterial properties. Further features and advantages of the invention are embodied in the following description of the invention and in the claims.

BRIEF DESCRIPTION OF THE DRAWINGS

c) Geometries of the noncanonical base pairs and base triples. Top panel, the three major groove base triples in the core of the structure: G1089-(U1090-U1101), G1071-(G1091-C1100), and C1072-(C1092-G1099). Bottom left panel, the minor groove docking interactions (U1082-A1086)-(G1056-A1103) and A1085-(G1054-C1104). Bottom right panel, the long-range pair A1088-U1060.

Figure 1C:
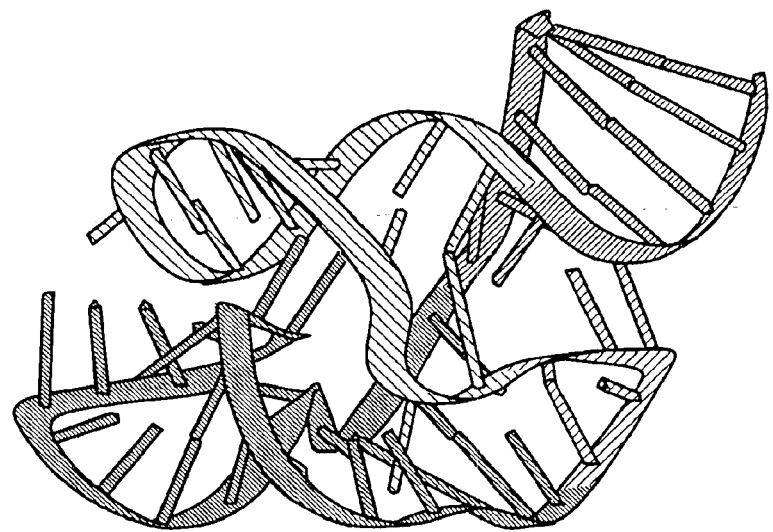
FIGS. 1*b* and 1*c* were made with the program RIBBONS (Carson, 1991).

Table II shows the atomic structure coordinates for the complex between ribosomal L11 protein and the GAR RNA as derived by X-ray diffraction from a crystal of L11 complexed with 23S rRNA nucleotides 1051–1108.

DETAILED DESCRIPTION OF THE INVENTION

The invention is based on the discovery of the crystal structure of the ribosomal GAR from the hyperthermophilic eubacterium *Thermotoga maritima*, which is disclosed herein Definitions As used herein, the term "binding site" or "binding pocket" refers to a region of a protein or protein/RNA complex which binds or interacts with a particular compound. It is understood that the composition of the protein or RNA residues and/or the protein or RNA backbone, as well as the interaction of such moieties with their solvent including ions defines the specificity of the binding pocket.

As used herein, the term "exposed residue" refers to an amino acid or RNA residue which is located on the surface of a protein, RNA or RNA/protein complex.

As used herein the term "N terminus" or "N terminal lobe" or "NTD" when used in reference to L11 means amino acids 1–70 of L11.

As used herein, the term "C terminus" or "C terminal lobe" or "CTD" when used in reference to L11 means amino acids 76–141 of L11.

As used herein, the term "tether" or "tether sequence" when used in reference to L11 means amino acids 71 to 75 of L11.

As used herein, the term "flexible" when applied to a protein or RNA domain means that that domain allows one or more domains adjoining or flanking it to move or flex in space relative to the flexible domain.

As used herein, the term "backbone" or "backbone residue" when applied to an RNA molecule refers to the sugar-phosphate moieties that are covalently linked to form an RNA polymer. When applied to a protein molecule, "backbone" or "backbone residue" refers to the alternating N—C—C—N moieties of amino acids that are covalently linked to form a peptide polymer.

As used herein, the term "interface" means the point or surface at which two or more domains of one or more molecules associate with each other.

As used herein, the term "GAR" refers to the region of the ribosome responsible for activating the GTPase activity of translation elongation factors. The term "GAR RNA" refers to nucleotides 1051 to 1108 of E. coli 23S rRNA or to its functional and structurally equivalent from any other bacterial rRNA. As used herein, GAR RNA refers to the nucleotides including and limited to (i.e., an RNA molecule consisting of GAR RNA) nucleotides 1051 to 1108 of E. Coli 23S rRNA (or the functionally and structurally equivalent region in other bacterial rRNAs); or it refers to that nucleotide region (1051 to 1108) within a longer nucleotide sequence (i.e., an RNA molecule consisting essentially of GAR RNA) where the GAR RNA (nucleotides 1051 to 1108) is the only active region in the longer sequence (in terms of binding and/or another activity), whether the extra sequence be a homologous sequence from the 23S rRNA (short of the complete sequence) or a heterologous sequence; or it refers to the 1051 to 1108 region within a complete functional 23S rRNA (i.e., an RNA molecule comprising the GAR RNA).

As used herein, the term "L11/GAR" refers to the portions of L 11 and GAR RNA which, when engaged in a complex, provide the L11/GAR binding site and/or activity, and preferably both the binding site and the activity. The term "L11/GAR" refers to a complex which consists of the ribosomal protein L11 and consists of the GAR RNA (nucleotides 1051 to 1108) in their native association; or it can refer to a complex consisting essentially of ribosomal protein L11 and consisting of or consisting essentially of or comprising GAR RNA (i.e., including other proteins which are inactive or do not otherwise affect the activity of the L11/GAR complex; or it can refer to a complex comprising ribosomal protein L11 and consisting of, consisting essentially of, or comprising GAR RNA. When ribosomal protein L11 is referred to, the complete protein is referred to; however, where an L11/GAR activity is referred to, the portion of L11 sufficient to provide the activity when associated in a complex with GAR ma be less than the complete L11 protein; "portion" referring to those combined L11 residues which provide for L11/GARcomplex formation and activity, the portions being one or more of the N-terminal, C-terminal or tether regions, as defined herein, or ant combination thereof.

"L11/GAR activity" may include one or more of the following: movement of the N-terminal lobe of L11; binding or displacement of thiostrepton or micrococcin; RNA translation, translation elongation, inhibition of amino acid addition, GTPase activity, and/or inhibition of elongation factor G (EF-G)-dependent GTP hydrolysis.

As used herein, the term "known L11/GAR binding activity" refers to an activity known in the art to associate with the L11/GAR either in vitro or in vivo. Known L11/GAR binding activities include, but are not limited to, the binding of agents such as thiostrepton and micrococcin.

As used herein, "stem loop" refers to a stretch of nucleic acid sequence on a single molecule comprising two lengths of sequence capable of forming hydrogen bonded base pairs with each other separated by a region which cannot participate in the same base pairing interaction, such that base pairing between the sequences capable of forming hydrogen bonded base pairs forms a loop of non-base paired nucleic acid consisting of the region which cannot participate in base pairing.

As used herein, the term "alpha helix" refers to a secondary structure arrangement of amino acids wherein hydrogen bonding between the C=O group of one peptide and the —NH group of the peptide bond four residues further down the same peptide polymer results in a right handed twist or helix formation.

As used herein, "four way junction" refers to a region in the tertiary structure of GAR RNA in which four helices interact simultaneously with each other, as defined by the crystal structure coordinates given in Table II.

As used herein, the term "translationally competent cell extract" refers to any fraction of a cell lysate, including a whole cell lysate, which is capable of directing the RNA-dependent polymerization of peptide bonds.

As used herein, the term "translatable RNA" refers to an RNA which, when incubated with factors necessary for translation can direct the synthesis of acid-precipitable protein.

As used herein, the term "decrease" when used in reference to a level of labeled RNA, a level of known L11/GAR binding activity, a level of translation, or a level of GTP hydrolysis means that the detected level is reduced by at least 10%, and preferably by 20% to 50% or more.

As used herein, the term "anti-bacterial properties" refers to the ability of a particular compound to inhibit the growth of bacteria. A compound can be said to have anti-bacterial properties if the rate of bacterial cell proliferation is reduced by at least 50%, and preferably by more than 50%.

As used herein, the term "naturally occurring amino acids" means the L-isomers of the naturally occurring amino acids. The naturally occurring amino acids are glycine (G, Gly), alanine (A, Ala), valine (V, Val), leucine (L, Leu), isoleucine (I, Ile), serine (S, Ser), methionine (M, Met), threonine (T, Thr), phenylalanine (F, Phe), tyrosine (Y, Tyr), tryptophan (W, Trp), cysteine (C, Cys), proline (P, Pro), histidine (H, His), aspartic acid (D, Asp), asparagine (N, Asn), glutamic acid (E, Glu), glutamine (Q, Gln), gamma-carboxyglutamic acid, arginine (R, Arg), ornithine and lysine (K, Lys). Unless specifically indicated, all amino acids referred to in this application are in the L-form.

As used herein, the term "unnatural amino acids" means amino acids that are not naturally found in proteins. Examples of unnatural amino acids used herein include racemic mixtures of selenocysteine and selenomethionine.

The term "positively charged amino acid" includes any naturally occurring or unnatural amino acid having a positively charged side chain under normal physiological conditions. Examples of positively charged naturally occurring amino acids are arginine, lysine and histidine.

The term "negatively charged amino acid" includes any naturally occurring or unnatural amino acid having a negatively charged side chain under normal physiological conditions. Examples of negatively charged naturally occurring amino acids are aspartic acid and glutamic acid.

The term "hydrophobic amino acid" means any amino acid having an uncharged, nonpolar side chain that is relatively insoluble in water. Examples of naturally occurring hydrophobic amino acids are alanine, leucine, isoleucine, valine, proline, phenylalanine, tryptophan and methionine.

The term "hydrophilic amino acid" means any amino acid having an uncharged, polar side chain that is relatively soluble in water. Examples of naturally occurring hydrophilic amino acids are serine, threonine, tyrosine, asparagine, glutamine, and cysteine.

As used herein, a "competitive" inhibitor is one that inhibits GAR activity by binding to the same kinetic form of the GAR as its accessory factors bind—thus directly competing with the accessory factors for the active site of the GAR. Competitive inhibition can be reversed completely by increasing the accessory factor concentration.

As used herein, the term "kinetic form" of the GAR means the condition of the GAR when either bound to an accessory factor or not, and in either its active or inactive state. That is, a kinetic form can be any conformation the GAR can assume under physiological conditions.

As used herein, the term "accessory factor" means an endogenous factor or protein that interacts with the L11/GAR. As used herein, EF-G is included in the term "accessory factor".

As used herein, an "uncompetitive" inhibitor is one that inhibits GAR activity by binding to a different kinetic form of the GAR than do the accessory factors. Such inhibitors bind to GAR already bound with the accessory factor and not to the accessory factor-free GAR. Uncompetitive inhibition cannot be reversed completely by increasing the accessory factor concentration.

As used herein, the term "co-complex" means L11 protein in covalent or non-covalent association with GAR RNA. As used herein, a co-complex may also encompass accessory factors and/or inhibitors or activators complexed with L11 or L11/GAR RNA.

As used herein, the terms "associates with" or "interacts with" refers to a condition of proximity between a chemical entity or compound, or portions thereof, with another chemical entity, compound or portion thereof. The association or interaction may be non-covalent—wherein the juxtaposition is energetically favored by hydrogen bonding or van der Waals or electrostatic interactions—or it may be covalent.

The term "beta-sheet" refers to the conformation of a polypeptide chain stretched into an extended zig-zig conformation. Portions of polypeptide chains that run "parallel" all run in the same direction. Polypeptide chains that are "antiparallel" run in the opposite direction from the parallel chains.

As used herein, the term "target" means a region of the L11/GAR complex, as defined by the crystal structure coordinates of Table II, which when bound by a candidate inhibitor or activator results in inhibition or activation of L11/GAR function.

As used herein, the term "modulate" refers to a change, either an increase or a decrease in some activity.

As used herein, the term "modulator" means a compound that modulates some activity.

As used herein, the term "inhibits" or "decreases" means that a candidate modulator reduces the activity of the L11/GAR. A candidate modulator may be said to inhibit or decrease activity if the activity of L11/GAR as measured by inhibition of GTP hydrolysis and/or translational activity is reduced by more than 50% in the presence of 50 uM or less of inhibitor compared to values obtained in the absence of inhibitor. Candidate modulators will preferably inhibit by more than 50% the presence of 10 uM or less of inhibitor and most preferably in the presence of 1 uM or less of inhibitor.

As used herein, the term "activates" or "increases" means that a candidate modulator raises the activity of the L11/GAR. A candidate modulator may be said to activate or increase activity if the activity of L11/GAR as measured by an increase of GTP hydrolysis by more than 50% in the presence of 50 uM or less of activator compared to values obtained in the absence of activator. Candidate modulators will preferably activate by more than 50% in the presence of 10 uM or less of inhibitor and most preferably in the presence of 1 uM or less of inhibitor.

As used herein, the term "structure coordinates" refers to mathematical coordinates derived from mathematical equations related to the patterns obtained on diffraction of a monochromatic beam of X-rays by the atoms (scattering centers) of an L11/GAR RNA complex in crystal form. The diffraction data are used to calculate an electron density map of the repeating unit of the crystal. The electron density maps are used to establish the positions of the individual atoms within the unit cell of the crystal.

As used herein, the term "heavy atom derivatization" refers to the method of producing a chemically modified form of a crystal of L11/GAR RNA. In practice, a crystal is soaked in a solution containing heavy metal atom salts, or organometallic compounds, e.g., methyl mercury nitrate, lead chloride, gold thiomalate, thimerosal or uranyl acetate, which can diffuse through the crystal and bind to the surface of the protein. The location(s) of the bound heavy metal atom(s) can be determined by X-ray diffraction analysis of the soaked crystal. This information, in turn, is used to generate the phase information used to construct three-dimensional structure of the protein or protein:RNA complex (Blundel, T. L. and N. L. Johnson, 1976, Protein Crystallography, Academic Press).

Those of skill in the art understand that a set of structure co-ordinates determined by X-ray crystallography is not without standard error. For the purpose of this invention, any set of structure coordinates for an L11/GAR RNA complex that has a root mean square deviation of protein backbone atoms (N, C$\alpha$, C and O) of less than 0.75 when superimposed on the structure coordinates of Table II, using backbone atoms, shall be considered identical.

The term "unit cell" refers to a basic parallelipiped shaped block. The entire volume of a crystal may be constructed by regular assembly of such blocks. Each unit cell comprises a complete representation of the unit of pattern, the repetition of which builds up the crystal. Using the structure coordinates of the L11/GAR RNA complex provided by this invention, molecular replacement may be used to determine the structure coordinates of a crystalline mutant or homologue of the L11/GAR RNA complex or of a different crystal form of the L11/GAR RNA complex.

Detailed Description of the High Resolution Structure of the L11/GAR Complex

The GAR RNA from the *T. maritima* 23S rRNA consists of nucleotides 1111–1168, which correspond to nucleotides 1051–1108 in the *E. coli* sequence. Hereafter, the *E. coli* numbering will be used in order to facilitate comparison with the available biochemical and genetic data. As described in detail in Example 1, crystals of the GAR RNA complexed with ribosomal protein L11 from *T. maritima* were prepared and used to solve the structure to 2.6 Å resolution using multi-wavelength anomalous diffraction on a mercury derivative of the crystal. Data collection, phasing and refinement statistics are shown in Table I. The asymmetric unit in the crystal consists of two 1:1 L11-RNA complexes stacked in a head-to-head manner. The two complexes are nearly identical except for a subtle bend in the terminal three base pairs of the RNA, and a difference in the degree of disorder of the two L11 N-terminal domains. Several observations strongly suggest that the conformation observed in the crystal structure is extremely similar to the structure of the GAR in situ in the ribosome. The RNA contains all of the predicted secondary structure; the two complexes in the asymmetric unit are virtually identical; and, most significantly, the structure explains most of the large body of experimental data on this system.

Structure of the GAR RNA

The predicted secondary structure of the GAR RNA (Glotz et al., 1981; Noller et al., 1981) is almost identical to that derived from the crystal structure (FIG. 1a). The RNA secondary structure contains four double-helical segments, referred to as the terminal stem (defined by nucleotides (nt) 1051–1056 base paired with nt 1103–1108), the 1067 stem-loop (defined by nt 1062–1076), the 1082 hairpin (defined by nt 1082–1086) and the 1095 stem-loop (defined by nt 1090–1101).

Figure 1B:
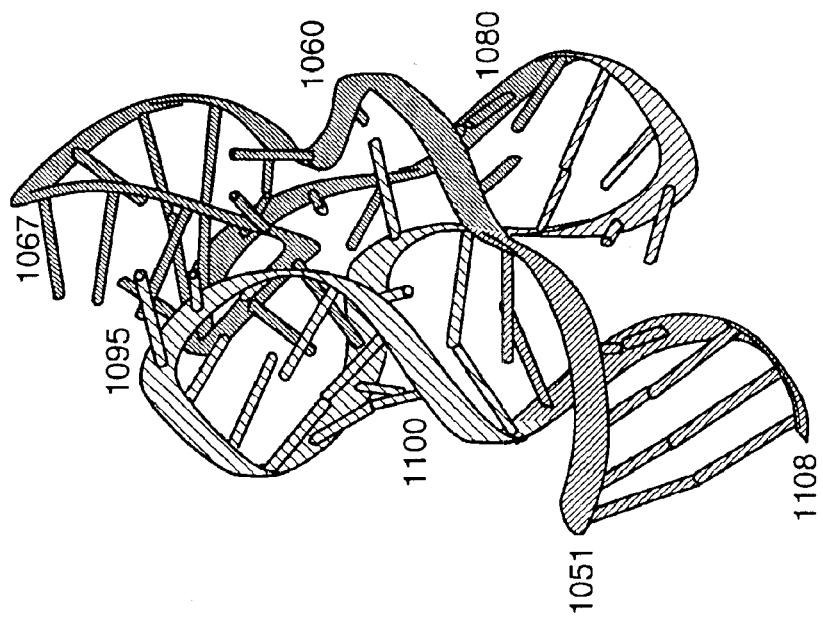
Figure 2A:
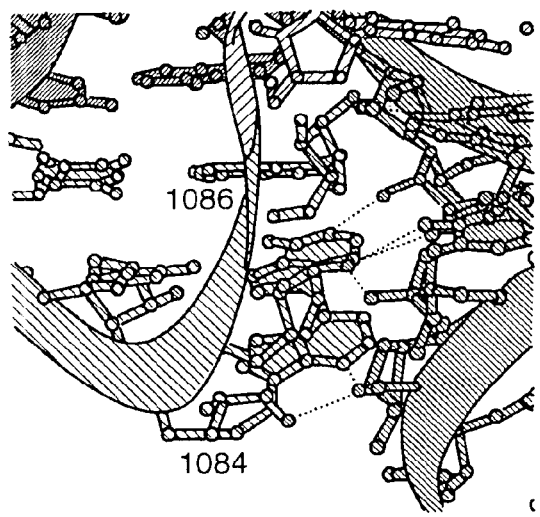
FIGS. 2*a* and 2*b* were made with RIBBONS (Carson, 1991); 2*c* with MOLSCRIPT (Kraulis, 1991).

In the tertiary structure, the terminal stem stacks on the 1095 stem-loop, and the 1067 stem-loop stacks on the 1082 hairpin. Thus the four double-helical segments stack pairwise to form two extended helical subdomains. These two subdomains have irregular yet complementary shapes, so that the entire GAR RNA folds into a single compact globular domain (FIGS. 1b, c). The helical subdomains associate in a roughly parallel fashion, with the terminal stem packed against the 1082 hairpin, and the 1067 and 1095 stem-loops packed against each other. Bulged-out residues in the 1067 and 1095 stem-loops mediate long-range tertiary interactions between the two subdomains. The fold requires two sharp turns in the backbone at the 1056–1057 and 1086–1087 phosphodiester linkages in the center of the junction, where the chain crosses over from one helical subdomain to the other. The molecule also contains a relatively large number of well-ordered metal ions that are integral to the A Ribose Zipper Joins the Terminal Stem and the 1082 Hairpin The association of the terminal stem with the 1082 hairpin occurs via their minor grooves. This rather intimate packing is stabilized primarily by a dense network of hydrogen bonds between the riboses of nucleotides A1084-A1086 and C1104-A1106 (FIG. 2a). A similar structural motif has been observed in the P4–P6 domain of the group I intron, and has been referred to as a ribose zipper (Cate et al., 1996). At the center of the four-way junction, the 2' OH of A1086 appears to be a particularly crucial component of the ribose zipper. It makes hydrogen bonds to A1103 N1 and G1056 2'OH, and also directly ligates a crucial central cadmium ion (see below). A1086 has an unusual syn conformation that is necessary for the very tight packing of its sugar against the G1056-A1103 pair, and for the reverse-Watson-Crick geometry of the U1082-A1086 pair (FIG. 2c). Another noteworthy feature of the ribose zipper is a minor groove A-(G-C) triple involving nucleotides A1085, G1055 and C1104 (FIG. 2c). This minor-groove triple has also been found previously in large RNA tertiary folds (Cate et al., 1996; Ferre-D'Amare et al., 1998).

Intimate Association of the 1067 and 1095 Stem-loops by Reciprocal Donation of Bulges The interaction between the 1067 and the 1095 stem-loops occurs primarily in their major grooves and is mediated largely by a reciprocal donation of highly conserved bulged-out bases. This unusually intimate major-groove packing is the primary reason for the compactness of the overall fold, and it requires substantial distortions from regular helical geometry. This portion of the structure contains a large number of tertiary interactions, some of which are novel structural motifs.

Figure 1A:
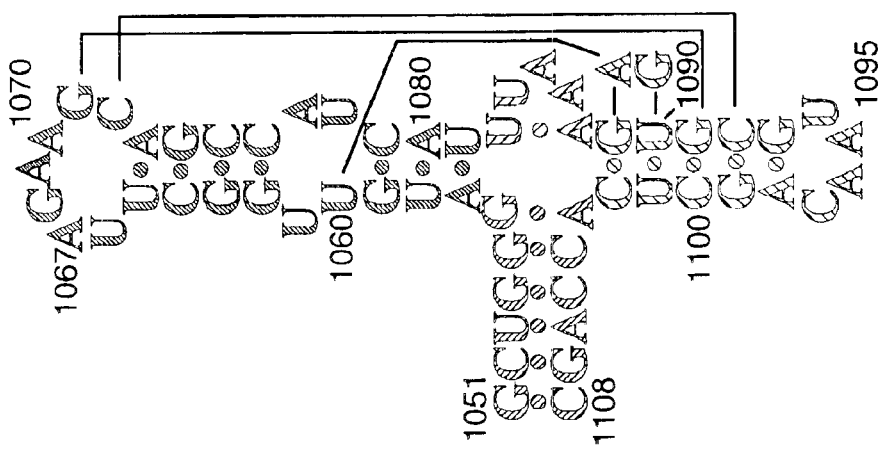
FIG. 1 shows an overview of the secondary and tertiary structure of the GTPase activating region RNA from *Thermotoga maritima*: a) RNA secondary structure derived from the crystal structure (RNA sequence is SEQ ID NO: 5). Lines indicate long-range base triples and the long-range 1088–1060 base pair; b) ribbon-and-stick schematic of the RNA tertiary structure (For clarity, protein L11 has been omitted from view); c) same as (b), but the view is down the major groove of the 1095 stem to emphasize the compactness to the RNA fold.

The 1095 stem donates a bulged-out base, A1088, to a pocket created by a distortion in the 1067 stem (FIG. 1). A1088 forms a universally conserved reverse-Hoogsteen pair with U1060 (FIG. 2c). Because of steric constraints, A1088 must be in the syn conformation, which together with the reverse-Hoogsteen pairing geometry requires that U1060 must be flipped over. The inversion of U1060 is in turn facilitated by bulging out of the base of U1061. This inversion-bulge, or S-turn motif, has an S-shaped backbone conformation that has been observed previously (Szewczak et al., 1993; Wimberly, 1994; Wimberly et al., 1993). The insertion of A1088 also requires that residues A1077 and U1078 are unpaired and rotated out to open up the pocket. The unpaired conformation of these residues is stabilized by three hydrogen bonds to the sugar-phosphate backbone of the 1095 stem loop at A1088 and G1089. Two of these hydrogen bonds are to the base of A1077 which explains its universal conservation.

Figure 2B:
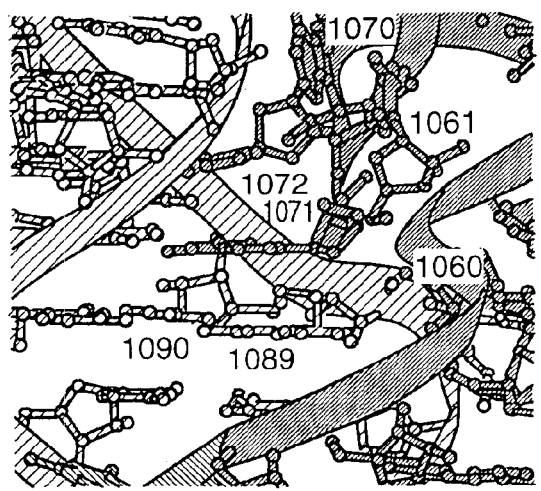
Figure 2C:
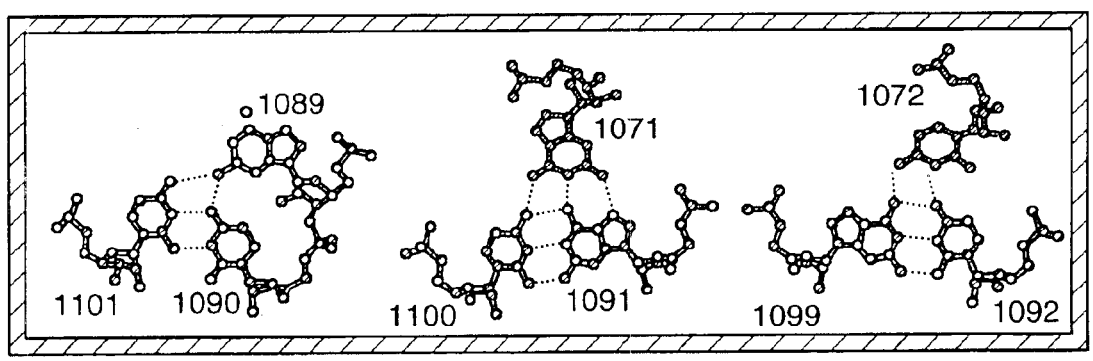
FIG. 2 shows selected details of the tertiary structure of the GTPase activating region RNA from *Thermotoga maritima*; in (a) and (b), the RNA backbone is represented by a ribbon and the phosphates are not shown: a) the ribose zipper that mediates the minor-groove to minor-groove association of the terminal stem and the 1082 hairpin loop (Hydrogen bonds are indicated by dotted lines); b) the major-groove to major-groove association of the 1067 and 1095 stem-loops, in a view emphasizing the high-five, S-turn, and dinucleotide platform motifs. The high-five motif consists of the long-range stacking of two bulged residues, U1061 and A1070. The S-turn comprises the inverted nucleotide U1060 and the bulged residue U1061. The dinucleotide platform motif consists of G1089 and U1090, on which the bulged residues G1071 and C1072 rest, as part of the long-range triples G1071-(G1091-C1100) and C1072-(C1092-G1099).
Figure 2C:
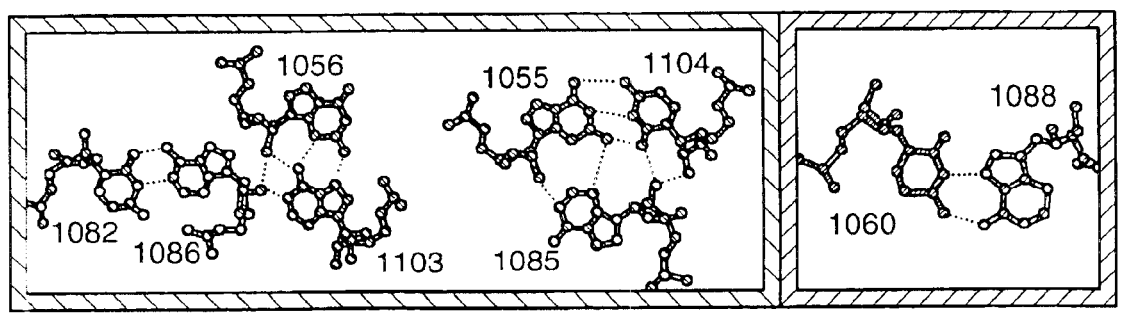

The reciprocal donation of a bulge from the 1067 stem-loop to the 1095 stem involves nucleotides G1071 and C1072, which form two novel interdomain base triples with the base pairs G1091-C1100 and C1092-G1099 respectively (FIGS. 2b, c). Within the 1095 stem loop, nucleotides G1089-(U1090-U1101) also form a triple (FIG. 2c), with G1089 acting as a stacking platform for the other two triples (FIG. 2b). The stacking of G1071 on G1089 is further stabilized by hydrogen bonds between the 1089 2' OH and 1071 N3, and between the 1071 2' OH and the 1089 phosphate. These three base triples explain the sequence conservation of all these residues. The 1072-(1092–1099) triple was previously predicted and subsequently experimentally confirmed, although the geometry proposed for the triple (Conn et al., 1998) differs from that seen in the crystal structure.

The 1067 and 1095 Hairpin Loops

The highly conserved 1067 hairpin loop consists of two parts, a hairpin portion (U1066-A1069) that stacks on the sheared U1065-A1073 pair, and a three-nucleotide bulge (A1070-C1072) that participates in two different long-range tertiary interactions. The hairpin portion has a conformation commonly found in small hairpin loops, with a U-turn motif (Quigley and Rich, 1976) at U1066 and regular stacking of A1067-G1068-A1069. A1069 stacks on A1073, and its 2' OH hydrogen bonds to the N3 of U1065, thereby stabilizing the location of the 1069 sugar as well as the sheared geometry of the U1065-A1073 pair. The three-nucleotide bulge has a corkscrew-like conformation in which A1070 is bulged to one side, and G1071 and C1072 are bulged into the major groove of the 1095 stem-loop. A1070 makes a novel long-range stacking interaction with U1061 which will be referred to herein as a "high-five" motif (FIG. 2b), while 1071 and 1072 participate in the long-range base triples described above. The high-five motif makes several hydrogen-bonding and van der Waals interactions with the 1095 hairpin loop, thereby stabilizing the relative orientations of the two hairpins.

The 1095 hairpin loop is also very highly conserved, and has a regular conformation stabilized by a U-turn at U1094 and a sheared G1093-A1098 pair. Part of the base of G1093 stacks over the base of C1072, so that the long-range base triples are tightly wedged between an overhang from the sheared G-A pair on one side, and the G1089-(U1090-U1101) triple on the other side. The structure of the 1095 hairpin loop is very similar to an NMR-derived structure of a small stem-loop containing the same hairpin loop sequence (Fountain et al., 1996). The structural basis for the very high sequence conservation of several of the residues in the 1095 hairpin loop (i.e. A1095, A1096 and U/C1097) is not completely clear, but it may arise from interactions with the N-terminal domain of L11 (see below) or with other components of the ribosome.

Metal Ion Interactions with RNA

Figure 3B:
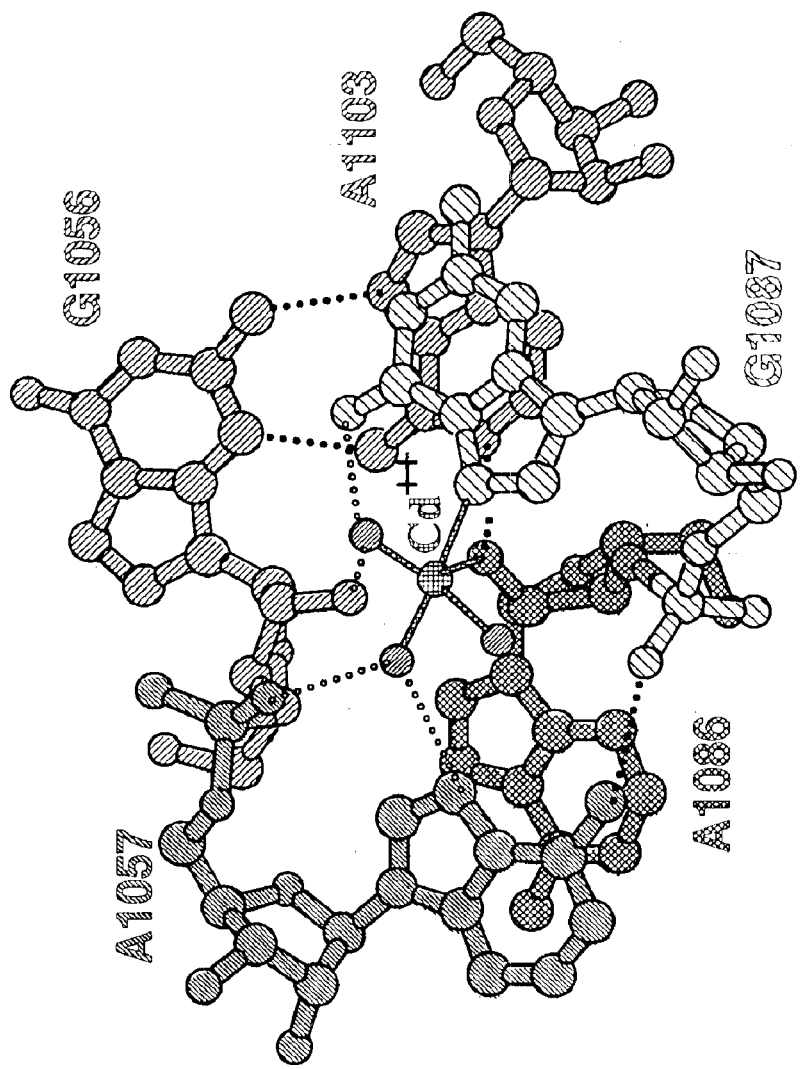
FIG. 3. RNA-metal ion interactions in the tertiary structure of the GTPase activating region RNA from *Thermotoga maritima:* a) overview of the locations of the metal ions, showing that they are primarily in the interacting major grooves of the 1067 and 1095 stems. Magnesium ions are gold, cadmium ions are magenta, and the mercury ion is rose. b) close-up of the central cadmium ion that stabilizes sharp turns at the 1056–1057 and 1086–1087 phosphodiester linkages at the center of the 4-way junction. Direct ligation of the cadmium ion is indicated by solid lines, and second-shell ligation is indicated by dotted lines.
FIG. 3*a* was made with RIBBONS (Carson, 1991), and FIG. 3*b* was made with MOLSCRIPT (Kraulis, 1991).
Figure 3A:
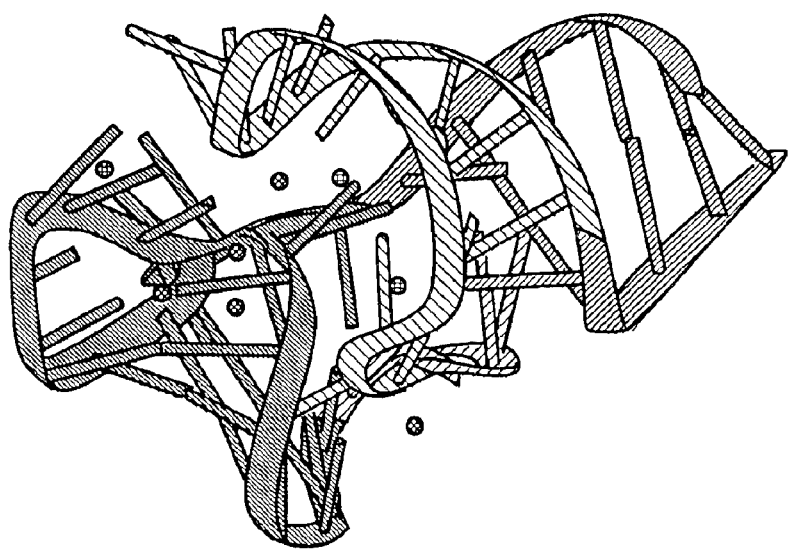

Three cadmium ions and at least seven magnesium ions are visible in the experimental electron density map. One of the cadmium ions stabilizes the association of the two complexes in the asymmetric unit, but the other two are integral to the RNA structure, and these two sites are probably occupied by magnesium ions in vivo. Most of the ions mediate the close approach of phosphates in the interacting major grooves of the 1067 and 1095 stems, and five of these ions stabilize the location and conformation of the 1070–1072 bulge between the 1067 and 1095 stems (FIG. 3a). A cadmium ion occupies a crucial location at the center of the four-way junction, where it makes either direct or water-mediated contacts with residues from all four double-helical stems (FIG. 3b). This ion appears to stabilize both of the sharp turns at the center of the junction, i.e. the 1056–1057 and 1086–1087 turns, and thereby plays an important role in determining the overall structure of the four-way junction.

Despite the accelerating pace of RNA structure determination, extremely little is known about RNA tertiary structure because only about five RNA folds have been determined. The crystal structure of the GAR RNA reveals an unexpectedly complex and compact fold that contains both well-known and novel structural motifs. The GAR RNA is in fact the most compact RNA structure yet reported, exposing only 138 Å$^2$ of solvent accessible surface area per nucleotide (Nicholls et al., 1991). This extreme compactness is a result of extensive tertiary interactions along the entire length of the structure, in both the major and minor grooves. The other relatively compact known RNA folds exhibit primarily minor-groove packing (e.g., the P4–P6 domain of the group I intron) or primarily major-groove packing (e.g., tRNA), and are therefore less efficiently folded. It is probable that very efficient packing of RNA will be found to be common in the ribosome.

The crystal structure explains the molecular basis for a number of important mutagenesis results. In particular, the RNA residues most sensitive to mutation are involved in tertiary interactions. For example, mutation of any of the universally conserved residues within the A1085-G1055-C1104 triple, a crucial part of the ribose zipper joining the terminal stem and the 1082 hairpin, dramatically destabilizes the RNA structure and greatly reduces the affinity for L11 (Lu and Draper, 1995). Mutation of C1072 to U within the 1072-(1092–1099) triple destroys the RNA tertiary structure, which demonstrates the energetic importance of this triple. Finally, the unusual observation that U1061A and U1061G mutants are more stable (Lu and Draper, 1994; Lu and Draper, 1995) is explained by the 1061–1070 "high five" tertiary stacking motif, since purine stacking is more stable than pyrimidine stacking.

Stabilization of the RNA Tertiary Structure by Metal Ions

The crystal structure also reveals important new information about how metal ions interact with and stabilize unusual RNA structures. Biochemical experiments suggest that the GAR RNA contains relatively high affinity binding sites for two divalent cations (Bukhman and Draper, 1997) and one K+ or NH4+ ion (Wang et al., 1993). The crystal structure reveals no fewer than seven magnesium sites and two cadmium sites, most of which stabilize the close approach of phosphates in the interacting major grooves of the 1067 and 1095 stem-loops. The metal-ion stabilization of the 1070–1072 bulge conformation is qualitatively similar—though different in detail—to that seen in the A-rich bulge of the P4–P6 domain of the group I intron (Cate et al., 1996). The striking structural role played by the central cadmium ion suggests that this site corresponds to one of the thermodynamically important ions. While more experiments will be necessary to test this hypothesis, it is worth noting that this cadmium ion is one of the two sites in the structure that ligates a guanosine N7. Both Mn$^{++}$ and Cd$^{++}$ preferentially bind to guanosine N7, and it has been observed that Mn$^{++}$ stabilizes the tertiary structure more than other divalent cations (Bukhman and Draper, 1997).

The Major-groove Dinucleotide Platform: a Generalization of the Adenosine Platform The crystal structure also reveals a new variant of a known tertiary structure motif, the adenosine platform. In the structure of the P4–P6 domain, two successive adenines adopt a coplanar conformation—an adenosine platform—that serves as a stacking platform for a long-range tertiary interaction (Cate et al., 1996). In the GAR structure, two successive nucleotides, G1089 and U1090, adopt the same conformation seen in the adenosine platform (FIG. 2C). The two bases are coplanar, with a single N2-O4 hydrogen bond between them, and they also serve as a stacking platform, for the 1071–1072 bulge involved in base triples (FIG. 2B). There are, however, some differences between the GU platform seen here and the AA platform. In the P4–P6 structure, the motif is displayed in the minor groove rather than in the major groove, as is seen here. Moreover, in the P4–P6 structure it is the 3' adenosine upon which the long-range stacking interaction occurs, while here G1071 rests upon the 5'residue of the motif, G1089. Finally, the tertiary stacking interaction occurs on opposite faces of the motif in the two structures. Despite these differences, the near-identity of the conformations and functions of the motifs in these two structures leads to the suggestion that the motif be referred to as a "dinucleotide platform", since it is clearly not restricted to adenosines. The few available data suggest that a GU dinucleotide platform may generally be more stable than an AA platform for major groove display. In the GAR, residues 1089 and 1090 are strictly conserved as either GU or AA, but mutation from AA to GU results in a significant stabilization of the RNA tertiary structure (Lu and Draper, 1994; Lu and Draper 1995). The major-groove GU dinucleotide platform motif has also been found in small RNA structures lacking tertiary interactions (Szewczak et al., 1993; Wimberly et al., 1993), which suggests that in large structured RNAs, the GU dinucleotide platform may in some cases function as a pre-formed stacking platform supporting major-groove base triples.

Methylmercury as a Phasing Vehicle for RNA Crystal Structures

Surprisingly, the primary mercury site used in phasing is not near a cysteine of L11, but is located 2.4 Å from the N3 atom of U1061, consistent with a covalent mercury-uridine N3 bond. A similar, minor mercury site at U1078 is also visible in the anomalous difference Fourier map. Although most mercury adducts of pyrimidines have been obtained at the O4 or 5 positions of the base, a mercury 1-methylthymine adduct at N3 has been obtained at alkaline pH (Kosturko et al., 1974), and methylmercury salts have been shown to denature AT-rich DNA, consistent with reaction at thymine N3 (Gruenwedel and Davidson, 1966; Gruenwedel and Davidson, 1967). Uracil is often preferred at bulge sites in RNA, so many larger RNA structures may contain solvent-accessible uracils. Therefore, methylmercury derivatization of RNA under native conditions, either prior or subsequent to crystallization, may be a generally useful method for obtaining heavy atom derivatives of RNA crystals, without the laborious incorporation of sulfur-containing ribonucleotides.

The Structure of Ribosomal Protein L11

Figure 4A:
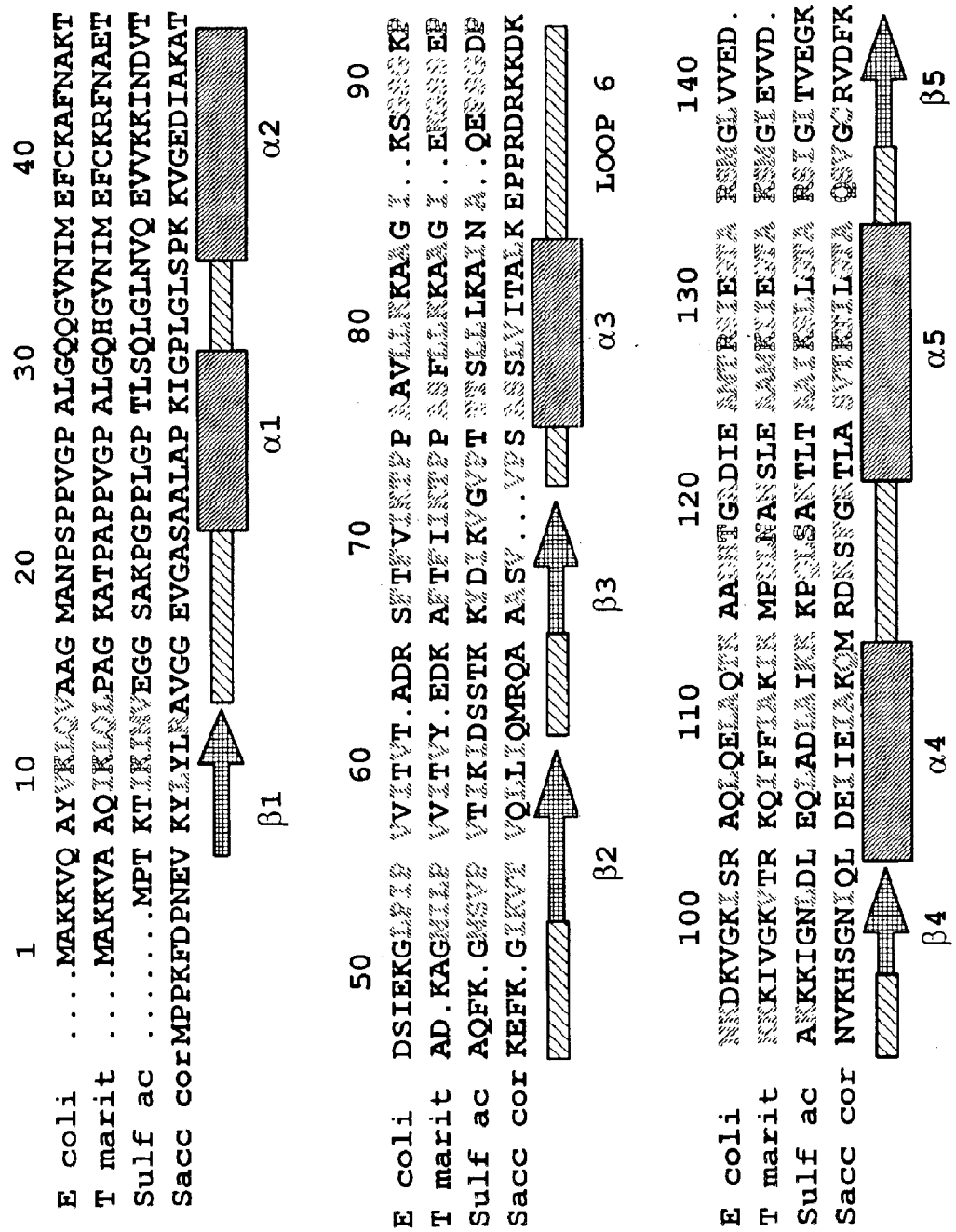
FIG. 4 shows the RNA-L11 complex within the GTPase activating region from *Thermotoga maritima*: a) alignment of four widely divergent L11 sequences ("*E coli*" is *Escherichia coli*, SEQ ID NO: 1; "T marit" is *Thermotoga maritima*, SEQ ID NO: 2; "Sulf ac" is *Sulfolobus acidocaldarius*, SEQ ID NO: 3; and "Sacc cor" is *Saccharomyces cerevisiae*, SEQ ID NO: 4), together with a schematic of the protein's secondary structure. The sidechains of residues shown in forward-slanting narrow hatch marks participate in the hydrophobic core in the crystal structure. Residues involved in RNA binding are shown with backward-slanting narrow hatch marks for side-chain contacts, backward slanting wide hatch marks for main-chain contacts or cross-hatched if both the side-chain and main-chain interact with RNA. Abbreviations: *E. coli, Echerichia coli* (eubacterium); *T. marit, Thermotoga maritima* (eubacterium); *Sulf ac, Sulfolobus acidocaldarius* (archaea); *Sacc cer, Saccharomyces cerevisiae* (eukaryote). The numbering is based on the *Thermotoga maritima* sequence present in the crystal structure. b) stereoview of the complex. The L11 N- and C-terminal domains are labled. Note that the N-terminal domain straddles the interface of the 1067 and 1095 stem-loops. c) orthogonal stereoview of the complex. This view emphasizes the relatively loose association of the L11 N-terminal domain with the RNA.
FIGS. 4*b* and 4*c* were made with RIBBONS (Carson, 1991).
Figure 4B:
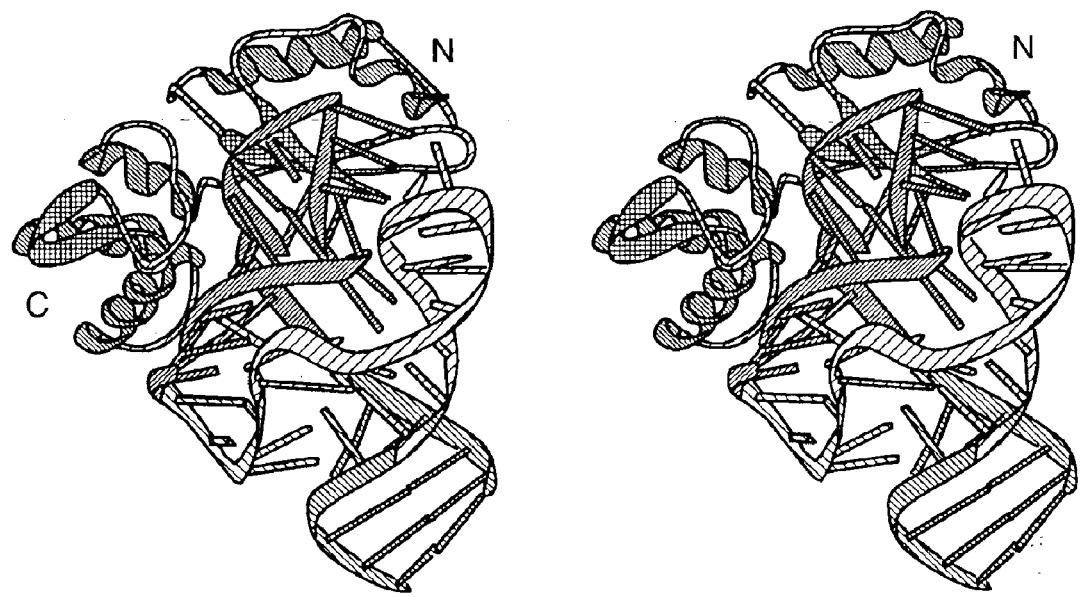
Figure 4C:
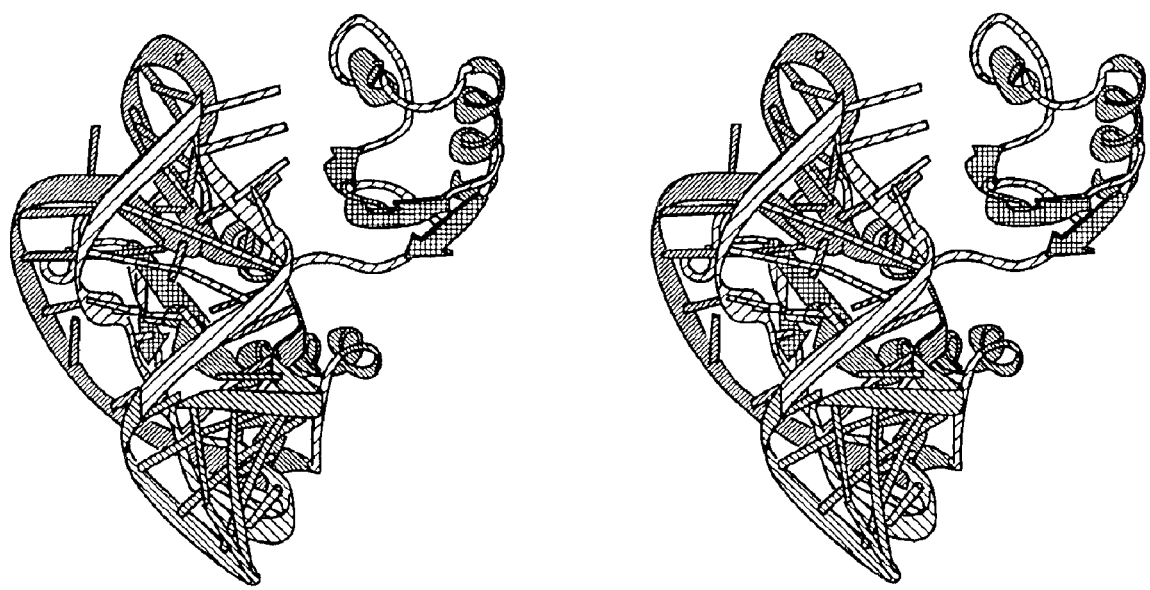

Ribosomal protein L11 consists of two globular domains connected by a linker region. The secondary structure and a sequence alignment of the protein are shown in FIG. 4a, and the tertiary fold is shown in FIGS. 4b and 4c in the context of the complex. As described below, there is some flexibility between the two domains, but the linker is short and it contains two conserved prolines (73 and 74) that provide inherent rigidity. Also, the domain interface consists primarily of conserved hydrophobic residues, notably Met52, Ile53, Pro55, Pro73 and Phe77. These observations suggest that relative orientation of the two domains has not been greatly perturbed by crystal packing requirements.

The structure of the L11 N-terminal domain (NTD) has not been previously reported. It consists of two helices packed against the concave surface of a three-stranded antiparallel beta sheet, with an overall β1-α1-α2-β2-β3 topology. The N-terminal 7 residues are disordered. One of the most distinctive and conserved regions of the L11 molecule is the proline-rich helix 1, which appears to have a crucial functional role, as described below. The electron density for this helix was weak, and the register of the sequence in this helix may be in error by one residue. The average main-chain B-factor for the domain is 72 Å$^2$ (for comparison, the average B-factor of the C-terminal domain (CTD) is 24 Å$^2$), indicating rigid body movement of the NTD within the crystal. This flexibility is consistent with the rather limited interactions seen between the NTD and other parts of the structure, and may have functional implications (see below).

The structure of the CTD is in good agreement with the previously determined NMR structures of the CTD, both in isolation (Markus et al., 1997; Xing et al., 1997) and in the context of the L11-RNA complex (Hinck et al., 1997). The domain consists of a three-helical bundle and a short parallel two-stranded β-ribbon, with an overall α3-β4-α4-α5-β5 topology. All five secondary structure elements contribute to a conserved hydrophobic core. The domain is characterized by two extended loops that are disordered in the absence of the RNA, but which have defined structures in the complex.

The RNA-protein Interaction

The two domains of L11 are very unequally associated with RNA. The CTD-RNA interface covers over 1700 Å$^2$ of solvent accessible surface area, while the NTD-RNA interface is less than 100 Å$^2$. This difference is consistent with the observation that the RNA-binding affinity of the CTD is essentially the same as that of the full-length protein (Xing and Draper, 1996).

Figure 5A:
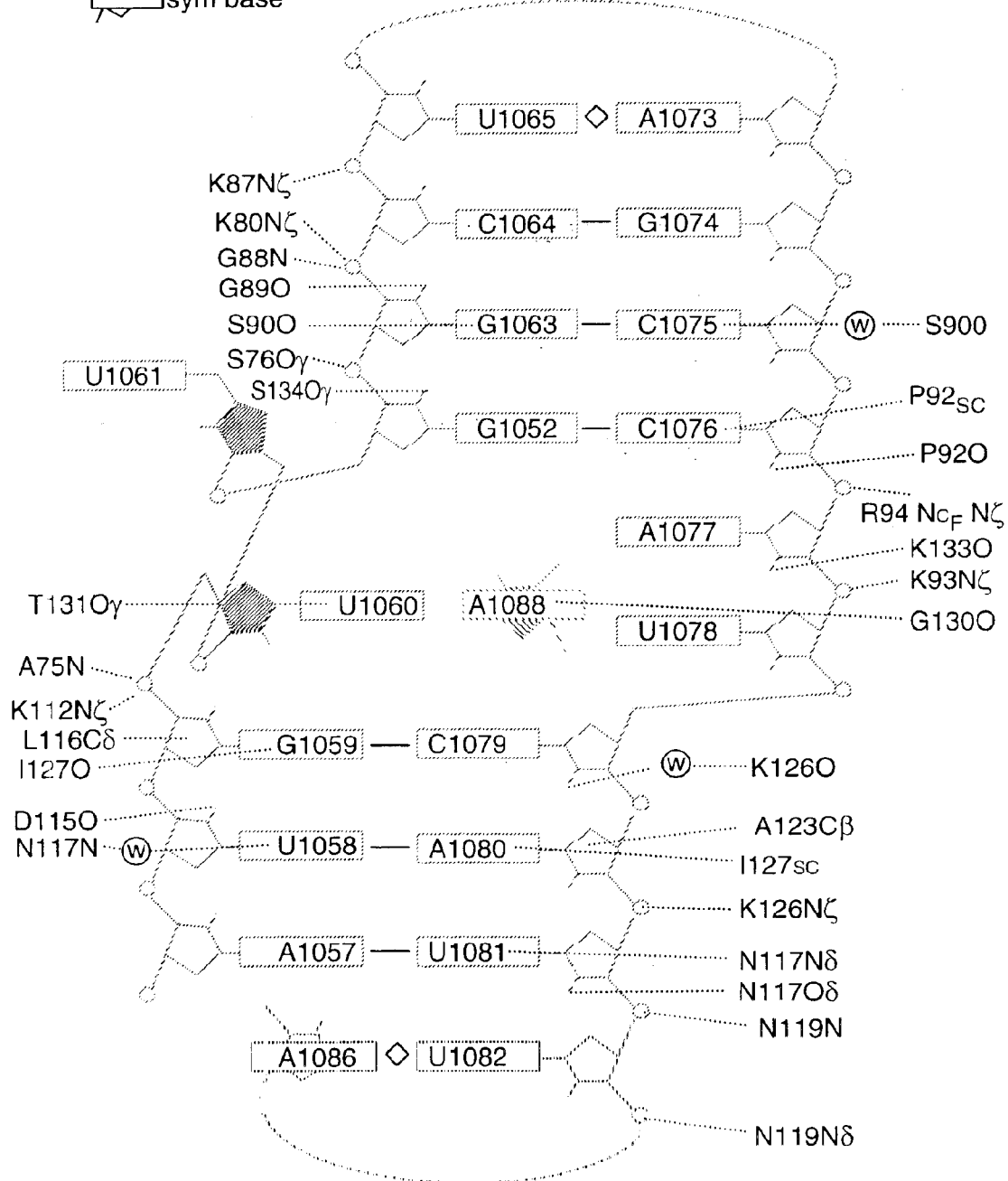
FIG. 5 shows Protein-RNA recognition within the GTPase activating region from *Thermotoga maritima:* a) schematic of RNA-CTD interactions observed in the crystal structure. Unusual RNA conformational features are also indicated (see inset for key). Water molecules that mediate protein-RNA interactions are indicated by a "W". b) Detail of the recognition of the conserved long-range A1088-U1060 pair by conserved L11 residues Gly 130 and Thr131 from helix 5, and by the N-terminus of helix 3.
FIG. 5*b* was made with MOLSCRIPT (Kraulis, 1991).

The CTD binds the minor groove of the 1067 stem (FIGS. 4b, c), which is bent and flatter than the minor groove of a canonical A-form double helix. The RNA-binding surface of the CTD consists of one face of helix 5, the N-terminal end of helix 3, and loops 6 and 7 that flank helix 5. Helix 5 is positioned lengthwise in the minor groove, and the flanking loops 6 and 7 extend this minor groove binding surface and also interact with the sugar-phosphate backbones on either side of the groove. A summary of the CTD-RNA interactions observed in the crystal structure (FIG. 5a) emphasizes that the recognition of the RNA minor groove by L11 involves primarily interactions between the protein backbone and the RNA 2' OH moieties. Approximately half of the RNA-CTD hydrogen bonds involve a main-chain amide or carbonyl, and over half of the 2'OH groups in the CTD footprint are hydrogen-bonded to the protein. This preponderance of protein backbone-RNA backbone interactions indicates that overall shape complementarity between the RNA and protein must be an important determinant of specificity.

Figure 5B:
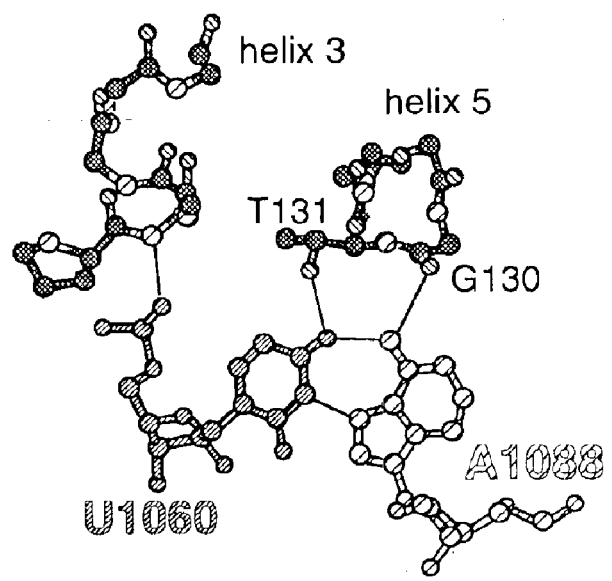

Although binding appears to depend less on electrostatic interactions than on shape complementarity, there are a number of important salt bridges between basic sidechains and phosphate groups: lysines 93, 126 and 133 and Arg94 interact with one side of the minor groove, and lysines 80, 87 and 112 with the other side. In the former group, the sidechains are splayed away from protein, and the hydrophobic part of the sidechain contributes to surface complementarity with the RNA. Sidechains at the N-terminus of α5 and within loop 7 make particularly intimate contact with the RNA, notably Ile127 and Asn117. Asn117 points directly into the minor groove making a number of hydrogen bonding interactions, and is one of the few sidechains that formally "reads" the local RNA sequence. Two of the most important recognition elements in the RNA are the universally conserved long-range pair U1060-A1088 and the surrounding RNA internal loop that distorts to accommodate the insertion of A1088. Significantly, the RNA footprint of helix 5 encompasses this entire region of distorted RNA. The importance of the U1060-A1088 pair for L11 specificity is shown by the extremely high conservation of Gly130 and Thr131 to which these bases are hydrogen-bonded (FIG. 5b).

The NTD bridges the interface between the 1067 and 1095 stem-loops, and it makes only a few specific interactions with the RNA (FIG. 4). Although its association with RNA is somewhat tenuous, which might be a result of its binding mode having been altered by crystal packing requirements, the high sequence conservation of the NTD residues interacting with RNA suggests that the binding mode observed in the crystal structure is relevant to the structure of the complex in solution. Moreover, as described above, the structure of the NTD-CTD interface also suggests that the orientation of the NTD has not been greatly perturbed by crystal packing. The NTD residues interacting with RNA include Lys10, Gln12, Gln30 and Lys71. Lys10 makes both main-chain and side-chain interactions with the RNA, and Gln30 probably interacts specifically with A1095. There is also electron density interacting with the Watson-Crick face of C1097, but it is not clear whether this density arises from the NTD; examination of an anomalous difference Fourier map reveals that some of this density must correspond to a mercury or cadmium site. Finally, although the proline-rich sequence in helix 1 is surface-exposed, highly conserved, and in the correct orientation for possible interactions with factors or antibiotics, it is close to but not in direct contact with RNA.

The Thiostrepton/micrococcin Binding Site

Figure 6:
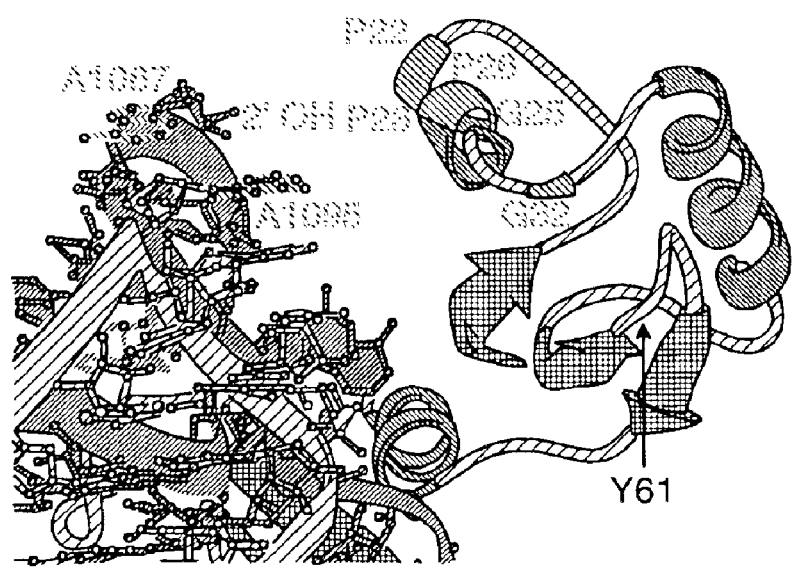
FIG. 6 shows that the sites of mutations conferring resistance to thiostrepton and micrococcin are clustered around a cleft between the RNA and the proline-rich helix in the L11 N-terminal domain. Residues implicated in thiostrepton binding (A1067, A1095, and Pro22) are labeled. The position of Tyr61, which is protected by thiostrepton in protein footprinting experiments, is also indicated. Other labeled residues are those that confer micrococcin resistance (see text for details). The figure was made with RIBBONS (Carson, 1991).

A1067 and A1095, at the ends of their respective stem-loops, have both been implicated in the binding of the antibiotics thiostrepton and micrococcin. Modification of A1067 by 2'-O methylation (Cundliffe and Thompson, 1979;

Thompson et al., 1982) or transversion mutations at either site (Rosendahl and Douthwaite, 1994) confers thiostrepton resistance. It has also been shown that thiostrepton affects the reactivity of both A1067 and A1095, suggesting that these two sites are close together (Rosendahl and Douthwaite, 1994) as indeed they are in the crystal structure. As for the role of L11 in antibiotic binding, it is known that L11 is required for high affinity binding of thiostrepton to the RNA, and that binding of L11 and thiostrepton to the RNA is cooperative. Thiostrepton has a much weaker affinity for the RNA alone (Kd=0.4 μM), and it does not bind isolated L11 (Thompson et al., 1979). Two sites within the NTD of the protein have been implicated in this interaction: the mutations Pro22Ser and Pro22Thr confer thiostrepton resistance, while the antibiotic protects Tyr61 (Tyr62 in $E.$ $coli$) in protein footprinting experiments (Porse et al., 1998). Recently, mutations that confer resistance to micrococcin have also been mapped to the NTD of L11 between residues 22 and 32 (Porse et al., 1999). All of these sites are located on a small surface of the NTD, near A1067 and A1095 on the RNA (FIG. 6). A prominent feature of this surface is the distinctive and highly conserved proline-rich helix, while Tyr61 is over 20 Å distant. The clustering of these sites of antibiotic resistance mutations, together with the cooperative binding data, strongly suggest that the antibiotics bind to the cleft between the RNA and the proline-rich helix 1 of the NTD.

The structure of the C-terminal domain (CTD) was previously determined by NMR in both the free (Markus et al., 1997; Xing et al., 1997) and RNA-bound (Hinck et al., 1997) forms. Our crystal structure of the CTD is similar to that of the RNA-bound form determined by NMR, except for the conformation of the large RNA-binding loop 6 which is poorly determined in the NMR studies (Hinck et al., 1997). The mean Cα root mean square difference (RMSD) for the crystal structure vs. NMR ensemble is 2.7 Å overall, or 1.6 Å when residues 86–97 of loop 6 are excluded. For comparison, the mean RMSD within the ensemble of NMR structures is 2.3 Å for main chain atoms.

Many ribosomal proteins show structural similarities to families of DNA- and RNA-binding proteins (Ramakrishnan and White, 1998). It was noted from the NMR structure that the CTD of L11 has a homeodomain-like fold (Markus et al., 1997; Xing et al., 1997), and further NMR studies on the complex suggested that the CTD uses the typical homeodomain helix to bind RNA (Hinck et al., 1997). Although the crystal structure reveals that this helix is indeed intimately associated with the RNA, its interaction does not bear any similarity to the base-specific recognition of a major groove by the homeodomains. Regarding the NTD, its overall α+β fold is similar to that seen in many other RNA-binding proteins (Ramakrishnan and White, 1998), but its β-α-α-β-β topology has not yet been observed in an RNA-binding protein.

RNA-protein Interaction

The L11-GAR RNA interaction has been probed by biochemical and NMR methods, and the crystal structure is in good agreement with the results of these studies, including a rather weak interaction between the RNA and the NTD. The RNA surface covered by the CTD corresponds fairly well to the residues protected by the binding of full-length L11 as shown by hydroxyl radical footprinting experiments (Rosendahl and Douthwaite, 1993). The RNA-binding surface of the CTD has been mapped by NMR chemical shift changes and relaxation studies (Hinck et al., 1997), and again the agreement with the crystal structure is excellent. The observation that L11 recognizes the RNA primarily by shape complementarity rather than by a sidechain-base reading of the RNA sequence is not surprising considering that the interaction occurs primarily via the minor groove. The interaction agrees with the prediction that relatively few highly conserved CTD residues would make specific sidechain contacts with RNA (Xing et al., 1997). However, the related prediction that RNA binding by the CTD would not involve extensive recognition of the RNA bases is incorrect, as most of the base pairs are recognized by either hydrogen bonding or hydrophobic interactions. However, most of these hydrogen bonds occur via main chain amides or carbonyls, rather than side chains. Finally, it is worth noting that L11 does not directly recognize the bulged-out nucleotides, which have previously been proposed as specificity determinants in ribosomal RNA-protein complexes.

Biochemical experiments have shown that L11 stabilizes the tertiary structure of the RNA, and that this is a property of the CTD (Draper and Xing, 1995; Xing and Draper, 1995). Since nearly all of the direct RNA-protein contacts within the complex are to the 1067 stem, the resulting stabilization of the RNA tertiary structure appears to be indirect. The binding of one face of helix 5 with both strands of the 1067 stem is extensive and universally conserved, and this interaction must be particularly important for stabilization of the RNA tertiary structure. Consistent with a crucial role in RNA binding, helix 5 contains most of the mutation sites that have the greatest adverse effect on binding affinity (T131V, G130A, K126A, and S134A) (Xing et al., 1997). As for the RNA-binding loops 6 and 7, both are disordered when not bound to RNA (Markus et al., 1997), but they are highly ordered in the complex, and their conformations match the groove surface perfectly. The loops contain conserved structural features, which are important in the complex and which may predispose them for RNA-binding. Although it makes many interactions with RNA and contains the other two sites most sensitive to mutation (G88P and P92G), the longer RNA-binding loop 6 is relatively poorly conserved between kingdoms, with the bacterial and archaeal loops differing significantly from the eukaryotic loops (FIG. 4A). This variability in the protein sequence correlates with variability between phylogenetic kingdoms in the base-pairing of the upper portion of the 1067 stem.

The NTD as a Molecular Switch

Prior to these structural studies, the molecular basis for cooperative binding within the RNA-L11-thiostrepton ternary complex was unknown. The crystal structure now provides a very straightforward explanation that also rationalizes the particular importance of the L11 NTD. The model also provides insights into how the GAR might function as a molecular switch.

The putative thiostrepton/micrococcin binding site is centered on a small gap between helix 1 of the NTD and the 1067/1095 region of the RNA (FIG. 6). The antibiotics are proposed to bind within this gap, possibly enlarging it somewhat, making specific interactions with the RNA on one side and further interactions with the NTD on the other side. In the absence of the NTD, the antibiotic's binding affinity would be greatly compromised, thus explaining the importance of the NTD for antibiotic binding (Xing and Draper, 1996). An alternative proposal, that thiostrepton binds directly only to the RNA and that this RNA conformation requires the presence of the NTD, is unlikely because the NTD does not appear to stabilize the RNA tertiary structure significantly, and because the NTD sites of resistance mutations are not in contact with the RNA. In a model that better accounts for previously known data and agrees with the crystal structure reported herein, the mechanism for the resistance to thiostrepton in Pro22 mutants would be a disruption of direct thiostrepton-Pro22 interaction. A similar mechanism must hold true for the micrococcin sites given the more recent data (Porse et al., 1999). Regarding the details of the interaction of thiostrepton and micrococcin with RNA, we note that these antibiotics contain an array of thiazole rings that resembles the array of prolines in the conserved proline-rich NTD helix.

The data disclosed herein suggests a potential mechanism of thiostrepton inhibition of factor-dependent GTPase activity involves restriction or "trapping" of one of the many conformational states that must occur during elongation (Cundliffe, 1986) by the antibiotic. In their analysis of the effects of the Pro22Ser and Pro22Thr mutations, Porse et al. (1998) suggest that thiostrepton binding may affect the ability of the L11 NTD to undergo a conformational change, an idea which merits closer examination in light of the crystal structure. In the structure, the CTD is rather firmly anchored to one of the two RNA subdomains, while the NTD is somewhat tenuously bound across the RNA subdomain-subdomain interface. Even in the absence of other data, this overall architecture suggests that the NTD may function as a molecular switch that reversibly associates with the GAR RNA during the elongation cycle. In light of the other data—in particular the cooperative binding of thiostrepton and full-length L11 to RNA, and the clustering of antibiotic resistance mutations to the cleft defined by A1067/A1095 and the proline-rich NTD helix—it appears even more likely that the NTD functions as a molecular switch, and that the thiazole antibiotics work by binding to the NTD-RNA interface, thereby preventing the NTD from switching between RNA-bound and RNA-free states. It is possible that the switch is coupled to, or triggered by, the binding of elongation factors. It is important to note that the NTD itself cannot provide the actual GTPase enhancing activity since L11 is not required for viability in *E. coli* (Stöffler et al., 1980). Therefore, the switch appears likely to function by controlling either the accessibility or the conformation of the GAR RNA.

This switch hypothesis could also explain why EF-Tu and IF2 do not footprint the 1067/1095 region of RNA, while EF-G does, even though all these factors interact with the sarcin/ricin loop (Moazed et al., 1988). The sarcin/ricin loop is known to bind to a nearby (Wilson and Noller, 1998) but distinct (Munishkin and Wool, 1997) site on EF-G. The EF-Tu-tRNA complex is similar in structure to EF-G, and the similarity is thought to be a case of molecular mimicry, with the factors binding to the same general region of the ribosome (Nissen et al., 1995). Thus the footprinting differences could be explained if EF-Tu and IF2 recognize a different conformation of the switch than EF-G does. This reasoning suggests that the two conformations of the GAR molecular switch correspond to different functional states of the ribosome.

The structure features a complex and very compact RNA fold stabilized by many bound metal ions, by a dense network of RNA tertiary interactions, and by extensive interactions with the protein. The overall architecture of the complex suggests that the N-terminal domain functions as a molecular switch, either by facilitating changes in the tertiary structure of the GAR RNA, or by controlling access to the RNA. Thiostrepton and micrococcin are proposed to bind to the NTD-RNA interface, thus locking the switch and disrupting GAR function.

Uses of the Crystal Structure Coordinates of the L11/GAR Complex

One approach enabled by the X-ray crystal structure disclosed herein is the use of the crystal coordinates for the rational design of GAR activity modulators, either de novo or by modification of known compounds. The modulators identified through use of the crystal structure coordinates will be useful for altering the rate of bacterial protein synthesis, and thereby the rate of bacterial cell growth. It is expected that, for example, an inhibitor of GAR function will inhibit bacterial cell proliferation, and will thus potentially have immediate medical usefulness.

One of skill in the art may use the structure data disclosed herein and the computer-modeling techniques described herein to develop models of target domains also selected through analysis of the crystal structure data (see below). These models can be used to provide a detailed analysis of the binding surfaces, including factors such as van der Waals contacts, electrostatic interactions and hydrogen-bonding opportunities. This information is then used with computer simulation techniques to map the favorable interaction positions for functional groups such as protons, hydroxyl groups, amine groups, divalent cations, aromatic and aliphatic functional groups, acetamide, methanol, etc. These groups may then be designed into a synthetic ligand.

The L11/GAR structure coordinates may be used to screen computationally small molecule data bases for chemical entities or compounds that may bind in whole, or in part, to the L11/GAR, to GAR, or to L11.

In addition, because the L11/GAR RNA complex may be crystallized in more than one crystal form (e.g, as a co-crystal with another factor, such as EF-G), the structure coordinates of the L11/GAR RNA, or portions thereof, as provided by this invention are useful to solve the structure of those other crystal forms of the L11/GAR RNA complex. One method that may be employed for this purpose is molecular replacement. In this method, the unknown crystal structure (i.e., that of the co-complex) may be determined using the L11/GAR complex structure coordinates of this invention as provided in FIG. 7. This method will provide an accurate structural form for the unknown crystal more quickly and efficiently than attempting to determine such information from first principles.

In addition, in accordance with this invention, the L11/GAR complex may be crystallized in co-complex with known GAR inhibitors (e.g., thiostrepton, micrococcin). The crystal structures of such complexes may then be solved by molecular replacement and compared with that of inhibitor-free L11/GAR complex. Critical sites for interaction of the known inhibitor with the L11/GAR may thus be identified at high resoultion. This information provides an additional tool for determining the most efficient binding interactions, for example, increased hydrophobic interactions, between L 11/GAR and a chemical entity or compound.

All of the complexes referred to above may be studied using well-known X-ray diffraction techniques and may be refined versus 2–3 Å resolution X-ray data to an R value of about 0.20 or less using computer software, such as X-PLOR (Yale University, ©1992, distributed by Molecular Simulations, Inc.). See, e.g., Blundel & Johnson, supra; Methods in Enzymology, 1985, vol. 114 & 115, H. W. Wyckoff et al., eds., Academic Press. The crystallographic information disclosed herein may thus be used to optimize known classes of L11/GAR inhibitors or activators.

Importantly, the X-ray crystal data disclosed herein also allows the design and synthesis of novel classes of L11/GAR inhibitors or activators (i.e., modulators). The design of compounds that bind to or modulate L11/GAR function according to this invention generally involves consideration of several factors. In particular, the compound must be capable of physically and structurally associating with L11/GAR. Non-covalent molecular interactions important in the functional association of L11/GAR with its accessory factors include hydrogen bonding, van der Waals, electrostatic and hydrophobic interactions.

It is recognized that although certain portions of the compound will not directly participate in this association with the L11/GAR, those portions may still influence the overall conformation of the molecule. This, in turn, may have a significant impact on potency. Such conformational requirements include the overall three-dimensional structure and orientation of the chemical entity or compound in relation to all or a portion of the binding site, or the spacing between functional groups of a compound comprising several chemical entities that directly interact with L11/GAR.

The potential modulating or binding effect of a chemical compound on the L11/GAR may be analyzed prior to its actual synthesis and testing by the use of computer modelling techniques. If the theoretical structure of the given compound suggests insufficient interaction and association between it and the L11/GAR, synthesis and testing of the compound is obviated. However, if computer modelling indicates a strong interaction, the molecule may then be synthesized and tested for its ability to bind to the L11/GAR domain and to inhibit using the assays described herein. In this manner, synthesis of inoperative compounds may be avoided.

A modulating or binding compound of the L11/GAR may be computationally evaluated and designed by means of a series of steps in which chemical entities or fragments are screened and selected for their ability to associate with the individual binding targets on the L11/GAR.

One skilled in the art may use one of several methods to screen chemical entities or fragments for their ability to associate with L11/GAR and more particularly with the individual binding domains comprising the L11/GAR active sites. This process may begin by visual inspection of, for example, the active site on the computer screen based on the L11/GAR RNA coordinates in FIG. 7. Selected fragments or chemical entities may then be positioned in a variety of orientations, or "docked", within an individual binding target site of the L11/GAR as defined herein from analysis of the crystal structure data. Docking may be accomplished using software such as Quanta (Molecular Simulations, Inc., San Diego, Calif.) and Sybyl (Tripos, Inc., St. Louis, Mo.) followed by energy minimization and molecular dynamics with standard molecular mechanics forcefields, such as CHARMM (Molecular Simulations, Inc., San Diego, Calif.) and AMBER (University of California at San Francisco).

Specialized computer programs may also assist in the process of selecting fragments or chemical entities. These include:

1. GRID (Goodford, P. J., "A Computational Procedure for Determining Energetically Favorable Binding Sites on Biologically Important Macromolecules", J. Med. Chem., 28, pp. 849–857 (1985)). GRID is available from Oxford University, Oxford, UK.
2. MCSS (Miranker, A. and M. Karplus, "Functionality Maps of Binding Sites: A Multiple Copy Simultaneous Search Method." Proteins: Structure. Function and Genetics, 11, pp. 29–34 (1991)). MCSS is available from Molecular Simulations, San Diego, Calif.
3. AUTODOCK (Goodseil, D. S. and A. J. Olsen, "Automated Docking of Substrates to Proteins by Simulated Annealing", Proteins: Structure. Function, and Genetics, 8, pp. 195–202 (1990)). AUTODOCK is available from Scripps Research Institute, La Jolla, Calif.
4. DOCK (Kuntz, I. D. et al., "A Geometric Approach to Macromolecule-Ligand Interactions", J. Mol. Biol., 161, pp. 269–288 (1982)). DOCK is available from University of California, San Francisco, Calif.
5. CERIUS II (available from Molecular Simulations, Inc., San Diego, Calif.).
6. Flexx (Rarey et al., 1996, J. Mol. Biol. 261: 470–489).

Once suitable chemical entities or fragments have been selected, they can be assembled into a single compound or modulator. Assembly may proceed by visual inspection of the relationship of the fragments to each other on the three-dimensional image displayed on a computer screen in relation to the structure coordinates of the L11/GAR. This would be followed by manual model building using software such as Quanta or Sybyl.

Useful programs to aid one of skill in the art in connecting the individual chemical entities or fragments include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., Royal Chem. Soc., 78, pp. 182–196 (1989)). CAVEAT is available from the University of California, Berkeley, Calif.
2. 3D Database systems such as MACCS-3D (MDL Information Systems, San Leandro, Calif.). This area is reviewed in Martin, Y. C., "3D Database Searching in Drug Design", J. Med. Chem., 35, pp. 2145–2154 (1992)).
3. HOOK (available from Molecular Simulations Inc., San Diego, Calif.).

Instead of proceeding to build an L11/GAR modulator in a step-wise fashion one fragment or chemical entity at a time as described above, modulatory L11/GAR binding compounds may be designed as a whole or "de novo" using either an empty active site or optionally including some portion(s) of a known inhibitor(s). These methods include:

1. LUDI (Bohm, H.-J., "The Computer Program LUDI: A New Method for the De Novo Design of Enzyme Inhibitors", J. Comp. Aid. Molec. Design, 6, pp. 61–78 (1992)). LUDI is available from Molecular Simulations, Inc., San Diego, Calif.
2. LEGEND (Nishibata, Y. and A. Itai, Tetrahedron, 47, p. 8985 (1991)). LEGEND is available from Molecular Simulations, San Diego, Calif.
3. LeapFrog (available from Tripos Associates, St. Louis, Mo.).

Other molecular modelling techniques may also be employed in accordance with this invention. See, e.g., Cohen, N. C. et al., "Molecular Modeling Software and Methods for Medicinal Chemistry", J. Med. Chem., 33, pp. 883–894 (1990). See also, Navia, M. A. and M. A. Murcko, "The Use of Structural Information in Drug Design", Current Opinions in Structural Biology, 2, pp. 202–210 (1992); Hubbard, "Can Drugs Be Designed?", Curr. Opin. Biotechnol., 8, pp. 696–700 (1997); and Afshar et al., "Structure-Based and Combinatorial Search for New RNA-Binding Drugs", Curr. Opin. Biotechnol., 10, pp.59–63 (1999).

Once a compound has been designed or selected by the above methods, the efficiency with which that compound may bind to L11/GAR may be tested and optimized by computational evaluation. For example, a compound may be optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the modulator and the enzyme when the modulator is bound to L11/GAR preferably make a neutral or favorable contribution to the enthalpy of binding.

Specific computer software is available in the art to evaluate compound deformation energy and electrostatic interaction. Examples of programs designed for such uses include:

Gaussian 92, revision C [M. J. Frisch, Gaussian, Inc., Pittsburgh, Pa. ©1992]; AMBER, version 4.0 [P. A. Kollman, University of California at San Francisco, ©1994];
QUANTA/CHARMM
[Molecular Simulations, Inc., San Diego, Calif. ©.1994]; and Insight II/Discover (Biosysm Technologies Inc., San Diego, Calif. ©1994). These programs may be implemented, for instance, using a Silicon Graphics workstation, 02-R10000 or IBM RISC/6000 workstation model 550. Other hardware systems and software packages will be known to those skilled in the art.

Once an L11/GAR-binding compound has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to L11/GAR by the same computer methods described in detail, above.

Targets for Modification of L11/GAR Function

The X-ray crystal structure co-ordinates disclosed herein may be used to define structural features of the L11/GAR which represent targets for inhibition or activation of the GTPase activity of the ribosome. The following regions of the L11/GAR, defined by the X-ray co-ordinate data, represent particularly useful targets for the development of inhibitory or activating compounds.

1. L11 N Terminus:GAR RNA Interface

The putative site for binding of the antibiotics thiostrepton and micrococcin to the GAR is between the N terminus of L11 and the interface between the 1067 and 1095 stem loops of the GAR RNA. The structural data as disclosed in Table II and described herein above suggest that the N terminal lobe of L11 behaves as a rigid body that flexes about the so-called "tether sequence" between the C terminal and N terminal lobes of the protein. Therefore, the binding pocket is not limited to those residues at the interface of the L11 N terminus and the GAR RNA that are in direct contact. The binding pocket can include all of the following:

A) all exposed residues from the L11 N terminus;
B) all exposed residues from the GAR RNA that are on its L11 binding surface, including A1070, U1061, A1095, A1096, C1097, and A1098;
C) L11 amino acid residues that are in direct contact with the GAR RNA, including K10, Q12, Q30 and K71;
D) L11 amino acid residues from the helical region between P20 and H31; and
E) the L11 β sheet between Q8 and P14, and neighboring I53.

Computer simulation techniques may be used to determine which parameters of the binding pocket may be exploited in designing or screening compounds that interact with the binding pocket. Such techniques allow for the construction of structural models that can then be used in designing inhibitory/activating compounds targeted to the L11/GAR binding pocket. These techniques may involve any of the software packages described above or known in the art, and include:

A) Interactive movement of the L11 N terminus as a rigid body with concurrent geometry optimization, using, for example, Quanta.
B) Molecular dynamics simulation of the GAR RNA-L11 complex using. For example, CHARMM and/or AMBER.
C) Normal mode dynamics simulation of the GAR RNA-L11 complex using, for example, CHARMM.
D) Molecular docking of thiostrepton and/or micrococcin to the models of the binding pocket.

2. The L11 Flexible Tether or the Flexible Tether:GAR RNA Interface

The flexible tether domain of L11 and the GAR RNA surfaces that the tether domain interacts with are defined by the crystal structure coordinates disclosed in Table II and discussed herein above. The X-ray crystal data suggest that the L11 N terminus may act as a molecular switch that triggers the GTPase activity. It is thought that thiostrepton and micrococcin act by modifying the interaction between the L11 N terminus and the GAR RNA. Therefore, the region tethering the N terminal and C terminal lobes of L11, (i.e., amino acids K71 through A75) represent a target for the development of compounds that inhibit or activate GAR function, as does the domain comprising the interface of the tether region with GAR RNA residues. The GAR RNA domain interacting with the tether includes U1061, the backbone of U1060, and G1059. Any molecule that could modify the relative positioning of the L11 NTD and CTD may disrupt the funtion of the molecular switch and thereby modulate the function of the GAR. For example, this could be performed by a molecule interacting with the L11 tether domain and/or the GAR in close contact with the tether. Any molecule that could interact with both the C terminal and N terminal lobes of L11 and stabilize one orientation of the lobes relative to the alternate orientation may disrupt the function of the molecular switch and thereby disrupt the function of the GAR.

Computer simulation techniques similar to those described above for modeling the L11 N terminus:GAR RNA interface may be used to determine which parameters of the 4 way junction and $Cd^{++}$ coordination site may be exploited in designing or screening compounds that interact with or disrupt the junction/$Cd^{++}$ coordination site and/or modify the activity of the GTPase.

3. The GAR RNA:EF-G Interface

The interaction of translational elongation factor EF-G with the ribosome has been mapped by directed hydroxyl radical probing (Wilson & Noller, 1998, Cell 92: 131–139). This approach indicated that GAR RNA residues in the region of A1070 and in the region of C1100 are involved in the binding of EF-G. A1070 is included in the GAR RNA:L11 N terminal interface discussed as a target above, but is nonetheless of interest in approaches aimed at disrupting or modifying EF-G binding.

The crystal structure coordinates disclosed in Table II and discussed herein above define the structure of the GAR RNA at C1100, and the RNA bases and L11 amino acid residues around it. This structure defines a novel target for the design and/or selection of molecules that can disrupt the GAR RNA:EF-G interaction.

Computer simulation techniques similar to those described above for modeling the L11 NTD: GAR RNA interface may be used to determine which parameters of the binding pocket may be exploited in designing or screening compounds that modify the relative positioning of L11 NTD and CTD and modify the activity of the GTPase.

4. RNA Folding/Stability

The X-ray crystal structure coordinates disclosed in Table II and discussed herein above define the structure of a novel "4 way junction" fold in the ribosomal RNA in the L11/GARcomplex. The data further reveal the importance of a $Cd^{++}$ ion that occupies the center of the four way junction between bases 1056–1057 and 1086–1087. Because a ligand that can modify the folding of the RNA would be predicted to disrupt or otherwise modify the GTPase activity, this folded RNA structure represents a strong target for development of inhibitors or activators of the GTPase. Because the $Cd^{++}$ ion likely stabilizes the unusual RNA fold, the region defined by those amino acid and RNA residues interacting with the $Cd^{++}$ ion is particularly attractive as a target.

5. The L11 C Terminus:GAR RNA Interface

The domain comprising the interaction surface of the C terminal lobe of L11 and the GAR RNA is defined by the crystal structure data disclosed in Table II (X-ray co-ord's) and is described herein above. The crystal data indicate that the C terminus of L11 interacts very tightly with the GAR RNA. As such, the interaction may be difficult to disrupt. Computer simulation techniques similar to those described above for modeling the L11 N terminus:GAR RNA interface may be used to determine which parameters of the binding pocket may be exploited in designing or screening compounds that interact with the C terminal L11: GAR RNA interface domain and/or modify the activity of the GTPase.

The analysis of the various targets made possible by the crystal structure coordinate data disclosed herein, including the GAR RNA:L11 interface, the GAR RNA:L11: Micrococcin interface, the L11 N terminus:L11 C terminus interface (with or without GAR RNA), the GAR RNA:EF-G interface, and the GAR RNA:L11:EF-G interface, may be used to define specific features (e.g., a pattern of hydrogen bond donors and acceptors, a hydrophobic patch, etc.) of these targets. These features in turn define a three dimensional "pharmacophore" pattern. This pattern can then be used to screen virtual libraries of existing compounds, such as the Available Chemical Directory (MDL, Inc.) for compounds exhibiting the desired combination of chemical entities. In this screening, the quality of fit of such entities or compounds to the target site may be judged by a scoring function. The scoring function can account for shape complementarity (Katchalski-Katzir et al., 1992, Proc. Natl. Acad. Sci. USA, 89, pp.2195–2199.), estimated interaction energy (Meng et al., 1992, J.Comp. Chem., 13, pp. 505–524), surface accessibility, or a combination of these (see for example, Bohm, 1994, J. Comp. Aided Mol. Design, pp.243–256). A program such as Catalyst (MSI) can perform this task. Libraries of compounds can also be screened virtually using the coordinates of the targets and molecular docking programs such as DOCK (UCSF) or FLEXX.

Once one or more compounds have been identified as potential ligands using any of the methods described above, they may be screened for biological activity.

A variety of assays can be used to evaluate the activity of compounds designed to inhbit the activity of the L11/GAR. These include, but are not limited to: inhibition of bacterial growth, inhibition of in vitro protein synthesis using messenger RNA as a template, inhibition of the elongation phase of in vitro protein synthesis using polyU as a template, inhibition of GTP hydrolysis mediated by EF-G as described by Pestka (1970) and Rodnina et al. (1997); activation of GTP hydrolysis mediated by EF-G as described by Cundliffe and Thompson (1981). Binding of EF-G to both the L11/GAR complex and to the sarcin/ricin domain can be measured as described by Munishkin and Wool (1997, Proc. Natl. Acad. Sci. USA 94, 12280–12284; "The ribosome in pieces: Binding of elongation factor EF-G to oligoribonucleotides that mimic the sarcin/ricin and thiostrepton domains of 23S ribosomal RNA").

In addition, compound interaction with the L11/GAR complex can be evaluated by direct binding assays. Filter binding assays that measure the ability of thiostrepton to cause retention of radiolabelled GAR RNA to nitrocellulose filters have been described by GuhaThakurta and Draper (1999; Biochemistry, 38, 3633–3640 "Protein-RNA sequence covariation in a ribosomal protein-rRNA complex"). As revealed herein, these assays can be modified to evaluate small molecules that competitively inhibit the binding of thiostrepton and/or micrococcin to the L11/GAR complex or to GAR. For molecules that do not themselves cause filter retention, the RNA may be labelled. For molecules that do cause filter retention, the RNA and/or RNA-protein complex can be immobilised on a solid support and the binding of radiolabelled thiostrepton or other known L11/GAR binding compound can be measured. Thiostrepton or micrococcin can be labelled metabolically by incorporation of 35S, 3H or 14C labelled precursors, or post-synthetically by modifcation of the molecule with radiolablled precursors. In addition thiostrepton or micrococcin can be labelled with another detectable group, including, but not limited to, fluorescent and luminescent groups.

Displacement assays can also be performed by using as reporter molecules any labelled molecule that binds to the L11/GAR complex or GAR RNA with an affinity of 50 uM or less. Suitable reporters include, but are not limited to, oligonucleotides, peptides and oligonucleotide-peptide conjugates.

Libraries for Screening According to the Invention

Inhibitors and/or activators identified according to the methods of the invention may be provided from libraries of compounds available from a number of sources or may be derived by combinatorial chemistry approaches known in the art. Such libraries include but are not limited to the available Chemical Directory, Maybridge, and natural product collections.

Compounds identified as ligands using the methods described herein may be further optimized to improve binding activity. Using the docked models of the known ligands thiostrepton and micrococcin, it is possible to identify structures of the ligand that may be altered to improve binding affinity. Similarly, features of a ligand that are identified as unimportant for binding may be excluded to reduce the molecular weight of the ligand.

EXAMPLES

In order that the invention described herein may be more fully understood, the following examples are set forth. It should be understood that these examples are for illustrative purposes only and are not to be construed as limiting this invention in any manner.

Example 1

Preparation and Analysis of L11/GAR RNA Crystal

A. Sample Preparation

The gene for *T. maritima* ribosomal protein L11 was cloned and overexpressed in *E. coli* using the T7-based expression system (Studier et al., 1990). The protein was purified b a combination of cation-exchange, hydroxylapatite and size-exclusion chromatography as reported for the purification of ribosomal protein S7 (Wimberly et al., 1997). For cocrystallization with RNA, the protein was dialysed into a buffer A containing 0.1 M KCl, 5 mM Na-cacodylate pH 6.0, 0.1 mM Na2EDTA, 1 mM DTT. A fragment of RNA corresponding to nucleotides 1111–1168 of *T. maritima* 23S rRNA was synthesized by in vitro run-off transcription from a linearized plasmid using T7 RNA polymerase. The plasmid contained the following elements: a T7 promoter, a self-cleaving hammerhead ribozyme to generate a homogeneous RNA 5' end (Price et al., 1995), a template for the target RNA sequence, and a Pst I site used for plasmid linearization. RNA was purified on denaturing polyacrylamide slab gels, eluted, concentrated by ethanol precipitation, and dialyzed into buffer A. The RNA was reannealed by heating to 90° C. and slow cooling. L11 protein was added to yield a 1:1 RNA:protein mixture, which was concentrated to 0.15 mM in each component for crystallization experiments.

B. Crystallization and Structure Determination

Crystals of the complex were obtained at 4° C. using the hanging drop technique. The equimolar mixture of L11 and RNA in dialysis buffer A was mixed with an equal volume of well solution (25% glycerol, 15% PEG 4000, 0.2 M KCl, 50 mM MgCl2, 20 mM CdCl2, 1 mM DTT, 50 mM Tris pH 7.5 at 22° C.). The crystals were in the space group P212121, with cell dimensions of a=63.9 Å, b=84.3 Å and c=155.5 Å, and diffracted to better than 2.6 Å resolution using a synchrotron source. Diffraction data were collected under cryogenic conditions, and the crystals were flash-frozen by plunging into liquid nitrogen. For mercury derivatization, crystals were soaked for 24 hours in the well solution containing 1 mM CH3HgNO3 but lacking DTT. Efforts to obtain cocrystals of RNA with selenomethione-substituted L11 were unsuccessful, apparently because the preparation of selenomethionyl L11 used was at least partly misfolded.

The structure was solved using a multiwavelength anomalous diffraction (MAD) experiment (Hendrickson, 1991) on the methylmercury derivative. Straightforward isomorphous replacement was not possible because the derivative is not isomorphous with native crystals. Because the mercury L11 edge does not have a significant white line, data were collected at just two wavelengths, the inflection point of the mercury edge at 1.01 Å and a remote wavelength at 0.98 Å. This remote wavelength is near the maximum f" for accurate measurement of anomalous differences, and is also sufficiently remote from the inflection point to give useful isomorphous differences. Data were collected from a single flash-cooled crystal at beamline X12-C of the NSLS. To optimize measurement of anomalous differences, we used the inverse beam method in which pairs of sweeps separated by 180 degrees in were collected every 30 degrees. The data were integrated and scaled using the HKL suite of programs (Otwinowski and Minor, 1997).

Phasing was done by treating MAD as a special case of MIR (Ramakrishnan and Biou, 1997; Ramakrishnan et al., 1993). Local scaling of the data, determination of initial heavy atom sites, and initial phasing was done using the program SOLVE (Terwilliger and Berendzen, 1999). Subsequent phasing was done using the program SHARP (de la Fortelle and Bricogne, 1997). A significant improvement in phasing was obtained by including several well-ordered cadmium sites in a final round of SHARP heavy atom refinement. Each round of phasing was followed by density modification with Solomon (Abrahams and Leslie, 1996). The unaveraged, solvent-flattened map revealed virtually unbroken main-chain density for the RNA and the L11 C-terminal domains of both complexes in the asymmetric unit, which were easily built using the program O (Jones and Kjeldgaard, 1997). Twofold non-crystallographic symmetry (NCS) averaging followed by solvent flattening was then carried out using NCS and solvent masks based on the RNA and C-terminal domain coordinates. The resulting map was of high quality and revealed a few minor building errors, but the L11 N-terminal domain density was still of insufficient quality to permit unambiguous fitting. Interpretation of the density for the entire L11 N-terminal domain was possible only from iterative rounds of refinement and $2F_o$-$F_c$ maps. The final model was refined to an Rfree of 27% using the program X-PLOR (Brünger, 1988) using standard parameters for protein (Engh and Huber, 1991) and nucleic acid (Parkinson et al., 1996) structure refinement. Magnesium and cadmium ions were distinguished by inspection of an anomalous difference Fourier map. Magnesium ions were distinguished from ordered waters by inspection of $2F_o$-$F_c$ maps, in which an octahedral coordination of magnesium by water and RNA ligands was often visible. A Ramachandran plot of the protein revealed only three outliers, Lys93 in the C-terminal domain, which clearly has a positive phi angle in the original experimental map, and Ala21 and Val24 in the N-terminal domain, for which the side chains are very poorly defined. Details of the data collection, phasing and refinement are shown in Table I.

Example 2

Use of the Ribosomal Protein L11/GAR Crystal Structure Coordinates to Design a Modulator of GAR Activity Example 1 illustrates the methods involved in generating a structure of the L11/GAR RNA complex at atomic resolution. The crystal structure data make clear, for example, that the N terminus of L11 can move within the context of the L11/GAR. Because the crystal structure data, in conjunction with available biochemical data, point to a molecular switch mechanism whereby the relative position of the L11 N terminal lobe determines the activity of the GAR, it is of interest to select or design compounds that can effect restriction of modification of this movement.

1. Modeling the movement and interactions of the L11 N terminal lobe.

One of skill in the art may use the crystal structure coordinates, along with the software package Quanta to interactively model the movement of the L11 N terminus as a rigid body relative to the other GAR surfaces. This model will provide information on the many possible interactions between the L11 N terminus and the other amino acid and nucleotide residues comprising the GAR, as well as solvent interactions.

To develop a more detailed picture of the molecular interactions involving the L11 N terminal lobe in the GAR, the software packages CHARMM and AMBER may be applied by one of skill in the art to the crystal structure coordinates. These will provide a molecular dynamics simulation of the N terminal lobe of L11 within the L11/GAR RNA complex.

Similarly, CHARMM may be used by one of skill in the art to provide a normal mode dynamics simulation of the L11 N terminal lobe within the L11/GAR context.

Finally, the crystal structure coordinates allow the use of software packages such as DOCK or to simulate docking of the known GAR modulators thiostrepton and micrococcin with the GAR, thereby providing a finely detailed description of those interactions within the GAR critical to its function.

Used in combination, the software approaches described above can manipulate the crystal structure coordinate data to provide a very high resolution three dimensional model of the L11 N terminal lobe and its interactions with other portions of the GAR including van der Waals contacts, electrostatic interactions and hydrogen bonding opportunities.

2. Design of a candidate modulator compound.

Once a detailed three dimensional model of the L11/GAR has been created as described above, one of skill in the art may use the grid-based software approaches GRID or CERIUS II, and MCSS techniques (see, for example, Castro et al., 1999, Medicinal Chem. Res. 9: 98–107) to map favorable interaction positions for functional groups such as protons, hydroxyl groups, anime groups, divalent cations, aromatic and aliphatic functional groups, acetamide, methanol, etc. Once a set of favorable groups for each position are predicted, one of skill in the art may take one of two different approaches to designing a modulator.

First, one may assemble the moieties predicted to interact with the various critical parts of the L11/GAR surfaces into a single molecule. This may be accomplished by one of skill in the art using the software packages CAVEAT, MACCS-3D or HOOK. One of skill in the art may then synthesize the selected compounds for in vitro and in vivo testing for effects on GAR activity.

Alternatively, one may screen a database, such as the MDL Available Chemical Directory to potentially find existing compounds that combine the required moieties in a favorable conformation for GAR binding. The software packages Catalyst, DOCK and FLEXX may be used to advantage for this purpose by one of skill in the art.

Example 3

Assaying the Activity of a Candidate Modulator by Displacement of Thiostrepton from the GAR Thiostrepton binding to GTPase centre RNA can be monitored by a filter binding assays (Uchiumi et al., 1995, Biol. Chem., 270(50):29889–93; Draper et al., 1988, Methods Enzymol., 164:203–20). The filter binding assay can be transformed to a 96-well format using Millipore MHAB (mixed cellulose ester) 96-well plates. The dissociation constant for the thiostrepton/GTPase centre-59 mer complex of 1 uM is in good accordance with the literature. Additionally, filter binding can show the cooperativity in binding of thiostrepton and L11. Thermotoga maritima ribosomes are known to be sensitive to thiostrepton (Londei et al., 1988, J. Bacteriol., 170(9):4353–60), although 100-fold less than *B. stearothermophilus* ribosomes. The affinity of thiostrepton for Thermotoga GTPase center RNA in vitro has not yet been determined.

$^{35}$S- or $^{32}$P-labelled RNA is prepared by transcription in the presence of radiolabelled nucleotides. The labelled RNAs are purified by gel electrophoresis or chromatography by reverse-phase. For filter binding assays the RNA are renatured and 3,000 to 10,000 cpm of RNA are used per assay. Association constants between RNA and thiostrepton in the presence or absence of inhbitor are determined in 100 ul reactions containing 10 mM Tris-HCl (pH 7.4), 3 mM MgCl2, 175 mM NH4Cl and 5% v/v DMSO. The reaction mixtures also contain between 2 and 10 uM thiostrepton and a range of inhibitor concentrations up to 50 uM. The RNA-thiostrepton-inhibitor mixtures are incubated for 15 min at room temperature (approximately 22° C.) prior to filtration through the nitrocellulose filter membranes.

For high-throughput screening, the assay can be performed in 96-well filter plates (Multiscreen HA filtration plates, Millipore) with nitrocellulose membranes incorporated into the bottom of each well and filtered using Multiscreen vacuum Manifold (Millipore). The filters are washed once with 100 ul buffer before determining their radioactivities using Microbeta Liquid Scintillation Counter (Wallac).

The relative amounts of RNA retained in the presence and absence of inhibitor can be determined by quantitation of the radioactivity on each filter. Compounds that reduce the amount of RNA retained on the filter in a concentration dependent manner are competitive inhibitors of thiostrepton binding to the RNA.

Example 4

Binding Assays with Radioactive Thiostrepton

Binding of [$^{35}$S]-labelled thiostrepton to 23S RNA and ribosomes has been shown by gel filtration of RNA and RNA/L11 complexes together with thiostrepton as well as by charcoal (Norit) absorption of unbound [$^{35}$S]thiostrepton (Thompson et al., 1979. Eur. J. Biochem., 98(1):261–5). Using equilibrium dialysis, the dissociation constant of thiostrepton/23S RNA has been determined as 0.23 uM (Thompson & Cundliffe, 1991, Biochimie 1991, 73(7–8) :1131–5). The affinity to intact ribosomes is 100–1000fold higher (Pestka et al., 1976, Anal. Biochem., 71(1):137–42).

The ability of biotinylated GTPase centre-59 mer to bind thiostrepton (as shown by filter binding) gives a route for a displacement assay employing displacement of [$^{3}$H]-labelled thiostrepton (Amersham) from an immobilised GTPase centre RNA/L11 complex or from ribosomes.

Example 5

Luciferase Translation Assay

Using an *E. coli* S30 lysate and luciferase mRNA (Promega *E. coli* S30 extract system for linear templates; Cat No: L1030) the active luciferase protein can be synthesised in vitro and the relative amount of luciferase generated is monitored in a bioluminescence assay. The mRNA is either provided by coupled transcription/translation using the linearized plasmid pBESTLucTM as a template or by adding purified luciferase mRNA.

The addition of ribosome-inactivating compounds or antibiotics directed to protein biosynthesis (thiostrepton, kanamycin, chloramphenicol and others) leads to a decrease in yield of active luciferase compared to the control. Compound and antibiotic titrations can be used to determine IC50 values (see Langer et al., 1996, Anal. Biochem., 243(1):150–3).

Example 6

Additional Translation Assays

An S30 transcription/translation system (Promega) can be used to incorporate [$^{35}$S]methionine into protein translated from MS2 phage RNA. Translation yield is quantified after alkaline hydrolysis by acid precipitation of the synthesised peptides and scintillation counting. Whole-cell protein synthesis can be measured adding [$^{14}$C]leucine to exponentially growing *E. coli* cells and measuring the incorporation into protein by alkaline hydrolysis and TCA precipitation (see Shinabarger et al., 1997, Antimicrob. Agents Chemother., 41(10):2132–6).

Example 7

Assay of Translation Elongation

Translation elongation is measured using isolated polysomes from *E. coli* MRE600 (Girbes et al., 1979, Methods Enzymol., 59:353–62), S100 extract from *E. coli* and poly (U) (Sigma) as a template (e.g. Grise-Miron et al., 1981, Biochim. Biophys. Acta, 656(1):103–10). Incorporation of [$^3$H]phenylalanine into polyphenylalanine is quantified by acid precipitation and scintillation counting.

Example 8

In vitro EF-G-dependent GTP Hydrolysis

Thiostrepton acts on the tRNA translocation step of translation elongation and inhibits elongation factor G (EF-G)-dependent GTP hydrolysis (Pestka et al., 1970, Biochem. Biophys. Res. Commun., 40(3):667–74; Rodnina et al., 1997, Nature, 385:37–41). EF-G is known to contact the GTPase centre region of 23S RNA (Skold et al., 1983, Nucleic Acids Res., 11(14):4923–32; Moazed & Noller, 1986, Nature, 334:362–4). 70S ribosomes support GTP hydrolysis by EF-G in the absence of other factors normally necessary for protein synthesis. Uncoupled GTP hydrolysis and the inhibition by thiostrepton or other compounds can be measured in an assay containing purified ribosomes, purified EF-G and gamma-[$^{32}$P]-GTP (Stark&Cundliffe, 1979, J. Mol. Biol., 134(4):767–9; Lill et al., 1988, EMBO J., 8(12):3933–8).

References

Abrahams, J. P., and Leslie, A. G. W. (1996). Methods used in the structure determination of bovine mitochondrial F1 ATPase. Acta Cryst. D52, 30–42.

Briones, E., Briones, C., Remacha, M., and Ballesta, J. P. (1998). The GTPase center protein L12 is required for correct ribosomal stalk assembly but not for Saccharomyces cerevisiae viability. J Biol Chem 273, 31956–61.

Brünger, A. T. (1988). Crystallographic refinement by simulated annealing. Application to a 2.8 Å structure of aspartate aminotransferase. J. Mol. Biol. 203, 803–16.

Bukhman, Y. V., and Draper, D. E. (1997). Affinities and selectivities of divalent cation binding sites within an RNA tertiary structure. J Mol Biol 273, 1020–31.

Carson, M. (1991). Ribbons 2.0. J.Appl.Cryst. 24, 958–961.

Cate, J., Gooding, A., Podell, E., Zhou, K., Golden, B., Szewczack, A., Kundrot, C., Cech, T., and Doudna, J. (1996). RNA Tertiary Structure Mediation by Adenosine Platforms. Science 273, 1696–1699.

Cate, J. H., Gooding, A. R., Podell, E., Zhou, K., Golden, B. L., Kundrot, C. E., Cech, T. R., and Doudna, J. A. (1996). Crystal structure of a group I ribozyme domain: principles of RNA packing. Science 273, 1678–85.

Conn, G. L., Gutell, R. R., and Draper, D. E. (1998). A functional ribosomal RNA tertiary structure involves a base triple interaction. Biochemistry 37, 11980–8.

Cundliffe, E. (1986). Involvement of specific portions of rRNA in defined ribosomal functions: a study utilizing antibiotics. In Structure, Function and Genetics of Ribosomes, B. Hardesty and G. Kramer, eds. (New York: Springer-Verlag), pp. 586–604.

Cundliffe, E., and Thompson, J. (1981). Concerning the mode of action of micrococcin upon bacterial protein synthesis. Eur J Biochem 118, 47–52.

Cundliffe, E., and Thompson, J. (1979). Ribose methylation and resistance to thiostrepton. Nature 278, 859–61.

de la Fortelle, E., and Bricogne, G. (1997). Maximum-likelihood heavy-atom parameter refinement for multiple isomorphous replacement and multiwavelength anomalous diffraction methods. In Methods in Enzymology, C. W. Carter, Jr. and R. M. Sweet, eds. (New York: Academic Press), pp. 472–93.

Donner, D., Villems, R., Liljas, A., and Kurland, C. G. (1978). Guanosinetriphosphatase activity dependent on elongation factor Tu and ribosomal protein L7/L12. Proc Natl Acad Sci USA 75, 3192–5.

Draper, D. E., and Xing, Y. (1995). Protein recognition of a ribosomal RNA tertiary structure. Nucleic Acids Symp Ser 33, 5–7.

Engh, R. A., and Huber, R. (1991). Accurate bond and angle parameters for x-ray protein structure refinement. Acta Cryst. A47, 392–400.

Ferre-D'Amare, A. R., Zhou, K., and Doudna, J. A. (1998). Crystal structure of a hepatitis delta virus ribozyme. Nature 395, 567–74.

Fountain, M. A., Serra, M. J., Krugh, T. R., and Turner, D. H. (1996). Structural features of a six-nucleotide RNA hairpin loop found in ribosomal RNA. Biochemistry 35, 6539–48.

Glotz, C., Zwieb, C., Brimacombe, R., Edwards, K., and K össel, H. (1981). Secondary structure of the large subunit ribosomal RNA from *Escherichia coli, Zea mays* chloroplast, and human and mouse mitochondrial ribosomes. Nucleic Acids Res 9, 3287–306.

Gruenwedel, D. W., and Davidson, N. (1966). Complexing and denaturation of DNA by methylmercuric hydroxide. I. Spectrophotometric studies. J Mol Biol 21, 129–44.

Gruenwedel, D. W., and Davidson, N. (1967). Complexing and denaturation of DNA by methylmercuric hydroxide. II. Ultracentrifugation studies. Biopolymers 5, 847–61.

Hendrickson, W. A. (1991). Determination of macromolecular structures from anomalous diffraction of synchrotron radiation. Science 254, 51–58.

Hinck, A. P., Markus, M. A., Huang, S., Grzesiek, S., Kustonovich, I., Draper, D. E., and Torchia, D. A. (1997). The RNA binding domain of ribosomal protein L11: three-dimensional structure of the RNA-bound form of the protein and its interaction with 23 S rRNA. J Mol Biol 274, 101–13.

Jones, T. A., and Kjeldgaard, M. (1997). Electron-density map interpretation. Meth. Enzymol. 277B, 173–207.

Kosturko, L. D., Folzer, C., and Stewart, R. F. (1974). The crystal and molecular structure of a 2:1 complex of 1-methylthymine-mercury (II). Biochemistry 13, 3949–52.

Kraulis, P. (1991). MOLSCRIPT: A program to produce both detailed and schematic plots of protein structures. J. Appl. Crystallogr. 24, 946–50.

Lu, M., and Draper, D. E. (1994). Bases defining an ammonium and magnesium ion-dependent tertiary structure within the large subunit ribosomal RNA. J Mol Biol 244, 572–85.

Lu, M., and Draper, D. E. (1995). On the role of rRNA tertiary structure in recognition of ribosomal protein L11 and thiostrepton. Nucleic Acids Res 23, 3426–33.

Markus, M. A., Hinck, A. P., Huang, S., Draper, D. E., and Torchia, D. A. (1997). High resolution solution structure of ribosomal protein L11-C76, a helical protein with a flexible loop that becomes structured upon binding to RNA. Nat Struct Biol 4, 70–7.

Moazed, D., Robertson, J. M., and Noller, H. F. (1988). Interaction of elongation factors EF-G and EF-Tu with a conserved loop in 23S RNA. Nature 334, 362–4.

Munishkin, A., and Wool, I. G. (1997). The ribosome-in-pieces: binding of elongation factor EF-G to oligoribo-nucleotides that mimic the sarcin/ricin and thiostrepton domains of 23S ribosomal RNA. Proc Natl Acad Sci USA 94, 12280–4.

Nicholls, A., Sharp, K. A., and Honig, B. (1991). Protein folding and association: insights from the interfacial and thermodynamic properties of hydrocarbons. Proteins 11, 281–96.

Nissen, P., Kjeldgaard, M., Thirup, S., Polekhina, G., Reshetnikova, L., Clark, B. F., and Nyborg, J. (1995). Crystal structure of the ternary complex of Phe-tRNAPhe, EF-TU, and a GTP and Science 270, 4–72.

Noller, H. F., Kop, J., Wheaton, V., Brosius, J., Gutell, R. R., Kopylov, A. M., Dohme, F., Herr, W., Stahl, D. A., Gupta, R., and Waese, C. R. (1981). Secondary structure model for 23S ribosomal RNA. Nucleic Acids Res 9, 6167–89.

Otwinowski, Z., and Minor, W. (1997). Processing of x-ray diffraction data collected in oscillation mode. In Methods in Enzymology, C. W. J. Carter and R. M. Sweet, eds. (New York: Academic Press), pp. 307–25.

Parkinson, G., Vojtechovsky, J., Clowney, L., Brünger, A. T., and Berman, H. M. (1996). New parameters for the refinement of nucleic acid containing structures. Acta Cryst. D52, 57–64.

Pestka, S. (1970). Thiostrepton: a ribosomal inhibitor of translocation. Biochem Biophys Res Commun 40, 667–74.

Porse, B. T., Cundliffe, E., and Garrett, R. A. (1999). The antibiotic micrococcin acts on protein L11 at the riboso-mal GTPase centre. J. Mol. Biol. 287, 33–45.

Porse, B. T., Leviev, I., Mankin, A. S., and Garrett, R. A. (1998). The antibiotic thiostrepton inhibits a functional transition within protein L11 at the ribosomal GTPase centre. J Mol Biol 276, 391–404.

Price, S. R., Ito, N., Oubridge, C., Avis, J. M., and Nagai, K. (1995). Crystallisation of RNA-protein complexes. I. Methods for the large-scale preparation of RNA suitable for crystallographic studies. J. Mol. Biol. 249, 398–408.

Quigley, G. J., and Rich, A. (1976). Structural domains of transfer RNA molecules. Science 194, 796–806.

Ramakrishnan, V., and Biou, V. (1997). Treatment of mul-tiwavelength anomalous diffraction data as a special case of multiple isomorphous replacement. In Meth. Enzymol., C. W. Carter, Jr. and R. M. Sweet, eds. (New York: Academic Press), pp. 538–57.

Ramakrishnan, V., Finch, J. T., Graziano, V., Lee, P. L., and Sweet, R. M. (1993). Crystal structure of globular domain of histone H5 and its implications for nucleosome bind-ing. Nature 362, 219–23.

Ramakrishnan, V., and White, S. W. (1998). Ribosomal protein structures: insights into the architecture, machin-ery and evolution of the ribosome. Trends Biochem Sci 23, 208–12.

Rodnina, M. V., Savelsbergh, A., Katunin, V. I., and Wintermeyer, W. (1997). Hydrolysis of GTP by elonga-tion factor G drives tRNA movement on the ribosome. Nature 385, 37–41.

Rosendahl, G., and Douthwaite, S. (1994). The antibiotics micrococcin and thiostrepton interact directly with 23S rRNA nucleotides 1067A and 1095A. Nucleic Acids Res 22, 357–63.

Rosendahl, G., and Douthwaite, S. (1993). Ribosomal pro-teins L11 and L10.(L12)4 and the antibiotic thiostrepton interact with overlapping regions of the 23 S rRNA backbone in the ribosomal GTPase centre. J Mol Biol 234, 1013–20.

Schmidt, F. J., Thompson, J., Lee, K., Dijk, J., and Cundliffe, E. (1981). The binding site for ribosomal protein L11 within 23 S ribosomal RNA of Escherichia coli. J Biol Chem 256, 12301–5.

Sopori, M. L., and Lengyel, P. (1972). Components of the 50S ribosomal subunit involved in GTP cleavage. Bio-chem Biophys Res Commun 46, 238–44.

Spahn, C. M., and Nierhaus, K. H. (1998). Models of the elongation cycle: an evaluation. Biol Chem 379, 753–72.

Stöffler, G., Cundliffe, E., Stoffler-Meilicke, M., and Dabbs, E. R. (1980). Mutants of Escherichia coli lacking ribo-somal protein L11. J Biol Chem 255, 10517–22.

Studier, F. W., Rosenberg, A. H., Dunn, J. J., and Dubendorff, J. W. (1990). Use of T7 RNA polymerase to direct expression of cloned genes. Meth. Enzymol. 185, 61–89.

Szewczak, A. A., Moore, P. B., Chang, Y. L., and Wool, I. G. (1993). The conformation of the sarcin/ricin loop from 28S ribosomal RNA. Proc Natl Acad Sci USA 90, 9581–5.

Terwilliger, T., and Berendzen, J. (1999). Automated MAD and MIR structure determination. Acta Cryst D (in press).

Thompson, J., Cundliffe, E., and Stark, M. (1979). Binding of thiostrepton to a complex of 23 -S rRNA with riboso-mal protein L11. Bur J Biochem 98, 261–5.

Thompson, J., Schmidt, F., and Cundliffe, E. (1982). Site of action of a ribosomal RNA methylase conferring resis-tance to thiostrepton. J Biol Chem 257, 7915–7.

Wang, Y. X., Lu, M., and Draper, D. E. (1993). Specific ammonium ion requirement for functional ribosomal RNA tertiary structure. Biochemistry 32, 12279–82.

Wilson, K. S., and Noller, H. F. (1998). Mapping the position of translational elongation factor EF-G in the ribosome by directed hydroxyl radical probing. Cell 92, 131–9.

Wilson, K. S., and Noller, H. F. (1998). Molecular move-ment inside the translational engine. Cell 92, 337–49.

Wimberly, B. (1994). A common RNA loop motif as a docking module and its function in the hammerhead ribozyme. Nat Struct Biol 1, 820–7.

Wimberly, B., Varani, G., and Tinoco, I., Jr. (1993). The conformation of loop E of eukaryotic 5S ribosomal RNA. Biochemistry 32, 1078–87.

Wimberly, B. T., White, S. W., and Ramakrishnan, V. (1997). The structure of ribosomal protein S7 at 1.9 A resolution reveals a beta-hairpin motif that binds double-stranded nucleic acids. Structure 5, 1187–98.

Xing, Y., and Draper, D. E. (1996). Cooperative interactions of RNA and thiostrepton antibiotic with two domains of ribosomal protein L11. Biochemistry 35, 15 81–8.

Xing, Y., and Draper, D. E. (1995). Stabilization of a ribosomal RNA tertiary structure by ribosomal protein L11. J Mol Biol 249, 319–31.

Xing, Y., Guha Thakurta, D., and Draper, D. E. (1997). The RNA binding domain of ribosomal protein L11 is struc-turally similar to homeodomains. Nat Struct Biol 4, 24–7.

TABLE I

| Crystallographic statistics | | |
|---|---|---|
| Data collection | λ1 (1.008 Å) | λ2 (0.980 Å) |
| Reflections | 104,096 | 107,907 |
| Independent reflections | 25,927 | 25,894 |
| Completeness | 99% (98%)* | 98% (97%)* |
| Mean (I/sigma (I)) | 20 (4.2)* | 20 (4.5)* |
| $R_{sym}$ | 4.1% (17%)* | 4.2% (17%)* |
| $d_{min}$ (Å) | 2.6 | 2.6 |

TABLE I-continued

| | λ1–λ2 isomorphous | λ1 anomalous | λ2 anomalous |
|---|---|---|---|
| ƒ' (Hg) (electrons)** | | −12.0 | −9.0 |
| ƒ" (Hg) (electrons)** | | 6.4 | 8.0 |
| ƒ' (Cd) (electrons)** | | −0.42 | −0.46 |
| ƒ" (Cd) (electrons)** | | 2.3 | 2.2 |
| Phasing | | | |
| $R_{Cullis}$ (centrics) | 0.50 | — | — |
| $R_{Kraut}$ (acentrics) | 0.09 | 0.025 | 0.023 |
| Phasing power (acentrics) | 1.25 | 1.54 | 1.52 |
| Mean figure of merit (acentrics) | 0.39 | | |
| Mean figure of merit (centrics) | 0.23 | | |

| Refinement | |
|---|---|
| Number of atoms | 4196 (2474 RNA, 1524 protein, 198 water & ions) |
| $R_{cryst}/R_{free}$ (5% of data) | 0.228/0.253 |
| RMS deviation from ideal geometry | |
| bond lengths | 0.005 Å |
| bond angles | 1.2 degrees |

*Values in parentheses refer to the highest resolution shell.
**Values after SHARP refinement.

TABLE II

| | |
|---|---|
| HEADER | RNA-PROTEIN COMPLEX 14-APR-99 |
| ONHOLD | ONE-YEAR HOLD; EXPERIMENTAL DATA, ONE-YEAR HOLD |
| TITLE | CRYSTAL STRUCTURE OF THE RIBOSOMAL PROTEIN L11-RNA COMPLEX |
| COMPND | MOL_ID: 1; |
| COMPND 2 | MOLECULE: 23S RIBOSOMAL RNA; |
| COMPND 3 | CHAIN: C, D; |
| COMPND 4 | FRAGMENT: FRAGMENT 1051–1108; |
| COMPND 5 | MUTATION: U1108C; |
| COMPND 6 | OTHER_DETAILS: COVALENT MERCURY LIGAND AT U1061; |
| COMPND 7 | MOL_ID: 2; |
| COMPND 8 | MOLECULE: RIBOSOMAL PROTEIN L11; |
| COMPND 9 | CHAIN: A, B; |
| COMPND 10 | ENGINEERED: YES; |
| COMPND 11 | OTHER_DETAILS: COVALENT MERCURY LIGAND AT CYS39 |
| SOURCE | MOL_ID: 1; |
| SOURCE 2 | ORGANISM_SCIENTIFIC: THERMOTOGA MARITIMA; |
| SOURCE 3 | OTHER_DETAILS: IN VITRO TRANSCRIBED RNA; |
| SOURCE 4 | MOL_ID: 2; |
| SOURCE 5 | ORGANISM_SCIENTIFIC: THERMOTOGA MARITIMA; |
| SOURCE 6 | EXPRESSION_SYSTEM: ESCHERICHIA COLI; |
| SOURCE 7 | EXPRESSION_SYSTEM_STRAIN: BL21(DE3); |
| SOURCE 8 | EXPRESSION_SYSTEM_PLASMID: PET13A; |
| SOURCE 9 | OTHER_DETAILS: RECOMBINANT PROTEIN |
| KEYWDS | RNA-PROTEIN COMPLEX, RNA, RIBOSOME, TRANSLOCATION, |
| KEYWDS 2 | THIOSTREPTON |
| EXPDTA | X-RAY DIFFRACTION |
| AUTHOR | B. T. WIMBERLY, R. GUYMON, J. P. MCCUTCHEON, S. W. WHITE, |
| AUTHOR 2 | V. RAMAKRISHNAN |
| REMARK 1 | |
| REMARK 1 | REFERENCE 1 |
| REMARK 1 | AUTH Y. XING, D. DRAPER |
| REMARK 1 | TITL COOPERATIVE INTERACTIONS OF RNA AND THIOSTREPTON |
| REMARK 1 | TITL 2 ANTIBIOTIC WITH TWO DOMAINS OF RIBOSOMAL PROTEIN |
| REMARK 1 | TITL 3 L11 |
| REMARK 1 | REF BIOCHEMISTRY   V. 35 1581 1996 |
| REMARK 1 | REFN ASTM BICHAW US ISSN 0006-2960 0033 |
| REMARK 1 | REFERENCE 2 |
| REMARK 1 | AUTH J. THOMPSON, F. SCHMIDT, E. CUNDLIFFE |
| REMARK 1 | TITL SITE OF ACTION OF A RIBOSOMAL RNA METHYLASE |
| REMARK 1 | TITL 2 CONFERRING RESISTANCE TO THIOSTREPTON |
| REMARK 1 | REF J. BIOL.CHEM.   V. 257 7915 1982 |
| REMARK 1 | REFN ASTM JBCHA3 US ISSN 0021-9258   0071 |
| REMARK 1 | REFERENCE 3 |
| REMARK 1 | AUTH J. THOMPSON, E. CUNDLIFFE, M. STARK |
| REMARK 1 | TITL BINDING OF THIOSTREPTON TO A COMPLEX OF 23S RNA |
| REMARK 1 | TITL 2 WITH RIBOSOMAL PROTEIN L11 |
| REMARK 1 | REF EUR. J. BIOCHEM.   V. 98 261 1979 |
| REMARK 1 | REFN ASTM EJBCAI IX ISSN 0014-2956   0262 |
| REMARK 2 | |
| REMARK 2 | RESOLUTION. 2.57 ANGSTROMS. |
| REMARK 3 | |
| REMARK 3 | REFINEMENT. |
| REMARK 3 | PROGRAM:  X-PLOR 3.851 |
| REMARK 3 | AUTHORS:  BRUNGER |
| REMARK 3 | |
| REMARK 3 | DATA USED IN REFINEMENT. |

TABLE II-continued

| | |
|---|---|
| REMARK 3 | RESOLUTION RANGE HIGH (ANGSTROMS): 2.57 |
| REMARK 3 | RESOLUTION RANGE LOW (ANGSTROMS): 20.0 |
| REMARK 3 | DATA CUTOFF    (SIGMA(F)): 0.0 |
| REMARK 3 | DATA CUTOFF HIGH    (ABS(F)): 1000000.0 |
| REMARK 3 | DATA CUTOFF LOW    (ABS(F)): 0.001 |
| REMARK 3 | COMPLETENESS (WORKING + TEST) (%): 95.5 |
| REMARK 3 | NUMBER OF REFLECTIONS:    49313 |
| REMARK 3 | |
| REMARK 3 | FIT TO DATA USED IN REFINEMENT. |
| REMARK 3 | CROSS-VALIDATION METHOD:    THROUGHOUT |
| REMARK 3 | FREE R VALUE TEST SET SELECTION: RANDOM |
| REMARK 3 | R VALUE    (WORKING SET): 0.219 |
| REMARK 3 | FREE R VALUE    : 0.254 |
| REMARK 3 | FREE R VALUE TEST SET SIZE (%): 4.9 |
| REMARK 3 | FREE R VALUE TEST SET COUNT:  2398 |
| REMARK 3 | ESTIMATED ERROR OF FREE R VALUE: 0.005 |
| REMARK 3 | |
| REMARK 3 | FIT IN THE HIGHEST RESOLUTION BIN. |
| REMARK 3 | TOTAL NUMBER OF BINS USED   : 6 |
| REMARK 3 | BIN RESOLUTION RANGE HIGH   (A): 2.57 |
| REMARK 3 | BIN RESOLUTION RANGE LOW   (A): 2.73 |
| REMARK 3 | BIN COMPLETENESS (WORKING + TEST) (%): 86.2 |
| REMARK 3 | REFLECTIONS IN BIN (WORKING SET): 7101 |
| REMARK 3 | BIN R VALUE   (WORKING SET): 0.386 |
| REMARK 3 | BIN FREE R VALUE    : 0.432 |
| REMARK 3 | BIN FREE R VALUE TEST SET SIZE (%): 4.5 |
| REMARK 3 | BIN FREE R VALUE TEST SET COUNT  : 331 |
| REMARK 3 | ESTIMATED ERROR OF BIN FREE R VALUE: 0.024 |
| REMARK 3 | |
| REMARK 3 | NUMBER OF NON-HYDROGEN ATOMS USED IN REFINEMENT. |
| REMARK 3 | PROTEIN ATOMS   : 1524 |
| REMARK 3 | NUCLEIC ACID ATOMS   : 2474 |
| REMARK 3 | HETEROGEN ATOMS   : 35 |
| REMARK 3 | SOLVENT ATOMS   : 142 |
| REMARK 3 | |
| REMARK 3 | B VALUES. |
| REMARK 3 | FROM WILSON PLOT   (A**2): 58.8 |
| REMARK 3 | MEAN B VALUE   (OVERALL, A**2): 42.8 |
| REMARK 3 | OVERALL ANISOTROPIC B VALUE. |
| REMARK 3 | B11 (A**2): NULL |
| REMARK 3 | B22 (A**2): NULL |
| REMARK 3 | B33 (A**2): NULL |
| REMARK 3 | B12 (A**2): NULL |
| REMARK 3 | B13 (A**2): NULL |
| REMARK 3 | B23 (A**2): NULL |
| REMARK 3 | |
| REMARK 3 | ESTIMATED COORDINATE ERROR. |
| REMARK 3 | ESD FROM LUZZATI PLOT   (A): 0.32 |
| REMARK 3 | ESD FROM SIGMAA   (A): 0.45 |
| REMARK 3 | LOW RESOLUTION CUTOFF   (A): 5.00 |
| REMARK 3 | |
| REMARK 3 | CROSS-VALIDATED ESTIMATED COORDINATE ERROR. |
| REMARK 3 | ESD FROM C-V LUZZATI PLOT   (A): 0.39 |
| REMARK 3 | ESD FROM C-V SIGMAA   (A): 0.50 |
| REMARK 3 | |
| REMARK 3 | RMS DEVIATIONS FROM IDEAL VALUES. |
| REMARK 3 | BOND LENGTHS   (A): 0.005 |
| REMARK 3 | BOND ANGLES   (DEGREES): 1.0 |
| REMARK 3 | DIHEDRAL ANGLES   (DEGREES): 28.8 |
| REMARK 3 | IMPROPER ANGLES (DEGREES): 1.40 |
| REMARK 3 | |
| REMARK 3 | ISOTROPIC THERMAL MODEL: RESTRAINED |
| REMARK 3 | |
| REMARK 3 | ISOTROPIC THERMAL FACTOR RESTRAINTS. RMS SIGMA |
| REMARK 3 | MAIN-CHAIN BOND   (A**2): 3.59; 1.50 |
| REMARK 3 | MAIN-CHAIN ANGLE   (A**2): 5.28; 2.00 |
| REMARK 3 | SIDE-CHAIN BOND   (A**2): 6.59; 2.00 |
| REMARK 3 | SIDE-CHAIN ANGLE   (A**2): 9.24; 2.50 |
| REMARK 3 | |
| REMARK 3 | NCS MODEL: RESTRAINTS |
| REMARK 3 | |
| REMARK 3 | NCS RESTRAINTS.    RMS SIGMA/WEIGHT |
| REMARK 3 | GROUP 1 POSITIONAL   (A): 0.07; 50 |
| REMARK 3 | GROUP 1 B-FACTOR   (A**2): 5.51; 2 |
| REMARK 3 | GROUP 2 POSITIONAL   (A): 0.07; 50 |
| REMARK 3 | GROUP 2 B-FACTOR   (A**2): 5.51; 2 |
| REMARK 3 | |
| REMARK 3 | PARAMETER FILE 1: DNA-RNA-MULTI-ENDO.PARAM |
| REMARK 3 | PARAMETER FILE 2: PROTEIN_REP.PARAM |

TABLE II-continued

| | |
|---|---|
| REMARK 3 | TOPOLOGY FILE 1: DNA-RNA-MULTI-ENDO.TOP |
| REMARK 3 | TOPOLOGY FILE 2: TOPHCSDX.PRO |
| REMARK 3 | TOPOLOGY FILE 3: TOPH19.SOL |
| REMARK 3 | |
| REMARK 3 | OTHER REFINEMENT REMARKS: NCS RESTRAINTS APPLIED TO RNA |
| REMARK 3 | THROUGHOUT, NOT TO PROTEIN |
| REMARK 5 | |
| REMARK 5 | WARNING |
| REMARK 5: | THIS IS LAYER 1 RELEASE. |
| REMARK 5 | |
| REMARK 5 | PLEASE NOTE THAT THIS ENTRY WAS RELEASED AFTER DEPOSITOR |
| REMARK 5 | CHECKING AND APPROVAL BUT WITHOUT PDB STAFF |
| | INTERVENTION. |
| REMARK 5 | AN AUXILIARY FILE, AUX.RPT, IS AVAILABLE FROM THE |
| REMARK 5 | PDB FTP SERVER AND IS ACCESSIBLE THROUGH THE 3DB BROWSER. |
| REMARK 5 | THE FILE CONTAINS THE OUTPUT OF THE PROGRAM WHAT_CHECK |
| | AND |
| REMARK 5 | OTHER DIAGNOSTICS. |
| REMARK 5 | |
| REMARK 5 | NOMENCLATURE IN THIS ENTRY, INCLUDING HET RESIDUE NAMES |
| REMARK 5 | AND HET ATOM NAMES, HAS NOT BEEN STANDARDIZED BY THE PDB |
| REMARK 5 | PROCESSING STAFF. A LAYER 2 ENTRY WILL BE RELEASED SHORTLY |
| REMARK 5 | AFTER THIS STANDARDIZATION IS COMPLETED AND APPROVED BY |
| | THE |
| REMARK 5 | DEPOSITOR. THE LAYER 2 ENTRY WILL BE TREATED AS A |
| REMARK 5 | CORRECTION TO THIS ONE, WITH THE APPROPRIATE REVDAT |
| | RECORD. |
| REMARK 5 | |
| REMARK 5 | FURTHER INFORMATION INCLUDING VALIDATION CRITERIA USED IN |
| REMARK 5 | CHECKING THIS ENTRY AND A LIST OF MANDATORY DATA FIELDS |
| REMARK 5 | ARE AVAILABLE FROM THE PDB WEB SITE AT |
| REMARK 5 | HTTP://WWW.PDB.BNL.GOV/. |
| REMARK 6 | |
| REMARK 6 | THE ASYMMETRIC UNIT CONTAINS TWO L11-RNA COMPLEXES. |
| | COMPLEX |
| REMARK 6 | 1 CONSISTS OF CHAINS A AND C, AND COMPLEX 2 CONSISTS OF |
| REMARK 6 | CHAINS B AAND D. RESIDUES 1–7 AND 141 OF CHAIN A ARE |
| REMARK 6 | DISORDERED. THE DENSITY FOR RESIDUES 8–70 OF CHAIN A WAS OF |
| REMARK 6 | SIGNIFICANTLY LOWER QUALITY THAN THE DENSITY FOR THE |
| REMARK 6 | REMAINDER OF THE ASYMMETRIC UNIT, AND THE QUALITY OF THE |
| REMARK 6 | MODEL FOR THIS N-TERMINAL DOMAIN IS LOWER THAN THAT OF |
| | THE |
| REMARK 6 | C-TERMINAL DOMAIN (RESIDUES 71–140). RESIDUES 1–70 AND 141 |
| REMARK 6 | OF CHAIN B ARE DISORDERED. THE RNA IS NUMBERED WITH THE E. |
| REMARK 6 | COLI NUMBERING TO FACILITATE COMPARISON WITH THE |
| | EXTENSIVE |
| REMARK 6 | BIOCHEMICAL DATA ON THE *E. COLI* RNA-L11 SYSTEM. THE *E. COLI* |
| REMARK 6 | RNA NUMBERING IS ALSO USED IN THE PRIMARY REFERENCE |
| REMARK 6 | DESCRIBING THIS STRUCTURE. |
| REMARK 7 | |
| REMARK 7 | TER |
| REMARK 7 | ASP: TERMINAL RESIDUE NOT SEEN IN MAPS |
| REMARK 7 | ASP: TERMINAL RESIDUE NOT SEEN IN MAPS |
| REMARK 200 | |
| REMARK 200 | EXPERIMENTAL DETAILS |
| REMARK 200 | EXPERIMENT TYPE:    X-RAY DIFFRACTION |
| REMARK 200 | DATE OF DATA COLLECTION  : 24-SEP-1998 |
| REMARK 200 | TEMPERATURE  (KELVIN): 100 |
| REMARK 200 | PH    : 8.3 |
| REMARK 200 | NUMBER OF CRYSTALS USED  : 1 |
| REMARK 200 | |
| REMARK 200 | SYNCHROTRON  (Y/N): Y |
| REMARK 200 | RADIATION SOURCE  : NSLS |
| REMARK 200 | BEAMLINE    : X12C |
| REMARK 200 | X-RAY GENERATOR MODEL  : NULL |
| REMARK 200 | MONOCHROMATIC OR LAUE (M/L): M |
| REMARK 200 | WAVELENGTH OR RANGE  (A): 0.98, 1.01 |
| REMARK 200 | MONOCHROMATOR     : SI CRYSTAL |
| REMARK 200 | OPTICS    : MIRRORS |
| REMARK 200 | |
| REMARK 200 | DETECTOR TYPE    : BRANDEIS 1K X 1 K CCD |
| REMARK 200 | DETECTOR MANUFACTURER  : NULL |
| REMARK 200 | INTENSITY-INTEGRATION SOFTWARE: DENZO |
| REMARK 200 | DATA SCALING SOFTWARE   : SCALEPACK |
| REMARK 200 | |
| REMARK 200 | NUMBER OF UNIQUE REFLECTIONS: 49313 |
| REMARK 200 | RESOLUTION RANGE HIGH   (A): 2.57 |
| REMARK 200 | RESOLUTION RANGE LOW   (A): 20.0 |
| REMARK 200 | REJECTION CRITERIA (SIGMA(I)): 0 |

TABLE II-continued

```
REMARK 200
REMARK 200  OVERALL.
REMARK 200  COMPLETENESS FOR RANGE (%): 95.5
REMARK 200  DATA REDUNDANCY   : 4.0
REMARK 200  R MERGE      (I): NULL
REMARK 200  R SYM        (I): 0.041
REMARK 200  < I/SIGMA(I)> FOR THE DATA SET: 20
REMARK 200
REMARK 200  IN THE HIGHEST RESOLUTION SHELL.
REMARK 200  HIGHEST RESOLUTION SHELL, RANGE HIGH (A): 2.57
REMARK 200  HIGHEST RESOLUTION SHELL, RANGE LOW (A): 2.73
REMARK 200  COMPLETENESS FOR SHELL (%): 86.2
REMARK 200  DATA REDUNDANCY IN SHELL: 3.4
REMARK 200  R MERGE FOR SHELL   (I): NULL
REMARK 200  R SYM FOR SHELL     (I): 0.17
REMARK 200  < I/SIGMA(I)> FOR SHELL    : 4.3
REMARK 200
REMARK 200  DIFFRACTION PROTOCOL: MAD
REMARK 200  METHOD USED TO DETERMINE THE STRUCTURE: MAD
REMARK 200  SOFTWARE USED: NULL
REMARK 200  STARTING MODEL: NULL
REMARK 200
REMARK 200  REMARK: TWO WAVELENGTH HG MAD
REMARK 280
REMARK 280  CRYSTAL
REMARK 280  SOLVENT CONTENT, VS (%): 55
REMARK 280  MATTHEWS COEFFICIENT, VM (ANGSTROMS**3/DA): 3.1
REMARK 280
REMARK 280  CRYSTALLIZATION CONDITIONS:
REMARK 280  25% GLYCEROL, 15% PEG 4000, 50 MM TRIS PH 7.5,
REMARK 280  50 MM MGCL2, 20 MM CDCL2, 0.2 M KCL,
REMARK 280  1 MM DITHIOTHREITOL, 4 DEGREES C
REMARK 290
REMARK 290  CRYSTALLOGRAPHIC SYMMETRY
REMARK 290  SYMMETRY OPERATORS FOR SPACE GROUP: P 21 21 21
REMARK 290
REMARK 290  SYMOP SYMMETRY
REMARK 290  NNNMMM OPERATOR
REMARK 290  1555 X, Y, Z
REMARK 290  2555 1/2 − X, −Y, 1/2 + Z
REMARK 290  3555 −X, 1/2 + Y, 1/2 − Z
REMARK 290  4555 1/2 + X, 1/2 − Y, −Z
REMARK 290
REMARK 290  WHERE NNN -> OPERATOR NUMBER
REMARK 290  MMM -> TRANSLATION VECTOR
REMARK 290
REMARK 290  CRYSTALLOGRAPHIC SYMMETRY TRANSFORMATIONS
REMARK 290  THE FOLLOWING TRANSFORMATIONS OPERATE ON THE
            ATOM/HETATM
REMARK 290  RECORDS IN THIS ENTRY TO PRODUCE CRYSTALLOGRAPHICALLY
REMARK 290  RELATED MOLECULES.
REMARK 290  SMTRY1   1   1.000000   0.000000   0.000000    0.00000
REMARK 290  SMTRY2   1   0.000000   1.000000   0.000000    0.00000
REMARK 290  SMTRY3   1   0.000000   0.000000   1.000000    0.00000
REMARK 290  SMTRY1   2  −1.000000   0.000000   0.000000   31.94480
REMARK 290  SMTRY2   2   0.000000  −1.000000   0.000000    0.00000
REMARK 290  SMTRY3   2   0.000000   0.000000   1.000000   77.76050
REMARK 290  SMTRY1   3  −1.000000   0.000000   0.000000    0.00000
REMARK 290  SMTRY2   3   0.000000   1.000000   0.000000   42.13010
REMARK 290  SMTRY3   3   0.000000   0.000000  −1.000000   77.76050
REMARK 290  SMTRY1   4   1.000000   0.000000   0.000000   31.94480
REMARK 290  SMTRY2   4   0.000000  −1.000000   0.000000   42.13010
REMARK 290  SMTRY3   4   0.000000   0.000000  −1.000000    0.00000
REMARK 290
REMARK 290  REMARK: NULL
REMARK 295
REMARK 295  NON-CRYSTALLOGRAPHIC SYMMETRY
REMARK 295  THE TRANSFORMATIONS PRESENTED ON THE MTRIX RECORDS
            BELOW
REMARK 295  DESCRIBE NON-CRYSTALLOGRAPHIC RELATIONSHIPS AMONG
            ATOMS
REMARK 295  IN THIS ENTRY. APPLYING THE APPROPRIATE MTRIX
REMARK 295  TRANSFORMATION TO THE RESIDUES LISTED FIRST WILL YIELD
REMARK 295  APPROXIMATE COORDINATES FOR THE RESIDUES LISTED SECOND.
REMARK 295  CHAIN IDENTIFIERS GIVEN AS "?" REFER TO CHAINS FOR WHICH
REMARK 295  ATOMS ARE NOT FOUND IN THIS ENTRY.
REMARK 295
REMARK 295      APPLIED TO    TRANSFORMED TO
REMARK 295  TRANSFORM CHAIN RESIDUES CHAIN RESIDUES RMSD
```

TABLE II-continued

```
REMARK 295  SSS
REMARK 295  M 1 C 1051 . . . 1108 D 1051 . . . 1108 0.07
REMARK 295  M 2 A 71 . . . 140 B 71 . . . 140 0.99
REMARK 295
REMARK 295  WHERE SSS -> COLUMNS 8–10 OF MTRIX RECORDS
REMARK 295
REMARK 295  REMARK:
REMARK 295  NCS RESTRAINTS NOT APPLIED TO PROTEIN
REMARK 465
REMARK 465  MISSING RESIDUES
REMARK 465  THE FOLLOWING RESIDUES WERE NOT LOCATED IN THE
REMARK 465  EXPERIMENT. (M = MODEL NUMBER; RES = RESIDUE NAME; C = CHA1N
REMARK 465  IDENTIFIER; SSSEQ = SEQUENCE NUMBER; I = INSERTION CODE):
REMARK 465
REMARK 465  M RES C SSSEQI
REMARK 465  ALA A 2
REMARK 465  LYS A 3
REMARK 465  LYS A 4
REMARK 465  VAL A 5
REMARK 465  ALA A 6
REMARK 465  ALA A 7
REMARK 465  ASP A 141
REMARK 465  ALA B 2 TO ILE B 70
REMARK 465  ASP B 141
REMARK 470
REMARK 470  MISSING ATOM
REMARK 470  THE FOLLOWING RESIDUES HAVE MISSING ATOMS (M = MODEL
            NUMBER;
REMARK 470  RES = RESIDUE NAME; C = CHAIN IDENTIFIER; SSEQ = SEQUENCE
            NUMBER;
REMARK 470  I = INSERTION CODE):
REMARK 470  M RES CSSEQI ATOMS
REMARK 470    G C1051 P O1P O2P
REMARK 470    G D1051 P O1P O2P
REMARK 550
REMARK 550  SEGID
REMARK 550  RNA1, RNA2
REMARK 550  L111, L112
REMARK 600
REMARK 600  HETEROGEN
REMARK 600  THERE ARE A TOTAL OF 8 CADMIUM IONS IN THE STRUCTURE
REMARK 600
REMARK 600  THERE ARE A TOTAL OF 19 MAGNESIUM IONS IN THE STRUCTURE
REMARK 600
REMARK 600  THERE ARE A TOTAL OF 8 METHYLMERCURY
REMARK 600  IONS IN THE STRUCTURE.
REMARK 600  THE METHYL GROUP HAS NOT BEEN MODELLED
REMARK 600  FOR ANY OF THESE IONS.
REMARK 600  TWO OF THE IONS ARE COVALENTLY BOUND
REMARK 600  TO CYS A 39.
REMARK 600  ONE IS COVALENTLY BOUND TO U C 1061.
REMARK 600  ONE IS COVALENTLY BOUND TO U D 1061.
REMARK 600
REMARK 800
REMARK 800  SITE
REMARK 800  SITE_IDENTIFIER: TSR
REMARK 800  SITE_DESCRIPTION:
REMARK 800  PUTATIVE THIOSTREPTON/MICROCOCCIN BINDING SITE
REMARK 800
REMARK 800  SITE_IDENTIFIER: TSR
REMARK 800  SITE_DESCRIPTION:
REMARK 800  PUTATIVE THIOSTREPTON/MICROCOCCIN BINDING SITE
REMARK 800
REMARK 800  SITE_IDENTIFIER: TSR
REMARK 800  SITE_DESCRIPTION:
REMARK 800  PUTATIVE THIOSTREPTON/MICROCOCCIN BINDING SITE
REMARK 800
DBREF A     8 140 SWS P29395 RL11_THEMA 1 141
DBREF B     71 140 SWS P29395 RL11_THEMA 1 141
DBREF C     1051 1108 PDB      1051 1108
DBREF D     1051 1108 PDB      1051 1108
SEQADV      RES C 1108 GI M67498 1168 ENGINEERED MUTATION
SEQADV      RES D 1108 GI M67498 1168 ENGINEERED MUTATION
SEQRES   1    A    140  ALA LYS LYS VAL ALA ALA GLN ILE LYS LEU GLN LEU PRO
SEQRES   2    A    140  ALA GLY LYS ALA THR PRO ALA PRO PRO VAL GLY PRO ALA
SEQRES   3    A    140  LEU GLY GLN HIS GLY VAL ASN ILE MET GLU PHE CYS LYS
SEQRES   4    A    140  ARG PHE ASN ALA GLU THR ALA ASP LYS ALA GLY MET ILE
SEQRES   5    A    140  LEU PRO VAL VAL ILE THR VAL TYR GLU ASP LYS SER PHE
SEQRES   6    A    140  THR PHE ILE ILE LYS THR PRO PRO ALA SER PHE LEU LEU
```

TABLE II-continued

| | | | | |
|---|---|---|---|---|
| SEQRES | 7 | A | 140 | LYS LYS ALA ALA GLY ILE GLU LYS GLY SER SER GLU PRO |
| SEQRES | 8 | A | 140 | LYS ARG LYS ILE VAL GLY LYS VAL THR ARG LYS GLN ILE |
| SEQRES | 9 | A | 140 | GLU GLU ILE ALA LYS THR LYS MET PRO ASP LEU ASN ALA |
| SEQRES | 10 | A | 140 | ASN SER LEU GLU ALA ALA MET LYS ILE ILE GLU GLY THR |
| SEQRES | 11 | A | 140 | ALA LYS SER MET GLY ILE GLU VAL VAL ASP |
| SEQRES | 1 | B | 140 | ALA LYS LYS VAL ALA ALA GLN ILE LYS LEU GLN LEU PRO |
| SEQRES | 2 | B | 140 | ALA GLY LYS ALA THR PRO ALA PRO PRO VAL GLY PRO ALA |
| SEQRES | 3 | B | 140 | LEU GLY GLN HIS GLY VAL ASN ILE MET GLU PHE CYS LYS |
| SEQRES | 4 | B | 140 | ARG PHE ASN ALA GLU THR ALA ASP LYS ALA GLY MET ILE |
| SEQRES | 5 | B | 140 | LEU PRO VAL VAL ILE THR VAL TYR GLU ASP LYS SER PHE |
| SEQRES | 6 | B | 140 | THR PHE ILE ILE LYS THR PRO PRO ALA SER PHE LEU LEU |
| SEQRES | 7 | B | 140 | LYS LYS ALA ALA GLY ILE GLU LYS GLY SER SER GLU PRO |
| SEQRES | 8 | B | 140 | LYS ARG LYS ILE VAL GLY LYS VAL THR ARG LYS GLN ILE |
| SEQRES | 9 | B | 140 | GLU GLU ILE ALA LYS THR LYS MET PRO ASP LEU ASN ALA |
| SEQRES | 10 | B | 140 | ASN SER LEU GLU ALA ALA MET LYS ILE ILE GLU GLY THR |
| SEQRES | 11 | B | 140 | ALA LYS SER MET GLY ILE GLU VAL VAL ASP |
| SEQRES | 1 | C | 58 | G C U G G G A U G U U G G |
| SEQRES | 2 | C | 58 | C U U A G A A G C A G C C |
| SEQRES | 3 | C | 58 | A U C A U U U A A A G A G |
| SEQRES | 4 | C | 58 | U G C G U A A C A G C U C |
| SEQRES | 5 | C | 58 | A C C A G C |
| SEQRES | 1 | D | 58 | G C U G G G A U G U U G G |
| SEQRES | 2 | D | 58 | C U U A G A A G C A G C C |
| SEQRES | 3 | D | 58 | A U C A U U U A A A G A G |
| SEQRES | 4 | D | 58 | U G C G U A A C A G C U C |
| SEQRES | 5 | D | 58 | A C C A G C |
| HET | CD | | 201 0 | |
| HET | CD | | 202 0 | |
| HET | CD | | 211 0 | |
| HET | CD | | 302 0 | |
| HET | CD | | 311 0 | |
| HET | CD | | 390 0 | |
| HET | CD | | 413 0 | |
| HET | CD | | 414 0 | SEE REMARK 600 |
| HET | MG | | 210 0 | |
| HET | MG | | 214 0 | |
| HET | MG | | 215 0 | |
| HET | MG | | 223 0 | |
| HET | MG | | 225 0 | |
| HET | MG | | 226 0 | |
| HET | MG | | 228 0 | |
| HET | MG | | 257 0 | |
| HET | MG | | 273 0 | |
| HET | MG | | 318 0 | |
| HET | MG | | 326 0 | |
| HET | MG | | 354 0 | |
| HET | MG | | 360 0 | |
| HET | MG | | 365 0 | |
| HET | MG | | 375 0 | |
| HET | MG | | 380 0 | |
| HET | MG | | 385 0 | |
| HET | MG | | 397 0 | |
| HET | MG | | 437 0 | SEE REMARK 600 |
| HET | HG | | 227 0 | |
| HET | HG | | 230 0 | |
| HET | HG | | 332 0 | |
| HET | HG | | 347 0 | |
| HET | HG | | 415 0 | |
| HET | HG | | 416 0 | |
| HET | HG | | 448 0 | |
| HET | HG | | 451 0 | SEE REMARK 600 |
| HETNAM | CD | | CD | |
| HETNAM | MG | | MG | |
| HETNAM | HG | | MMC | |
| HETSYN | CD | | CADMIUM (II) | |
| HETSYN | MG | | MAGNESIUM (II) | |
| HETSYN | HG | | METHYLMERCURY ION | |
| FORMUL 5 | CD | 8(CD1 2+) | | |
| FORMUL 6 | MG | 19(MG1 2+) | | |
| FORMUL 7 | HG | 8(C1 H3 HG1 1+) | | |
| FORMUL 8 | HOH | *142(H2 O1) | | |
| HELIX 1 | 1 PRO A | 26 GLN A | 30 | 1 5 |
| HELIX 2 | 2 ILE A | 35 ALA A | 47 | 1 13 |
| HELIX 3 | 3 ALA A | 75 ALA A | 83 | 1 9 |
| HELIX 4 | 4 ARG A | 102 ASP A | 115 | 1 14 |
| HELIX 5 | 5 LEU A | 121 SER A | 134 | 1 14 |
| HELIX 6 | 6 ALA B | 75 ALA B | 83 | 1 9 |
| HELIX 7 | 7 ARG B | 102 ASP B | 115 | 1 14 |
| HELIX 8 | 8 LEU B | 121 MET B | 135 | 1 15 |

TABLE II-continued

| | | | | | | | | | | | | | | |
|---|---|---|---|---|---|---|---|---|---|---|---|---|---|---|
| SHEET | 1 | A | 3 | LLE | A | 9 | PRO | A | 14 | 0 | | | | |
| SHEET | 2 | A | 3 | ILE | A | 53 | VAL | A | 60 | −1 N | ILE | A | 58 | O ILE A 9 |
| SHEET | 3 | A | 3 | PHE | A | 66 | ILE | A | 70 | −1 N | ILE | A | 69 | O VAL A 57 |
| SHEET | 1 | B | 2 | GLY | A | 98 | THR | A | 101 | 0 | | | | |
| SHEET | 2 | B | 2 | ILE | A | 137 | VAL | A | 140 | 1 N | GLU | A | 138 | O GLY A 98 |
| SHEET | 1 | C | 2 | GLY | B | 98 | VAL | B | 100 | 0 | | | | |
| SHEET | 2 | C | 2 | ILE | B | 137 | VAL | B | 139 | 1 N | GLU | B | 138 | O GLY B 98 |
| SITE | 1 | TSR | 2 | A | C | 1067 | A | C | 1095 | | | | | |
| SITE | 2 | TSR | 2 | A | D | 1067 | A | D | 1095 | | | | | |
| SITE | 3 | TSR | 3 | PRO | A | 22 | PRO | A | 23 PRO | A | 26 | | | |
| CRYST1 | | 63.890 | 84.260 | 155.510 | 90.00 | 90.00 | 90.00 | P 21 21 21 | 8 | | | | | |
| ORIGX1 | | 1.000000 | 0.000000 | 0.000000 | 0.00000 | | | | | | | | | |
| ORIGX2 | | 0.000000 | 1.000000 | 0.000000 | 0.00000 | | | | | | | | | |
| ORIGX3 | | 0.000000 | 0.000000 | 1.000000 | 0.00000 | | | | | | | | | |
| SCALE1 | | 0.015652 | 0.000000 | 0.000000 | 0.00000 | | | | | | | | | |
| SCALE2 | | 0.000000 | 0.011868 | 0.000000 | 0.00000 | | | | | | | | | |
| SCALE3 | | 0.000000 | 0.000000 | 0.006430 | 0.00000 | | | | | | | | | |
| MTRIX1 | 1 | 0.974505 | 0.101458 | −0.200117 | −4.54330 | 1 | | | | | | | | |
| MTRIX2 | 1 | 0.097433 | −0.994793 | −0.029885 | −3.74880 | 1 | | | | | | | | |
| MTRIX3 | 1 | −0.202107 | 0.009626 | −0.979316 | −50.69290 | 1 | | | | | | | | |
| MTRIX1 | 2 | 0.973477 | 0.098780 | −0.206364 | −4.89630 | 1 | | | | | | | | |
| MTRIX2 | 2 | 0.098758 | −0.995057 | −0.010432 | −2.89050 | 1 | | | | | | | | |
| MTRIX3 | 2 | −0.206374 | −0.010225 | −0.978420 | −50.97240 | 1 | | | | | | | | |
| ATOM | 1 | N | GLN | A | 8 | −7.803 | −11.096 | −9.783 | 1.00 | 71.77 | L111 | N | | |
| ATOM | 2 | CA | GLN | A | 8 | −8.476 | −9.887 | −9.223 | 1.00 | 79.42 | L111 | C | | |
| ATOM | 3 | C | GLN | A | 8 | −8.010 | −8.599 | −9.897 | 1.00 | 80.19 | L111 | C | | |
| ATOM | 4 | O | GLN | A | 8 | −6.857 | −8.190 | −9.748 | 1.00 | 77.92 | L111 | O | | |
| ATOM | 5 | CB | GLN | A | 8 | −8.212 | −9.788 | −7.722 | 1.00 | 79.86 | L111 | C | | |
| ATOM | 6 | CG | GLN | A | 8 | −9.065 | −8.752 | −7.016 | 1.00 | 80.16 | L111 | C | | |
| ATOM | 7 | CD | GLN | A | 8 | −9.072 | −8.948 | −5.518 | 1.00 | 80.58 | L111 | C | | |
| ATOM | 8 | OE1 | GLN | A | 8 | −8.020 | −8.963 | −4.881 | 1.00 | 82.16 | L111 | O | | |
| ATOM | 9 | NE2 | GLN | A | 8 | −10.261 | −9.104 | −4.946 | 1.00 | 79.20 | L111 | N | | |
| ATOM | 10 | N | ILE | A | 9 | −8.916 | −7.963 | −10.634 | 1.00 | 81.13 | L111 | N | | |
| ATOM | 11 | CA | ILE | A | 9 | −8.604 | −6.723 | −11.337 | 1.00 | 80.39 | L111 | C | | |
| ATOM | 12 | C | ILE | A | 9 | −9.312 | −5.530 | −10.699 | 1.00 | 79.13 | L111 | C | | |
| ATOM | 13 | O | ILE | A | 9 | −10.338 | −5.680 | −10.036 | 1.00 | 78.96 | L111 | O | | |
| ATOM | 14 | CB | ILE | A | 9 | −9.013 | −6.804 | −12.834 | 1.00 | 77.02 | L111 | C | | |
| ATOM | 15 | CG1 | ILE | A | 9 | −10.534 | −6.778 | −12.970 | 1.00 | 77.57 | L111 | C | | |
| ATOM | 16 | CG2 | ILE | A | 9 | −8.482 | −8.080 | −13.452 | 1.00 | 74.06 | L111 | C | | |
| ATOM | 17 | CD1 | ILE | A | 9 | −11.066 | −5.495 | −13.552 | 1.00 | 83.48 | L111 | C | | |
| ATOM | 18 | N | LYS | A | 10 | −8.752 | −4.343 | −10.900 | 1.00 | 80.87 | L111 | N | | |
| ATOM | 19 | CA | LYS | A | 10 | −9.330 | −3.121 | −10.360 | 1.00 | 77.55 | L111 | C | | |
| ATOM | 20 | C | LYS | A | 10 | −9.252 | −2.011 | −11.400 | 1.00 | 74.90 | L111 | C | | |
| ATOM | 21 | O | LYS | A | 10 | −8.308 | −1.945 | −12.191 | 1.00 | 69.61 | L111 | O | | |
| ATOM | 22 | CB | LYS | A | 10 | −8.590 | −2.696 | −9.089 | 1.00 | 78.72 | L111 | C | | |
| ATOM | 23 | CG | LYS | A | 10 | −7.080 | −2.607 | −9.243 | 1.00 | 76.53 | L111 | C | | |
| ATOM | 24 | CD | LYS | A | 10 | −6.482 | −1.615 | −8.256 | 1.00 | 76.55 | L111 | C | | |
| ATOM | 25 | CE | LYS | A | 10 | −6.047 | −2.300 | −6.968 | 1.00 | 78.93 | L111 | C | | |
| ATOM | 26 | NZ | LYS | A | 10 | −4.923 | −1.584 | −6.296 | 1.00 | 81.54 | L111 | N | | |
| ATOM | 27 | N | LEU | A | 11 | −10.261 | −1.149 | −11.403 | 1.00 | 72.26 | L111 | N | | |
| ATOM | 28 | CA | LEU | A | 11 | −10.311 | −0.037 | −12.342 | 1.00 | 77.13 | L111 | C | | |
| ATOM | 29 | C | LEU | A | 11 | −11.286 | 1.024 | −11.852 | 1.00 | 78.99 | L111 | C | | |
| ATOM | 30 | O | LEU | A | 11 | −12.052 | 0.790 | −10.915 | 1.00 | 78.52 | L111 | O | | |
| ATOM | 31 | CB | LEU | A | 11 | −10.744 | −0.525 | −13.728 | 1.00 | 77.54 | L111 | C | | |
| ATOM | 32 | CG | LEU | A | 11 | −11.051 | −2.014 | −13.906 | 1.00 | 72.58 | L111 | C | | |
| ATOM | 33 | CD1 | LEU | A | 11 | −12.511 | −2.199 | −14.290 | 1.00 | 68.73 | L111 | C | | |
| ATOM | 34 | CD2 | LEU | A | 11 | −10.128 | −2.590 | −14.969 | 1.00 | 73.75 | L111 | C | | |
| ATOM | 35 | N | GLN | A | 12 | −11.255 | 2.189 | −12.489 | 1.00 | 80.79 | L111 | N | | |
| ATOM | 36 | CA | GLN | A | 12 | −12.144 | 3.284 | −12.120 | 1.00 | 82.10 | L111 | C | | |
| ATOM | 37 | C | GLN | A | 12 | −13.115 | 3.582 | −13.261 | 1.00 | 80.51 | L111 | C | | |
| ATOM | 38 | O | GLN | A | 12 | −12.791 | 4.320 | −14.190 | 1.00 | 81.39 | L111 | O | | |
| ATOM | 39 | CB | GLN | A | 12 | −11.329 | 4.536 | −11.789 | 1.00 | 81.65 | L111 | C | | |
| ATOM | 40 | CG | GLN | A | 12 | −10.068 | 4.267 | −10.979 | 1.00 | 81.34 | L111 | C | | |
| ATOM | 41 | CD | GLN | A | 12 | −9.364 | 5.545 | −10.556 | 1.00 | 88.15 | L111 | C | | |
| ATOM | 42 | OE1 | GLN | A | 12 | −9.445 | 6.568 | −11.239 | 1.00 | 89.05 | L111 | O | | |
| ATOM | 43 | NE2 | GLN | A | 12 | −8.668 | 5.493 | −9.425 | 1.00 | 90.09 | L111 | N | | |
| ATOM | 44 | N | LEU | A | 13 | −14.308 | 3.003 | −13.184 | 1.00 | 80.02 | L111 | N | | |
| ATOM | 45 | CA | LEU | A | 13 | −15.320 | 3.197 | −14.214 | 1.00 | 79.90 | L111 | C | | |
| ATOM | 46 | C | LEU | A | 13 | −16.345 | 4.256 | −13.818 | 1.00 | 81.60 | L111 | C | | |
| ATOM | 47 | O | LEU | A | 13 | −16.761 | 4.331 | −12.659 | 1.00 | 82.22 | L111 | O | | |
| ATOM | 48 | CB | LEU | A | 13 | −16.033 | 1.873 | −14.502 | 1.00 | 73.75 | L111 | C | | |
| ATOM | 49 | CG | LEU | A | 13 | −15.191 | 0.615 | −14.276 | 1.00 | 73.16 | L111 | C | | |
| ATOM | 50 | CD1 | LEU | A | 13 | −16.100 | −0.586 | −14.059 | 1.00 | 74.99 | L111 | C | | |
| ATOM | 51 | CD2 | LEU | A | 13 | −14.277 | 0.397 | −15.470 | 1.00 | 68.58 | L111 | C | | |
| ATOM | 52 | N | PRO | A | 14 | −16.759 | 5.097 | −14.783 | 1.00 | 80.42 | L111 | N | | |
| ATOM | 53 | CA | PRO | A | 14 | −17.745 | 6.151 | −14.511 | 1.00 | 76.54 | L111 | C | | |
| ATOM | 54 | C | PRO | A | 14 | −19.065 | 5.553 | −14.041 | 1.00 | 74.17 | L111 | C | | |
| ATOM | 55 | O | PRO | A | 14 | −19.364 | 4.396 | −14.328 | 1.00 | 73.53 | L111 | O | | |

TABLE II-continued

| ATOM | 56 | CB | PRO | A | 14 | −17.877 | 6.880 | −15.846 | 1.00 | 74.99 | L111 | C |
|---|---|---|---|---|---|---|---|---|---|---|---|---|
| ATOM | 57 | CG | PRO | A | 14 | −17.358 | 5.919 | −16.870 | 1.00 | 77.83 | L111 | C |
| ATOM | 58 | CD | PRO | A | 14 | −16.315 | 5.101 | −16.188 | 1.00 | 76.88 | L111 | C |
| ATOM | 59 | N | ALA | A | 15 | −19.844 | 6.349 | −13.317 | 1.00 | 75.75 | L111 | N |
| ATOM | 60 | CA | ALA | A | 15 | −21.128 | 5.917 | −12.774 | 1.00 | 82.83 | L111 | C |
| ATOM | 61 | C | ALA | A | 15 | −21.947 | 5.008 | −13.691 | 1.00 | 89.65 | L111 | C |
| ATOM | 62 | O | ALA | A | 15 | −21.711 | 3.800 | −13.753 | 1.00 | 93.73 | L111 | O |
| ATOM | 63 | CB | ALA | A | 15 | −21.947 | 7.132 | −12.387 | 1.00 | 88.09 | L111 | C |
| ATOM | 64 | N | GLY | A | 16 | −22.921 | 5.590 | −14.387 | 1.00 | 94.26 | L111 | N |
| ATOM | 65 | CA | GLY | A | 16 | −23.761 | 4.810 | −15.282 | 1.00 | 98.24 | L111 | C |
| ATOM | 66 | C | GLY | A | 16 | −23.218 | 4.696 | −16.697 | 1.00 | 100.00 | L111 | C |
| ATOM | 67 | O | GLY | A | 16 | −23.672 | 5.395 | −17.607 | 1.00 | 100.00 | L111 | O |
| ATOM | 68 | N | LYS | A | 17 | −22.239 | 3.813 | −16.881 | 1.00 | 99.48 | L111 | N |
| ATOM | 69 | CA | LYS | A | 17 | −21.621 | 3.594 | −18.187 | 1.00 | 98.41 | L111 | C |
| ATOM | 70 | C | LYS | A | 17 | −20.588 | 2.467 | −18.117 | 1.00 | 99.13 | L111 | C |
| ATOM | 71 | O | LYS | A | 17 | −19.851 | 2.351 | −17.134 | 1.00 | 100.00 | L111 | O |
| ATOM | 72 | CB | LYS | A | 17 | −20.951 | 4.883 | −18.685 | 1.00 | 94.26 | L111 | C |
| ATOM | 73 | CG | LYS | A | 17 | −20.492 | 5.822 | −17.580 | 1.00 | 96.55 | L111 | C |
| ATOM | 74 | CD | LYS | A | 17 | −21.088 | 7.220 | −17.728 | 1.00 | 97.02 | L111 | C |
| ATOM | 75 | CE | LYS | A | 17 | −21.564 | 7.773 | −16.385 | 1.00 | 96.31 | L111 | C |
| ATOM | 76 | NZ | LYS | A | 17 | −20.459 | 8.345 | −15.556 | 1.00 | 90.28 | L111 | N |
| ATOM | 77 | N | ALA | A | 18 | −20.545 | 1.642 | −19.163 | 1.00 | 98.71 | L111 | N |
| ATOM | 78 | CA | ALA | A | 18 | −19.615 | 0.517 | −19.243 | 1.00 | 96.77 | L111 | C |
| ATOM | 79 | C | ALA | A | 18 | −19.707 | −0.148 | −20.614 | 1.00 | 96.63 | L111 | C |
| ATOM | 80 | O | ALA | A | 18 | −20.502 | 0.271 | −21.453 | 1.00 | 98.42 | L111 | O |
| ATOM | 81 | CB | ALA | A | 18 | −19.932 | −0.500 | −18.152 | 1.00 | 95.01 | L111 | C |
| ATOM | 82 | N | THR | A | 19 | −18.872 | −1.165 | −20.837 | 1.00 | 96.19 | L111 | N |
| ATOM | 83 | CA | THR | A | 19 | −18.843 | −1.936 | −22.089 | 1.00 | 98.62 | L111 | C |
| ATOM | 84 | C | THR | A | 19 | −17.834 | −1.538 | −23.177 | 1.00 | 98.30 | L111 | C |
| ATOM | 85 | O | THR | A | 19 | −17.439 | −2.379 | −23.987 | 1.00 | 94.28 | L111 | O |
| ATOM | 86 | CB | THR | A | 19 | −20.250 | −2.000 | −22.756 | 1.00 | 100.00 | L111 | C |
| ATOM | 87 | OG1 | THR | A | 19 | −21.255 | −2.212 | −21.753 | 1.00 | 100.00 | L111 | O |
| ATOM | 88 | CG2 | THR | A | 19 | −20.311 | −3.135 | −23.772 | 1.00 | 99.76 | L111 | C |
| ATOM | 89 | N | PRO | A | 20 | −17.392 | −0.267 | −23.212 | 1.00 | 100.00 | L111 | N |
| ATOM | 90 | CA | PRO | A | 20 | −16.433 | 0.087 | −24.268 | 1.00 | 100.00 | L111 | C |
| ATOM | 91 | C | PRO | A | 20 | −15.174 | −0.778 | −24.289 | 1.00 | 100.00 | L111 | C |
| ATOM | 92 | O | PRO | A | 20 | −14.692 | −1.220 | −23.246 | 1.00 | 100.00 | L111 | O |
| ATOM | 93 | CB | PRO | A | 20 | −16.117 | 1.561 | −23.995 | 1.00 | 100.00 | L111 | C |
| ATOM | 94 | CG | PRO | A | 20 | −16.510 | 1.782 | −22.568 | 1.00 | 100.00 | L111 | C |
| ATOM | 95 | CD | PRO | A | 20 | −17.690 | 0.887 | −22.347 | 1.00 | 100.00 | L111 | C |
| ATOM | 96 | N | ALA | A | 21 | −14.650 | −1.015 | −25.487 | 1.00 | 100.00 | L111 | N |
| ATOM | 97 | CA | ALA | A | 21 | −13.450 | −1.823 | −25.640 | 1.00 | 100.00 | L111 | C |
| ATOM | 98 | C | ALA | A | 21 | −12.238 | −1.115 | −25.030 | 1.00 | 100.00 | L111 | C |
| ATOM | 99 | O | ALA | A | 21 | −11.622 | −1.626 | −24.097 | 1.00 | 100.00 | L111 | O |
| ATOM | 100 | CB | ALA | A | 21 | −13.204 | −2.130 | −27.121 | 1.00 | 100.00 | L111 | C |
| ATOM | 101 | N | PRO | A | 22 | −11.886 | 0.079 | −25.542 | 1.00 | 100.00 | L111 | N |
| ATOM | 102 | CA | PRO | A | 22 | −10.725 | 0.773 | −24.969 | 1.00 | 100.00 | L111 | C |
| ATOM | 103 | C | PRO | A | 22 | −10.740 | 0.904 | −23.434 | 1.00 | 100.00 | L111 | C |
| ATOM | 104 | O | PRO | A | 22 | −9.793 | 0.478 | −22.768 | 1.00 | 100.00 | L111 | O |
| ATOM | 105 | CB | PRO | A | 22 | −10.726 | 2.127 | −25.683 | 1.00 | 100.00 | L111 | C |
| ATOM | 106 | CG | PRO | A | 22 | −11.439 | 1.862 | −26.979 | 1.00 | 100.00 | L111 | C |
| ATOM | 107 | CD | PRO | A | 22 | −12.496 | 0.845 | −26.645 | 1.00 | 100.00 | L111 | C |
| ATOM | 108 | N | PRO | A | 23 | −11.807 | 1.495 | −22.853 | 1.00 | 100.00 | L111 | N |
| ATOM | 109 | CA | PRO | A | 23 | −11.880 | 1.650 | −21.390 | 1.00 | 100.00 | L111 | C |
| ATOM | 110 | C | PRO | A | 23 | −11.941 | 0.338 | −20.592 | 1.00 | 100.00 | L111 | C |
| ATOM | 111 | O | PRO | A | 23 | −11.025 | 0.026 | −19.829 | 1.00 | 100.00 | L111 | O |
| ATOM | 112 | CB | PRO | A | 23 | −13.135 | 2.507 | −21.173 | 1.00 | 99.53 | L111 | C |
| ATOM | 113 | CG | PRO | A | 23 | −13.446 | 3.100 | −22.519 | 1.00 | 100.00 | L111 | C |
| ATOM | 114 | CD | PRO | A | 23 | −12.988 | 2.077 | −23.513 | 1.00 | 100.00 | L111 | C |
| ATOM | 115 | N | VAL | A | 24 | −13.020 | −0.423 | −20.767 | 1.00 | 100.00 | L111 | N |
| ATOM | 116 | CA | VAL | A | 24 | −13.199 | −1.689 | −20.051 | 1.00 | 95.98 | L111 | C |
| ATOM | 117 | C | VAL | A | 24 | −12.711 | −2.903 | −20.844 | 1.00 | 94.54 | L111 | C |
| ATOM | 118 | O | VAL | A | 24 | −11.538 | −3.272 | −20.773 | 1.00 | 88.41 | L111 | O |
| ATOM | 119 | CB | VAL | A | 24 | −14.688 | −1.923 | −19.689 | 1.00 | 92.89 | L111 | C |
| ATOM | 120 | CG1 | VAL | A | 24 | −14.809 | −2.320 | −18.232 | 1.00 | 90.90 | L111 | C |
| ATOM | 121 | CG2 | VAL | A | 24 | −15.504 | −0.668 | −19.969 | 1.00 | 91.81 | L111 | C |
| ATOM | 122 | N | GLY | A | 25 | −13.636 | −3.515 | −21.584 | 1.00 | 95.43 | L111 | N |
| ATOM | 123 | CA | GLY | A | 25 | −13.343 | −4.683 | −22.401 | 1.00 | 94.07 | L111 | C |
| ATOM | 124 | C | GLY | A | 25 | −11.973 | −5.312 | −22.224 | 1.00 | 94.21 | L111 | C |
| ATOM | 125 | O | GLY | A | 25 | −11.738 | −6.020 | −21.243 | 1.00 | 93.12 | L111 | O |
| ATOM | 126 | N | PRO | A | 26 | −11.051 | −5.081 | −23.176 | 1.00 | 93.73 | L111 | N |
| ATOM | 127 | CA | PRO | A | 26 | −9.684 | −5.606 | −23.165 | 1.00 | 93.06 | L111 | C |
| ATOM | 128 | C | PRO | A | 26 | −9.110 | −5.852 | −21.774 | 1.00 | 94.47 | L111 | C |
| ATOM | 129 | O | PRO | A | 26 | −8.633 | −6.947 | −21.480 | 1.00 | 96.39 | L111 | O |
| ATOM | 130 | CB | PRO | A | 26 | −8.893 | −4.546 | −23.929 | 1.00 | 91.97 | L111 | C |
| ATOM | 131 | CG | PRO | A | 26 | −9.909 | −3.882 | −24.840 | 1.00 | 86.86 | L111 | C |
| ATOM | 132 | CD | PRO | A | 26 | −11.299 | −4.278 | −24.385 | 1.00 | 89.82 | L111 | C |
| ATOM | 133 | N | ALA | A | 27 | −9.167 | −4.829 | −20.927 | 1.00 | 95.87 | L111 | N |
| ATOM | 134 | CA | ALA | A | 27 | −8.647 | −4.902 | −19.561 | 1.00 | 96.04 | L111 | C |

TABLE II-continued

| | | | | | | | | | | | | |
|---|---|---|---|---|---|---|---|---|---|---|---|---|
| ATOM | 135 | C | ALA | A | 27 | −8.916 | −6.234 | −18.858 | 1.00 | 93.76 | L111 | C |
| ATOM | 136 | O | ALA | A | 27 | −8.098 | −7.152 | −18.912 | 1.00 | 89.80 | L111 | O |
| ATOM | 137 | CB | ALA | A | 27 | −9.218 | −3.755 | −18.730 | 1.00 | 98.77 | L111 | C |
| ATOM | 138 | N | LEU | A | 28 | −10.057 | −6.326 | −18.185 | 1.00 | 92.88 | L111 | N |
| ATOM | 139 | CA | LEU | A | 28 | −10.424 | −7.543 | −17.473 | 1.00 | 92.03 | L111 | C |
| ATOM | 140 | C | LEU | A | 28 | −10.935 | −8.593 | −18.454 | 1.00 | 91.54 | L111 | C |
| ATOM | 141 | O | LEU | A | 28 | −10.992 | −9.782 | −18.137 | 1.00 | 91.91 | L111 | O |
| ATOM | 142 | CB | LEU | A | 28 | −11.495 | −7.237 | −16.422 | 1.00 | 92.11 | L111 | C |
| ATOM | 143 | CG | LEU | A | 28 | −12.912 | −6.897 | −16.898 | 1.00 | 91.83 | L111 | C |
| ATOM | 144 | CD1 | LEU | A | 28 | −13.728 | −6.405 | −15.711 | 1.00 | 87.53 | L111 | C |
| ATOM | 145 | CD2 | LEU | A | 28 | −12.870 | −5.837 | −17.996 | 1.00 | 89.79 | L111 | C |
| ATOM | 146 | N | GLY | A | 29 | −11.304 | −8.143 | −19.650 | 1.00 | 90.13 | L111 | N |
| ATOM | 147 | CA | GLY | A | 29 | −11.794 | −9.060 | −20.661 | 1.00 | 88.78 | L111 | C |
| ATOM | 148 | C | GLY | A | 29 | −10.732 | −10.074 | −21.044 | 1.00 | 88.80 | L111 | C |
| ATOM | 149 | O | GLY | A | 29 | −11.022 | −11.064 | −21.716 | 1.00 | 86.10 | L111 | O |
| ATOM | 150 | N | GLN | A | 30 | −9.497 | −9.826 | −20.616 | 1.00 | 89.64 | L111 | N |
| ATOM | 151 | CA | GLN | A | 30 | −8.389 | −10.726 | −20.919 | 1.00 | 91.11 | L111 | C |
| ATOM | 152 | C | GLN | A | 30 | −7.986 | −11.569 | −19.712 | 1.00 | 91.31 | L111 | C |
| ATOM | 153 | O | GLN | A | 30 | −6.980 | −12.277 | −19.747 | 1.00 | 89.05 | L111 | O |
| ATOM | 154 | CB | GLN | A | 30 | −7.177 | −9.932 | −21.439 | 1.00 | 92.85 | L111 | C |
| ATOM | 155 | CG | GLN | A | 30 | −6.545 | −8.965 | −20.440 | 1.00 | 90.47 | L111 | C |
| ATOM | 156 | CD | GLN | A | 30 | −5.431 | −8.119 | −21.055 | 1.00 | 92.62 | L111 | C |
| ATOM | 157 | OE1 | GLN | A | 30 | −4.260 | −8.511 | −21.057 | 1.00 | 93.46 | L111 | O |
| ATOM | 158 | NE2 | GLN | A | 30 | −5.796 | −6.955 | −21.584 | 1.00 | 92.21 | L111 | N |
| ATOM | 159 | N | HIS | A | 31 | −8.776 | −11.489 | −18.646 | 1.00 | 94.67 | L111 | N |
| ATOM | 160 | CA | HIS | A | 31 | −8.505 | −12.256 | −17.432 | 1.00 | 94.53 | L111 | C |
| ATOM | 161 | C | HIS | A | 31 | −9.521 | −13.393 | −17.329 | 1.00 | 93.97 | L111 | C |
| ATOM | 162 | O | HIS | A | 31 | −9.323 | −14.351 | −16.582 | 1.00 | 94.95 | L111 | O |
| ATOM | 163 | CB | HIS | A | 31 | −8.594 | −11.350 | −16.193 | 1.00 | 92.77 | L111 | C |
| ATOM | 164 | CG | HIS | A | 31 | −7.423 | −10.425 | −16.028 | 1.00 | 90.32 | L111 | C |
| ATOM | 165 | ND1 | HIS | A | 31 | −7.531 | −9.056 | −16.160 | 1.00 | 88.08 | L111 | N |
| ATOM | 166 | CD2 | HIS | A | 31 | −6.126 | −10.671 | −15.729 | 1.00 | 86.03 | L111 | C |
| ATOM | 167 | CE1 | HIS | A | 31 | −6.351 | −8.500 | −15.950 | 1.00 | 81.34 | L111 | C |
| ATOM | 168 | NE2 | HIS | A | 31 | −5.480 | −9.457 | −15.686 | 1.00 | 84.77 | L111 | N |
| ATOM | 169 | N | GLY | A | 32 | −10.604 | −13.278 | −18.094 | 1.00 | 93.26 | L111 | N |
| ATOM | 170 | CA | GLY | A | 32 | −11.637 | −14.299 | −18.091 | 1.00 | 90.69 | L111 | C |
| ATOM | 171 | C | GLY | A | 32 | −13.032 | −13.721 | −17.950 | 1.00 | 90.58 | L111 | C |
| ATOM | 172 | O | GLY | A | 32 | −14.022 | −14.353 | −18.323 | 1.00 | 91.06 | L111 | O |
| ATOM | 173 | N | VAL | A | 33 | −13.107 | −12.509 | −17.415 | 1.00 | 89.92 | L111 | N |
| ATOM | 174 | CA | VAL | A | 33 | −14.376 | −11.822 | −17.196 | 1.00 | 90.50 | L111 | C |
| ATOM | 175 | C | VAL | A | 33 | −15.254 | −11.711 | −18.443 | 1.00 | 88.55 | L111 | C |
| ATOM | 176 | O | VAL | A | 33 | −14.753 | −11.581 | −19.560 | 1.00 | 88.34 | L111 | O |
| ATOM | 177 | CB | VAL | A | 33 | −14.135 | −10.398 | −16.652 | 1.00 | 92.08 | L111 | C |
| ATOM | 178 | CG1 | VAL | A | 33 | −15.292 | −9.976 | −15.770 | 1.00 | 90.59 | L111 | C |
| ATOM | 179 | CG2 | VAL | A | 33 | −12.830 | −10.351 | −15.873 | 1.00 | 93.31 | L111 | C |
| ATOM | 180 | N | ASN | A | 34 | −16.568 | −11.766 | −18.237 | 1.00 | 89.80 | L111 | N |
| ATOM | 181 | CA | ASN | A | 34 | −17.533 | −11.650 | −19.327 | 1.00 | 94.89 | L111 | C |
| ATOM | 182 | C | ASN | A | 34 | −18.128 | −10.245 | −19.290 | 1.00 | 96.48 | L111 | C |
| ATOM | 183 | O | ASN | A | 34 | −19.141 | −10.008 | −18.630 | 1.00 | 97.04 | L111 | O |
| ATOM | 184 | CB | ASN | A | 34 | −18.661 | −12.681 | −19.182 | 1.00 | 97.83 | L111 | C |
| ATOM | 185 | CG | ASN | A | 34 | −18.405 | −13.683 | −18.072 | 1.00 | 100.00 | L111 | C |
| ATOM | 186 | OD1 | ASN | A | 34 | −19.205 | −13.813 | −17.141 | 1.00 | 100.00 | L111 | O |
| ATOM | 187 | ND2 | ASN | A | 34 | −17.291 | −14.405 | −18.167 | 1.00 | 100.00 | L111 | N |
| ATOM | 188 | N | ILE | A | 35 | −17.486 | −9.325 | −20.006 | 1.00 | 98.20 | L111 | N |
| ATOM | 189 | CA | ILE | A | 35 | −17.898 | −7.922 | −20.071 | 1.00 | 97.32 | L111 | C |
| ATOM | 190 | C | ILE | A | 35 | −19.392 | −7.651 | −19.844 | 1.00 | 99.75 | L111 | C |
| ATOM | 191 | O | ILE | A | 35 | −19.776 | −7.148 | −18.788 | 1.00 | 100.00 | L111 | O |
| ATOM | 192 | CB | ILE | A | 35 | −17.478 | −7.282 | −21.426 | 1.00 | 95.15 | L111 | C |
| ATOM | 193 | CG1 | ILE | A | 35 | −16.341 | −8.094 | −22.064 | 1.00 | 93.73 | L111 | C |
| ATOM | 194 | CG2 | ILE | A | 35 | −17.066 | −5.823 | −21.213 | 1.00 | 87.68 | L111 | C |
| ATOM | 195 | CD1 | ILE | A | 35 | −14.960 | −7.824 | −21.485 | 1.00 | 91.66 | L111 | C |
| ATOM | 196 | N | MET | A | 36 | −20.220 | −7.980 | −20.835 | 1.00 | 100.00 | L111 | N |
| ATOM | 197 | CA | MET | A | 36 | −21.672 | −7.767 | −20.773 | 1.00 | 99.82 | L111 | C |
| ATOM | 198 | C | MET | A | 36 | −22.294 | −7.868 | −19.376 | 1.00 | 97.54 | L111 | C |
| ATOM | 199 | O | MET | A | 36 | −23.032 | −6.975 | −18.950 | 1.00 | 95.12 | L111 | O |
| ATOM | 200 | CB | MET | A | 36 | −22.384 | −8.752 | −21.713 | 1.00 | 100.00 | L111 | C |
| ATOM | 201 | CG | MET | A | 36 | −23.911 | −8.645 | −21.709 | 1.00 | 100.00 | L111 | C |
| ATOM | 202 | SD | MET | A | 36 | −24.759 | −10.248 | −21.810 | 1.00 | 100.00 | L111 | S |
| ATOM | 203 | CE | MET | A | 36 | −25.601 | −10.300 | −20.213 | 1.00 | 97.00 | L111 | C |
| ATOM | 204 | N | GLU | A | 37 | −22.001 | −8.960 | −18.674 | 1.00 | 95.35 | L111 | N |
| ATOM | 205 | CA | GLU | A | 37 | −22.535 | −9.190 | −17.335 | 1.00 | 92.68 | L111 | C |
| ATOM | 206 | C | GLU | A | 37 | −22.124 | −8.100 | −16.349 | 1.00 | 93.66 | L111 | C |
| ATOM | 207 | O | GLU | A | 37 | −22.925 | −7.672 | −15.515 | 1.00 | 91.34 | L111 | O |
| ATOM | 208 | CB | GLU | A | 37 | −22.071 | −10.552 | −16.819 | 1.00 | 90.67 | L111 | C |
| ATOM | 209 | CG | GLU | A | 37 | −23.205 | −11.512 | −16.511 | 1.00 | 93.38 | L111 | C |
| ATOM | 210 | CD | GLU | A | 37 | −22.929 | −12.372 | −15.290 | 1.00 | 96.55 | L111 | C |
| ATOM | 211 | OE1 | GLU | A | 37 | −22.044 | −13.254 | −15.365 | 1.00 | 91.81 | L111 | O |
| ATOM | 212 | OE2 | GLU | A | 37 | −23.600 | −12.163 | −14.256 | 1.00 | 99.15 | L111 | O |
| ATOM | 213 | N | PHE | A | 38 | −20.872 | −7.657 | −16.449 | 1.00 | 94.99 | L111 | N |

TABLE II-continued

| ATOM | 214 | CA | PHE | A | 38 | −20.335 | −6.614 | −15.575 | 1.00 | 95.14 | L111 | C |
| --- | --- | --- | --- | --- | --- | --- | --- | --- | --- | --- | --- | --- |
| ATOM | 215 | C | PHE | A | 38 | −20.928 | −5.243 | −15.907 | 1.00 | 93.32 | L111 | C |
| ATOM | 216 | O | PHE | A | 38 | −21.382 | −4.527 | −15.017 | 1.00 | 92.65 | L111 | O |
| ATOM | 217 | CB | PHE | A | 38 | −18.802 | −6.565 | −15.693 | 1.00 | 93.51 | L111 | C |
| ATOM | 218 | CG | PHE | A | 38 | −18.139 | −5.586 | −14.748 | 1.00 | 96.97 | L111 | C |
| ATOM | 219 | CD1 | PHE | A | 38 | −18.716 | −5.269 | −13.518 | 1.00 | 98.99 | L111 | C |
| ATOM | 220 | CD2 | PHE | A | 38 | −16.935 | −4.978 | −15.094 | 1.00 | 96.40 | L111 | C |
| ATOM | 221 | CE1 | PHE | A | 38 | −18.106 | −4.355 | −12.651 | 1.00 | 95.25 | L111 | C |
| ATOM | 222 | CE2 | PHE | A | 38 | −16.318 | −4.064 | −14.233 | 1.00 | 96.95 | L111 | C |
| ATOM | 223 | CZ | PHE | A | 38 | −16.905 | −3.754 | −13.010 | 1.00 | 92.93 | L111 | C |
| ATOM | 224 | N | CYS | A | 39 | −20.925 | −4.884 | −17.187 | 1.00 | 94.43 | L111 | N |
| ATOM | 225 | CA | CYS | A | 39 | −21.461 | −3.597 | −17.632 | 1.00 | 95.64 | L111 | C |
| ATOM | 226 | C | CYS | A | 39 | −22.840 | −3.321 | −17.044 | 1.00 | 96.32 | L111 | C |
| ATOM | 227 | O | CYS | A | 39 | −23.051 | −2.295 | −16.392 | 1.00 | 95.48 | L111 | O |
| ATOM | 228 | CB | CYS | A | 39 | −21.540 | −3.563 | −19.159 | 1.00 | 93.89 | L111 | C |
| ATOM | 229 | SG | CYS | A | 39 | −19.986 | −3.992 | −19.971 | 1.00 | 100.00 | L111 | S |
| ATOM | 230 | N | LYS | A | 40 | −23.774 | −4.239 | −17.279 | 1.00 | 96.81 | L111 | N |
| ATOM | 231 | CA | LYS | A | 40 | −25.133 | −4.101 | −16.768 | 1.00 | 96.22 | L111 | C |
| ATOM | 232 | C | LYS | A | 40 | −25.135 | −4.168 | −15.240 | 1.00 | 95.74 | L111 | C |
| ATOM | 233 | O | LYS | A | 40 | −25.823 | −3.389 | −14.576 | 1.00 | 96.26 | L111 | O |
| ATOM | 234 | CB | LYS | A | 40 | −26.029 | −5.205 | −17.339 | 1.00 | 95.66 | L111 | C |
| ATOM | 235 | CG | LYS | A | 40 | −25.956 | −5.344 | −18.855 | 1.00 | 97.68 | L111 | C |
| ATOM | 236 | CD | LYS | A | 40 | −27.132 | −6.148 | −19.401 | 1.00 | 95.99 | L111 | C |
| ATOM | 237 | CE | LYS | A | 40 | −26.947 | −6.475 | −20.880 | 1.00 | 94.18 | L111 | C |
| ATOM | 238 | NZ | LYS | A | 40 | −28.171 | −6.189 | −21.684 | 1.00 | 88.70 | L111 | N |
| ATOM | 239 | N | ARG | A | 41 | −24.356 | −5.097 | −14.688 | 1.00 | 92.53 | L111 | N |
| ATOM | 240 | CA | ARG | A | 41 | −24.262 | −5.260 | −13.239 | 1.00 | 89.97 | L111 | C |
| ATOM | 241 | C | ARG | A | 41 | −23.694 | −4.003 | −12.582 | 1.00 | 90.13 | L111 | C |
| ATOM | 242 | O | ARG | A | 41 | −24.306 | −3.433 | −11.679 | 1.00 | 91.63 | L111 | O |
| ATOM | 243 | CB | ARG | A | 41 | −23.375 | −6.459 | −12.900 | 1.00 | 85.72 | L111 | C |
| ATOM | 244 | CG | ARG | A | 41 | −24.143 | −7.710 | −12.526 | 1.00 | 85.51 | L111 | C |
| ATOM | 245 | CD | ARG | A | 41 | −23.330 | −8.594 | −11.595 | 1.00 | 90.22 | L111 | C |
| ATOM | 246 | NE | ARG | A | 41 | −22.610 | −9.641 | −12.318 | 1.00 | 88.90 | L111 | N |
| ATOM | 247 | CZ | ARG | A | 41 | −21.670 | −10.412 | −11.778 | 1.00 | 87.28 | L111 | C |
| ATOM | 248 | NH1 | ARG | A | 41 | −21.332 | −10.257 | −10.501 | 1.00 | 84.21 | L111 | N |
| ATOM | 249 | NH2 | ARG | A | 41 | −21.070 | −11.340 | −12.511 | 1.00 | 80.87 | L111 | N |
| ATOM | 250 | N | PHE | A | 42 | −22.517 | −3.583 | −13.037 | 1.00 | 87.95 | L111 | N |
| ATOM | 251 | CA | PHE | A | 42 | −21.865 | −2.393 | −12.509 | 1.00 | 82.17 | L111 | C |
| ATOM | 252 | C | PHE | A | 42 | −22.838 | −1.228 | −12.587 | 1.00 | 83.84 | L111 | C |
| ATOM | 253 | O | PHE | A | 42 | −23.215 | −0.648 | −11.566 | 1.00 | 84.64 | L111 | O |
| ATOM | 254 | CB | PHE | A | 42 | −20.608 | −2.074 | −13.325 | 1.00 | 78.71 | L111 | C |
| ATOM | 255 | CG | PHE | A | 42 | −19.934 | −0.792 | −12.925 | 1.00 | 83.84 | L111 | C |
| ATOM | 256 | CD1 | PHE | A | 42 | −19.109 | −0.745 | −11.802 | 1.00 | 84.59 | L111 | C |
| ATOM | 257 | CD2 | PHE | A | 42 | −20.132 | 0.373 | −13.662 | 1.00 | 83.65 | L111 | C |
| ATOM | 258 | CE1 | PHE | A | 42 | −18.490 | 0.444 | −11.417 | 1.00 | 79.21 | L111 | C |
| ATOM | 259 | CE2 | PHE | A | 42 | −19.518 | 1.567 | −13.289 | 1.00 | 77.97 | L111 | C |
| ATOM | 260 | CZ | PHE | A | 42 | −18.695 | 1.602 | −12.162 | 1.00 | 81.55 | L111 | C |
| ATOM | 261 | N | ASN | A | 43 | −23.253 | −0.906 | −13.808 | 1.00 | 85.30 | L111 | N |
| ATOM | 262 | CA | ASN | A | 43 | −24.181 | 0.191 | −14.053 | 1.00 | 86.52 | L111 | C |
| ATOM | 263 | C | ASN | A | 43 | −25.488 | 0.062 | −13.284 | 1.00 | 85.43 | L111 | C |
| ATOM | 264 | O | ASN | A | 43 | −26.281 | 1.000 | −13.240 | 1.00 | 85.51 | L111 | O |
| ATOM | 265 | CB | ASN | A | 43 | −24.476 | 0.296 | −15.548 | 1.00 | 86.27 | L111 | C |
| ATOM | 266 | CG | ASN | A | 43 | −23.265 | 0.716 | −16.344 | 1.00 | 92.38 | L111 | C |
| ATOM | 267 | OD1 | ASN | A | 43 | −22.347 | 1.340 | −15.811 | 1.00 | 96.74 | L111 | O |
| ATOM | 268 | ND2 | ASN | A | 43 | −23.249 | 0.374 | −17.627 | 1.00 | 99.06 | L111 | N |
| ATOM | 269 | N | ALA | A | 44 | −25.712 | −1.098 | −12.679 | 1.00 | 85.49 | L111 | N |
| ATOM | 270 | CA | ALA | A | 44 | −26.930 | −1.319 | −11.912 | 1.00 | 84.79 | L111 | C |
| ATOM | 271 | C | ALA | A | 44 | −26.900 | −0.515 | −10.618 | 1.00 | 85.21 | L111 | C |
| ATOM | 272 | O | ALA | A | 44 | −27.668 | 0.433 | −10.452 | 1.00 | 84.84 | L111 | O |
| ATOM | 273 | CB | ALA | A | 44 | −27.092 | −2.797 | −11.603 | 1.00 | 86.85 | L111 | C |
| ATOM | 274 | N | GLU | A | 45 | −26.005 | −0.893 | −9.708 | 1.00 | 85.98 | L111 | N |
| ATOM | 275 | CA | GLU | A | 45 | −25.885 | −0.211 | −8.420 | 1.00 | 90.10 | L111 | C |
| ATOM | 276 | C | GLU | A | 45 | −25.222 | 1.158 | −8.536 | 1.00 | 89.46 | L111 | C |
| ATOM | 277 | O | GLU | A | 45 | −25.388 | 2.010 | −7.661 | 1.00 | 88.02 | L111 | O |
| ATOM | 278 | CB | GLU | A | 45 | −25.103 | −1.076 | −7.427 | 1.00 | 89.91 | L111 | C |
| ATOM | 279 | CG | GLU | A | 45 | −23.812 | −1.641 | −7.983 | 1.00 | 93.26 | L111 | C |
| ATOM | 280 | CD | GLU | A | 45 | −23.917 | −3.118 | −8.293 | 1.00 | 95.55 | L111 | C |
| ATOM | 281 | OE1 | GLU | A | 45 | −24.558 | −3.844 | −7.503 | 1.00 | 94.41 | L111 | O |
| ATOM | 282 | OE2 | GLU | A | 45 | −23.360 | −3.551 | −9.326 | 1.00 | 98.04 | L111 | O |
| ATOM | 283 | N | THR | A | 46 | −24.463 | 1.369 | −9.608 | 1.00 | 89.00 | L111 | N |
| ATOM | 284 | CA | THR | A | 46 | −23.806 | 2.655 | −9.810 | 1.00 | 91.97 | L111 | C |
| ATOM | 285 | C | THR | A | 46 | −24.849 | 3.680 | −10.261 | 1.00 | 95.20 | L111 | C |
| ATOM | 286 | O | THR | A | 46 | −24.516 | 4.737 | −10.806 | 1.00 | 95.92 | L111 | O |
| ATOM | 287 | CB | THR | A | 46 | −22.681 | 2.560 | −10.865 | 1.00 | 90.40 | L111 | C |
| ATOM | 288 | OG1 | THR | A | 46 | −23.232 | 2.170 | −12.129 | 1.00 | 88.41 | L111 | O |
| ATOM | 289 | CG2 | THR | A | 46 | −21.634 | 1.545 | −10.429 | 1.00 | 87.67 | L111 | C |
| ATOM | 290 | N | ALA | A | 47 | −26.116 | 3.343 | −10.031 | 1.00 | 95.70 | L111 | N |
| ATOM | 291 | CA | ALA | A | 47 | −27.237 | 4.208 | −10.374 | 1.00 | 93.30 | L111 | C |
| ATOM | 292 | C | ALA | A | 47 | −27.464 | 5.142 | −9.191 | 1.00 | 95.59 | L111 | C |

TABLE II-continued

| ATOM | 293 | O | ALA | A | 47 | −27.681 | 6.341 | −9.367 | 1.00 | 97.14 | L111 | O |
|---|---|---|---|---|---|---|---|---|---|---|---|---|
| ATOM | 294 | CB | ALA | A | 47 | −28.488 | 3.373 | −10.634 | 1.00 | 85.02 | L111 | C |
| ATOM | 295 | N | ASP | A | 48 | −27.409 | 4.580 | −7.985 | 1.00 | 98.95 | L111 | N |
| ATOM | 296 | CA | ASP | A | 48 | −27.589 | 5.360 | −6.764 | 1.00 | 100.00 | L111 | C |
| ATOM | 297 | C | ASP | A | 48 | −26.667 | 6.582 | −6.823 | 1.00 | 100.00 | L111 | C |
| ATOM | 298 | O | ASP | A | 48 | −27.065 | 7.697 | −6.477 | 1.00 | 100.00 | L111 | O |
| ATOM | 299 | CB | ASP | A | 48 | −27.248 | 4.515 | −5.526 | 1.00 | 100.00 | L111 | C |
| ATOM | 300 | CG | ASP | A | 48 | −27.577 | 3.038 | −5.706 | 1.00 | 100.00 | L111 | C |
| ATOM | 301 | OD1 | ASP | A | 48 | −28.633 | 2.721 | −6.297 | 1.00 | 100.00 | L111 | O |
| ATOM | 302 | OD2 | ASP | A | 48 | −26.777 | 2.191 | −5.249 | 1.00 | 100.00 | L111 | O |
| ATOM | 303 | N | LYS | A | 49 | −25.434 | 6.356 | −7.270 | 1.00 | 100.00 | L111 | N |
| ATOM | 304 | CA | LYS | A | 49 | −24.440 | 7.419 | −7.394 | 1.00 | 99.10 | L111 | C |
| ATOM | 305 | C | LYS | A | 49 | −24.009 | 7.547 | −8.859 | 1.00 | 98.06 | L111 | C |
| ATOM | 306 | O | LYS | A | 49 | −23.106 | 6.842 | −9.318 | 1.00 | 95.26 | L111 | O |
| ATOM | 307 | CB | LYS | A | 49 | −23.226 | 7.105 | −6.512 | 1.00 | 94.97 | L111 | C |
| ATOM | 308 | CG | LYS | A | 49 | −23.561 | 6.908 | −5.037 | 1.00 | 92.57 | L111 | C |
| ATOM | 309 | CD | LYS | A | 49 | −22.956 | 5.619 | −4.498 | 1.00 | 93.51 | L111 | C |
| ATOM | 310 | CE | LYS | A | 49 | −21.611 | 5.873 | −3.827 | 1.00 | 94.40 | L111 | C |
| ATOM | 311 | NZ | LYS | A | 49 | −20.528 | 4.998 | −4.365 | 1.00 | 88.97 | L111 | N |
| ATOM | 312 | N | ALA | A | 50 | −24.661 | 8.450 | −9.587 | 1.00 | 95.33 | L111 | N |
| ATOM | 313 | CA | ALA | A | 50 | −24.360 | 8.653 | −10.999 | 1.00 | 93.02 | L111 | C |
| ATOM | 314 | C | ALA | A | 50 | −23.680 | 9.985 | −11.305 | 1.00 | 91.25 | L111 | C |
| ATOM | 315 | O | ALA | A | 50 | −23.898 | 10.986 | −10.619 | 1.00 | 90.14 | L111 | O |
| ATOM | 316 | CB | ALA | A | 50 | −25.636 | 8.522 | −11.819 | 1.00 | 96.51 | L111 | C |
| ATOM | 317 | N | GLY | A | 51 | −22.861 | 9.984 | −12.353 | 1.00 | 89.39 | L111 | N |
| ATOM | 318 | CA | GLY | A | 51 | −22.153 | 11.186 | −12.752 | 1.00 | 90.09 | L111 | C |
| ATOM | 319 | C | GLY | A | 51 | −20.709 | 11.173 | −12.289 | 1.00 | 91.40 | L111 | C |
| ATOM | 320 | O | GLY | A | 51 | −19.828 | 11.733 | −12.943 | 1.00 | 91.06 | L111 | O |
| ATOM | 321 | N | MET | A | 52 | −20.465 | 10.520 | −11.158 | 1.00 | 91.81 | L111 | N |
| ATOM | 322 | CA | MET | A | 52 | −19.125 | 10.440 | −10.591 | 1.00 | 88.05 | L111 | C |
| ATOM | 323 | C | MET | A | 52 | −18.347 | 9.218 | −11.062 | 1.00 | 84.95 | L111 | C |
| ATOM | 324 | O | MET | A | 52 | −18.927 | 8.206 | −11.455 | 1.00 | 85.89 | L111 | O |
| ATOM | 325 | CB | MET | A | 52 | −19.207 | 10.425 | −9.065 | 1.00 | 85.66 | L111 | C |
| ATOM | 326 | CG | MET | A | 52 | −20.358 | 11.236 | −8.503 | 1.00 | 86.98 | L111 | C |
| ATOM | 327 | SD | MET | A | 52 | −20.028 | 11.840 | −6.840 | 1.00 | 94.43 | L111 | S |
| ATOM | 328 | CE | MET | A | 52 | −18.414 | 12.577 | −7.060 | 1.00 | 92.32 | L111 | C |
| ATOM | 329 | N | ILE | A | 53 | −17.025 | 9.330 | −11.021 | 1.00 | 80.70 | L111 | N |
| ATOM | 330 | CA | ILE | A | 53 | −16.145 | 8.242 | −11.415 | 1.00 | 76.40 | L111 | C |
| ATOM | 331 | C | ILE | A | 53 | −15.856 | 7.437 | −10.157 | 1.00 | 76.01 | L111 | C |
| ATOM | 332 | O | ILE | A | 53 | −15.214 | 7.937 | −9.238 | 1.00 | 80.34 | L111 | O |
| ATOM | 333 | CB | ILE | A | 53 | −14.815 | 8.781 | −11.987 | 1.00 | 72.67 | L111 | C |
| ATOM | 334 | CG1 | ILE | A | 53 | −15.035 | 9.279 | −13.421 | 1.00 | 73.66 | L111 | C |
| ATOM | 335 | CG2 | ILE | A | 53 | −13.735 | 7.706 | −11.897 | 1.00 | 69.87 | L111 | C |
| ATOM | 336 | CD1 | ILE | A | 53 | −14.073 | 8.712 | −14.461 | 1.00 | 67.81 | L111 | C |
| ATOM | 337 | N | LEU | A | 54 | −16.337 | 6.199 | −10.110 | 1.00 | 77.62 | L111 | N |
| ATOM | 338 | CA | LEU | A | 54 | −16.123 | 5.355 | −8.940 | 1.00 | 75.31 | L111 | C |
| ATOM | 339 | C | LEU | A | 54 | −15.263 | 4.129 | −9.242 | 1.00 | 73.26 | L111 | C |
| ATOM | 340 | O | LEU | A | 54 | −15.468 | 3.448 | −10.248 | 1.00 | 69.71 | L111 | O |
| ATOM | 341 | CB | LEU | A | 54 | −17.471 | 4.913 | −8.354 | 1.00 | 74.18 | L111 | C |
| ATOM | 342 | CG | LEU | A | 54 | −18.446 | 4.186 | −9.283 | 1.00 | 76.71 | L111 | C |
| ATOM | 343 | CD1 | LEU | A | 54 | −19.398 | 3.339 | −8.456 | 1.00 | 78.50 | L111 | C |
| ATOM | 344 | CD2 | LEU | A | 54 | −19.221 | 5.196 | −10.112 | 1.00 | 77.50 | L111 | C |
| ATOM | 345 | N | PRO | A | 55 | −14.277 | 3.841 | −8.368 | 1.00 | 73.50 | L111 | N |
| ATOM | 346 | CA | PRO | A | 55 | −13.379 | 2.694 | −8.531 | 1.00 | 73.63 | L111 | C |
| ATOM | 347 | C | PRO | A | 55 | −13.998 | 1.397 | −8.010 | 1.00 | 72.99 | L111 | C |
| ATOM | 348 | O | PRO | A | 55 | −14.516 | 1.349 | −6.895 | 1.00 | 76.87 | L111 | O |
| ATOM | 349 | CB | PRO | A | 55 | −12.139 | 3.096 | −7.736 | 1.00 | 69.02 | L111 | C |
| ATOM | 350 | CG | PRO | A | 55 | −12.654 | 4.000 | −6.669 | 1.00 | 66.68 | L111 | C |
| ATOM | 351 | CD | PRO | A | 55 | −13.950 | 4.617 | −7.157 | 1.00 | 72.43 | L111 | C |
| ATOM | 352 | N | VAL | A | 56 | −13.945 | 0.349 | −8.825 | 1.00 | 70.25 | L111 | N |
| ATOM | 353 | CA | VAL | A | 56 | −14.496 | −0.942 | −8.440 | 1.00 | 70.19 | L111 | C |
| ATOM | 354 | C | VAL | A | 56 | −13.399 | −1.999 | −8.486 | 1.00 | 70.07 | L111 | C |
| ATOM | 355 | O | VAL | A | 56 | −12.502 | −1.937 | −9.329 | 1.00 | 67.23 | L111 | O |
| ATOM | 356 | CB | VAL | A | 56 | −15.654 | −1.361 | −9.384 | 1.00 | 67.10 | L111 | C |
| ATOM | 357 | CG1 | VAL | A | 56 | −15.246 | −1.161 | −10.828 | 1.00 | 67.75 | L111 | C |
| ATOM | 358 | CG2 | VAL | A | 56 | −16.034 | −2.808 | −9.143 | 1.00 | 62.26 | L111 | C |
| ATOM | 359 | N | VAL | A | 57 | −13.459 | −2.956 | −7.565 | 1.00 | 72.09 | L111 | N |
| ATOM | 360 | CA | VAL | A | 57 | −12.472 | −4.027 | −7.527 | 1.00 | 73.93 | L111 | C |
| ATOM | 361 | C | VAL | A | 57 | −13.121 | −5.341 | −7.934 | 1.00 | 76.94 | L111 | C |
| ATOM | 362 | O | VAL | A | 57 | −13.788 | −6.001 | −7.131 | 1.00 | 78.31 | L111 | O |
| ATOM | 363 | CB | VAL | A | 57 | −11.849 | −4.189 | −6.127 | 1.00 | 68.90 | L111 | C |
| ATOM | 364 | CG1 | VAL | A | 57 | −10.940 | −5.410 | −6.104 | 1.00 | 66.82 | L111 | C |
| ATOM | 365 | CG2 | VAL | A | 57 | −11.058 | −2.948 | −5.767 | 1.00 | 67.57 | L111 | C |
| ATOM | 366 | N | ILE | A | 58 | −12.923 | −5.702 | −9.197 | 1.00 | 79.04 | L111 | N |
| ATOM | 367 | CA | ILE | A | 58 | −13.467 | −6.930 | −9.756 | 1.00 | 77.59 | L111 | C |
| ATOM | 368 | C | ILE | A | 58 | −12.611 | −8.115 | −9.319 | 1.00 | 77.59 | L111 | C |
| ATOM | 369 | O | ILE | A | 58 | −11.383 | −8.023 | −9.262 | 1.00 | 73.20 | L111 | O |
| ATOM | 370 | CB | ILE | A | 58 | −13.490 | −6.863 | −11.307 | 1.00 | 76.77 | L111 | C |
| ATOM | 371 | CG1 | ILE | A | 58 | −14.689 | −6.033 | −11.773 | 1.00 | 79.34 | L111 | C |

TABLE II-continued

| ATOM | 372 | CG2 | ILE | A | 58 | −13.526 | −8.267 | −11.904 | 1.00 | 73.40 | L111 | C |
|---|---|---|---|---|---|---|---|---|---|---|---|---|
| ATOM | 373 | CD1 | ILE | A | 58 | −15.970 | −6.832 | −11.963 | 1.00 | 82.47 | L111 | C |
| ATOM | 374 | N | THR | A | 59 | −13.270 | −9.224 | −8.999 | 1.00 | 82.32 | L111 | N |
| ATOM | 375 | CA | THR | A | 59 | −12.581 | −10.444 | −8.589 | 1.00 | 82.77 | L111 | C |
| ATOM | 376 | C | THR | A | 59 | −13.114 | −11.602 | −9.430 | 1.00 | 83.16 | L111 | C |
| ATOM | 377 | O | THR | A | 59 | −14.312 | −11.888 | −9.417 | 1.00 | 78.62 | L111 | O |
| ATOM | 378 | CB | THR | A | 59 | −12.815 | −10.761 | −7.091 | 1.00 | 81.80 | L111 | C |
| ATOM | 379 | OG1 | THR | A | 59 | −12.872 | −9.539 | −6.341 | 1.00 | 79.00 | L111 | O |
| ATOM | 380 | CG2 | THR | A | 59 | −11.682 | −11.629 | −6.552 | 1.00 | 74.95 | L111 | C |
| ATOM | 381 | N | VAL | A | 60 | −12.221 | −12.256 | −10.168 | 1.00 | 84.63 | L111 | N |
| ATOM | 382 | CA | VAL | A | 60 | −12.603 | −13.377 | −11.022 | 1.00 | 85.45 | L111 | C |
| ATOM | 383 | C | VAL | A | 60 | −12.140 | −14.723 | −10.466 | 1.00 | 85.80 | L111 | C |
| ATOM | 384 | O | VAL | A | 60 | −10.947 | −14.934 | −10.228 | 1.00 | 83.46 | L111 | O |
| ATOM | 385 | CB | VAL | A | 60 | −12.030 | −13.211 | −12.445 | 1.00 | 85.69 | L111 | C |
| ATOM | 386 | CG1 | VAL | A | 60 | −12.984 | −12.383 | −13.295 | 1.00 | 80.95 | L111 | C |
| ATOM | 387 | CG2 | VAL | A | 60 | −10.653 | −12.563 | −12.380 | 1.00 | 84.62 | L111 | C |
| ATOM | 388 | N | TYR | A | 61 | −13.098 | −15.629 | −10.272 | 1.00 | 86.41 | L111 | N |
| ATOM | 389 | CA | TYR | A | 61 | −12.827 | −16.965 | −9.747 | 1.00 | 88.03 | L111 | C |
| ATOM | 390 | C | TYR | A | 61 | −12.459 | −17.915 | −10.877 | 1.00 | 89.54 | L111 | C |
| ATOM | 391 | O | TYR | A | 61 | −12.885 | −17.721 | −12.015 | 1.00 | 93.25 | L111 | O |
| ATOM | 392 | CB | TYR | A | 61 | −14.056 | −17.486 | −8.998 | 1.00 | 87.73 | L111 | C |
| ATOM | 393 | CG | TYR | A | 61 | −14.589 | −16.487 | −7.999 | 1.00 | 91.62 | L111 | C |
| ATOM | 394 | CD1 | TYR | A | 61 | −13.873 | −16.187 | −6.837 | 1.00 | 89.76 | L111 | C |
| ATOM | 395 | CD2 | TYR | A | 61 | −15.772 | −15.788 | −8.244 | 1.00 | 89.94 | L111 | C |
| ATOM | 396 | CE1 | TYR | A | 61 | −14.316 | −15.214 | −5.947 | 1.00 | 89.76 | L111 | C |
| ATOM | 397 | CE2 | TYR | A | 61 | −16.225 | −14.810 | −7.358 | 1.00 | 92.12 | L111 | C |
| ATOM | 398 | CZ | TYR | A | 61 | −15.489 | −14.526 | −6.214 | 1.00 | 92.07 | L111 | C |
| ATOM | 399 | OH | TYR | A | 61 | −15.910 | −13.543 | −5.347 | 1.00 | 94.51 | L111 | O |
| ATOM | 400 | N | GLU | A | 62 | −11.666 | −18.936 | −10.557 | 1.00 | 89.59 | L111 | N |
| ATOM | 401 | CA | GLU | A | 62 | −11.218 | −19.921 | −11.541 | 1.00 | 86.30 | L111 | C |
| ATOM | 402 | C | GLU | A | 62 | −12.248 | −20.245 | −12.626 | 1.00 | 84.38 | L111 | C |
| ATOM | 403 | O | GLU | A | 62 | −11.886 | −20.480 | −13.779 | 1.00 | 83.12 | L111 | O |
| ATOM | 404 | CB | GLU | A | 62 | −10.798 | −21.217 | −10.835 | 1.00 | 86.59 | L111 | C |
| ATOM | 405 | CG | GLU | A | 62 | −11.842 | −21.781 | −9.872 | 1.00 | 98.78 | L111 | C |
| ATOM | 406 | CD | GLU | A | 62 | −12.709 | −22.865 | −10.502 | 1.00 | 100.00 | L111 | C |
| ATOM | 407 | OE1 | GLU | A | 62 | −12.149 | −23.866 | −11.007 | 1.00 | 100.00 | L111 | O |
| ATOM | 408 | OE2 | GLU | A | 62 | −13.952 | −22.711 | −10.490 | 1.00 | 100.00 | L111 | O |
| ATOM | 409 | N | ASP | A | 63 | −13.527 | −20.246 | −12.261 | 1.00 | 83.04 | L111 | N |
| ATOM | 410 | CA | ASP | A | 63 | −14.593 | −20.554 | −13.210 | 1.00 | 83.65 | L111 | C |
| ATOM | 411 | C | ASP | A | 63 | −15.045 | −19.360 | −14.066 | 1.00 | 89.63 | L111 | C |
| ATOM | 412 | O | ASP | A | 63 | −16.153 | −19.364 | −14.609 | 1.00 | 90.46 | L111 | O |
| ATOM | 413 | CB | ASP | A | 63 | −15.795 | −21.132 | −12.461 | 1.00 | 80.07 | L111 | C |
| ATOM | 414 | CG | ASP | A | 63 | −16.738 | −20.061 | −11.968 | 1.00 | 79.27 | L111 | C |
| ATOM | 415 | OD1 | ASP | A | 63 | −16.275 | −19.146 | −11.254 | 1.00 | 85.70 | L111 | O |
| ATOM | 416 | OD2 | ASP | A | 63 | −17.941 | −20.130 | −12.298 | 1.00 | 76.37 | L111 | O |
| ATOM | 417 | N | LYS | A | 64 | −14.188 | −18.347 | −14.185 | 1.00 | 91.01 | L111 | N |
| ATOM | 418 | CA | LYS | A | 64 | −14.481 | −17.150 | −14.976 | 1.00 | 89.76 | L111 | C |
| ATOM | 419 | C | LYS | A | 64 | −15.585 | −16.261 | −14.398 | 1.00 | 89.42 | L111 | C |
| ATOM | 420 | O | LYS | A | 64 | −15.809 | −15.149 | −14.882 | 1.00 | 91.74 | L111 | O |
| ATOM | 421 | CB | LYS | A | 64 | −14.833 | −17.540 | −16.418 | 1.00 | 92.48 | L111 | C |
| ATOM | 422 | CG | LYS | A | 64 | −13.737 | −17.237 | −17.436 | 1.00 | 92.64 | L111 | C |
| ATOM | 423 | CD | LYS | A | 64 | −12.362 | −17.682 | −16.936 | 1.00 | 89.88 | L111 | C |
| ATOM | 424 | CE | LYS | A | 64 | −11.520 | −18.269 | −18.060 | 1.00 | 87.02 | L111 | C |
| ATOM | 425 | NZ | LYS | A | 64 | −12.331 | −18.548 | −19.280 | 1.00 | 89.34 | L111 | N |
| ATOM | 426 | N | SER | A | 65 | −16.280 | −16.748 | −13.373 | 1.00 | 88.30 | L111 | N |
| ATOM | 427 | CA | SER | A | 65 | −17.336 | −15.966 | −12.738 | 1.00 | 87.60 | L111 | C |
| ATOM | 428 | C | SER | A | 65 | −16.668 | −14.827 | −11.979 | 1.00 | 90.25 | L111 | C |
| ATOM | 429 | O | SER | A | 65 | −15.443 | −14.800 | −11.857 | 1.00 | 94.42 | L111 | O |
| ATOM | 430 | CB | SER | A | 65 | −18.138 | −16.830 | −11.766 | 1.00 | 83.90 | L111 | C |
| ATOM | 431 | OG | SER | A | 65 | −19.255 | −16.115 | −11.265 | 1.00 | 86.12 | L111 | O |
| ATOM | 432 | N | PHE | A | 66 | −17.459 | −13.895 | −11.456 | 1.00 | 89.68 | L111 | N |
| ATOM | 433 | CA | PHE | A | 66 | −16.872 | −12.769 | −10.737 | 1.00 | 86.65 | L111 | C |
| ATOM | 434 | C | PHE | A | 66 | −17.824 | −11.963 | −9.852 | 1.00 | 84.85 | L111 | C |
| ATOM | 435 | O | PHE | A | 66 | −19.049 | −12.065 | −9.956 | 1.00 | 84.96 | L111 | O |
| ATOM | 436 | CB | PHE | A | 66 | −16.207 | −11.819 | −11.740 | 1.00 | 83.79 | L111 | C |
| ATOM | 437 | CG | PHE | A | 66 | −17.166 | −11.224 | −12.736 | 1.00 | 84.15 | L111 | C |
| ATOM | 438 | CD1 | PHE | A | 66 | −17.849 | −10.044 | −12.446 | 1.00 | 84.23 | L111 | C |
| ATOM | 439 | CD2 | PHE | A | 66 | −17.402 | −11.851 | −13.955 | 1.00 | 85.47 | L111 | C |
| ATOM | 440 | CE1 | PHE | A | 66 | −18.756 | −9.496 | −13.358 | 1.00 | 83.49 | L111 | C |
| ATOM | 441 | CE2 | PHE | A | 66 | −18.307 | −11.312 | −14.875 | 1.00 | 85.83 | L111 | C |
| ATOM | 442 | CZ | PHE | A | 66 | −18.985 | −10.132 | −14.574 | 1.00 | 81.40 | L111 | C |
| ATOM | 443 | N | THR | A | 67 | −17.223 | −11.166 | −8.975 | 1.00 | 83.77 | L111 | N |
| ATOM | 444 | CA | THR | A | 67 | −17.937 | −10.279 | −8.065 | 1.00 | 79.66 | L111 | C |
| ATOM | 445 | C | THR | A | 67 | −17.102 | −9.009 | −8.062 | 1.00 | 79.21 | L111 | C |
| ATOM | 446 | O | THR | A | 67 | −16.005 | −8.985 | −8.623 | 1.00 | 78.86 | L111 | O |
| ATOM | 447 | CB | THR | A | 67 | −17.990 | −10.835 | −6.630 | 1.00 | 77.12 | L111 | C |
| ATOM | 448 | OG1 | THR | A | 67 | −16.660 | −11.101 | −6.169 | 1.00 | 71.17 | L111 | O |
| ATOM | 449 | CG2 | THR | A | 67 | −18.807 | −12.112 | −6.585 | 1.00 | 76.03 | L111 | C |
| ATOM | 450 | N | PHE | A | 68 | −17.603 | −7.954 | −7.439 | 1.00 | 77.92 | L111 | N |

TABLE II-continued

| | | | | | | | | | | | |
|---|---|---|---|---|---|---|---|---|---|---|---|
| ATOM | 451 | CA | PHE | A | 68 | −16.850 | −6.711 | −7.409 | 1.00 | 76.33 | L111 | C |
| ATOM | 452 | C | PHE | A | 68 | −17.396 | −5.750 | −6.379 | 1.00 | 74.52 | L111 | C |
| ATOM | 453 | O | PHE | A | 68 | −18.609 | −5.594 | −6.241 | 1.00 | 74.74 | L111 | O |
| ATOM | 454 | CB | PHE | A | 68 | −16.871 | −6.046 | −8.789 | 1.00 | 79.76 | L111 | C |
| ATOM | 455 | CG | PHE | A | 68 | −18.255 | −5.772 | −9.311 | 1.00 | 78.43 | L111 | C |
| ATOM | 456 | CD1 | PHE | A | 68 | −18.994 | −6.781 | −9.922 | 1.00 | 77.56 | L111 | C |
| ATOM | 457 | CD2 | PHE | A | 68 | −18.821 | −4.506 | −9.193 | 1.00 | 77.06 | L111 | C |
| ATOM | 458 | CE1 | PHE | A | 68 | −20.276 | −6.532 | −10.409 | 1.00 | 79.65 | L111 | C |
| ATOM | 459 | CE2 | PHE | A | 68 | −20.103 | −4.247 | −9.677 | 1.00 | 76.90 | L111 | C |
| ATOM | 460 | CZ | PHE | A | 68 | −20.831 | −5.263 | −10.285 | 1.00 | 77.56 | L111 | C |
| ATOM | 461 | N | ILE | A | 69 | −16.491 | −5.105 | −5.656 | 1.00 | 73.94 | L111 | N |
| ATOM | 462 | CA | ILE | A | 69 | −16.885 | −4.142 | −4.644 | 1.00 | 70.90 | L111 | C |
| ATOM | 463 | C | ILE | A | 69 | −16.752 | −2.736 | −5.218 | 1.00 | 71.09 | L111 | C |
| ATOM | 464 | O | ILE | A | 69 | −15.773 | −2.420 | −5.901 | 1.00 | 68.28 | L111 | O |
| ATOM | 465 | CB | ILE | A | 69 | −16.010 | −4.273 | −3.377 | 1.00 | 65.36 | L111 | C |
| ATOM | 466 | CG1 | ILE | A | 69 | −14.550 | −3.966 | −3.709 | 1.00 | 63.63 | L111 | C |
| ATOM | 467 | CG2 | ILE | A | 69 | −16.119 | −5.682 | −2.820 | 1.00 | 61.98 | L111 | C |
| ATOM | 468 | CD1 | ILE | A | 69 | −13.850 | −3.146 | −2.650 | 1.00 | 54.75 | L111 | C |
| ATOM | 469 | N | ILE | A | 70 | −17.753 | −1.903 | −4.962 | 1.00 | 68.20 | L111 | N |
| ATOM | 470 | CA | ILE | A | 70 | −17.740 | −0.530 | −5.443 | 1.00 | 65.88 | L111 | C |
| ATOM | 471 | C | ILE | A | 70 | −17.350 | 0.388 | −4.283 | 1.00 | 61.84 | L111 | C |
| ATOM | 472 | O | ILE | A | 70 | −17.975 | 0.367 | −3.222 | 1.00 | 60.58 | L111 | O |
| ATOM | 473 | CB | ILE | A | 70 | −19.126 | −0.135 | −6.022 | 1.00 | 66.46 | L111 | C |
| ATOM | 474 | CG1 | ILE | A | 70 | −19.030 | −0.026 | −7.545 | 1.00 | 67.64 | L111 | C |
| ATOM | 475 | CG2 | ILE | A | 70 | −19.608 | 1.187 | −5.432 | 1.00 | 69.87 | L111 | C |
| ATOM | 476 | CD1 | ILE | A | 70 | −19.695 | −1.163 | −8.283 | 1.00 | 63.00 | L111 | C |
| ATOM | 477 | N | LYS | A | 71 | −16.301 | 1.179 | −4.489 | 1.00 | 55.49 | L111 | N |
| ATOM | 478 | CA | LYS | A | 71 | −15.820 | 2.092 | −3.463 | 1.00 | 49.56 | L111 | C |
| ATOM | 479 | C | LYS | A | 71 | −16.181 | 3.531 | −3.773 | 1.00 | 51.89 | L111 | C |
| ATOM | 480 | O | LYS | A | 71 | −16.814 | 3.826 | −4.787 | 1.00 | 58.09 | L111 | O |
| ATOM | 481 | CB | LYS | A | 71 | −14.301 | 1.996 | −3.325 | 1.00 | 41.23 | L111 | C |
| ATOM | 482 | CG | LYS | A | 71 | −13.736 | 0.617 | −3.549 | 1.00 | 45.62 | L111 | C |
| ATOM | 483 | CD | LYS | A | 71 | −12.280 | 0.573 | −3.134 | 1.00 | 47.82 | L111 | C |
| ATOM | 484 | CE | LYS | A | 71 | −12.066 | −0.371 | −1.962 | 1.00 | 53.59 | L111 | C |
| ATOM | 485 | NZ | LYS | A | 71 | −10.785 | −1.130 | −2.085 | 1.00 | 54.56 | L111 | N |
| ATOM | 486 | N | THR | A | 72 | −15.763 | 4.424 | −2.883 | 1.00 | 51.64 | L111 | N |
| ATOM | 487 | CA | THR | A | 72 | −16.005 | 5.851 | −3.034 | 1.00 | 48.54 | L111 | C |
| ATOM | 488 | C | THR | A | 72 | −15.040 | 6.390 | −4.088 | 1.00 | 47.19 | L111 | C |
| ATOM | 489 | O | THR | A | 72 | −13.919 | 5.896 | −4.227 | 1.00 | 51.43 | L111 | O |
| ATOM | 490 | CB | THR | A | 72 | −15.758 | 6.584 | −1.711 | 1.00 | 49.44 | L111 | C |
| ATOM | 491 | OG1 | THR | A | 72 | −14.374 | 6.469 | −1.356 | 1.00 | 56.76 | L111 | O |
| ATOM | 492 | CG2 | THR | A | 72 | −16.598 | 5.975 | −0.602 | 1.00 | 49.50 | L111 | C |
| ATOM | 493 | N | PRO | A | 73 | −15.463 | 7.409 | −4.850 | 1.00 | 43.35 | L111 | N |
| ATOM | 494 | CA | PRO | A | 73 | −14.603 | 7.989 | −5.890 | 1.00 | 39.98 | L111 | C |
| ATOM | 495 | C | PRO | A | 73 | −13.260 | 8.487 | −5.357 | 1.00 | 38.40 | L111 | C |
| ATOM | 496 | O | PRO | A | 73 | −13.153 | 8.908 | −4.206 | 1.00 | 41.41 | L111 | O |
| ATOM | 497 | CB | PRO | A | 73 | −15.449 | 9.117 | −6.483 | 1.00 | 40.56 | L111 | C |
| ATOM | 498 | CG | PRO | A | 73 | −16.536 | 9.360 | −5.490 | 1.00 | 44.56 | L111 | C |
| ATOM | 499 | CD | PRO | A | 73 | −16.775 | 8.071 | −4.781 | 1.00 | 42.40 | L111 | C |
| ATOM | 500 | N | PRO | A | 74 | −12.217 | 8.453 | −6.198 | 1.00 | 36.48 | L111 | N |
| ATOM | 501 | CA | PRO | A | 74 | −10.882 | 8.904 | −5.788 | 1.00 | 35.21 | L111 | C |
| ATOM | 502 | C | PRO | A | 74 | −10.881 | 10.296 | −5.162 | 1.00 | 32.68 | L111 | C |
| ATOM | 503 | O | PRO | A | 74 | −11.778 | 11.102 | −5.406 | 1.00 | 30.40 | L111 | O |
| ATOM | 504 | CB | PRO | A | 74 | −10.066 | 8.856 | −7.082 | 1.00 | 37.87 | L111 | C |
| ATOM | 505 | CG | PRO | A | 74 | −10.787 | 7.880 | −7.956 | 1.00 | 31.11 | L111 | C |
| ATOM | 506 | CD | PRO | A | 74 | −12.244 | 8.000 | −7.601 | 1.00 | 35.28 | L111 | C |
| ATOM | 507 | N | ALA | A | 75 | −9.868 | 10.570 | −4.348 | 1.00 | 31.58 | L111 | N |
| ATOM | 508 | CA | ALA | A | 75 | −9.763 | 11.862 | −3.698 | 1.00 | 29.59 | L111 | C |
| ATOM | 509 | C | ALA | A | 75 | −9.517 | 12.901 | −4.774 | 1.00 | 34.00 | L111 | C |
| ATOM | 510 | O | ALA | A | 75 | −10.210 | 13.915 | −4.837 | 1.00 | 37.52 | L111 | O |
| ATOM | 511 | CB | ALA | A | 75 | −8.618 | 11.856 | −2.694 | 1.00 | 34.28 | L111 | C |
| ATOM | 512 | N | SER | A | 76 | −8.532 | 12.638 | −5.627 | 1.00 | 30.09 | L111 | N |
| ATOM | 513 | CA | SER | A | 76 | −8.211 | 13.561 | −6.702 | 1.00 | 31.31 | L111 | C |
| ATOM | 514 | C | SER | A | 76 | −9.467 | 13.929 | −7.483 | 1.00 | 31.25 | L111 | C |
| ATOM | 515 | O | SER | A | 76 | −9.661 | 15.091 | −7.825 | 1.00 | 36.66 | L111 | O |
| ATOM | 516 | CB | SER | A | 76 | −7.169 | 12.951 | −7.643 | 1.00 | 32.45 | L111 | C |
| ATOM | 517 | OG | SER | A | 76 | −7.473 | 11.608 | −7.957 | 1.00 | 36.38 | L111 | O |
| ATOM | 518 | N | PHE | A | 77 | −10.323 | 12.946 | −7.752 | 1.00 | 31.85 | L111 | N |
| ATOM | 519 | CA | PHE | A | 77 | −11.564 | 13.194 | −8.489 | 1.00 | 34.16 | L111 | C |
| ATOM | 520 | C | PHE | A | 77 | −12.502 | 14.125 | −7.734 | 1.00 | 38.37 | L111 | C |
| ATOM | 521 | O | PHE | A | 77 | −12.919 | 15.160 | −8.251 | 1.00 | 41.67 | L111 | O |
| ATOM | 522 | CB | PHE | A | 77 | −12.307 | 11.894 | −8.769 | 1.00 | 33.17 | L111 | C |
| ATOM | 523 | CG | PHE | A | 77 | −13.623 | 12.095 | −9.468 | 1.00 | 40.76 | L111 | C |
| ATOM | 524 | CD1 | PHE | A | 77 | −13.667 | 12.357 | −10.837 | 1.00 | 47.11 | L111 | C |
| ATOM | 525 | CD2 | PHE | A | 77 | −14.818 | 12.034 | −8.761 | 1.00 | 42.42 | L111 | C |
| ATOM | 526 | CE1 | PHE | A | 77 | −14.880 | 12.554 | −11.492 | 1.00 | 38.82 | L111 | C |
| ATOM | 527 | CE2 | PHE | A | 77 | −16.041 | 12.230 | −9.409 | 1.00 | 42.68 | L111 | C |
| ATOM | 528 | CZ | PHE | A | 77 | −16.069 | 12.491 | −10.777 | 1.00 | 38.85 | L111 | C |
| ATOM | 529 | N | LEU | A | 78 | −12.852 | 13.743 | −6.514 | 1.00 | 39.27 | L111 | N |

TABLE II-continued

| ATOM | 530 | CA | LEU | A | 78 | −13.732 | 14.568 | −5.703 | 1.00 | 42.01 | L111 | C |
| --- | --- | --- | --- | --- | --- | --- | --- | --- | --- | --- | --- | --- |
| ATOM | 531 | C | LEU | A | 78 | −13.162 | 15.986 | −5.625 | 1.00 | 44.64 | L111 | C |
| ATOM | 532 | O | LEU | A | 78 | −13.892 | 16.967 | −5.777 | 1.00 | 45.86 | L111 | O |
| ATOM | 533 | CB | LEU | A | 78 | −13.861 | 13.966 | −4.303 | 1.00 | 42.80 | L111 | C |
| ATOM | 534 | CG | LEU | A | 78 | −14.640 | 12.646 | −4.258 | 1.00 | 47.12 | L111 | C |
| ATOM | 535 | CD1 | LEU | A | 78 | −14.485 | 11.973 | −2.899 | 1.00 | 38.14 | L111 | C |
| ATOM | 536 | CD2 | LEU | A | 78 | −16.108 | 12.925 | −4.548 | 1.00 | 50.88 | L111 | C |
| ATOM | 537 | N | LEU | A | 79 | −11.851 | 16.081 | −5.406 | 1.00 | 43.07 | L111 | N |
| ATOM | 538 | CA | LEU | A | 79 | −11.164 | 17.367 | −5.309 | 1.00 | 34.91 | L111 | C |
| ATOM | 539 | C | LEU | A | 79 | −11.352 | 18.182 | −6.580 | 1.00 | 35.68 | L111 | C |
| ATOM | 540 | O | LEU | A | 79 | −11.701 | 19.355 | −6.522 | 1.00 | 36.29 | L111 | O |
| ATOM | 541 | CB | LEU | A | 79 | −9.676 | 17.150 | −5.056 | 1.00 | 32.85 | L111 | C |
| ATOM | 542 | CG | LEU | A | 79 | −9.326 | 16.833 | −3.603 | 1.00 | 29.72 | L111 | C |
| ATOM | 543 | CD1 | LEU | A | 79 | −7.848 | 16.529 | −3.480 | 1.00 | 33.33 | L111 | C |
| ATOM | 544 | CD2 | LEU | A | 79 | −9.703 | 18.013 | −2.730 | 1.00 | 29.46 | L111 | C |
| ATOM | 545 | N | LYS | A | 80 | −11.113 | 17.558 | −7.727 | 1.00 | 39.06 | L111 | N |
| ATOM | 546 | CA | LYS | A | 80 | −11.292 | 18.235 | −9.006 | 1.00 | 38.30 | L111 | C |
| ATOM | 547 | C | LYS | A | 80 | −12.692 | 18.832 | −8.990 | 1.00 | 39.56 | L111 | C |
| ATOM | 548 | O | LYS | A | 80 | −12.872 | 20.036 | −9.144 | 1.00 | 44.34 | L111 | O |
| ATOM | 549 | CB | LYS | A | 80 | −11.191 | 17.239 | −10.163 | 1.00 | 32.02 | L111 | C |
| ATOM | 550 | CG | LYS | A | 80 | −9.805 | 17.066 | −10.750 | 1.00 | 32.26 | L111 | C |
| ATOM | 551 | CD | LYS | A | 80 | −9.758 | 15.821 | −11.628 | 1.00 | 37.75 | L111 | C |
| ATOM | 552 | CE | LYS | A | 80 | −8.410 | 15.660 | −12.313 | 1.00 | 49.50 | L111 | C |
| ATOM | 553 | NZ | LYS | A | 80 | −8.046 | 14.224 | −12.490 | 1.00 | 54.98 | L111 | N |
| ATOM | 554 | N | LYS | A | 81 | −13.681 | 17.969 | −8.789 | 1.00 | 39.53 | L111 | N |
| ATOM | 555 | CA | LYS | A | 81 | −15.070 | 18.386 | −8.754 | 1.00 | 38.23 | L111 | C |
| ATOM | 556 | C | LYS | A | 81 | −15.268 | 19.576 | −7.832 | 1.00 | 41.10 | L111 | C |
| ATOM | 557 | O | LYS | A | 81 | −15.797 | 20.603 | −8.242 | 1.00 | 50.63 | L111 | O |
| ATOM | 558 | CB | LYS | A | 81 | −15.949 | 17.230 | −8.290 | 1.00 | 40.15 | L111 | C |
| ATOM | 559 | CG | LYS | A | 81 | −17.433 | 17.521 | −8.367 | 1.00 | 56.64 | L111 | C |
| ATOM | 560 | CD | LYS | A | 81 | −18.209 | 16.317 | −8.878 | 1.00 | 68.16 | L111 | C |
| ATOM | 561 | CE | LYS | A | 81 | −19.133 | 15.761 | −7.799 | 1.00 | 76.64 | L111 | C |
| ATOM | 562 | NZ | LYS | A | 81 | −18.420 | 15.535 | −6.502 | 1.00 | 78.09 | L111 | N |
| ATOM | 563 | N | ALA | A | 82 | −14.836 | 19.435 | −6.585 | 1.00 | 45.28 | L111 | N |
| ATOM | 564 | CA | ALA | A | 82 | −14.976 | 20.500 | −5.598 | 1.00 | 43.40 | L111 | C |
| ATOM | 565 | C | ALA | A | 82 | −14.384 | 21.832 | −6.056 | 1.00 | 49.00 | L111 | C |
| ATOM | 566 | O | ALA | A | 82 | −15.003 | 22.884 | −5.892 | 1.00 | 53.59 | L111 | O |
| ATOM | 567 | CB | ALA | A | 82 | −14.330 | 20.076 | −4.290 | 1.00 | 42.16 | L111 | C |
| ATOM | 568 | N | ALA | A | 83 | −13.183 | 21.790 | −6.621 | 1.00 | 48.31 | L111 | N |
| ATOM | 569 | CA | ALA | A | 83 | −12.527 | 23.004 | −7.089 | 1.00 | 44.61 | L111 | C |
| ATOM | 570 | C | ALA | A | 83 | −13.115 | 23.458 | −8.416 | 1.00 | 44.02 | L111 | C |
| ATOM | 571 | O | ALA | A | 83 | −12.693 | 24.467 | −8.978 | 1.00 | 50.26 | L111 | O |
| ATOM | 572 | CB | ALA | A | 83 | −11.042 | 22.764 | −7.236 | 1.00 | 40.08 | L111 | C |
| ATOM | 573 | N | GLY | A | 84 | −14.086 | 22.699 | −8.912 | 1.00 | 42.49 | L111 | N |
| ATOM | 574 | CA | GLY | A | 84 | −14.727 | 23.029 | −10.169 | 1.00 | 37.87 | L111 | C |
| ATOM | 575 | C | GLY | A | 84 | −13.804 | 22.971 | −11.370 | 1.00 | 39.67 | L111 | C |
| ATOM | 576 | O | GLY | A | 84 | −14.127 | 23.511 | −12.424 | 1.00 | 50.03 | L111 | O |
| ATOM | 577 | N | ILE | A | 85 | −12.654 | 22.323 | −11.226 | 1.00 | 37.41 | L111 | N |
| ATOM | 578 | CA | ILE | A | 85 | −11.715 | 22.219 | −12.334 | 1.00 | 37.65 | L111 | C |
| ATOM | 579 | C | ILE | A | 85 | −11.826 | 20.868 | −13.037 | 1.00 | 41.62 | L111 | C |
| ATOM | 580 | O | ILE | A | 85 | −12.532 | 19.974 | −12.571 | 1.00 | 45.50 | L111 | O |
| ATOM | 581 | CB | ILE | A | 85 | −10.261 | 22.429 | −11.863 | 1.00 | 37.93 | L111 | C |
| ATOM | 582 | CG1 | ILE | A | 85 | −9.905 | 21.408 | −10.784 | 1.00 | 32.73 | L111 | C |
| ATOM | 583 | CG2 | ILE | A | 85 | −10.088 | 23.845 | −11.336 | 1.00 | 42.04 | L111 | C |
| ATOM | 584 | CD1 | ILE | A | 85 | −8.435 | 21.395 | −10.442 | 1.00 | 22.67 | L111 | C |
| ATOM | 585 | N | GLU | A | 86 | −11.126 | 20.728 | −14.159 | 1.00 | 45.67 | L111 | N |
| ATOM | 586 | CA | GLU | A | 86 | −11.156 | 19.499 | −14.948 | 1.00 | 47.13 | L111 | C |
| ATOM | 587 | C | GLU | A | 86 | −9.874 | 18.675 | −14.831 | 1.00 | 47.71 | L111 | C |
| ATOM | 588 | O | GLU | A | 86 | −9.882 | 17.460 | −15.044 | 1.00 | 48.51 | L111 | O |
| ATOM | 589 | CB | GLU | A | 86 | −11.408 | 19.839 | −16.421 | 1.00 | 57.79 | L111 | C |
| ATOM | 590 | CG | GLU | A | 86 | −12.374 | 18.896 | −17.128 | 1.00 | 77.13 | L111 | C |
| ATOM | 591 | CD | GLU | A | 86 | −13.815 | 19.383 | −17.078 | 1.00 | 86.58 | L111 | C |
| ATOM | 592 | OE1 | GLU | A | 86 | −14.025 | 20.594 | −16.849 | 1.00 | 90.24 | L111 | O |
| ATOM | 593 | OE2 | GLU | A | 86 | −14.734 | 18.553 | −17.268 | 1.00 | 89.81 | L111 | O |
| ATOM | 594 | N | LYS | A | 87 | −8.771 | 19.335 | −14.499 | 1.00 | 39.94 | L111 | N |
| ATOM | 595 | CA | LYS | A | 87 | −7.499 | 18.645 | −14.366 | 1.00 | 38.76 | L111 | C |
| ATOM | 596 | C | LYS | A | 87 | −6.699 | 19.204 | −13.204 | 1.00 | 34.61 | L111 | C |
| ATOM | 597 | O | LYS | A | 87 | −6.981 | 20.291 | −12.715 | 1.00 | 46.69 | L111 | O |
| ATOM | 598 | CB | LYS | A | 87 | −6.686 | 18.784 | −15.656 | 1.00 | 41.37 | L111 | C |
| ATOM | 599 | CG | LYS | A | 87 | −7.279 | 18.057 | −16.847 | 1.00 | 47.04 | L111 | C |
| ATOM | 600 | CD | LYS | A | 87 | −6.550 | 18.426 | −18.128 | 1.00 | 53.23 | L111 | C |
| ATOM | 601 | CE | LYS | A | 87 | −5.833 | 17.224 | −18.724 | 1.00 | 60.76 | L111 | C |
| ATOM | 602 | NZ | LYS | A | 87 | −6.109 | 15.961 | −17.979 | 1.00 | 61.63 | L111 | N |
| ATOM | 603 | N | GLY | A | 88 | −5.703 | 18.452 | −12.759 | 1.00 | 34.29 | L111 | N |
| ATOM | 604 | CA | GLY | A | 88 | −4.871 | 18.914 | −11.669 | 1.00 | 33.53 | L111 | C |
| ATOM | 605 | C | GLY | A | 88 | −3.718 | 19.688 | −12.261 | 1.00 | 35.94 | L111 | C |
| ATOM | 606 | O | GLY | A | 88 | −3.422 | 19.547 | −13.445 | 1.00 | 37.03 | L111 | O |
| ATOM | 607 | N | SER | A | 89 | −3.065 | 20.511 | −11.453 | 1.00 | 35.86 | L111 | N |
| ATOM | 608 | CA | SER | A | 89 | −1.941 | 21.285 | −11.951 | 1.00 | 31.79 | L111 | C |

TABLE II-continued

| ATOM | 609 | C | SER | A | 89 | -0.968 | 20.358 | -12.658 | 1.00 | 33.45 | L111 | C |
| --- | --- | --- | --- | --- | --- | --- | --- | --- | --- | --- | --- | --- |
| ATOM | 610 | O | SER | A | 89 | -0.868 | 19.185 | -12.317 | 1.00 | 36.12 | L111 | O |
| ATOM | 611 | CB | SER | A | 89 | -1.227 | 21.987 | -10.801 | 1.00 | 30.17 | L111 | C |
| ATOM | 612 | OG | SER | A | 89 | 0.141 | 22.195 | -11.114 | 1.00 | 29.65 | L111 | O |
| ATOM | 613 | N | SER | A | 90 | -0.260 | 20.881 | -13.651 | 1.00 | 36.82 | L111 | N |
| ATOM | 614 | CA | SER | A | 90 | 0.716 | 20.083 | -14.372 | 1.00 | 35.62 | L111 | C |
| ATOM | 615 | C | SER | A | 90 | 1.981 | 20.112 | -13.530 | 1.00 | 35.74 | L111 | C |
| ATOM | 616 | O | SER | A | 90 | 2.879 | 19.287 | -13.692 | 1.00 | 37.58 | L111 | O |
| ATOM | 617 | CB | SER | A | 90 | 0.976 | 20.682 | -15.758 | 1.00 | 37.33 | L111 | C |
| ATOM | 618 | OG | SER | A | 90 | 1.955 | 21.708 | -15.701 | 1.00 | 51.94 | L111 | O |
| ATOM | 619 | N | GLU | A | 91 | 2.034 | 21.083 | -12.625 | 1.00 | 33.32 | L111 | N |
| ATOM | 620 | CA | GLU | A | 91 | 3.166 | 21.246 | -11.726 | 1.00 | 38.55 | L111 | C |
| ATOM | 621 | C | GLU | A | 91 | 2.619 | 21.648 | -10.362 | 1.00 | 37.86 | L111 | C |
| ATOM | 622 | O | GLU | A | 91 | 2.553 | 22.832 | -10.026 | 1.00 | 36.53 | L111 | O |
| ATOM | 623 | CB | GLU | A | 91 | 4.115 | 22.317 | -12.262 | 1.00 | 42.92 | L111 | C |
| ATOM | 624 | CG | GLU | A | 91 | 4.927 | 21.857 | -13.457 | 1.00 | 56.44 | L111 | C |
| ATOM | 625 | CD | GLU | A | 91 | 6.025 | 22.832 | -13.841 | 1.00 | 69.04 | L111 | C |
| ATOM | 626 | OE1 | GLU | A | 91 | 6.223 | 23.832 | -13.113 | 1.00 | 67.53 | L111 | O |
| ATOM | 627 | OE2 | GLU | A | 91 | 6.692 | 22.593 | -14.876 | 1.00 | 73.04 | L111 | O |
| ATOM | 628 | N | PRO | A | 92 | 2.199 | 20.652 | -9.561 | 1.00 | 39.75 | L111 | N |
| ATOM | 629 | CA | PRO | A | 92 | 1.643 | 20.871 | -8.222 | 1.00 | 37.71 | L111 | C |
| ATOM | 630 | C | PRO | A | 92 | 2.536 | 21.749 | -7.365 | 1.00 | 33.98 | L111 | C |
| ATOM | 631 | O | PRO | A | 92 | 3.760 | 21.633 | -7.418 | 1.00 | 31.75 | L111 | O |
| ATOM | 632 | CB | PRO | A | 92 | 1.505 | 19.459 | -7.655 | 1.00 | 34.90 | L111 | C |
| ATOM | 633 | CG | PRO | A | 92 | 1.371 | 18.596 | -8.852 | 1.00 | 30.25 | L111 | C |
| ATOM | 634 | CD | PRO | A | 92 | 2.246 | 19.219 | -9.898 | 1.00 | 39.42 | L111 | C |
| ATOM | 635 | N | LYS | A | 93 | 1.910 | 22.625 | -6.584 | 1.00 | 30.90 | L111 | N |
| ATOM | 636 | CA | LYS | A | 93 | 2.620 | 23.544 | -5.703 | 1.00 | 36.65 | L111 | C |
| ATOM | 637 | C | LYS | A | 93 | 3.250 | 24.695 | -6.477 | 1.00 | 36.64 | L111 | C |
| ATOM | 638 | O | LYS | A | 93 | 3.181 | 25.841 | -6.044 | 1.00 | 45.57 | L111 | O |
| ATOM | 639 | CB | LYS | A | 93 | 3.699 | 22.800 | -4.907 | 1.00 | 42.76 | L111 | C |
| ATOM | 640 | CG | LYS | A | 93 | 4.532 | 23.681 | -3.993 | 1.00 | 47.27 | L111 | C |
| ATOM | 641 | CD | LYS | A | 93 | 4.991 | 22.907 | -2.768 | 1.00 | 53.52 | L111 | C |
| ATOM | 642 | CE | LYS | A | 93 | 5.915 | 23.744 | -1.894 | 1.00 | 54.40 | L111 | C |
| ATOM | 643 | NZ | LYS | A | 93 | 7.235 | 23.085 | -1.673 | 1.00 | 61.73 | L111 | N |
| ATOM | 644 | N | ARG | A | 94 | 3.864 | 24.394 | -7.616 | 1.00 | 35.63 | L111 | N |
| ATOM | 645 | CA | ARG | A | 94 | 4.486 | 25.432 | -8.430 | 1.00 | 29.80 | L111 | C |
| ATOM | 646 | C | ARG | A | 94 | 3.408 | 26.252 | -9.125 | 1.00 | 32.19 | L111 | C |
| ATOM | 647 | O | ARG | A | 94 | 3.593 | 27.443 | -9.371 | 1.00 | 36.21 | L111 | O |
| ATOM | 648 | CB | ARG | A | 94 | 5.418 | 24.817 | -9.475 | 1.00 | 21.41 | L111 | C |
| ATOM | 649 | CG | ARG | A | 94 | 6.818 | 24.559 | -8.966 | 1.00 | 26.71 | L111 | C |
| ATOM | 650 | CD | ARG | A | 94 | 7.779 | 24.180 | -10.088 | 1.00 | 28.16 | L111 | C |
| ATOM | 651 | NE | ARG | A | 94 | 9.002 | 23.582 | -9.551 | 1.00 | 40.63 | L111 | N |
| ATOM | 652 | CZ | ARG | A | 94 | 10.016 | 23.133 | -10.289 | 1.00 | 42.98 | L111 | C |
| ATOM | 653 | NH1 | ARG | A | 94 | 9.965 | 23.212 | -11.610 | 1.00 | 45.19 | L111 | N |
| ATOM | 654 | NH2 | ARG | A | 94 | 11.085 | 22.606 | -9.704 | 1.00 | 48.46 | L111 | N |
| ATOM | 655 | N | LYS | A | 95 | 2.284 | 25.612 | -9.440 | 1.00 | 28.46 | L111 | N |
| ATOM | 656 | CA | LYS | A | 95 | 1.177 | 26.298 | -10.104 | 1.00 | 30.94 | L111 | C |
| ATOM | 657 | C | LYS | A | 95 | -0.145 | 25.834 | -9.542 | 1.00 | 28.39 | L111 | C |
| ATOM | 658 | O | LYS | A | 95 | -0.511 | 24.679 | -9.700 | 1.00 | 40.28 | L111 | O |
| ATOM | 659 | CB | LYS | A | 95 | 1.169 | 26.024 | -11.614 | 1.00 | 36.77 | L111 | C |
| ATOM | 660 | CG | LYS | A | 95 | 2.531 | 25.791 | -12.244 | 1.00 | 49.47 | L111 | C |
| ATOM | 661 | CD | LYS | A | 95 | 2.426 | 25.746 | -13.765 | 1.00 | 48.94 | L111 | C |
| ATOM | 662 | CE | LYS | A | 95 | 3.782 | 25.970 | -14.420 | 1.00 | 50.63 | L111 | C |
| ATOM | 663 | NZ | LYS | A | 95 | 3.730 | 25.733 | -15.886 | 1.00 | 46.96 | L111 | N |
| ATOM | 664 | N | ILE | A | 96 | -0.872 | 26.728 | -8.892 | 1.00 | 30.02 | L111 | N |
| ATOM | 665 | CA | ILE | A | 96 | -2.162 | 26.357 | -8.337 | 1.00 | 31.34 | L111 | C |
| ATOM | 666 | C | ILE | A | 96 | -3.209 | 26.537 | -9.425 | 1.00 | 35.19 | L111 | C |
| ATOM | 667 | O | ILE | A | 96 | -3.286 | 27.593 | -10.048 | 1.00 | 42.96 | L111 | O |
| ATOM | 668 | CB | ILE | A | 96 | -2.502 | 27.231 | -7.115 | 1.00 | 33.87 | L111 | C |
| ATOM | 669 | CG1 | ILE | A | 96 | -1.379 | 27.115 | -6.079 | 1.00 | 33.04 | L111 | C |
| ATOM | 670 | CG2 | ILE | A | 96 | -3.840 | 26.812 | -6.518 | 1.00 | 28.64 | L111 | C |
| ATOM | 671 | CD1 | ILE | A | 96 | -0.892 | 25.695 | -5.843 | 1.00 | 35.36 | L111 | C |
| ATOM | 672 | N | VAL | A | 97 | -4.008 | 25.504 | -9.664 | 1.00 | 32.56 | L111 | N |
| ATOM | 673 | CA | VAL | A | 97 | -5.022 | 25.570 | -10.704 | 1.00 | 29.74 | L111 | C |
| ATOM | 674 | C | VAL | A | 97 | -6.427 | 25.650 | -10.148 | 1.00 | 36.58 | L111 | C |
| ATOM | 675 | O | VAL | A | 97 | -7.399 | 25.737 | -10.905 | 1.00 | 38.60 | L111 | O |
| ATOM | 676 | CB | VAL | A | 97 | -4.930 | 24.351 | -11.648 | 1.00 | 38.47 | L111 | C |
| ATOM | 677 | CG1 | VAL | A | 97 | -3.502 | 24.185 | -12.123 | 1.00 | 37.01 | L111 | C |
| ATOM | 678 | CG2 | VAL | A | 97 | -5.403 | 23.086 | -10.940 | 1.00 | 37.97 | L111 | C |
| ATOM | 679 | N | GLY | A | 98 | -6.531 | 25.623 | -8.823 | 1.00 | 35.02 | L111 | N |
| ATOM | 680 | CA | GLY | A | 98 | -7.836 | 25.690 | -8.192 | 1.00 | 35.16 | L111 | C |
| ATOM | 681 | C | GLY | A | 98 | -7.744 | 25.779 | -6.683 | 1.00 | 38.01 | L111 | C |
| ATOM | 682 | O | GLY | A | 98 | -6.648 | 25.832 | -6.117 | 1.00 | 38.34 | L111 | O |
| ATOM | 683 | N | LYS | A | 99 | -8.896 | 25.801 | -6.023 | 1.00 | 35.14 | L111 | N |
| ATOM | 684 | CA | LYS | A | 99 | -8.911 | 25.883 | -4.575 | 1.00 | 40.57 | L111 | C |
| ATOM | 685 | C | LYS | A | 99 | -10.230 | 25.403 | -3.991 | 1.00 | 42.95 | L111 | C |
| ATOM | 686 | O | LYS | A | 99 | -11.264 | 25.396 | -4.663 | 1.00 | 42.23 | L111 | O |
| ATOM | 687 | CB | LYS | A | 99 | -8.634 | 27.320 | -4.130 | 1.00 | 50.99 | L111 | C |

TABLE II-continued

| | | | | | | | | | | | |
|---|---|---|---|---|---|---|---|---|---|---|---|
| ATOM | 688 | CG | LYS | A | 99 | −9.850 | 28.231 | −4.172 | 1.00 | 60.57 | L111 C |
| ATOM | 689 | CD | LYS | A | 99 | −9.469 | 29.678 | −3.885 | 1.00 | 65.97 | L111 C |
| ATOM | 690 | CE | LYS | A | 99 | −10.646 | 30.614 | −4.127 | 1.00 | 63.49 | L111 C |
| ATOM | 691 | NZ | LYS | A | 99 | −10.216 | 31.886 | −4.768 | 1.00 | 65.04 | L111 N |
| ATOM | 692 | N | VAL | A | 100 | −10.180 | 24.992 | −2.731 | 1.00 | 40.70 | L111 N |
| ATOM | 693 | CA | VAL | A | 100 | −11.361 | 24.511 | −2.036 | 1.00 | 41.33 | L111 C |
| ATOM | 694 | C | VAL | A | 100 | −11.330 | 24.980 | −0.592 | 1.00 | 41.84 | L111 C |
| ATOM | 695 | O | VAL | A | 100 | −10.263 | 25.188 | −0.012 | 1.00 | 40.91 | L111 O |
| ATOM | 696 | CB | VAL | A | 100 | −11.440 | 22.973 | −2.057 | 1.00 | 42.37 | L111 C |
| ATOM | 697 | CG1 | VAL | A | 100 | −11.840 | 22.498 | −3.442 | 1.00 | 43.81 | L111 C |
| ATOM | 698 | CG2 | VAL | A | 100 | −10.102 | 22.377 | −1.651 | 1.00 | 37.38 | L111 C |
| ATOM | 699 | N | THR | A | 101 | −12.511 | 25.145 | −0.016 | 1.00 | 43.68 | L111 N |
| ATOM | 700 | CA | THR | A | 101 | −12.629 | 25.595 | 1.355 | 1.00 | 42.43 | L111 C |
| ATOM | 701 | C | THR | A | 101 | −12.362 | 24.454 | 2.321 | 1.00 | 45.89 | L111 C |
| ATOM | 702 | O | THR | A | 101 | −12.495 | 23.284 | 1.963 | 1.00 | 46.60 | L111 O |
| ATOM | 703 | CB | THR | A | 101 | −14.026 | 26.153 | 1.610 | 1.00 | 45.72 | L111 C |
| ATOM | 704 | OG1 | THR | A | 101 | −15.005 | 25.154 | 1.293 | 1.00 | 40.56 | L111 O |
| ATOM | 705 | CG2 | THR | A | 101 | −14.260 | 27.380 | 0.738 | 1.00 | 42.52 | L111 C |
| ATOM | 706 | N | ARG | A | 102 | −11.981 | 24.799 | 3.545 | 1.00 | 49.33 | L111 N |
| ATOM | 707 | CA | ARG | A | 102 | −11.701 | 23.797 | 4.565 | 1.00 | 49.44 | L111 C |
| ATOM | 708 | C | ARG | A | 102 | −12.925 | 22.925 | 4.792 | 1.00 | 49.34 | L111 C |
| ATOM | 709 | O | ARG | A | 102 | −12.807 | 21.744 | 5.115 | 1.00 | 53.45 | L111 O |
| ATOM | 710 | CB | ARG | A | 102 | −11.301 | 24.469 | 5.879 | 1.00 | 51.60 | L111 C |
| ATOM | 711 | CG | ARG | A | 102 | −10.126 | 23.806 | 6.574 | 1.00 | 64.32 | L111 C |
| ATOM | 712 | CD | ARG | A | 102 | −10.579 | 23.003 | 7.777 | 1.00 | 72.71 | L111 C |
| ATOM | 713 | NE | ARG | A | 102 | −10.495 | 23.786 | 9.006 | 1.00 | 86.85 | L111 N |
| ATOM | 714 | CZ | ARG | A | 102 | −10.080 | 23.304 | 10.174 | 1.00 | 96.04 | L111 C |
| ATOM | 715 | NH1 | ARG | A | 102 | −9.710 | 22.033 | 10.275 | 1.00 | 95.91 | L111 N |
| ATOM | 716 | NH2 | ARG | A | 102 | −10.033 | 24.095 | 11.242 | 1.00 | 96.71 | L111 N |
| ATOM | 717 | N | LYS | A | 103 | −14.103 | 23.514 | 4.626 | 1.00 | 50.48 | L111 N |
| ATOM | 718 | CA | LYS | A | 103 | −15.341 | 22.774 | 4.811 | 1.00 | 51.76 | L111 C |
| ATOM | 719 | C | LYS | A | 103 | −15.441 | 21.718 | 3.719 | 1.00 | 51.34 | L111 C |
| ATOM | 720 | O | LYS | A | 103 | −15.884 | 20.600 | 3.966 | 1.00 | 59.36 | L111 O |
| ATOM | 721 | CB | LYS | A | 103 | −16.545 | 23.721 | 4.751 | 1.00 | 53.67 | L111 C |
| ATOM | 722 | CG | LYS | A | 103 | −17.839 | 23.135 | 5.319 | 1.00 | 62.90 | L111 C |
| ATOM | 723 | CD | LYS | A | 103 | −17.717 | 22.781 | 6.806 | 1.00 | 65.48 | L111 C |
| ATOM | 724 | CE | LYS | A | 103 | −18.840 | 21.841 | 7.257 | 1.00 | 63.76 | L111 C |
| ATOM | 725 | NZ | LYS | A | 103 | −19.077 | 21.884 | 8.732 | 1.00 | 58.26 | L111 N |
| ATOM | 726 | N | GLN | A | 104 | −15.013 | 22.073 | 2.512 | 1.00 | 51.89 | L111 N |
| ATOM | 727 | CA | GLN | A | 104 | −15.052 | 21.145 | 1.388 | 1.00 | 44.08 | L111 C |
| ATOM | 728 | C | GLN | A | 104 | −14.161 | 19.939 | 1.664 | 1.00 | 42.43 | L111 C |
| ATOM | 729 | O | GLN | A | 104 | −14.519 | 18.804 | 1.347 | 1.00 | 40.53 | L111 O |
| ATOM | 730 | CB | GLN | A | 104 | −14.602 | 21.850 | 0.110 | 1.00 | 42.64 | L111 C |
| ATOM | 731 | CG | GLN | A | 104 | −15.663 | 22.751 | −0.484 | 1.00 | 35.82 | L111 C |
| ATOM | 732 | CD | GLN | A | 104 | −15.242 | 23.354 | −1.804 | 1.00 | 44.67 | L111 C |
| ATOM | 733 | OE1 | GLN | A | 104 | −14.303 | 24.154 | −1.867 | 1.00 | 37.53 | L111 O |
| ATOM | 734 | NE2 | GLN | A | 104 | −15.936 | 22.975 | −2.873 | 1.00 | 35.39 | L111 N |
| ATOM | 735 | N | ILE | A | 105 | −12.998 | 20.186 | 2.254 | 1.00 | 39.32 | L111 N |
| ATOM | 736 | CA | ILE | A | 105 | −12.088 | 19.103 | 2.584 | 1.00 | 35.57 | L111 C |
| ATOM | 737 | C | ILE | A | 105 | −12.846 | 18.187 | 3.525 | 1.00 | 41.32 | L111 C |
| ATOM | 738 | O | ILE | A | 105 | −12.770 | 16.965 | 3.411 | 1.00 | 46.00 | L111 O |
| ATOM | 739 | CB | ILE | A | 105 | −10.832 | 19.624 | 3.298 | 1.00 | 33.68 | L111 C |
| ATOM | 740 | CG1 | ILE | A | 105 | −9.873 | 20.242 | 2.277 | 1.00 | 32.96 | L111 C |
| ATOM | 741 | CG2 | ILE | A | 105 | −10.154 | 18.495 | 4.061 | 1.00 | 34.33 | L111 C |
| ATOM | 742 | CD1 | ILE | A | 105 | −9.501 | 19.321 | 1.131 | 1.00 | 34.42 | L111 C |
| ATOM | 743 | N | GLU | A | 106 | −13.584 | 18.800 | 4.448 | 1.00 | 47.08 | L111 N |
| ATOM | 744 | CA | GLU | A | 106 | −14.382 | 18.068 | 5.428 | 1.00 | 53.52 | L111 C |
| ATOM | 745 | C | GLU | A | 106 | −15.411 | 17.186 | 4.719 | 1.00 | 55.13 | L111 C |
| ATOM | 746 | O | GLU | A | 106 | −15.606 | 16.027 | 5.087 | 1.00 | 59.36 | L111 O |
| ATOM | 747 | CB | GLU | A | 106 | −15.094 | 19.051 | 6.381 | 1.00 | 50.72 | L111 C |
| ATOM | 748 | CG | GLU | A | 106 | −15.480 | 18.464 | 7.748 | 1.00 | 55.56 | L111 C |
| ATOM | 749 | CD | GLU | A | 106 | −16.029 | 19.504 | 8.734 | 1.00 | 62.03 | L111 C |
| ATOM | 750 | OE1 | GLU | A | 106 | −15.308 | 20.476 | 9.054 | 1.00 | 63.26 | L111 O |
| ATOM | 751 | OE2 | GLU | A | 106 | −17.182 | 19.345 | 9.199 | 1.00 | 53.90 | L111 O |
| ATOM | 752 | N | GLU | A | 107 | −16.061 | 17.731 | 3.695 | 1.00 | 51.75 | L111 N |
| ATOM | 753 | CA | GLU | A | 107 | −17.071 | 16.982 | 2.954 | 1.00 | 52.07 | L111 C |
| ATOM | 754 | C | GLU | A | 107 | −16.476 | 15.755 | 2.282 | 1.00 | 50.13 | L111 C |
| ATOM | 755 | O | GLU | A | 107 | −16.990 | 14.642 | 2.417 | 1.00 | 49.53 | L111 O |
| ATOM | 756 | CB | GLU | A | 107 | −17.720 | 17.871 | 1.891 | 1.00 | 56.84 | L111 C |
| ATOM | 757 | CG | GLU | A | 107 | −17.859 | 19.328 | 2.293 | 1.00 | 73.20 | L111 C |
| ATOM | 758 | CD | GLU | A | 107 | −18.843 | 20.088 | 1.422 | 1.00 | 81.27 | L111 C |
| ATOM | 759 | OE1 | GLU | A | 107 | −19.271 | 19.540 | 0.382 | 1.00 | 84.05 | L111 O |
| ATOM | 760 | OE2 | GLU | A | 107 | −19.187 | 21.237 | 1.779 | 1.00 | 86.15 | L111 O |
| ATOM | 761 | N | ILE | A | 108 | −15.391 | 15.973 | 1.549 | 1.00 | 46.89 | L111 N |
| ATOM | 762 | CA | ILE | A | 108 | −14.719 | 14.900 | 0.844 | 1.00 | 39.41 | L111 C |
| ATOM | 763 | C | ILE | A | 108 | −14.222 | 13.854 | 1.829 | 1.00 | 40.77 | L111 C |
| ATOM | 764 | O | ILE | A | 108 | −14.441 | 12.658 | 1.637 | 1.00 | 43.65 | L111 O |
| ATOM | 765 | CB | ILE | A | 108 | −13.542 | 15.447 | 0.019 | 1.00 | 38.05 | L111 C |
| ATOM | 766 | CG1 | ILE | A | 108 | −14.072 | 16.428 | −1.032 | 1.00 | 36.44 | L111 C |

TABLE II-continued

| | | | | | | | | | | | | |
|---|---|---|---|---|---|---|---|---|---|---|---|---|
| ATOM | 767 | CG2 | ILE | A | 108 | −12.796 | 14.305 | −0.649 | 1.00 | 41.19 | L111 | C |
| ATOM | 768 | CD1 | ILE | A | 108 | −13.004 | 17.084 | −1.882 | 1.00 | 31.78 | L111 | C |
| ATOM | 769 | N | ALA | A | 109 | −13.561 | 14.303 | 2.891 | 1.00 | 40.57 | L111 | N |
| ATOM | 770 | CA | ALA | A | 109 | −13.053 | 13.380 | 3.895 | 1.00 | 42.41 | L111 | C |
| ATOM | 771 | C | ALA | A | 109 | −14.205 | 12.546 | 4.429 | 1.00 | 44.77 | L111 | C |
| ATOM | 772 | O | ALA | A | 109 | −14.051 | 11.356 | 4.685 | 1.00 | 48.40 | L111 | O |
| ATOM | 773 | CB | ALA | A | 109 | −12.393 | 14.140 | 5.032 | 1.00 | 38.72 | L111 | C |
| ATOM | 774 | N | LYS | A | 110 | −15.365 | 13.174 | 4.589 | 1.00 | 47.97 | L111 | N |
| ATOM | 775 | CA | LYS | A | 110 | −16.537 | 12.474 | 5.099 | 1.00 | 44.59 | L111 | C |
| ATOM | 776 | C | LYS | A | 110 | −17.027 | 11.474 | 4.066 | 1.00 | 45.30 | L111 | C |
| ATOM | 777 | O | LYS | A | 110 | −17.377 | 10.342 | 4.401 | 1.00 | 44.67 | L111 | O |
| ATOM | 778 | CB | LYS | A | 110 | −17.651 | 13.469 | 5.422 | 1.00 | 45.45 | L111 | C |
| ATOM | 779 | CG | LYS | A | 110 | −17.991 | 13.562 | 6.902 | 1.00 | 47.29 | L111 | C |
| ATOM | 780 | CD | LYS | A | 110 | −17.733 | 14.963 | 7.448 | 1.00 | 51.84 | L111 | C |
| ATOM | 781 | CE | LYS | A | 110 | −18.991 | 15.558 | 8.070 | 1.00 | 53.58 | L111 | C |
| ATOM | 782 | NZ | LYS | A | 110 | −18.712 | 16.257 | 9.356 | 1.00 | 55.16 | L111 | N |
| ATOM | 783 | N | THR | A | 111 | −17.043 | 11.902 | 2.807 | 1.00 | 44.49 | L111 | N |
| ATOM | 784 | CA | THR | A | 111 | −17.492 | 11.060 | 1.705 | 1.00 | 42.63 | L111 | C |
| ATOM | 785 | C | THR | A | 111 | −16.635 | 9.810 | 1.548 | 1.00 | 44.42 | L111 | C |
| ATOM | 786 | O | THR | A | 111 | −17.149 | 8.707 | 1.375 | 1.00 | 44.77 | L111 | O |
| ATOM | 787 | CB | THR | A | 111 | −17.452 | 11.830 | 0.376 | 1.00 | 40.13 | L111 | C |
| ATOM | 788 | OG1 | THR | A | 111 | −18.545 | 12.754 | 0.325 | 1.00 | 46.15 | L111 | O |
| ATOM | 789 | CG2 | THR | A | 111 | −17.552 | 10.871 | −0.799 | 1.00 | 43.65 | L111 | C |
| ATOM | 790 | N | LYS | A | 112 | −15.323 | 9.995 | 1.609 | 1.00 | 42.25 | L111 | N |
| ATOM | 791 | CA | LYS | A | 112 | −14.382 | 8.898 | 1.448 | 1.00 | 42.77 | L111 | C |
| ATOM | 792 | C | LYS | A | 112 | −14.081 | 8.127 | 2.732 | 1.00 | 43.93 | L111 | C |
| ATOM | 793 | O | LYS | A | 112 | −13.321 | 7.157 | 2.713 | 1.00 | 47.28 | L111 | O |
| ATOM | 794 | CB | LYS | A | 112 | −13.072 | 9.442 | 0.873 | 1.00 | 44.33 | L111 | C |
| ATOM | 795 | CG | LYS | A | 112 | −13.129 | 9.772 | −0.607 | 1.00 | 40.93 | L111 | C |
| ATOM | 796 | CD | LYS | A | 112 | −11.806 | 9.474 | −1.281 | 1.00 | 35.66 | L111 | C |
| ATOM | 797 | CE | LYS | A | 112 | −11.377 | 8.032 | −1.062 | 1.00 | 31.03 | L111 | C |
| ATOM | 798 | NZ | LYS | A | 112 | −11.960 | 7.113 | −2.076 | 1.00 | 28.57 | L111 | N |
| ATOM | 799 | N | MET | A | 113 | −14.673 | 8.554 | 3.842 | 1.00 | 42.32 | L111 | N |
| ATOM | 800 | CA | MET | A | 113 | −14.436 | 7.911 | 5.132 | 1.00 | 41.26 | L111 | C |
| ATOM | 801 | C | MET | A | 113 | −14.492 | 6.379 | 5.116 | 1.00 | 39.35 | L111 | C |
| ATOM | 802 | O | MET | A | 113 | −13.619 | 5.717 | 5.688 | 1.00 | 39.20 | L111 | O |
| ATOM | 803 | CB | MET | A | 113 | −15.410 | 8.457 | 6.177 | 1.00 | 39.84 | L111 | C |
| ATOM | 804 | CG | MET | A | 113 | −14.931 | 8.283 | 7.609 | 1.00 | 45.81 | L111 | C |
| ATOM | 805 | SD | MET | A | 113 | −13.481 | 9.269 | 8.040 | 1.00 | 47.31 | L111 | S |
| ATOM | 806 | CE | MET | A | 113 | −14.261 | 10.787 | 8.610 | 1.00 | 49.60 | L111 | C |
| ATOM | 807 | N | PRO | A | 114 | −15.524 | 5.793 | 4.484 | 1.00 | 32.93 | L111 | N |
| ATOM | 808 | CA | PRO | A | 114 | −15.582 | 4.328 | 4.458 | 1.00 | 29.51 | L111 | C |
| ATOM | 809 | C | PRO | A | 114 | −14.301 | 3.703 | 3.912 | 1.00 | 35.05 | L111 | C |
| ATOM | 810 | O | PRO | A | 114 | −13.918 | 2.609 | 4.314 | 1.00 | 41.74 | L111 | O |
| ATOM | 811 | CB | PRO | A | 114 | −16.791 | 4.013 | 3.575 | 1.00 | 27.80 | L111 | C |
| ATOM | 812 | CG | PRO | A | 114 | −17.214 | 5.307 | 2.967 | 1.00 | 23.57 | L111 | C |
| ATOM | 813 | CD | PRO | A | 114 | −16.678 | 6.411 | 3.811 | 1.00 | 31.92 | L111 | C |
| ATOM | 814 | N | ASP | A | 115 | −13.629 | 4.408 | 3.008 | 1.00 | 38.82 | L111 | N |
| ATOM | 815 | CA | ASP | A | 115 | −12.399 | 3.898 | 2.419 | 1.00 | 36.41 | L111 | C |
| ATOM | 816 | C | ASP | A | 115 | −11.138 | 4.462 | 3.069 | 1.00 | 36.55 | L111 | C |
| ATOM | 817 | O | ASP | A | 115 | −10.025 | 4.080 | 2.713 | 1.00 | 40.35 | L111 | O |
| ATOM | 818 | CB | ASP | A | 115 | −12.385 | 4.193 | 0.919 | 1.00 | 48.68 | L111 | C |
| ATOM | 819 | CG | ASP | A | 115 | −13.453 | 3.418 | 0.162 | 1.00 | 57.41 | L111 | C |
| ATOM | 820 | OD1 | ASP | A | 115 | −13.653 | 2.221 | 0.464 | 1.00 | 51.55 | L111 | O |
| ATOM | 821 | OD2 | ASP | A | 115 | −14.090 | 4.009 | −0.737 | 1.00 | 58.21 | L111 | O |
| ATOM | 822 | N | LEU | A | 116 | −11.311 | 5.368 | 4.024 | 1.00 | 38.89 | L111 | N |
| ATOM | 823 | CA | LEU | A | 116 | −10.178 | 5.969 | 4.720 | 1.00 | 33.57 | L111 | C |
| ATOM | 824 | C | LEU | A | 116 | −9.916 | 5.199 | 6.007 | 1.00 | 32.97 | L111 | C |
| ATOM | 825 | O | LEU | A | 116 | −10.817 | 4.567 | 6.547 | 1.00 | 40.69 | L111 | O |
| ATOM | 826 | CB | LEU | A | 116 | −10.482 | 7.427 | 5.055 | 1.00 | 38.53 | L111 | C |
| ATOM | 827 | CG | LEU | A | 116 | −9.930 | 8.533 | 4.156 | 1.00 | 37.13 | L111 | C |
| ATOM | 828 | CD1 | LEU | A | 116 | −9.839 | 8.062 | 2.720 | 1.00 | 34.98 | L111 | C |
| ATOM | 829 | CD2 | LEU | A | 116 | −10.837 | 9.742 | 4.261 | 1.00 | 33.33 | L111 | C |
| ATOM | 830 | N | ASN | A | 117 | −8.686 | 5.256 | 6.501 | 1.00 | 32.67 | L111 | N |
| ATOM | 831 | CA | ASN | A | 117 | −8.336 | 4.549 | 7.725 | 1.00 | 33.28 | L111 | C |
| ATOM | 832 | C | ASN | A | 117 | −8.052 | 5.502 | 8.889 | 1.00 | 39.76 | L111 | C |
| ATOM | 833 | O | ASN | A | 117 | −7.373 | 5.140 | 9.851 | 1.00 | 36.63 | L111 | O |
| ATOM | 834 | CB | ASN | A | 117 | −7.117 | 3.666 | 7.475 | 1.00 | 23.35 | L111 | C |
| ATOM | 835 | CG | ASN | A | 117 | −5.872 | 4.470 | 7.208 | 1.00 | 24.02 | L111 | C |
| ATOM | 836 | OD1 | ASN | A | 117 | −5.949 | 5.659 | 6.916 | 1.00 | 31.18 | L111 | O |
| ATOM | 837 | ND2 | ASN | A | 117 | −4.714 | 3.828 | 7.306 | 1.00 | 18.87 | L111 | N |
| ATOM | 838 | N | ALA | A | 118 | −8.572 | 6.720 | 8.799 | 1.00 | 41.20 | L111 | N |
| ATOM | 839 | CA | ALA | A | 118 | −8.363 | 7.710 | 9.846 | 1.00 | 41.18 | L111 | C |
| ATOM | 840 | C | ALA | A | 118 | −9.297 | 7.443 | 11.018 | 1.00 | 43.82 | L111 | C |
| ATOM | 841 | O | ALA | A | 118 | −10.455 | 7.069 | 10.827 | 1.00 | 45.81 | L111 | O |
| ATOM | 842 | CB | ALA | A | 118 | −8.604 | 9.103 | 9.296 | 1.00 | 41.30 | L111 | C |
| ATOM | 843 | N | ASN | A | 119 | −8.793 | 7.644 | 12.230 | 1.00 | 42.07 | L111 | N |
| ATOM | 844 | CA | ASN | A | 119 | −9.589 | 7.419 | 13.429 | 1.00 | 42.41 | L111 | C |
| ATOM | 845 | C | ASN | A | 119 | −10.370 | 8.660 | 13.847 | 1.00 | 48.14 | L111 | C |

TABLE II-continued

| | | | | | | | | | | | |
|---|---|---|---|---|---|---|---|---|---|---|---|
| ATOM | 846 | O | ASN | A | 119 | −11.141 | 8.625 | 14.807 | 1.00 | 53.14 | L111 | O |
| ATOM | 847 | CB | ASN | A | 119 | −8.684 | 6.981 | 14.575 | 1.00 | 37.27 | L111 | C |
| ATOM | 848 | CG | ASN | A | 119 | −8.180 | 5.575 | 14.400 | 1.00 | 33.45 | L111 | C |
| ATOM | 849 | OD1 | ASN | A | 119 | −8.886 | 4.714 | 13.876 | 1.00 | 31.47 | L111 | O |
| ATOM | 850 | ND2 | ASN | A | 119 | −6.951 | 5.328 | 14.837 | 1.00 | 38.73 | L111 | N |
| ATOM | 851 | N | SER | A | 120 | −10.168 | 9.756 | 13.125 | 1.00 | 48.44 | L111 | N |
| ATOM | 852 | CA | SER | A | 120 | −10.851 | 11.005 | 13.430 | 1.00 | 43.86 | L111 | C |
| ATOM | 853 | C | SER | A | 120 | −11.091 | 11.809 | 12.163 | 1.00 | 45.90 | L111 | C |
| ATOM | 854 | O | SER | A | 120 | −10.321 | 11.715 | 11.208 | 1.00 | 53.71 | L111 | O |
| ATOM | 855 | CB | SER | A | 120 | −10.010 | 11.834 | 14.401 | 1.00 | 38.80 | L111 | C |
| ATOM | 856 | OG | SER | A | 120 | −8.642 | 11.834 | 14.030 | 1.00 | 32.06 | L111 | O |
| ATOM | 857 | N | LEU | A | 121 | −12.157 | 12.601 | 12.156 | 1.00 | 46.97 | L111 | N |
| ATOM | 858 | CA | LEU | A | 121 | −12.476 | 13.429 | 11.000 | 1.00 | 44.83 | L111 | C |
| ATOM | 859 | C | LEU | A | 121 | −11.297 | 14.333 | 10.678 | 1.00 | 45.31 | L111 | C |
| ATOM | 860 | O | LEU | A | 121 | −11.078 | 14.693 | 9.526 | 1.00 | 52.25 | L111 | O |
| ATOM | 861 | CB | LEU | A | 121 | −13.705 | 14.291 | 11.277 | 1.00 | 39.77 | L111 | C |
| ATOM | 862 | CG | LEU | A | 121 | −13.904 | 15.469 | 10.325 | 1.00 | 41.18 | L111 | C |
| ATOM | 863 | CD1 | LEU | A | 121 | −14.063 | 14.958 | 8.900 | 1.00 | 41.06 | L111 | C |
| ATOM | 864 | CD2 | LEU | A | 121 | −15.128 | 16.260 | 10.751 | 1.00 | 41.00 | L111 | C |
| ATOM | 865 | N | GLU | A | 122 | −10.542 | 14.701 | 11.705 | 1.00 | 46.54 | L111 | N |
| ATOM | 866 | CA | GLU | A | 122 | −9.383 | 15.562 | 11.522 | 1.00 | 47.46 | L111 | C |
| ATOM | 867 | C | GLU | A | 122 | −8.327 | 14.834 | 10.702 | 1.00 | 45.12 | L111 | C |
| ATOM | 868 | O | GLU | A | 122 | −7.781 | 15.383 | 9.747 | 1.00 | 51.65 | L111 | O |
| ATOM | 869 | CB | GLU | A | 122 | −8.807 | 15.962 | 12.881 | 1.00 | 45.32 | L111 | C |
| ATOM | 870 | CG | GLU | A | 122 | −9.646 | 16.987 | 13.629 | 1.00 | 57.78 | L111 | C |
| ATOM | 871 | CD | GLU | A | 122 | −10.643 | 16.353 | 14.588 | 1.00 | 63.03 | L111 | C |
| ATOM | 872 | OE1 | GLU | A | 122 | −10.380 | 15.234 | 15.075 | 1.00 | 64.43 | L111 | O |
| ATOM | 873 | OE2 | GLU | A | 122 | −11.690 | 16.979 | 14.857 | 1.00 | 69.35 | L111 | O |
| ATOM | 874 | N | ALA | A | 123 | −8.045 | 13.593 | 11.083 | 1.00 | 41.17 | L111 | N |
| ATOM | 875 | CA | ALA | A | 123 | −7.062 | 12.786 | 10.381 | 1.00 | 38.97 | L111 | C |
| ATOM | 876 | C | ALA | A | 123 | −7.516 | 12.566 | 8.944 | 1.00 | 41.17 | L111 | C |
| ATOM | 877 | O | ALA | A | 123 | −6.701 | 12.562 | 8.022 | 1.00 | 41.16 | L111 | O |
| ATOM | 878 | CB | ALA | A | 123 | −6.891 | 11.452 | 11.081 | 1.00 | 36.50 | L111 | C |
| ATOM | 879 | N | ALA | A | 124 | −8.822 | 12.389 | 8.760 | 1.00 | 36.64 | L111 | N |
| ATOM | 880 | CA | ALA | A | 124 | −9.390 | 12.168 | 7.432 | 1.00 | 36.26 | L111 | C |
| ATOM | 881 | C | ALA | A | 124 | −9.133 | 13.362 | 6.533 | 1.00 | 35.14 | L111 | C |
| ATOM | 882 | O | ALA | A | 124 | −8.742 | 13.207 | 5.379 | 1.00 | 41.09 | L111 | O |
| ATOM | 883 | CB | ALA | A | 124 | −10.886 | 11.914 | 7.533 | 1.00 | 32.82 | L111 | C |
| ATOM | 884 | N | MET | A | 125 | −9.358 | 14.555 | 7.072 | 1.00 | 38.73 | L111 | N |
| ATOM | 885 | CA | MET | A | 125 | −9.158 | 15.785 | 6.322 | 1.00 | 34.84 | L111 | C |
| ATOM | 886 | C | MET | A | 125 | −7.686 | 15.968 | 6.003 | 1.00 | 31.87 | L111 | C |
| ATOM | 887 | O | MET | A | 125 | −7.330 | 16.458 | 4.938 | 1.00 | 42.09 | L111 | O |
| ATOM | 888 | CB | MET | A | 125 | −9.671 | 16.977 | 7.126 | 1.00 | 35.51 | L111 | C |
| ATOM | 889 | CG | MET | A | 125 | −11.072 | 16.769 | 7.695 | 1.00 | 40.88 | L111 | C |
| ATOM | 890 | SD | MET | A | 125 | −12.008 | 18.287 | 7.948 | 1.00 | 45.99 | L111 | S |
| ATOM | 891 | CE | MET | A | 125 | −10.675 | 19.462 | 8.286 | 1.00 | 44.96 | L111 | C |
| ATOM | 892 | N | LYS | A | 126 | −6.831 | 15.567 | 6.930 | 1.00 | 28.09 | L111 | N |
| ATOM | 893 | CA | LYS | A | 126 | −5.397 | 15.684 | 6.730 | 1.00 | 28.15 | L111 | C |
| ATOM | 894 | C | LYS | A | 126 | −5.007 | 14.801 | 5.551 | 1.00 | 30.29 | L111 | C |
| ATOM | 895 | O | LYS | A | 126 | −4.107 | 15.129 | 4.781 | 1.00 | 32.85 | L111 | O |
| ATOM | 896 | CB | LYS | A | 126 | −4.652 | 15.229 | 7.989 | 1.00 | 34.95 | L111 | C |
| ATOM | 897 | CG | LYS | A | 126 | −4.010 | 16.351 | 8.781 | 1.00 | 28.05 | L111 | C |
| ATOM | 898 | CD | LYS | A | 126 | −4.465 | 16.328 | 10.229 | 1.00 | 31.31 | L111 | C |
| ATOM | 899 | CE | LYS | A | 126 | −3.431 | 15.676 | 11.140 | 1.00 | 39.80 | L111 | C |
| ATOM | 900 | NZ | LYS | A | 126 | −2.064 | 16.271 | 11.016 | 1.00 | 45.29 | L111 | N |
| ATOM | 901 | N | ILE | A | 127 | −5.691 | 13.669 | 5.417 | 1.00 | 32.92 | L111 | N |
| ATOM | 902 | CA | ILE | A | 127 | −5.414 | 12.748 | 4.325 | 1.00 | 29.89 | L111 | C |
| ATOM | 903 | C | ILE | A | 127 | −5.820 | 13.405 | 3.014 | 1.00 | 30.60 | L111 | C |
| ATOM | 904 | O | ILE | A | 127 | −5.024 | 13.492 | 2.086 | 1.00 | 36.08 | L111 | O |
| ATOM | 905 | CB | ILE | A | 127 | −6.179 | 11.423 | 4.501 | 1.00 | 23.98 | L111 | C |
| ATOM | 906 | CG1 | ILE | A | 127 | −5.591 | 10.649 | 5.689 | 1.00 | 33.32 | L111 | C |
| ATOM | 907 | CG2 | ILE | A | 127 | −6.074 | 10.590 | 3.234 | 1.00 | 26.83 | L111 | C |
| ATOM | 908 | CD1 | ILE | A | 127 | −6.427 | 9.465 | 6.152 | 1.00 | 25.44 | L111 | C |
| ATOM | 909 | N | ILE | A | 128 | −7.060 | 13.875 | 2.947 | 1.00 | 30.31 | L111 | N |
| ATOM | 910 | CA | ILE | A | 128 | −7.559 | 14.543 | 1.756 | 1.00 | 27.70 | L111 | C |
| ATOM | 911 | C | ILE | A | 128 | −6.681 | 15.730 | 1.359 | 1.00 | 30.19 | L111 | C |
| ATOM | 912 | O | ILE | A | 128 | −6.406 | 15.939 | 0.181 | 1.00 | 37.83 | L111 | O |
| ATOM | 913 | CB | ILE | A | 128 | −8.980 | 15.065 | 1.974 | 1.00 | 29.26 | L111 | C |
| ATOM | 914 | CG1 | ILE | A | 128 | −9.911 | 13.906 | 2.325 | 1.00 | 27.20 | L111 | C |
| ATOM | 915 | CG2 | ILE | A | 128 | −9.454 | 15.802 | 0.731 | 1.00 | 29.10 | L111 | C |
| ATOM | 916 | CD1 | ILE | A | 128 | −9.915 | 12.793 | 1.304 | 1.00 | 21.41 | L111 | C |
| ATOM | 917 | N | GLU | A | 129 | −6.245 | 16.507 | 2.342 | 1.00 | 27.35 | L111 | N |
| ATOM | 918 | CA | GLU | A | 129 | −5.412 | 17.669 | 2.065 | 1.00 | 28.43 | L111 | C |
| ATOM | 919 | C | GLU | A | 129 | −4.116 | 17.249 | 1.418 | 1.00 | 25.38 | L111 | C |
| ATOM | 920 | O | GLU | A | 129 | −3.554 | 17.983 | 0.613 | 1.00 | 33.17 | L111 | O |
| ATOM | 921 | CB | GLU | A | 129 | −5.092 | 18.429 | 3.348 | 1.00 | 39.34 | L111 | C |
| ATOM | 922 | CG | GLU | A | 129 | −6.223 | 19.289 | 3.870 | 1.00 | 49.18 | L111 | C |
| ATOM | 923 | CD | GLU | A | 129 | −6.093 | 19.546 | 5.355 | 1.00 | 57.36 | L111 | C |
| ATOM | 924 | OE1 | GLU | A | 129 | −4.942 | 19.571 | 5.849 | 1.00 | 62.27 | L111 | O |

TABLE II-continued

| | | | | | | | | | | | |
|---|---|---|---|---|---|---|---|---|---|---|---|
| ATOM | 925 | OE2 | GLU | A | 129 | −7.136 | 19.716 | 6.024 | 1.00 | 61.09 | L111 | O |
| ATOM | 926 | N | GLY | A | 130 | −3.634 | 16.071 | 1.785 | 1.00 | 24.18 | L111 | N |
| ATOM | 927 | CA | GLY | A | 130 | −2.394 | 15.591 | 1.210 | 1.00 | 21.91 | L111 | C |
| ATOM | 928 | C | GLY | A | 130 | −2.536 | 15.392 | −0.285 | 1.00 | 23.19 | L111 | C |
| ATOM | 929 | O | GLY | A | 130 | −1.597 | 15.625 | −1.042 | 1.00 | 21.99 | L111 | O |
| ATOM | 930 | N | THR | A | 131 | −3.720 | 14.962 | −0.705 | 1.00 | 22.49 | L111 | N |
| ATOM | 931 | CA | THR | A | 131 | −4.005 | 14.723 | −2.111 | 1.00 | 25.94 | L111 | C |
| ATOM | 932 | C | THR | A | 131 | −4.160 | 16.049 | −2.849 | 1.00 | 28.86 | L111 | C |
| ATOM | 933 | O | THR | A | 131 | −3.629 | 16.229 | −3.946 | 1.00 | 31.66 | L111 | O |
| ATOM | 934 | CB | THR | A | 131 | −5.292 | 13.896 | −2.270 | 1.00 | 27.10 | L111 | C |
| ATOM | 935 | OG1 | THR | A | 131 | −5.078 | 12.577 | −1.747 | 1.00 | 26.23 | L111 | O |
| ATOM | 936 | CG2 | THR | A | 131 | −5.694 | 13.808 | −3.734 | 1.00 | 27.07 | L111 | C |
| ATOM | 937 | N | ALA | A | 132 | −4.887 | 16.979 | −2.241 | 1.00 | 27.56 | L111 | N |
| ATOM | 938 | CA | ALA | A | 132 | −5.096 | 18.292 | −2.835 | 1.00 | 26.64 | L111 | C |
| ATOM | 939 | C | ALA | A | 132 | −3.753 | 18.974 | −3.058 | 1.00 | 28.30 | L111 | C |
| ATOM | 940 | O | ALA | A | 132 | −3.524 | 19.602 | −4.084 | 1.00 | 30.29 | L111 | O |
| ATOM | 941 | CB | ALA | A | 132 | −5.954 | 19.134 | −1.922 | 1.00 | 32.54 | L111 | C |
| ATOM | 942 | N | LYS | A | 133 | −2.866 | 18.843 | −2.082 | 1.00 | 29.52 | L111 | N |
| ATOM | 943 | CA | LYS | A | 133 | −1.545 | 19.443 | −2.158 | 1.00 | 27.21 | L111 | C |
| ATOM | 944 | C | LYS | A | 133 | −0.754 | 18.848 | −3.311 | 1.00 | 30.72 | L111 | C |
| ATOM | 945 | O | LYS | A | 133 | 0.190 | 19.458 | −3.813 | 1.00 | 34.77 | L111 | O |
| ATOM | 946 | CB | LYS | A | 133 | −0.784 | 19.205 | −0.846 | 1.00 | 30.61 | L111 | C |
| ATOM | 947 | CG | LYS | A | 133 | −0.843 | 20.371 | 0.138 | 1.00 | 38.23 | L111 | C |
| ATOM | 948 | CD | LYS | A | 133 | −0.782 | 19.897 | 1.581 | 1.00 | 35.27 | L111 | C |
| ATOM | 949 | CE | LYS | A | 133 | 0.653 | 19.826 | 2.079 | 1.00 | 45.39 | L111 | C |
| ATOM | 950 | NZ | LYS | A | 133 | 0.737 | 19.680 | 3.568 | 1.00 | 50.50 | L111 | N |
| ATOM | 951 | N | SER | A | 134 | −1.141 | 17.650 | −3.729 | 1.00 | 31.51 | L111 | N |
| ATOM | 952 | CA | SER | A | 134 | −0.441 | 16.966 | −4.807 | 1.00 | 33.04 | L111 | C |
| ATOM | 953 | C | SER | A | 134 | −0.969 | 17.300 | −6.202 | 1.00 | 30.13 | L111 | C |
| ATOM | 954 | O | SER | A | 134 | −0.345 | 16.952 | −7.198 | 1.00 | 27.50 | L111 | O |
| ATOM | 955 | CB | SER | A | 134 | −0.510 | 15.452 | −4.588 | 1.00 | 31.88 | L111 | C |
| ATOM | 956 | OG | SER | A | 134 | −1.741 | 14.927 | −5.055 | 1.00 | 23.70 | L111 | O |
| ATOM | 957 | N | MET | A | 135 | −2.107 | 17.977 | −6.276 | 1.00 | 26.88 | L111 | N |
| ATOM | 958 | CA | MET | A | 135 | −2.691 | 18.308 | −7.563 | 1.00 | 25.82 | L111 | C |
| ATOM | 959 | C | MET | A | 135 | −2.887 | 19.801 | −7.783 | 1.00 | 31.45 | L111 | C |
| ATOM | 960 | O | MET | A | 135 | −3.737 | 20.209 | −8.581 | 1.00 | 30.19 | L111 | O |
| ATOM | 961 | CB | MET | A | 135 | −4.029 | 17.597 | −7.711 | 1.00 | 27.23 | L111 | C |
| ATOM | 962 | CG | MET | A | 135 | −4.974 | 17.857 | −6.574 | 1.00 | 22.80 | L111 | C |
| ATOM | 963 | SD | MET | A | 135 | −6.230 | 16.597 | −6.491 | 1.00 | 37.09 | L111 | S |
| ATOM | 964 | CE | MET | A | 135 | −7.008 | 16.793 | −8.089 | 1.00 | 41.07 | L111 | C |
| ATOM | 965 | N | GLY | A | 136 | −2.105 | 20.613 | −7.078 | 1.00 | 27.82 | L111 | N |
| ATOM | 966 | CA | GLY | A | 136 | −2.215 | 22.050 | −7.228 | 1.00 | 22.84 | L111 | C |
| ATOM | 967 | C | GLY | A | 136 | −3.569 | 22.630 | −6.854 | 1.00 | 27.99 | L111 | C |
| ATOM | 968 | O | GLY | A | 136 | −4.068 | 23.538 | −7.515 | 1.00 | 33.90 | L111 | O |
| ATOM | 969 | N | ILE | A | 137 | −4.181 | 22.099 | −5.806 | 1.00 | 27.75 | L111 | N |
| ATOM | 970 | CA | ILE | A | 137 | −5.458 | 22.621 | −5.345 | 1.00 | 29.45 | L111 | C |
| ATOM | 971 | C | ILE | A | 137 | −5.207 | 23.141 | −3.934 | 1.00 | 37.77 | L111 | C |
| ATOM | 972 | O | ILE | A | 137 | −4.722 | 22.409 | −3.066 | 1.00 | 42.44 | L111 | O |
| ATOM | 973 | CB | ILE | A | 137 | −6.553 | 21.535 | −5.334 | 1.00 | 29.74 | L111 | C |
| ATOM | 974 | CG1 | ILE | A | 137 | −6.755 | 20.994 | −6.751 | 1.00 | 30.99 | L111 | C |
| ATOM | 975 | CG2 | ILE | A | 137 | −7.864 | 22.117 | −4.842 | 1.00 | 21.17 | L111 | C |
| ATOM | 976 | CD1 | ILE | A | 137 | −7.883 | 19.989 | −6.877 | 1.00 | 23.63 | L111 | C |
| ATOM | 977 | N | GLU | A | 138 | −5.508 | 24.419 | −3.723 | 1.00 | 40.79 | L111 | N |
| ATOM | 978 | CA | GLU | A | 138 | −5.299 | 25.058 | −2.435 | 1.00 | 39.24 | L111 | C |
| ATOM | 979 | C | GLU | A | 138 | −6.528 | 25.003 | −1.549 | 1.00 | 43.73 | L111 | C |
| ATOM | 980 | O | GLU | A | 138 | −7.640 | 24.799 | −2.031 | 1.00 | 48.97 | L111 | O |
| ATOM | 981 | CB | GLU | A | 138 | −4.903 | 26.506 | −2.644 | 1.00 | 41.53 | L111 | C |
| ATOM | 982 | CG | GLU | A | 138 | −3.466 | 26.787 | −2.294 | 1.00 | 59.35 | L111 | C |
| ATOM | 983 | CD | GLU | A | 138 | −3.094 | 28.228 | −2.556 | 1.00 | 67.14 | L111 | C |
| ATOM | 984 | OE1 | GLU | A | 138 | −3.950 | 28.970 | −3.098 | 1.00 | 59.01 | L111 | O |
| ATOM | 985 | OE2 | GLU | A | 138 | −1.950 | 28.613 | −2.220 | 1.00 | 67.00 | L111 | O |
| ATOM | 986 | N | VAL | A | 139 | −6.316 | 25.193 | −0.251 | 1.00 | 48.03 | L111 | N |
| ATOM | 987 | CA | VAL | A | 139 | −7.404 | 25.171 | 0.725 | 1.00 | 52.55 | L111 | C |
| ATOM | 988 | C | VAL | A | 139 | −7.561 | 26.549 | 1.370 | 1.00 | 53.32 | L111 | C |
| ATOM | 989 | O | VAL | A | 139 | −6.578 | 27.164 | 1.782 | 1.00 | 54.50 | L111 | O |
| ATOM | 990 | CB | VAL | A | 139 | −7.144 | 24.122 | 1.838 | 1.00 | 47.09 | L111 | C |
| ATOM | 991 | CG1 | VAL | A | 139 | −7.486 | 22.741 | 1.332 | 1.00 | 46.28 | L111 | C |
| ATOM | 992 | CG2 | VAL | A | 139 | −5.689 | 24.171 | 2.281 | 1.00 | 54.07 | L111 | C |
| ATOM | 993 | N | VAL | A | 140 | −8.799 | 27.028 | 1.454 | 1.00 | 57.53 | L111 | N |
| ATOM | 994 | CA | VAL | A | 140 | −9.076 | 28.334 | 2.045 | 1.00 | 58.40 | L111 | C |
| ATOM | 995 | C | VAL | A | 140 | −10.295 | 28.298 | 2.970 | 1.00 | 64.90 | L111 | C |
| ATOM | 966 | O | VAL | A | 140 | −11.243 | 27.540 | 2.674 | 1.00 | 63.16 | L111 | O |
| ATOM | 997 | CB | VAL | A | 140 | −9.321 | 29.394 | 0.950 | 1.00 | 56.76 | L111 | C |
| ATOM | 998 | CG1 | VAL | A | 140 | −8.207 | 29.343 | −0.082 | 1.00 | 48.47 | L111 | C |
| ATOM | 999 | CG2 | VAL | A | 140 | −10.667 | 29.156 | 0.288 | 1.00 | 56.93 | L111 | C |
| ATOM | 1000 | OXT | VAL | A | 140 | −10.290 | 29.036 | 3.980 | 1.00 | 72.53 | L111 | O |
| TER | 1001 | | VAL | A | 140 | | | | | | | |
| ATOM | 1002 | N | LYS | B | 71 | −21.043 | −5.854 | −42.905 | 1.00 | 63.31 | L112 | N |
| ATOM | 1003 | CA | LYS | B | 71 | −20.335 | −6.681 | −43.925 | 1.00 | 62.12 | L112 | C |

TABLE II-continued

| ATOM | 1004 | C | LYS | B | 71 | −20.331 | −8.162 | −43.563 | 1.00 | 64.08 | L112 | C |
|------|------|------|-----|---|----|---------|--------|---------|------|-------|------|---|
| ATOM | 1005 | O | LYS | B | 71 | −20.688 | −8.546 | −42.446 | 1.00 | 64.38 | L112 | O |
| ATOM | 1006 | CB | LYS | B | 71 | −18.892 | −6.202 | −44.080 | 1.00 | 58.09 | L112 | C |
| ATOM | 1007 | CG | LYS | B | 71 | −18.753 | −4.928 | −44.883 | 1.00 | 57.55 | L112 | C |
| ATOM | 1008 | CD | LYS | B | 71 | −17.414 | −4.877 | −45.584 | 1.00 | 59.51 | L112 | C |
| ATOM | 1009 | CE | LYS | B | 71 | −17.502 | −4.091 | −46.883 | 1.00 | 73.52 | L112 | C |
| ATOM | 1010 | NZ | LYS | B | 71 | −16.276 | −3.277 | −47.136 | 1.00 | 74.38 | L112 | N |
| ATOM | 1011 | N | THR | B | 72 | −19.922 | −8.992 | −44.517 | 1.00 | 60.82 | L112 | N |
| ATOM | 1012 | CA | THR | B | 72 | −19.866 | −10.432 | −44.305 | 1.00 | 53.90 | L112 | C |
| ATOM | 1013 | C | THR | B | 72 | −18.602 | −10.793 | −43.534 | 1.00 | 45.75 | L112 | C |
| ATOM | 1014 | O | THR | B | 72 | −17.573 | −10.123 | −43.661 | 1.00 | 42.26 | L112 | O |
| ATOM | 1015 | CB | THR | B | 72 | −19.881 | −11.190 | −45.647 | 1.00 | 54.39 | L112 | C |
| ATOM | 1016 | OG1 | THR | B | 72 | −20.261 | −10.291 | −46.695 | 1.00 | 53.11 | L112 | O |
| ATOM | 1017 | CG2 | THR | B | 72 | −20.877 | −12.340 | −45.603 | 1.00 | 54.95 | L112 | C |
| ATOM | 1018 | N | PRO | B | 73 | −18.664 | −11.860 | −42.721 | 1.00 | 37.48 | L112 | N |
| ATOM | 1019 | CA | PRO | B | 73 | −17.507 | −12.290 | −41.935 | 1.00 | 34.20 | L112 | C |
| ATOM | 1020 | C | PRO | B | 73 | −16.302 | −12.518 | −42.828 | 1.00 | 36.67 | L112 | C |
| ATOM | 1021 | O | PRO | B | 73 | −16.441 | −12.715 | −44.034 | 1.00 | 42.32 | L112 | O |
| ATOM | 1022 | CB | PRO | B | 73 | −17.977 | −13.578 | −41.271 | 1.00 | 35.95 | L112 | C |
| ATOM | 1023 | CG | PRO | B | 73 | −19.465 | −13.478 | −41.261 | 1.00 | 38.50 | L112 | C |
| ATOM | 1024 | CD | PRO | B | 73 | −19.831 | −12.733 | −42.504 | 1.00 | 38.65 | L112 | C |
| ATOM | 1025 | N | PRO | B | 74 | −15.097 | −12.500 | −42.247 | 1.00 | 30.98 | L112 | N |
| ATOM | 1026 | CA | PRO | B | 74 | −13.896 | −12.712 | −43.056 | 1.00 | 29.22 | L112 | C |
| ATOM | 1027 | C | PRO | B | 74 | −13.949 | −14.071 | −43.737 | 1.00 | 30.46 | L112 | C |
| ATOM | 1028 | O | PRO | B | 74 | −14.664 | −14.971 | −43.292 | 1.00 | 34.58 | L112 | O |
| ATOM | 1029 | CB | PRO | B | 74 | −12.755 | −12.620 | −42.042 | 1.00 | 26.89 | L112 | C |
| ATOM | 1030 | CG | PRO | B | 74 | −13.334 | −11.909 | −40.876 | 1.00 | 16.14 | L112 | C |
| ATOM | 1031 | CD | PRO | B | 74 | −14.773 | −12.302 | −40.828 | 1.00 | 24.82 | L112 | C |
| ATOM | 1032 | N | ALA | B | 75 | −13.196 | −14.217 | −44.819 | 1.00 | 26.98 | L112 | N |
| ATOM | 1033 | CA | ALA | B | 75 | −13.162 | −15.472 | −45.540 | 1.00 | 21.93 | L112 | C |
| ATOM | 1034 | C | ALA | B | 75 | −12.623 | −16.534 | −44.597 | 1.00 | 29.69 | L112 | C |
| ATOM | 1035 | O | ALA | B | 75 | −13.190 | −17.619 | −44.481 | 1.00 | 33.14 | L112 | O |
| ATOM | 1036 | CB | ALA | B | 75 | −12.264 | −15.346 | −46.760 | 1.00 | 29.99 | L112 | C |
| ATOM | 1037 | N | SER | B | 76 | −11.530 | −16.210 | −43.912 | 1.00 | 29.96 | L112 | N |
| ATOM | 1038 | CA | SER | B | 76 | −10.911 | −17.143 | −42.978 | 1.00 | 31.14 | L112 | C |
| ATOM | 1039 | C | SER | B | 76 | −11.908 | −17.595 | −41.918 | 1.00 | 36.21 | L112 | C |
| ATOM | 1040 | O | SER | B | 76 | −11.922 | −18.760 | −41.517 | 1.00 | 38.58 | L112 | O |
| ATOM | 1041 | CB | SER | B | 76 | −9.700 | −16.496 | −42.305 | 1.00 | 28.76 | L112 | C |
| ATOM | 1042 | OG | SER | B | 76 | −10.103 | −15.622 | −41.266 | 1.00 | 33.61 | L112 | O |
| ATOM | 1043 | N | PHE | B | 77 | −12.748 | −16.674 | −41.465 | 1.00 | 35.12 | L112 | N |
| ATOM | 1044 | CA | PHE | B | 77 | −13.731 | −17.018 | −40.457 | 1.00 | 36.06 | L112 | C |
| ATOM | 1045 | C | PHE | B | 77 | −14.684 | −18.047 | −41.025 | 1.00 | 38.63 | L112 | C |
| ATOM | 1046 | O | PHE | B | 77 | −14.874 | −19.116 | −40.448 | 1.00 | 43.61 | L112 | O |
| ATOM | 1047 | CB | PHE | B | 77 | −14.518 | −15.787 | −40.025 | 1.00 | 44.62 | L112 | C |
| ATOM | 1048 | CG | PHE | B | 77 | −15.644 | −16.097 | −39.080 | 1.00 | 47.58 | L112 | C |
| ATOM | 1049 | CD1 | PHE | B | 77 | −15.388 | −16.347 | −37.733 | 1.00 | 44.42 | L112 | C |
| ATOM | 1050 | CD2 | PHE | B | 77 | −16.959 | −16.151 | −39.536 | 1.00 | 44.81 | L112 | C |
| ATOM | 1051 | CE1 | PHE | B | 77 | −16.424 | −16.646 | −36.855 | 1.00 | 40.74 | L112 | C |
| ATOM | 1052 | CE2 | PHE | B | 77 | −18.003 | −16.449 | −38.667 | 1.00 | 42.72 | L112 | C |
| ATOM | 1053 | CZ | PHE | B | 77 | −17.736 | −16.697 | −37.322 | 1.00 | 44.82 | L112 | C |
| ATOM | 1054 | N | LEU | B | 78 | −15.288 | −17.719 | −42.161 | 1.00 | 37.81 | L112 | N |
| ATOM | 1055 | CA | LEU | B | 78 | −16.228 | −18.625 | −42.810 | 1.00 | 36.34 | L112 | C |
| ATOM | 1056 | C | LEU | B | 78 | −15.574 | −19.970 | −43.100 | 1.00 | 31.89 | L112 | C |
| ATOM | 1057 | O | LEU | B | 78 | −16.204 | −21.017 | −42.980 | 1.00 | 35.90 | L112 | O |
| ATOM | 1058 | CB | LEU | B | 78 | −16.743 | −17.998 | −44.105 | 1.00 | 34.71 | L112 | C |
| ATOM | 1059 | CG | LEU | B | 78 | −17.603 | −16.750 | −43.895 | 1.00 | 33.80 | L112 | C |
| ATOM | 1060 | CD1 | LEU | B | 78 | −18.030 | −16.182 | −45.238 | 1.00 | 29.39 | L112 | C |
| ATOM | 1061 | CD2 | LEU | B | 78 | −18.817 | −17.113 | −43.052 | 1.00 | 29.74 | L112 | C |
| ATOM | 1062 | N | LEU | B | 79 | −14.302 | −19.936 | −43.474 | 1.00 | 26.28 | L112 | N |
| ATOM | 1063 | CA | LEU | B | 79 | −13.566 | −21.153 | −43.765 | 1.00 | 31.61 | L112 | C |
| ATOM | 1064 | C | LEU | B | 79 | −13.420 | −22.002 | −42.498 | 1.00 | 39.25 | L112 | C |
| ATOM | 1065 | O | LEU | B | 79 | −13.727 | −23.194 | −42.508 | 1.00 | 40.69 | L112 | O |
| ATOM | 1066 | CB | LEU | B | 79 | −12.192 | −20.799 | −44.344 | 1.00 | 31.36 | L112 | C |
| ATOM | 1067 | CG | LEU | B | 79 | −12.229 | −20.369 | −45.816 | 1.00 | 25.54 | L112 | C |
| ATOM | 1068 | CD1 | LEU | B | 79 | −10.852 | −19.971 | −46.314 | 1.00 | 21.73 | L112 | C |
| ATOM | 1069 | CD2 | LEU | B | 79 | −12.763 | −21.520 | −46.635 | 1.00 | 23.94 | L112 | C |
| ATOM | 1070 | N | LYS | B | 80 | −12.960 | −21.384 | −41.411 | 1.00 | 44.27 | L112 | N |
| ATOM | 1071 | CA | LYS | B | 80 | −12.794 | −22.078 | −40.131 | 1.00 | 39.57 | L112 | C |
| ATOM | 1072 | C | LYS | B | 80 | −14.075 | −22.822 | −39.785 | 1.00 | 35.79 | L112 | C |
| ATOM | 1073 | O | LYS | B | 80 | −14.049 | −23.993 | −39.418 | 1.00 | 37.45 | L112 | O |
| ATOM | 1074 | CB | LYS | B | 80 | −12.500 | −21.077 | −39.008 | 1.00 | 44.26 | L112 | C |
| ATOM | 1075 | CG | LYS | B | 80 | −11.028 | −20.840 | −38.710 | 1.00 | 46.47 | L112 | C |
| ATOM | 1076 | CD | LYS | B | 80 | −10.839 | −19.591 | −37.850 | 1.00 | 45.33 | L112 | C |
| ATOM | 1077 | CE | LYS | B | 80 | −9.377 | −19.388 | −37.474 | 1.00 | 50.24 | L112 | C |
| ATOM | 1078 | NZ | LYS | B | 80 | −9.071 | −17.963 | −37.174 | 1.00 | 50.61 | L112 | N |
| ATOM | 1079 | N | LYS | B | 81 | −15.197 | −22.122 | −39.907 | 1.00 | 34.23 | L112 | N |
| ATOM | 1080 | CA | LYS | B | 81 | −16.508 | −22.682 | −39.609 | 1.00 | 39.48 | L112 | C |
| ATOM | 1081 | C | LYS | B | 81 | −16.845 | −23.880 | −40.485 | 1.00 | 42.52 | L112 | C |
| ATOM | 1082 | O | LYS | B | 81 | −17.253 | −24.929 | −39.991 | 1.00 | 49.15 | L112 | O |

TABLE II-continued

| ATOM | 1083 | CB | LYS | B | 81 | −17.580 | −21.607 | −39.787 | 1.00 | 41.03 | L112 | C |
|---|---|---|---|---|---|---|---|---|---|---|---|---|
| ATOM | 1084 | CG | LYS | B | 81 | −18.306 | −21.234 | −38.510 | 1.00 | 52.41 | L112 | C |
| ATOM | 1085 | CD | LYS | B | 81 | −19.812 | −21.200 | −38.730 | 1.00 | 68.51 | L112 | C |
| ATOM | 1086 | CE | LYS | B | 81 | −20.234 | −19.983 | −39.549 | 1.00 | 73.66 | L112 | C |
| ATOM | 1087 | NZ | LYS | B | 81 | −20.152 | −20.217 | −41.023 | 1.00 | 71.12 | L112 | N |
| ATOM | 1088 | N | ALA | B | 82 | −16.678 | −23.722 | −41.792 | 1.00 | 45.81 | L112 | N |
| ATOM | 1089 | CA | ALA | B | 82 | −16.979 | −24.800 | −42.725 | 1.00 | 44.23 | L112 | C |
| ATOM | 1090 | C | ALA | B | 82 | −16.154 | −26.049 | −42.431 | 1.00 | 40.55 | L112 | C |
| ATOM | 1091 | O | ALA | B | 82 | −16.662 | −27.165 | −42.503 | 1.00 | 39.77 | L112 | O |
| ATOM | 1092 | CB | ALA | B | 82 | −16.729 | −24.336 | −44.149 | 1.00 | 42.43 | L112 | C |
| ATOM | 1093 | N | ALA | B | 83 | −14.882 | −25.855 | −42.101 | 1.00 | 35.34 | L112 | N |
| ATOM | 1094 | CA | ALA | B | 83 | −13.990 | −26.967 | −41.807 | 1.00 | 33.10 | L112 | C |
| ATOM | 1095 | C | ALA | B | 83 | −14.259 | −27.559 | −40.431 | 1.00 | 40.90 | L112 | C |
| ATOM | 1096 | O | ALA | B | 83 | −13.797 | −28.659 | −40.123 | 1.00 | 42.00 | L112 | O |
| ATOM | 1097 | CB | ALA | B | 83 | −12.544 | −26.514 | −41.898 | 1.00 | 30.83 | L112 | C |
| ATOM | 1098 | N | GLY | B | 84 | −15.000 | −26.823 | −39.605 | 1.00 | 43.37 | L112 | N |
| ATOM | 1099 | CA | GLY | B | 84 | −15.320 | −27.292 | −38.267 | 1.00 | 40.61 | L112 | C |
| ATOM | 1100 | C | GLY | B | 84 | −14.164 | −27.194 | −37.287 | 1.00 | 41.90 | L112 | C |
| ATOM | 1101 | O | GLY | B | 84 | −14.061 | −27.997 | −36.361 | 1.00 | 45.63 | L112 | O |
| ATOM | 1102 | N | ILE | B | 85 | −13.283 | −26.222 | −37.495 | 1.00 | 40.72 | L112 | N |
| ATOM | 1103 | CA | ILE | B | 85 | −12.141 | −26.025 | −36.612 | 1.00 | 39.23 | L112 | C |
| ATOM | 1104 | C | ILE | B | 85 | −12.283 | −24.664 | −35.944 | 1.00 | 44.21 | L112 | C |
| ATOM | 1105 | O | ILE | B | 85 | −13.168 | −23.884 | −36.304 | 1.00 | 48.06 | L112 | O |
| ATOM | 1106 | CB | ILE | B | 85 | −10.801 | −26.081 | −37.388 | 1.00 | 34.91 | L112 | C |
| ATOM | 1107 | CG1 | ILE | B | 85 | −10.738 | −24.959 | −38.423 | 1.00 | 34.57 | L112 | C |
| ATOM | 1108 | CG2 | ILE | B | 85 | −10.657 | −27.425 | −38.076 | 1.00 | 33.20 | L112 | C |
| ATOM | 1109 | CD1 | ILE | B | 85 | −9.477 | −24.973 | −39.258 | 1.00 | 32.16 | L112 | C |
| ATOM | 1110 | N | GLU | B | 86 | −11.422 | −24.380 | −34.972 | 1.00 | 45.20 | L112 | N |
| ATOM | 1111 | CA | GLU | B | 86 | −11.484 | −23.108 | −34.266 | 1.00 | 43.68 | L112 | C |
| ATOM | 1112 | C | GLU | B | 86 | −10.261 | −22.245 | −34.544 | 1.00 | 41.68 | L112 | C |
| ATOM | 1113 | O | GLU | B | 86 | −10.258 | −21.049 | −34.257 | 1.00 | 47.94 | L112 | O |
| ATOM | 1114 | CB | GLU | B | 86 | −11.632 | −23.347 | −32.760 | 1.00 | 46.15 | L112 | C |
| ATOM | 1115 | CG | GLU | B | 86 | −10.322 | −23.581 | −32.020 | 1.00 | 65.68 | L112 | C |
| ATOM | 1116 | CD | GLU | B | 86 | −10.394 | −23.163 | −30.561 | 1.00 | 76.24 | L112 | C |
| ATOM | 1117 | OE1 | GLU | B | 86 | −11.440 | −23.417 | −29.922 | 1.00 | 79.61 | L112 | O |
| ATOM | 1118 | OE2 | GLU | B | 86 | −9.409 | −22.580 | −30.054 | 1.00 | 77.24 | L112 | O |
| ATOM | 1119 | N | LYS | B | 87 | −9.222 | −22.850 | −35.103 | 1.00 | 33.13 | L112 | N |
| ATOM | 1120 | CA | LYS | B | 87 | −8.011 | −22.109 | −35.416 | 1.00 | 40.07 | L112 | C |
| ATOM | 1121 | C | LYS | B | 87 | −7.423 | −22.570 | −36.741 | 1.00 | 40.26 | L112 | C |
| ATOM | 1122 | O | LYS | B | 87 | −7.610 | −23.712 | −37.150 | 1.00 | 46.66 | L112 | O |
| ATOM | 1123 | CB | LYS | B | 87 | −6.973 | −22.293 | −34.306 | 1.00 | 43.57 | L112 | C |
| ATOM | 1124 | CG | LYS | B | 87 | −7.240 | −21.468 | −33.057 | 1.00 | 57.30 | L112 | C |
| ATOM | 1125 | CD | LYS | B | 87 | −6.210 | −21.759 | −31.970 | 1.00 | 60.56 | L112 | C |
| ATOM | 1126 | CE | LYS | B | 87 | −5.750 | −20.483 | −31.279 | 1.00 | 59.04 | L112 | C |
| ATOM | 1127 | NZ | LYS | B | 87 | −6.112 | −19.261 | −32.054 | 1.00 | 64.31 | L112 | N |
| ATOM | 1128 | N | GLY | B | 88 | −6.725 | −21.671 | −37.418 | 1.00 | 34.46 | L112 | N |
| ATOM | 1129 | CA | GLY | B | 88 | −6.110 | −22.038 | −38.672 | 1.00 | 33.11 | L112 | C |
| ATOM | 1130 | C | GLY | B | 88 | −4.818 | −22.742 | −38.333 | 1.00 | 31.13 | L112 | C |
| ATOM | 1131 | O | GLY | B | 88 | −4.402 | −22.747 | −37.180 | 1.00 | 34.45 | L112 | O |
| ATOM | 1132 | N | SER | B | 89 | −4.183 | −23.345 | −39.325 | 1.00 | 31.44 | L112 | N |
| ATOM | 1133 | CA | SER | B | 89 | −2.935 | −24.043 | −39.093 | 1.00 | 29.45 | L112 | C |
| ATOM | 1134 | C | SER | B | 89 | −1.871 | −23.027 | −38.709 | 1.00 | 37.64 | L112 | C |
| ATOM | 1135 | O | SER | B | 89 | −1.904 | −21.889 | −39.167 | 1.00 | 39.44 | L112 | O |
| ATOM | 1136 | CB | SER | B | 89 | −2.519 | −24.789 | −40.357 | 1.00 | 30.04 | L112 | C |
| ATOM | 1137 | OG | SER | B | 89 | −1.138 | −25.097 | −40.339 | 1.00 | 30.69 | L112 | O |
| ATOM | 1138 | N | SER | B | 90 | −0.932 | −23.437 | −37.863 | 1.00 | 34.79 | L112 | N |
| ATOM | 1139 | CA | SER | B | 90 | 0.145 | −22.556 | −37.434 | 1.00 | 36.73 | L112 | C |
| ATOM | 1140 | C | SER | B | 90 | 1.250 | −22.593 | −38.480 | 1.00 | 37.59 | L112 | C |
| ATOM | 1141 | O | SER | B | 90 | 2.173 | −21.778 | −38.474 | 1.00 | 38.46 | L112 | O |
| ATOM | 1142 | CB | SER | B | 90 | 0.698 | −23.023 | −36.092 | 1.00 | 42.80 | L112 | C |
| ATOM | 1143 | OG | SER | B | 90 | 1.368 | −24.265 | −36.234 | 1.00 | 57.39 | L112 | O |
| ATOM | 1144 | N | GLU | B | 91 | 1.153 | −23.565 | −39.373 | 1.00 | 40.27 | L112 | N |
| ATOM | 1145 | CA | GLU | B | 91 | 2.122 | −23.726 | −40.445 | 1.00 | 44.62 | L112 | C |
| ATOM | 1146 | C | GLU | B | 91 | 1.352 | −24.125 | −41.697 | 1.00 | 42.72 | L112 | C |
| ATOM | 1147 | O | GLU | B | 91 | 1.316 | −25.295 | −42.067 | 1.00 | 49.13 | L112 | O |
| ATOM | 1148 | CB | GLU | B | 91 | 3.135 | −24.812 | −40.085 | 1.00 | 47.12 | L112 | C |
| ATOM | 1149 | CG | GLU | B | 91 | 4.520 | −24.289 | −39.768 | 1.00 | 58.48 | L112 | C |
| ATOM | 1150 | CD | GLU | B | 91 | 5.431 | −25.364 | −39.208 | 1.00 | 65.15 | L112 | C |
| ATOM | 1151 | OE1 | GLU | B | 91 | 5.935 | −26.197 | −39.997 | 1.00 | 68.92 | L112 | O |
| ATOM | 1152 | OE2 | GLU | B | 91 | 5.643 | −25.374 | −37.976 | 1.00 | 74.00 | L112 | O |
| ATOM | 1153 | N | PRO | B | 92 | 0.699 | −23.154 | −42.352 | 1.00 | 40.19 | L112 | N |
| ATOM | 1154 | CA | PRO | B | 92 | −0.071 | −23.435 | −43.566 | 1.00 | 40.89 | L112 | C |
| ATOM | 1155 | C | PRO | B | 92 | 0.736 | −24.213 | −44.603 | 1.00 | 42.71 | L112 | C |
| ATOM | 1156 | O | PRO | B | 92 | 1.955 | −24.035 | −44.720 | 1.00 | 32.77 | L112 | O |
| ATOM | 1157 | CB | PRO | B | 92 | −0.467 | −22.049 | −44.062 | 1.00 | 43.77 | L112 | C |
| ATOM | 1158 | CG | PRO | B | 92 | −0.489 | −21.217 | −42.818 | 1.00 | 42.90 | L112 | C |
| ATOM | 1159 | CD | PRO | B | 92 | 0.642 | −21.729 | −41.987 | 1.00 | 35.83 | L112 | C |
| ATOM | 1160 | N | LYS | B | 93 | 0.043 | −25.074 | −45.346 | 1.00 | 45.71 | L112 | N |
| ATOM | 1161 | CA | LYS | B | 93 | 0.656 | −25.905 | −46.380 | 1.00 | 42.76 | L112 | C |

TABLE II-continued

| | | | | | | | | | | | |
|---|---|---|---|---|---|---|---|---|---|---|---|
| ATOM | 1162 | C | LYS | B | 93 | 1.431 | −27.073 | −45.773 | 1.00 | 42.07 | L112 | C |
| ATOM | 1163 | O | LYS | B | 93 | 1.296 | −28.210 | −46.223 | 1.00 | 47.50 | L112 | O |
| ATOM | 1164 | CB | LYS | B | 93 | 1.588 | −25.068 | −47.267 | 1.00 | 46.12 | L112 | C |
| ATOM | 1165 | CG | LYS | B | 93 | 1.163 | −24.984 | −48.735 | 1.00 | 52.73 | L112 | C |
| ATOM | 1166 | CD | LYS | B | 93 | −0.145 | −24.214 | −48.924 | 1.00 | 53.15 | L112 | C |
| ATOM | 1167 | CE | LYS | B | 93 | 0.025 | −23.038 | −49.883 | 1.00 | 56.74 | L112 | C |
| ATOM | 1168 | NZ | LYS | B | 93 | 0.637 | −23.435 | −51.187 | 1.00 | 65.38 | L112 | N |
| ATOM | 1169 | N | ARG | B | 94 | 2.232 | −26.790 | −44.748 | 1.00 | 39.69 | L112 | N |
| ATOM | 1170 | CA | ARG | B | 94 | 3.028 | −27.815 | −44.077 | 1.00 | 28.33 | L112 | C |
| ATOM | 1171 | C | ARG | B | 94 | 2.200 | −28.678 | −43.134 | 1.00 | 27.71 | L112 | C |
| ATOM | 1172 | O | ARG | B | 94 | 2.515 | −29.841 | −42.919 | 1.00 | 39.31 | L112 | O |
| ATOM | 1173 | CB | ARG | B | 94 | 4.159 | −27.172 | −43.282 | 1.00 | 22.60 | L112 | C |
| ATOM | 1174 | CG | ARG | B | 94 | 5.305 | −26.668 | −44.121 | 1.00 | 29.42 | L112 | C |
| ATOM | 1175 | CD | ARG | B | 94 | 6.358 | −26.019 | −43.246 | 1.00 | 31.23 | L112 | C |
| ATOM | 1176 | NE | ARG | B | 94 | 7.463 | −25.486 | −44.033 | 1.00 | 42.70 | L112 | N |
| ATOM | 1177 | CZ | ARG | B | 94 | 8.628 | −25.108 | −43.516 | 1.00 | 56.07 | L112 | C |
| ATOM | 1178 | NH1 | ARG | B | 94 | 8.833 | −25.207 | −42.207 | 1.00 | 58.35 | L112 | N |
| ATOM | 1179 | NH2 | ARG | B | 94 | 9.584 | −24.628 | −44.304 | 1.00 | 57.97 | L112 | N |
| ATOM | 1180 | N | LYS | B | 95 | 1.146 | −28.110 | −42.568 | 1.00 | 27.38 | L112 | N |
| ATOM | 1181 | CA | LYS | B | 95 | 0.301 | −28.850 | −41.645 | 1.00 | 29.34 | L112 | C |
| ATOM | 1182 | C | LYS | B | 95 | −1.150 | −28.482 | −41.891 | 1.00 | 30.96 | L112 | C |
| ATOM | 1183 | O | LYS | B | 95 | −1.551 | −27.342 | −41.680 | 1.00 | 36.81 | L112 | O |
| ATOM | 1184 | CB | LYS | B | 95 | 0.688 | −28.513 | −40.200 | 1.00 | 39.33 | L112 | C |
| ATOM | 1185 | CG | LYS | B | 95 | 0.177 | −29.500 | −39.158 | 1.00 | 54.73 | L112 | C |
| ATOM | 1186 | CD | LYS | B | 95 | −0.879 | −28.870 | −38.249 | 1.00 | 67.65 | L112 | C |
| ATOM | 1187 | CE | LYS | B | 95 | −0.393 | −28.746 | −36.801 | 1.00 | 74.12 | L112 | C |
| ATOM | 1188 | NZ | LYS | B | 95 | −0.959 | −27.548 | −36.096 | 1.00 | 63.57 | L112 | N |
| ATOM | 1189 | N | ILE | B | 96 | −1.937 | −29.446 | −42.345 | 1.00 | 32.10 | L112 | N |
| ATOM | 1190 | CA | ILE | B | 96 | −3.347 | −29.195 | −42.614 | 1.00 | 32.15 | L112 | C |
| ATOM | 1191 | C | ILE | B | 96 | −4.165 | −29.436 | −41.353 | 1.00 | 33.56 | L112 | C |
| ATOM | 1192 | O | ILE | B | 96 | −4.075 | −30.496 | −40.739 | 1.00 | 42.84 | L112 | O |
| ATOM | 1193 | CB | ILE | B | 96 | −3.863 | −30.103 | −43.759 | 1.00 | 28.05 | L112 | C |
| ATOM | 1194 | CG1 | ILE | B | 96 | −3.017 | −29.876 | −45.014 | 1.00 | 11.50 | L112 | C |
| ATOM | 1195 | CG2 | ILE | B | 96 | −5.330 | −29.814 | −44.048 | 1.00 | 19.38 | L112 | C |
| ATOM | 1196 | CD1 | ILE | B | 96 | −2.904 | −28.429 | −45.429 | 1.00 | 19.93 | L112 | C |
| ATOM | 1197 | N | VAL | B | 97 | −4.964 | −28.448 | −40.973 | 1.00 | 32.84 | L112 | N |
| ATOM | 1198 | CA | VAL | B | 97 | −5.776 | −28.552 | −39.770 | 1.00 | 29.62 | L112 | C |
| ATOM | 1199 | C | VAL | B | 97 | −7.232 | −28.853 | −40.066 | 1.00 | 29.20 | L112 | C |
| ATOM | 1200 | O | VAL | B | 97 | −8.015 | −29.112 | −39.156 | 1.00 | 36.19 | L112 | O |
| ATOM | 1201 | CB | VAL | B | 97 | −5.717 | −27.246 | −38.949 | 1.00 | 28.85 | L112 | C |
| ATOM | 1202 | CG1 | VAL | B | 97 | −4.288 | −26.945 | −38.556 | 1.00 | 28.11 | L112 | C |
| ATOM | 1203 | CG2 | VAL | B | 97 | −6.291 | −26.094 | −39.760 | 1.00 | 28.49 | L112 | C |
| ATOM | 1204 | N | GLY | B | 98 | −7.605 | −28.811 | −41.337 | 1.00 | 34.31 | L112 | N |
| ATOM | 1205 | CA | GLY | B | 98 | −8.988 | −29.072 | −41.685 | 1.00 | 28.21 | L112 | C |
| ATOM | 1206 | C | GLY | B | 98 | −9.152 | −29.147 | −43.181 | 1.00 | 30.18 | L112 | C |
| ATOM | 1207 | O | GLY | B | 98 | −8.192 | −28.965 | −43.923 | 1.00 | 30.67 | L112 | O |
| ATOM | 1208 | N | LYS | B | 99 | −10.373 | −29.402 | −43.627 | 1.00 | 29.50 | L112 | N |
| ATOM | 1209 | CA | LYS | B | 99 | −10.634 | −29.516 | −45.046 | 1.00 | 32.51 | L112 | C |
| ATOM | 1210 | C | LYS | B | 99 | −12.080 | −29.187 | −45.374 | 1.00 | 36.44 | L112 | C |
| ATOM | 1211 | O | LYS | B | 99 | −12.976 | −29.448 | −44.575 | 1.00 | 35.95 | L112 | O |
| ATOM | 1212 | CB | LYS | B | 99 | −10.315 | −30.937 | −45.507 | 1.00 | 39.97 | L112 | C |
| ATOM | 1213 | CG | LYS | B | 99 | −10.933 | −32.025 | −44.639 | 1.00 | 41.83 | L112 | C |
| ATOM | 1214 | CD | LYS | B | 99 | −11.335 | −33.237 | −45.469 | 1.00 | 51.41 | L112 | C |
| ATOM | 1215 | CE | LYS | B | 99 | −10.486 | −34.453 | −45.134 | 1.00 | 53.02 | L112 | C |
| ATOM | 1216 | NZ | LYS | B | 99 | −11.298 | −35.553 | −44.538 | 1.00 | 66.17 | L112 | N |
| ATOM | 1217 | N | VAL | B | 100 | −12.298 | −28.609 | −46.555 | 1.00 | 40.79 | L112 | N |
| ATOM | 1218 | CA | VAL | B | 100 | −13.642 | −28.263 | −47.010 | 1.00 | 40.95 | L112 | C |
| ATOM | 1219 | C | VAL | B | 100 | −13.871 | −28.788 | −48.419 | 1.00 | 41.23 | L112 | C |
| ATOM | 1220 | O | VAL | B | 100 | −12.927 | −28.948 | −49.199 | 1.00 | 37.76 | L112 | O |
| ATOM | 1221 | CB | VAL | B | 100 | −13.877 | −26.742 | −47.033 | 1.00 | 42.14 | L112 | C |
| ATOM | 1222 | CG1 | VAL | B | 100 | −14.062 | −26.228 | −45.623 | 1.00 | 47.48 | L112 | C |
| ATOM | 1223 | CG2 | VAL | B | 100 | −12.714 | −26.049 | −47.719 | 1.00 | 46.52 | L112 | C |
| ATOM | 1224 | N | THR | B | 101 | −15.134 | −29.054 | −48.737 | 1.00 | 43.68 | L112 | N |
| ATOM | 1225 | CA | THR | B | 101 | −15.505 | −29.556 | −50.052 | 1.00 | 44.90 | L112 | C |
| ATOM | 1226 | C | THR | B | 101 | −15.572 | −28.401 | −51.030 | 1.00 | 46.97 | L112 | C |
| ATOM | 1227 | O | THR | B | 101 | −15.847 | −27.266 | −50.641 | 1.00 | 49.23 | L112 | O |
| ATOM | 1228 | CB | THR | B | 101 | −16.882 | −30.228 | −50.037 | 1.00 | 44.59 | L112 | C |
| ATOM | 1229 | OG1 | THR | B | 101 | −17.875 | −29.262 | −49.670 | 1.00 | 47.42 | L112 | O |
| ATOM | 1230 | CG2 | THR | B | 101 | −16.904 | −31.382 | −49.050 | 1.00 | 37.18 | L112 | C |
| ATOM | 1231 | N | ARG | B | 102 | −15.319 | −28.692 | −52.301 | 1.00 | 47.23 | L112 | N |
| ATOM | 1232 | CA | ARG | B | 102 | −15.376 | −27.664 | −53.324 | 1.00 | 42.99 | L112 | C |
| ATOM | 1233 | C | ARG | B | 102 | −16.760 | −27.046 | −53.255 | 1.00 | 39.27 | L112 | C |
| ATOM | 1234 | O | ARG | B | 102 | −16.947 | −25.888 | −53.609 | 1.00 | 51.83 | L112 | O |
| ATOM | 1235 | CB | ARG | B | 102 | −15.140 | −28.272 | −54.708 | 1.00 | 50.12 | L112 | C |
| ATOM | 1236 | CG | ARG | B | 102 | −14.295 | −27.405 | −55.639 | 1.00 | 58.67 | L112 | C |
| ATOM | 1237 | CD | ARG | B | 102 | −12.884 | −27.964 | −55.821 | 1.00 | 61.68 | L112 | C |
| ATOM | 1238 | NE | ARG | B | 102 | −12.827 | −29.413 | −55.632 | 1.00 | 63.94 | L112 | N |
| ATOM | 1239 | CZ | ARG | B | 102 | −11.703 | −30.124 | −55.623 | 1.00 | 67.71 | L112 | C |
| ATOM | 1240 | NH1 | ARG | B | 102 | −10.534 | −29.517 | −55.793 | 1.00 | 66.40 | L112 | N |

TABLE II-continued

| | | | | | | | | | | | |
|---|---|---|---|---|---|---|---|---|---|---|---|
| ATOM | 1241 | NH2 | ARG | B | 102 | −11.747 | −31.442 | −55.443 | 1.00 | 60.88 | L112 | N |
| ATOM | 1242 | N | LYS | B | 103 | −17.730 | −27.823 | −52.786 | 1.00 | 37.67 | L112 | N |
| ATOM | 1243 | CA | LYS | B | 103 | −19.096 | −27.333 | −52.664 | 1.00 | 41.92 | L112 | C |
| ATOM | 1244 | C | LYS | B | 103 | −19.160 | −26.308 | −51.547 | 1.00 | 44.83 | L112 | C |
| ATOM | 1245 | O | LYS | B | 103 | −19.856 | −25.298 | −51.649 | 1.00 | 49.24 | L112 | O |
| ATOM | 1246 | CB | LYS | B | 103 | −20.056 | −28.483 | −52.354 | 1.00 | 49.35 | L112 | C |
| ATOM | 1247 | CG | LYS | B | 103 | −21.265 | −28.079 | −51.510 | 1.00 | 57.47 | L112 | C |
| ATOM | 1248 | CD | LYS | B | 103 | −22.244 | −27.221 | −52.298 | 1.00 | 66.45 | L112 | C |
| ATOM | 1249 | CE | LYS | B | 103 | −23.683 | −27.670 | −52.075 | 1.00 | 76.17 | L112 | C |
| ATOM | 1250 | NZ | LYS | B | 103 | −24.099 | −27.557 | −50.645 | 1.00 | 75.72 | L112 | N |
| ATOM | 1251 | N | GLN | B | 104 | −18.434 | −26.578 | −50.471 | 1.00 | 44.97 | L112 | N |
| ATOM | 1252 | CA | GLN | B | 104 | −18.412 | −25.662 | −49.347 | 1.00 | 43.50 | L112 | C |
| ATOM | 1253 | C | GLN | B | 104 | −17.766 | −24.359 | −49.796 | 1.00 | 37.68 | L112 | C |
| ATOM | 1254 | O | GLN | B | 104 | −18.268 | −23.277 | −49.500 | 1.00 | 38.95 | L112 | O |
| ATOM | 1255 | CB | GLN | B | 104 | −17.640 | −26.279 | −48.181 | 1.00 | 47.34 | L112 | C |
| ATOM | 1256 | CG | GLN | B | 104 | −18.442 | −27.328 | −47.425 | 1.00 | 42.38 | L112 | C |
| ATOM | 1257 | CD | GLN | B | 104 | −17.693 | −27.890 | −46.237 | 1.00 | 42.53 | L112 | C |
| ATOM | 1258 | OE1 | GLN | B | 104 | −16.603 | −28.446 | −46.380 | 1.00 | 35.56 | L112 | O |
| ATOM | 1259 | NE2 | GLN | B | 104 | −18.275 | −27.745 | −45.050 | 1.00 | 36.61 | L112 | N |
| ATOM | 1260 | N | ILE | B | 105 | −16.660 | −24.471 | −50.525 | 1.00 | 30.76 | L112 | N |
| ATOM | 1261 | CA | ILE | B | 105 | −15.962 | −23.296 | −51.026 | 1.00 | 35.17 | L112 | C |
| ATOM | 1262 | C | ILE | B | 105 | −16.931 | −22.427 | −51.811 | 1.00 | 39.38 | L112 | C |
| ATOM | 1263 | O | ILE | B | 105 | −16.880 | −21.202 | −51.736 | 1.00 | 44.28 | L112 | O |
| ATOM | 1264 | CB | ILE | B | 105 | −14.808 | −23.678 | −51.962 | 1.00 | 26.23 | L112 | C |
| ATOM | 1265 | CG1 | ILE | B | 105 | −13.674 | −24.314 | −51.159 | 1.00 | 35.32 | L112 | C |
| ATOM | 1266 | CG2 | ILE | B | 105 | −14.320 | −22.442 | −52.714 | 1.00 | 30.76 | L112 | C |
| ATOM | 1267 | CD1 | ILE | B | 105 | −12.778 | −23.317 | −50.444 | 1.00 | 30.65 | L112 | C |
| ATOM | 1268 | N | GLU | B | 106 | −17.815 | −23.074 | −52.563 | 1.00 | 44.23 | L112 | N |
| ATOM | 1269 | CA | GLU | B | 106 | −18.800 | −22.367 | −53.366 | 1.00 | 48.57 | L112 | C |
| ATOM | 1270 | C | GLU | B | 106 | −19.776 | −21.590 | −52.488 | 1.00 | 50.45 | L112 | C |
| ATOM | 1271 | O | GLU | B | 106 | −20.083 | −20.430 | −52.769 | 1.00 | 52.09 | L112 | O |
| ATOM | 1272 | CB | GLU | B | 106 | −19.563 | −23.358 | −54.249 | 1.00 | 56.57 | L112 | C |
| ATOM | 1273 | CG | GLU | B | 106 | −20.814 | −22.786 | −54.920 | 1.00 | 65.87 | L112 | C |
| ATOM | 1274 | CD | GLU | B | 106 | −21.335 | −23.664 | −56.053 | 1.00 | 68.27 | L112 | C |
| ATOM | 1275 | OE1 | GLU | B | 106 | −20.505 | −24.254 | −56.781 | 1.00 | 62.09 | L112 | O |
| ATOM | 1276 | OE2 | GLU | B | 106 | −22.573 | −23.762 | −56.214 | 1.00 | 66.69 | L112 | O |
| ATOM | 1277 | N | GLU | B | 107 | −20.258 | −22.222 | −51.422 | 1.00 | 48.38 | L112 | N |
| ATOM | 1278 | CA | GLU | B | 107 | −21.204 | −21.567 | −50.523 | 1.00 | 50.26 | L112 | C |
| ATOM | 1279 | C | GLU | B | 107 | −20.610 | −20.317 | −49.890 | 1.00 | 50.25 | L112 | C |
| ATOM | 1280 | O | GLU | B | 107 | −21.311 | −19.332 | −49.661 | 1.00 | 52.98 | L112 | O |
| ATOM | 1281 | CB | GLU | B | 107 | −21.648 | −22.527 | −49.425 | 1.00 | 52.51 | L112 | C |
| ATOM | 1282 | CG | GLU | B | 107 | −22.481 | −23.685 | −49.921 | 1.00 | 72.08 | L112 | C |
| ATOM | 1283 | CD | GLU | B | 107 | −22.371 | −24.896 | −49.016 | 1.00 | 86.41 | L112 | C |
| ATOM | 1284 | OE1 | GLU | B | 107 | −21.249 | −25.188 | −48.545 | 1.00 | 91.57 | L112 | O |
| ATOM | 1285 | OE2 | GLU | B | 107 | −23.405 | −25.554 | −48.772 | 1.00 | 92.70 | L112 | O |
| ATOM | 1286 | N | ILE | B | 108 | −19.315 | −20.355 | −49.602 | 1.00 | 46.38 | L112 | N |
| ATOM | 1287 | CA | ILE | B | 108 | −18.667 | −19.206 | −48.999 | 1.00 | 43.09 | L112 | C |
| ATOM | 1288 | C | ILE | B | 108 | −18.525 | −18.099 | −50.030 | 1.00 | 42.47 | L112 | C |
| ATOM | 1289 | O | ILE | B | 108 | −18.815 | −16.937 | −49.748 | 1.00 | 47.10 | L112 | O |
| ATOM | 1290 | CB | ILE | B | 108 | −17.272 | −19.565 | −48.449 | 1.00 | 42.76 | L112 | C |
| ATOM | 1291 | CG1 | ILE | B | 108 | −17.407 | −20.613 | −47.345 | 1.00 | 35.09 | L112 | C |
| ATOM | 1292 | CG2 | ILE | B | 108 | −16.592 | −18.317 | −47.891 | 1.00 | 31.13 | L112 | C |
| ATOM | 1293 | CD1 | ILE | B | 108 | −16.084 | −21.041 | −46.747 | 1.00 | 41.11 | L112 | C |
| ATOM | 1294 | N | ALA | B | 109 | −18.081 | −18.464 | −51.229 | 1.00 | 38.62 | L112 | N |
| ATOM | 1295 | CA | ALA | B | 109 | −17.900 | −17.486 | −52.293 | 1.00 | 38.24 | L112 | C |
| ATOM | 1296 | C | ALA | B | 109 | −19.208 | −16.761 | −52.539 | 1.00 | 37.79 | L112 | C |
| ATOM | 1297 | O | ALA | B | 109 | −19.222 | −15.562 | −52.807 | 1.00 | 37.18 | L112 | O |
| ATOM | 1298 | CB | ALA | B | 109 | −17.436 | −18.172 | −53.562 | 1.00 | 38.10 | L112 | C |
| ATOM | 1299 | N | LYS | B | 110 | −20.309 | −17.497 | −52.437 | 1.00 | 38.29 | L112 | N |
| ATOM | 1300 | CA | LYS | B | 110 | −21.626 | −16.917 | −52.647 | 1.00 | 42.58 | L112 | C |
| ATOM | 1301 | C | LYS | B | 110 | −21.945 | −15.951 | −51.518 | 1.00 | 45.99 | L112 | C |
| ATOM | 1302 | O | LYS | B | 110 | −22.468 | −14.858 | −51.747 | 1.00 | 55.26 | L112 | O |
| ATOM | 1303 | CB | LYS | B | 110 | −22.689 | −18.016 | −52.702 | 1.00 | 39.40 | L112 | C |
| ATOM | 1304 | CG | LYS | B | 110 | −22.558 | −18.947 | −53.898 | 1.00 | 51.26 | L112 | C |
| ATOM | 1305 | CD | LYS | B | 110 | −23.911 | −19.512 | −54.329 | 1.00 | 60.46 | L112 | C |
| ATOM | 1306 | CE | LYS | B | 110 | −23.897 | −19.968 | −55.790 | 1.00 | 63.75 | L112 | C |
| ATOM | 1307 | NZ | LYS | B | 110 | −24.464 | −21.340 | −55.985 | 1.00 | 64.25 | L112 | N |
| ATOM | 1308 | N | THR | B | 111 | −21.620 | −16.357 | −50.297 | 1.00 | 40.79 | L112 | N |
| ATOM | 1309 | CA | THR | B | 111 | −21.876 | −15.527 | −49.134 | 1.00 | 38.24 | L112 | C |
| ATOM | 1310 | C | THR | B | 111 | −21.088 | −14.231 | −49.196 | 1.00 | 42.37 | L112 | C |
| ATOM | 1311 | O | THR | B | 111 | −21.644 | −13.152 | −48.998 | 1.00 | 48.64 | L112 | O |
| ATOM | 1312 | CB | THR | B | 111 | −21.490 | −16.256 | −47.845 | 1.00 | 42.62 | L112 | C |
| ATOM | 1313 | OG1 | THR | B | 111 | −22.140 | −17.531 | −47.812 | 1.00 | 49.22 | L112 | O |
| ATOM | 1314 | CG2 | THR | B | 111 | −21.899 | −15.441 | −46.630 | 1.00 | 41.08 | L112 | C |
| ATOM | 1315 | N | LYS | B | 112 | −19.794 | −14.346 | −49.479 | 1.00 | 41.09 | L112 | N |
| ATOM | 1316 | CA | LYS | B | 112 | −18.900 | −13.194 | −49.544 | 1.00 | 38.50 | L112 | C |
| ATOM | 1317 | C | LYS | B | 112 | −18.910 | −12.449 | −50.879 | 1.00 | 43.09 | L112 | C |
| ATOM | 1318 | O | LYS | B | 112 | −18.246 | −11.424 | −51.018 | 1.00 | 40.13 | L112 | O |
| ATOM | 1319 | CB | LYS | B | 112 | −17.467 | −13.640 | −49.240 | 1.00 | 35.11 | L112 | C |

TABLE II-continued

| | | | | | | | | | | | |
|---|---|---|---|---|---|---|---|---|---|---|---|
| ATOM | 1320 | CG | LYS | B | 112 | −17.124 | −13.715 | −47.764 | 1.00 | 33.43 | L112 | C |
| ATOM | 1321 | CD | LYS | B | 112 | −16.011 | −12.742 | −47.409 | 1.00 | 29.28 | L112 | C |
| ATOM | 1322 | CE | LYS | B | 112 | −16.567 | −11.530 | −46.680 | 1.00 | 35.42 | L112 | C |
| ATOM | 1323 | NZ | LYS | B | 112 | −15.524 | −10.509 | −46.385 | 1.00 | 31.34 | L112 | N |
| ATOM | 1324 | N | MET | B | 113 | −19.654 | −12.957 | −51.857 | 1.00 | 50.88 | L112 | N |
| ATOM | 1325 | CA | MET | B | 113 | −19.709 | −12.331 | −53.180 | 1.00 | 51.11 | L112 | C |
| ATOM | 1326 | C | MET | B | 113 | −19.879 | −10.807 | −53.156 | 1.00 | 49.15 | L112 | C |
| ATOM | 1327 | O | MET | B | 113 | −19.130 | −10.081 | −53.813 | 1.00 | 50.15 | L112 | O |
| ATOM | 1328 | CB | MET | B | 113 | −20.824 | −12.962 | −54.022 | 1.00 | 51.18 | L112 | C |
| ATOM | 1329 | CG | MET | B | 113 | −20.717 | −12.654 | −55.515 | 1.00 | 47.98 | L112 | C |
| ATOM | 1330 | SD | MET | B | 113 | −19.263 | −13.400 | −56.298 | 1.00 | 49.73 | L112 | S |
| ATOM | 1331 | CE | MET | B | 113 | −18.549 | −11.969 | −57.088 | 1.00 | 52.43 | L112 | C |
| ATOM | 1332 | N | PRO | B | 114 | −20.870 | −10.301 | −52.409 | 1.00 | 42.31 | L112 | N |
| ATOM | 1333 | CA | PRO | B | 114 | −21.051 | −8.849 | −52.369 | 1.00 | 41.88 | L112 | C |
| ATOM | 1334 | C | PRO | B | 114 | −19.781 | −8.079 | −51.997 | 1.00 | 44.88 | L112 | C |
| ATOM | 1335 | O | PRO | B | 114 | −19.589 | −6.945 | −52.439 | 1.00 | 51.97 | L112 | O |
| ATOM | 1336 | CB | PRO | B | 114 | −22.171 | −8.646 | −51.345 | 1.00 | 38.22 | L112 | C |
| ATOM | 1337 | CG | PRO | B | 114 | −22.290 | −9.946 | −50.621 | 1.00 | 43.79 | L112 | C |
| ATOM | 1338 | CD | PRO | B | 114 | −21.870 | −11.000 | −51.588 | 1.00 | 46.66 | L112 | C |
| ATOM | 1339 | N | ASP | B | 115 | −18.912 | −8.690 | −51.197 | 1.00 | 46.07 | L112 | N |
| ATOM | 1340 | CA | ASP | B | 115 | −17.673 | −8.030 | −50.785 | 1.00 | 45.61 | L112 | C |
| ATOM | 1341 | C | ASP | B | 115 | −16.506 | −8.353 | −51.709 | 1.00 | 42.88 | L112 | C |
| ATOM | 1342 | O | ASP | B | 115 | −15.435 | −7.758 | −51.598 | 1.00 | 47.89 | L112 | O |
| ATOM | 1343 | CB | ASP | B | 115 | −17.292 | −8.429 | −49.355 | 1.00 | 51.51 | L112 | C |
| ATOM | 1344 | CG | ASP | B | 115 | −18.431 | −8.252 | −48.368 | 1.00 | 50.88 | L112 | C |
| ATOM | 1345 | OD1 | ASP | B | 115 | −19.514 | −7.787 | −48.779 | 1.00 | 57.98 | L112 | O |
| ATOM | 1346 | OD2 | ASP | B | 115 | −18.240 | −8.582 | −47.178 | 1.00 | 59.37 | L112 | O |
| ATOM | 1347 | N | LEU | B | 116 | −16.713 | −9.298 | −52.618 | 1.00 | 40.70 | L112 | N |
| ATOM | 1348 | CA | LEU | B | 116 | −15.669 | −9.698 | −53.553 | 1.00 | 37.46 | L112 | C |
| ATOM | 1349 | C | LEU | B | 116 | −15.698 | −8.849 | −54.819 | 1.00 | 37.00 | L112 | C |
| ATOM | 1350 | O | LEU | B | 116 | −16.757 | −8.385 | −55.242 | 1.00 | 38.81 | L112 | O |
| ATOM | 1351 | CB | LEU | B | 116 | −15.851 | −11.169 | −53.939 | 1.00 | 40.60 | L112 | C |
| ATOM | 1352 | CG | LEU | B | 116 | −15.289 | −12.293 | −53.065 | 1.00 | 35.62 | L112 | C |
| ATOM | 1353 | CD1 | LEU | B | 116 | −14.872 | −11.765 | −51.707 | 1.00 | 42.51 | L112 | C |
| ATOM | 1354 | CD2 | LEU | B | 116 | −16.347 | −13.368 | −52.923 | 1.00 | 33.28 | L112 | C |
| ATOM | 1355 | N | ASN | B | 117 | −14.535 | −8.653 | −55.429 | 1.00 | 32.39 | L112 | N |
| ATOM | 1356 | CA | ASN | B | 117 | −14.467 | −7.886 | −56.662 | 1.00 | 32.20 | L112 | C |
| ATOM | 1357 | C | ASN | B | 117 | −14.427 | −8.835 | −57.867 | 1.00 | 37.64 | L112 | C |
| ATOM | 1358 | O | ASN | B | 117 | −14.193 | −8.415 | −59.001 | 1.00 | 35.01 | L112 | O |
| ATOM | 1359 | CB | ASN | B | 117 | −13.235 | −6.984 | −56.655 | 1.00 | 24.31 | L112 | C |
| ATOM | 1360 | CG | ASN | B | 117 | −11.952 | −7.762 | −56.709 | 1.00 | 29.72 | L112 | C |
| ATOM | 1361 | OD1 | ASN | B | 117 | −11.914 | −8.941 | −56.354 | 1.00 | 32.78 | L112 | O |
| ATOM | 1362 | ND2 | ASN | B | 117 | −10.883 | −7.110 | −57.154 | 1.00 | 25.55 | L112 | N |
| ATOM | 1363 | N | ALA | B | 118 | −14.662 | −10.117 | −57.608 | 1.00 | 39.75 | L112 | N |
| ATOM | 1364 | CA | ALA | B | 118 | −14.665 | −11.130 | −58.656 | 1.00 | 41.80 | L112 | C |
| ATOM | 1365 | C | ALA | B | 118 | −15.862 | −10.910 | −59.567 | 1.00 | 45.30 | L112 | C |
| ATOM | 1366 | O | ALA | B | 118 | −16.863 | −10.330 | −59.156 | 1.00 | 53.58 | L112 | O |
| ATOM | 1367 | CB | ALA | B | 118 | −14.734 | −12.512 | −58.043 | 1.00 | 30.65 | L112 | C |
| ATOM | 1368 | N | ASN | B | 119 | −15.760 | −11.381 | −60.804 | 1.00 | 46.03 | L112 | N |
| ATOM | 1369 | CA | ASN | B | 119 | −16.840 | −11.216 | −61.766 | 1.00 | 48.46 | L112 | C |
| ATOM | 1370 | C | ASN | B | 119 | −17.574 | −12.516 | −62.081 | 1.00 | 50.16 | L112 | C |
| ATOM | 1371 | O | ASN | B | 119 | −18.557 | −12.512 | −62.817 | 1.00 | 55.94 | L112 | O |
| ATOM | 1372 | CB | ASN | B | 119 | −16.287 | −10.625 | −63.061 | 1.00 | 49.26 | L112 | C |
| ATOM | 1373 | CG | ASN | B | 119 | −16.023 | −9.137 | −62.958 | 1.00 | 50.05 | L112 | C |
| ATOM | 1374 | OD1 | ASN | B | 119 | −16.747 | −8.407 | −62.269 | 1.00 | 48.95 | L112 | O |
| ATOM | 1375 | ND2 | ASN | B | 119 | −14.981 | −8.674 | −63.646 | 1.00 | 48.05 | L112 | N |
| ATOM | 1376 | N | SER | B | 120 | −17.096 | −13.624 | −61.527 | 1.00 | 51.92 | L112 | N |
| ATOM | 1377 | CA | SER | B | 120 | −17.711 | −14.924 | −61.771 | 1.00 | 47.70 | L112 | C |
| ATOM | 1378 | C | SER | B | 120 | −17.599 | −15.828 | −60.555 | 1.00 | 50.21 | L112 | C |
| ATOM | 1379 | O | SER | B | 120 | −16.614 | −15.770 | −59.823 | 1.00 | 58.54 | L112 | O |
| ATOM | 1380 | CB | SER | B | 120 | −17.034 | −15.609 | −62.964 | 1.00 | 46.48 | L112 | C |
| ATOM | 1381 | OG | SER | B | 120 | −15.617 | −15.558 | −62.866 | 1.00 | 29.64 | L112 | O |
| ATOM | 1382 | N | LEU | B | 121 | −18.607 | −16.670 | −60.346 | 1.00 | 49.76 | L112 | N |
| ATOM | 1383 | CA | LEU | B | 121 | −18.591 | −17.600 | −59.225 | 1.00 | 44.29 | L112 | C |
| ATOM | 1384 | C | LEU | B | 121 | −17.276 | −18.369 | −59.261 | 1.00 | 42.13 | L112 | C |
| ATOM | 1385 | O | LEU | B | 121 | −16.669 | −18.628 | −58.229 | 1.00 | 45.70 | L112 | O |
| ATOM | 1386 | CB | LEU | B | 121 | −19.760 | −18.578 | −59.327 | 1.00 | 41.45 | L112 | C |
| ATOM | 1387 | CG | LEU | B | 121 | −19.784 | −19.676 | −58.262 | 1.00 | 41.89 | L112 | C |
| ATOM | 1388 | CD1 | LEU | B | 121 | −19.585 | −19.051 | −56.890 | 1.00 | 40.55 | L112 | C |
| ATOM | 1389 | CD2 | LEU | B | 121 | −21.102 | −20.431 | −58.320 | 1.00 | 32.73 | L112 | C |
| ATOM | 1390 | N | GLU | B | 122 | −16.842 | −18.722 | −60.465 | 1.00 | 39.88 | L112 | N |
| ATOM | 1391 | CA | GLU | B | 122 | −15.593 | −19.447 | −60.666 | 1.00 | 40.08 | L112 | C |
| ATOM | 1392 | C | GLU | B | 122 | −14.444 | −18.620 | −60.091 | 1.00 | 38.04 | L112 | C |
| ATOM | 1393 | O | GLU | B | 122 | −13.606 | −19.135 | −59.355 | 1.00 | 43.79 | L112 | O |
| ATOM | 1394 | CB | GLU | B | 122 | −15.377 | −19.699 | −62.170 | 1.00 | 47.41 | L112 | C |
| ATOM | 1395 | CG | GLU | B | 122 | −14.120 | −20.496 | −62.548 | 1.00 | 66.40 | L112 | C |
| ATOM | 1396 | CD | GLU | B | 122 | −14.105 | −20.935 | −64.023 | 1.00 | 79.56 | L112 | C |
| ATOM | 1397 | OE1 | GLU | B | 122 | −15.061 | −21.614 | −64.461 | 1.00 | 83.56 | L112 | O |
| ATOM | 1398 | OE2 | GLU | B | 122 | −13.137 | −20.604 | −64.747 | 1.00 | 80.21 | L112 | O |

TABLE II-continued

| | | | | | | | | | | | |
|---|---|---|---|---|---|---|---|---|---|---|---|
| ATOM | 1399 | N | ALA | B | 123 | −14.416 | −17.332 | −60.422 | 1.00 | 37.15 | L112 | N |
| ATOM | 1400 | CA | ALA | B | 123 | −13.369 | −16.432 | −59.946 | 1.00 | 31.33 | L112 | C |
| ATOM | 1401 | C | ALA | B | 123 | −13.466 | −16.220 | −58.440 | 1.00 | 32.49 | L112 | C |
| ATOM | 1402 | O | ALA | B | 123 | −12.458 | −16.207 | −57.736 | 1.00 | 32.50 | L112 | O |
| ATOM | 1403 | CB | ALA | B | 123 | −13.472 | −15.096 | −60.655 | 1.00 | 28.73 | L112 | C |
| ATOM | 1404 | N | ALA | B | 124 | −14.689 | −16.042 | −57.958 | 1.00 | 26.80 | L112 | N |
| ATOM | 1405 | CA | ALA | B | 124 | −14.937 | −15.835 | −56.545 | 1.00 | 22.39 | L112 | C |
| ATOM | 1406 | C | ALA | B | 124 | −14.365 | −16.994 | −55.736 | 1.00 | 30.24 | L112 | C |
| ATOM | 1407 | O | ALA | B | 124 | −13.632 | −16.790 | −54.773 | 1.00 | 32.38 | L112 | O |
| ATOM | 1408 | CB | ALA | B | 124 | −16.434 | −15.714 | −56.304 | 1.00 | 19.73 | L112 | C |
| ATOM | 1409 | N | MET | B | 125 | −14.695 | −18.214 | −56.147 | 1.00 | 38.83 | L112 | N |
| ATOM | 1410 | CA | MET | B | 125 | −14.232 | −19.422 | −55.468 | 1.00 | 34.24 | L112 | C |
| ATOM | 1411 | C | MET | B | 125 | −12.718 | −19.546 | −55.464 | 1.00 | 30.68 | L112 | C |
| ATOM | 1412 | O | MET | B | 125 | −12.142 | −20.147 | −54.562 | 1.00 | 39.64 | L112 | O |
| ATOM | 1413 | CB | MET | B | 125 | −14.839 | −20.659 | −56.125 | 1.00 | 37.17 | L112 | C |
| ATOM | 1414 | CG | MET | B | 125 | −16.346 | −20.783 | −55.948 | 1.00 | 34.83 | L112 | C |
| ATOM | 1415 | SD | MET | B | 125 | −16.993 | −22.386 | −56.480 | 1.00 | 44.61 | L112 | S |
| ATOM | 1416 | CE | MET | B | 125 | −15.586 | −23.063 | −57.397 | 1.00 | 33.28 | L112 | C |
| ATOM | 1417 | N | LYS | B | 126 | −12.074 | −18.991 | −56.480 | 1.00 | 26.30 | L112 | N |
| ATOM | 1418 | CA | LYS | B | 126 | −10.622 | −19.038 | −56.558 | 1.00 | 27.93 | L112 | C |
| ATOM | 1419 | C | LYS | B | 126 | −10.072 | −18.083 | −55.503 | 1.00 | 30.79 | L112 | C |
| ATOM | 1420 | O | LYS | B | 126 | −8.932 | −18.220 | −55.056 | 1.00 | 35.96 | L112 | O |
| ATOM | 1421 | CB | LYS | B | 126 | −10.146 | −18.601 | −57.946 | 1.00 | 32.20 | L112 | C |
| ATOM | 1422 | CG | LYS | B | 126 | −10.107 | −19.703 | −58.994 | 1.00 | 27.48 | L112 | C |
| ATOM | 1423 | CD | LYS | B | 126 | −8.844 | −19.598 | −59.850 | 1.00 | 40.52 | L112 | C |
| ATOM | 1424 | CE | LYS | B | 126 | −9.159 | −19.142 | −61.268 | 1.00 | 32.95 | L112 | C |
| ATOM | 1425 | NZ | LYS | B | 126 | −9.919 | −20.188 | −62.011 | 1.00 | 51.40 | L112 | N |
| ATOM | 1426 | N | ILE | B | 127 | −10.895 | −17.110 | −55.114 | 1.00 | 31.30 | L112 | N |
| ATOM | 1427 | CA | ILE | B | 127 | −10.511 | −16.117 | −54.111 | 1.00 | 30.96 | L112 | C |
| ATOM | 1428 | C | ILE | B | 127 | −10.523 | −16.741 | −52.718 | 1.00 | 28.53 | L112 | C |
| ATOM | 1429 | O | ILE | B | 127 | −9.570 | −16.587 | −51.952 | 1.00 | 27.30 | L112 | O |
| ATOM | 1430 | CB | ILE | B | 127 | −11.469 | −14.899 | −54.139 | 1.00 | 27.50 | L112 | C |
| ATOM | 1431 | CG1 | ILE | B | 127 | −11.203 | −14.064 | −55.391 | 1.00 | 29.44 | L112 | C |
| ATOM | 1432 | CG2 | ILE | B | 127 | −11.268 | −14.038 | −52.902 | 1.00 | 28.00 | L112 | C |
| ATOM | 1433 | CD1 | ILE | B | 127 | −12.047 | −12.810 | −55.482 | 1.00 | 31.68 | L112 | C |
| ATOM | 1434 | N | ILE | B | 128 | −11.608 | −17.439 | −52.396 | 1.00 | 20.75 | L112 | N |
| ATOM | 1435 | CA | ILE | B | 128 | −11.731 | −18.104 | −51.111 | 1.00 | 18.60 | L112 | C |
| ATOM | 1436 | C | ILE | B | 128 | −10.637 | −19.152 | −50.969 | 1.00 | 23.21 | L112 | C |
| ATOM | 1437 | O | ILE | B | 128 | −9.936 | −19.202 | −49.960 | 1.00 | 34.11 | L112 | O |
| ATOM | 1438 | CB | ILE | B | 128 | −13.084 | −18.796 | −50.975 | 1.00 | 17.63 | L112 | C |
| ATOM | 1439 | CG1 | ILE | B | 128 | −14.208 | −17.807 | −51.280 | 1.00 | 17.94 | L112 | C |
| ATOM | 1440 | CG2 | ILE | B | 128 | −13.236 | −19.348 | −49.581 | 1.00 | 23.67 | L112 | C |
| ATOM | 1441 | CD1 | ILE | B | 128 | −14.138 | −16.529 | −50.469 | 1.00 | 20.35 | L112 | C |
| ATOM | 1442 | N | GLU | B | 129 | −10.488 | −19.985 | −51.989 | 1.00 | 23.93 | L112 | N |
| ATOM | 1443 | CA | GLU | B | 129 | −9.473 | −21.025 | −51.982 | 1.00 | 27.79 | L112 | C |
| ATOM | 1444 | C | GLU | B | 129 | −8.116 | −20.447 | −51.612 | 1.00 | 28.96 | L112 | C |
| ATOM | 1445 | O | GLU | B | 129 | −7.332 | −21.079 | −50.907 | 1.00 | 34.08 | L112 | O |
| ATOM | 1446 | CB | GLU | B | 129 | −9.379 | −21.666 | −53.359 | 1.00 | 43.68 | L112 | C |
| ATOM | 1447 | CG | GLU | B | 129 | −9.007 | −23.129 | −53.344 | 1.00 | 54.25 | L112 | C |
| ATOM | 1448 | CD | GLU | B | 129 | −9.708 | −23.894 | −54.445 | 1.00 | 67.26 | L112 | C |
| ATOM | 1449 | OE1 | GLU | B | 129 | −10.697 | −23.356 | −54.998 | 1.00 | 58.57 | L112 | O |
| ATOM | 1450 | OE2 | GLU | B | 129 | −9.272 | −25.027 | −54.754 | 1.00 | 76.46 | L112 | O |
| ATOM | 1451 | N | GLY | B | 130 | −7.836 | −19.248 | −52.108 | 1.00 | 29.13 | L112 | N |
| ATOM | 1452 | CA | GLY | B | 130 | −6.571 | −18.609 | −51.809 | 1.00 | 23.84 | L112 | C |
| ATOM | 1453 | C | GLY | B | 130 | −6.440 | −18.423 | −50.315 | 1.00 | 27.27 | L112 | C |
| ATOM | 1454 | O | GLY | B | 130 | −5.372 | −18.629 | −49.735 | 1.00 | 29.16 | L112 | O |
| ATOM | 1455 | N | THR | B | 131 | −7.536 | −18.031 | −49.680 | 1.00 | 19.93 | L112 | N |
| ATOM | 1456 | CA | THR | B | 131 | −7.521 | −17.839 | −48.242 | 1.00 | 27.52 | L112 | C |
| ATOM | 1457 | C | THR | B | 131 | −7.337 | −19.204 | −47.579 | 1.00 | 28.05 | L112 | C |
| ATOM | 1458 | O | THR | B | 131 | −6.453 | −19.383 | −46.741 | 1.00 | 33.97 | L112 | O |
| ATOM | 1459 | CB | THR | B | 131 | −8.832 | −17.187 | −47.758 | 1.00 | 25.95 | L112 | C |
| ATOM | 1460 | OG1 | THR | B | 131 | −8.954 | −15.883 | −48.335 | 1.00 | 19.66 | L112 | O |
| ATOM | 1461 | CG2 | THR | B | 131 | −8.836 | −17.050 | −46.255 | 1.00 | 29.87 | L112 | C |
| ATOM | 1462 | N | ALA | B | 132 | −8.164 | −20.167 | −47.977 | 1.00 | 23.92 | L112 | N |
| ATOM | 1463 | CA | ALA | B | 132 | −8.101 | −21.523 | −47.436 | 1.00 | 21.36 | L112 | C |
| ATOM | 1464 | C | ALA | B | 132 | −6.704 | −22.108 | −47.505 | 1.00 | 21.61 | L112 | C |
| ATOM | 1465 | O | ALA | B | 132 | −6.253 | −22.768 | −46.575 | 1.00 | 34.50 | L112 | O |
| ATOM | 1466 | CB | ALA | B | 132 | −9.060 | −22.428 | −48.182 | 1.00 | 19.47 | L112 | C |
| ATOM | 1467 | N | LYS | B | 133 | −6.015 | −21.870 | −48.610 | 1.00 | 25.84 | L112 | N |
| ATOM | 1468 | CA | LYS | B | 133 | −4.674 | −22.405 | −48.779 | 1.00 | 29.20 | L112 | C |
| ATOM | 1469 | C | LYS | B | 133 | −3.693 | −21.721 | −47.851 | 1.00 | 27.88 | L112 | C |
| ATOM | 1470 | O | LYS | B | 133 | −2.642 | −22.270 | −47.530 | 1.00 | 37.04 | L112 | O |
| ATOM | 1471 | CB | LYS | B | 133 | −4.213 | −22.232 | −50.230 | 1.00 | 33.18 | L112 | C |
| ATOM | 1472 | CG | LYS | B | 133 | −5.011 | −23.052 | −51.235 | 1.00 | 37.46 | L112 | C |
| ATOM | 1473 | CD | LYS | B | 133 | −4.884 | −22.487 | −52.640 | 1.00 | 50.67 | L112 | C |
| ATOM | 1474 | CE | LYS | B | 133 | −3.636 | −23.010 | −53.343 | 1.00 | 51.75 | L112 | C |
| ATOM | 1475 | NZ | LYS | B | 133 | −3.389 | −22.329 | −54.654 | 1.00 | 54.53 | L112 | N |
| ATOM | 1476 | N | SER | B | 134 | −4.042 | −20.518 | −47.416 | 1.00 | 36.66 | L112 | N |
| ATOM | 1477 | CA | SER | B | 134 | −3.168 | −19.747 | −46.539 | 1.00 | 36.64 | L112 | C |

TABLE II-continued

| | | | | | | | | | | | |
|---|---|---|---|---|---|---|---|---|---|---|---|
| ATOM | 1478 | C    | SER | B | 134 | −3.344  | −20.080 | −45.066 | 1.00 | 33.11 | L112 C |
| ATOM | 1479 | O    | SER | B | 134 | −2.635  | −19.541 | −44.223 | 1.00 | 37.50 | L112 O |
| ATOM | 1480 | CB   | SER | B | 134 | −3.414  | −18.252 | −46.741 | 1.00 | 34.18 | L112 C |
| ATOM | 1481 | OG   | SER | B | 134 | −4.603  | −17.857 | −46.080 | 1.00 | 23.48 | L112 O |
| ATOM | 1482 | N    | MET | B | 135 | −4.281  | −20.964 | −44.748 | 1.00 | 29.84 | L112 N |
| ATOM | 1483 | CA   | MET | B | 135 | −4.509  | −21.312 | −43.357 | 1.00 | 23.70 | L112 C |
| ATOM | 1484 | C    | MET | B | 135 | −4.602  | −22.808 | −43.089 | 1.00 | 29.55 | L112 C |
| ATOM | 1485 | O    | MET | B | 135 | −5.283  | −23.242 | −42.161 | 1.00 | 23.32 | L112 O |
| ATOM | 1486 | CB   | MET | B | 135 | −5.768  | −20.618 | −42.857 | 1.00 | 22.94 | L112 C |
| ATOM | 1487 | CG   | MET | B | 135 | −7.034  | −21.139 | −43.448 | 1.00 | 17.81 | L112 C |
| ATOM | 1488 | SD   | MET | B | 135 | −8.303  | −19.898 | −43.327 | 1.00 | 34.08 | L112 S |
| ATOM | 1489 | CE   | MET | B | 135 | −9.264  | −20.525 | −41.959 | 1.00 | 35.79 | L112 C |
| ATOM | 1490 | N    | GLY | B | 136 | −3.914  | −23.592 | −43.910 | 1.00 | 35.43 | L112 N |
| ATOM | 1491 | CA   | GLY | B | 136 | −3.911  | −25.030 | −43.728 | 1.00 | 27.07 | L112 C |
| ATOM | 1492 | C    | GLY | B | 136 | −5.245  | −25.737 | −43.854 | 1.00 | 28.44 | L112 C |
| ATOM | 1493 | O    | GLY | B | 136 | −5.524  | −26.683 | −43.120 | 1.00 | 30.60 | L112 O |
| ATOM | 1494 | N    | ILE | B | 137 | −6.088  | −25.289 | −44.770 | 1.00 | 27.95 | L112 N |
| ATOM | 1495 | CA   | ILE | B | 137 | −7.357  | −25.966 | −44.963 | 1.00 | 31.48 | L112 C |
| ATOM | 1496 | C    | ILE | B | 137 | −7.358  | −26.505 | −46.389 | 1.00 | 36.97 | L112 C |
| ATOM | 1497 | O    | ILE | B | 137 | −7.192  | −25.752 | −47.350 | 1.00 | 43.45 | L112 O |
| ATOM | 1498 | CB   | ILE | B | 137 | −8.547  | −25.019 | −44.736 | 1.00 | 31.35 | L112 C |
| ATOM | 1499 | CG1  | ILE | B | 137 | −8.702  | −24.756 | −43.233 | 1.00 | 30.66 | L112 C |
| ATOM | 1500 | CG2  | ILE | B | 137 | −9.826  | −25.634 | −45.302 | 1.00 | 23.26 | L112 C |
| ATOM | 1501 | CD1  | ILE | B | 137 | −9.853  | −23.843 | −42.859 | 1.00 | 19.47 | L112 C |
| ATOM | 1502 | N    | GLU | B | 138 | −7.516  | −27.820 | −46.508 | 1.00 | 34.70 | L112 N |
| ATOM | 1503 | CA   | GLU | B | 138 | −7.523  | −28.504 | −47.793 | 1.00 | 24.78 | L112 C |
| ATOM | 1504 | C    | GLU | B | 138 | −8.909  | −28.509 | −48.402 | 1.00 | 30.83 | L112 C |
| ATOM | 1505 | O    | GLU | B | 138 | −9.911  | −28.509 | −47.685 | 1.00 | 25.06 | L112 O |
| ATOM | 1506 | CB   | GLU | B | 138 | −7.065  | −29.949 | −47.617 | 1.00 | 33.57 | L112 C |
| ATOM | 1507 | CG   | GLU | B | 138 | −5.717  | −30.270 | −48.240 | 1.00 | 53.60 | L112 C |
| ATOM | 1508 | CD   | GLU | B | 138 | −5.435  | −31.769 | −48.293 | 1.00 | 61.48 | L112 C |
| ATOM | 1509 | OE1  | GLU | B | 138 | −6.286  | −32.555 | −47.810 | 1.00 | 52.54 | L112 O |
| ATOM | 1510 | OE2  | GLU | B | 138 | −4.359  | −32.152 | −48.818 | 1.00 | 61.92 | L112 O |
| ATOM | 1511 | N    | VAL | B | 139 | −8.962  | −28.518 | −49.733 | 1.00 | 36.08 | L112 N |
| ATOM | 1512 | CA   | VAL | B | 139 | −10.234 | −28.552 | −50.450 | 1.00 | 32.76 | L112 C |
| ATOM | 1513 | C    | VAL | B | 139 | −10.392 | −29.933 | −51.077 | 1.00 | 35.50 | L112 C |
| ATOM | 1514 | O    | VAL | B | 139 | −9.434  | −30.484 | −51.624 | 1.00 | 35.56 | L112 O |
| ATOM | 1515 | CB   | VAL | B | 139 | −10.293 | −27.477 | −51.557 | 1.00 | 24.66 | L112 C |
| ATOM | 1516 | CG1  | VAL | B | 139 | −11.653 | −27.507 | −52.234 | 1.00 | 22.09 | L112 C |
| ATOM | 1517 | CG2  | VAL | B | 139 | −10.044 | −26.102 | −50.959 | 1.00 | 19.96 | L112 C |
| ATOM | 1518 | N    | VAL | B | 140 | −11.593 | −30.499 | −50.978 | 1.00 | 39.97 | L112 N |
| ATOM | 1519 | CA   | VAL | B | 140 | −11.862 | −31.825 | −51.534 | 1.00 | 47.65 | L112 C |
| ATOM | 1520 | C    | VAL | B | 140 | −13.287 | −31.934 | −52.091 | 1.00 | 51.84 | L112 C |
| ATOM | 1521 | O    | VAL | B | 140 | −13.610 | −32.955 | −52.740 | 1.00 | 48.50 | L112 O |
| ATOM | 1522 | CB   | VAL | B | 140 | −11.651 | −32.933 | −50.467 | 1.00 | 46.88 | L112 C |
| ATOM | 1523 | CG1  | VAL | B | 140 | −11.479 | −34.280 | −51.152 | 1.00 | 53.45 | L112 C |
| ATOM | 1524 | CG2  | VAL | B | 140 | −10.421 | −32.628 | −49.615 | 1.00 | 37.90 | L112 C |
| ATOM | 1525 | OXT  | VAL | B | 140 | −14.071 | −30.988 | −51.877 | 1.00 | 56.26 | L112 O |
| TER  | 1526 |      | VAL | B | 140 |         |         |         |      |       |        |
| ATOM | 1527 | O5*  | G   | C | 1051 | 24.335 | −12.173 | 6.313  | 1.00 | 73.26 | RNA1 O |
| ATOM | 1528 | C5*  | G   | C | 1051 | 22.929 | −12.367 | 6.147  | 1.00 | 60.23 | RNA1 C |
| ATOM | 1529 | C4*  | G   | C | 1051 | 22.454 | −13.612 | 6.854  | 1.00 | 60.92 | RNA1 C |
| ATOM | 1530 | O4*  | G   | C | 1051 | 22.709 | −13.474 | 8.275  | 1.00 | 63.63 | RNA1 O |
| ATOM | 1531 | C3*  | G   | C | 1051 | 20.961 | −13.878 | 6.747  | 1.00 | 62.37 | RNA1 C |
| ATOM | 1532 | O3*  | G   | C | 1051 | 20.640 | −14.594 | 5.557  | 1.00 | 56.24 | RNA1 O |
| ATOM | 1533 | C2*  | G   | C | 1051 | 20.665 | −14.668 | 8.018  | 1.00 | 60.79 | RNA1 C |
| ATOM | 1534 | O2*  | G   | C | 1051 | 20.939 | −16.050 | 7.900  | 1.00 | 63.11 | RNA1 O |
| ATOM | 1535 | C1*  | G   | C | 1051 | 21.637 | −14.032 | 9.016  | 1.00 | 57.61 | RNA1 C |
| ATOM | 1536 | N9   | G   | C | 1051 | 21.014 | −12.959 | 9.786  | 1.00 | 54.68 | RNA1 N |
| ATOM | 1537 | C8   | G   | C | 1051 | 21.204 | −11.607 | 9.624  | 1.00 | 57.52 | RNA1 C |
| ATOM | 1538 | N7   | G   | C | 1051 | 20.474 | −10.887 | 10.430 | 1.00 | 63.57 | RNA1 N |
| ATOM | 1539 | C5   | G   | C | 1051 | 19.766 | −11.817 | 11.176 | 1.00 | 60.31 | RNA1 C |
| ATOM | 1540 | C6   | G   | C | 1051 | 18.808 | −11.631 | 12.205 | 1.00 | 65.69 | RNA1 C |
| ATOM | 1541 | O6   | G   | C | 1051 | 18.372 | −10.568 | 12.669 | 1.00 | 71.42 | RNA1 O |
| ATOM | 1542 | N1   | G   | C | 1051 | 18.347 | −12.847 | 12.698 | 1.00 | 61.97 | RNA1 N |
| ATOM | 1543 | C2   | G   | C | 1051 | 18.751 | −14.081 | 12.257 | 1.00 | 58.15 | RNA1 C |
| ATOM | 1544 | N2   | G   | C | 1051 | 18.193 | −15.135 | 12.861 | 1.00 | 61.86 | RNA1 N |
| ATOM | 1545 | N3   | G   | C | 1051 | 19.636 | −14.269 | 11.294 | 1.00 | 58.41 | RNA1 N |
| ATOM | 1546 | C4   | G   | C | 1051 | 20.099 | −13.101 | 10.802 | 1.00 | 56.62 | RNA1 C |
| ATOM | 1547 | P    | C   | C | 1052 | 19.126 | −14.611 | 5.015  | 1.00 | 50.79 | RNA1 P |
| ATOM | 1548 | O1P  | C   | C | 1052 | 18.620 | −13.217 | 4.973  | 1.00 | 58.55 | RNA1 O |
| ATOM | 1549 | O2P  | C   | C | 1052 | 19.094 | −15.438 | 3.784  | 1.00 | 67.52 | RNA1 O |
| ATOM | 1550 | O5*  | C   | C | 1052 | 18.323 | −15.374 | 6.155  | 1.00 | 48.31 | RNA1 O |
| ATOM | 1551 | C5*  | C   | C | 1052 | 18.502 | −16.781 | 6.372  | 1.00 | 35.63 | RNA1 C |
| ATOM | 1552 | C4*  | C   | C | 1052 | 17.510 | −17.267 | 7.392  | 1.00 | 38.42 | RNA1 C |
| ATOM | 1553 | O4*  | C   | C | 1052 | 17.824 | −16.686 | 8.682  | 1.00 | 47.16 | RNA1 O |
| ATOM | 1554 | C3*  | C   | C | 1052 | 16.087 | −16.825 | 7.117  | 1.00 | 44.09 | RNA1 C |
| ATOM | 1555 | O3*  | C   | C | 1052 | 15.438 | −17.673 | 6.200  | 1.00 | 49.32 | RNA1 O |
| ATOM | 1556 | C2*  | C   | C | 1052 | 15.449 | −16.814 | 8.499  | 1.00 | 46.87 | RNA1 C |

TABLE II-continued

| ATOM | 1557 | O2* | C | C | 1052 | 14.978 | -18.071 | 8.935 | 1.00 | 46.62 | RNA1 | O |
|------|------|-----|---|---|------|--------|---------|-------|------|-------|------|---|
| ATOM | 1558 | C1* | C | C | 1052 | 16.623 | -16.360 | 9.368 | 1.00 | 48.30 | RNA1 | C |
| ATOM | 1559 | N1 | C | C | 1052 | 16.588 | -14.902 | 9.601 | 1.00 | 47.59 | RNA1 | N |
| ATOM | 1560 | C2 | C | C | 1052 | 15.778 | -14.405 | 10.629 | 1.00 | 47.88 | RNA1 | C |
| ATOM | 1561 | O2 | C | C | 1052 | 15.145 | -15.205 | 11.338 | 1.00 | 45.47 | RNA1 | O |
| ATOM | 1562 | N3 | C | C | 1052 | 15.706 | -13.069 | 10.824 | 1.00 | 51.51 | RNA1 | N |
| ATOM | 1563 | C4 | C | C | 1052 | 16.406 | -12.242 | 10.045 | 1.00 | 47.87 | RNA1 | C |
| ATOM | 1564 | N4 | C | C | 1052 | 16.289 | -10.929 | 10.263 | 1.00 | 45.35 | RNA1 | N |
| ATOM | 1565 | C5 | C | C | 1052 | 17.252 | -12.720 | 9.006 | 1.00 | 42.28 | RNA1 | C |
| ATOM | 1566 | C6 | C | C | 1052 | 17.314 | -14.043 | 8.821 | 1.00 | 43.16 | RNA1 | C |
| ATOM | 1567 | P | U | C | 1053 | 14.314 | -17.067 | 5.236 | 1.00 | 53.77 | RNA1 | P |
| ATOM | 1568 | O1P | U | C | 1053 | 14.776 | -15.724 | 4.784 | 1.00 | 61.48 | RNA1 | O |
| ATOM | 1569 | O2P | U | C | 1053 | 13.984 | -18.106 | 4.231 | 1.00 | 67.30 | RNA1 | O |
| ATOM | 1570 | O5* | U | C | 1053 | 13.059 | -16.888 | 6.196 | 1.00 | 51.10 | RNA1 | O |
| ATOM | 1571 | C5* | U | C | 1053 | 12.448 | -18.032 | 6.809 | 1.00 | 47.98 | RNA1 | C |
| ATOM | 1572 | C4* | U | C | 1053 | 11.467 | -17.603 | 7.868 | 1.00 | 47.08 | RNA1 | C |
| ATOM | 1573 | O4* | U | C | 1053 | 12.170 | -16.895 | 8.917 | 1.00 | 48.31 | RNA1 | O |
| ATOM | 1574 | C3* | U | C | 1053 | 10.382 | -16.641 | 7.423 | 1.00 | 49.60 | RNA1 | C |
| ATOM | 1575 | O3* | U | C | 1053 | 9.295 | -17.321 | 6.812 | 1.00 | 61.44 | RNA1 | O |
| ATOM | 1576 | C2* | U | C | 1053 | 9.993 | -15.961 | 8.730 | 1.00 | 50.47 | RNA1 | C |
| ATOM | 1577 | O2* | U | C | 1053 | 9.119 | -16.731 | 9.531 | 1.00 | 43.66 | RNA1 | O |
| ATOM | 1578 | C1* | U | C | 1053 | 11.339 | -15.875 | 9.443 | 1.00 | 44.87 | RNA1 | C |
| ATOM | 1579 | N1 | U | C | 1053 | 12.003 | -14.575 | 9.247 | 1.00 | 55.73 | RNA1 | N |
| ATOM | 1580 | C2 | U | C | 1053 | 11.564 | -13.505 | 10.018 | 1.00 | 53.37 | RNA1 | C |
| ATOM | 1581 | O2 | U | C | 1053 | 10.644 | -13.591 | 10.824 | 1.00 | 47.71 | RNA1 | O |
| ATOM | 1582 | N3 | U | C | 1053 | 12.240 | -12.328 | 9.807 | 1.00 | 43.32 | RNA1 | N |
| ATOM | 1583 | C4 | U | C | 1053 | 13.281 | -12.110 | 8.928 | 1.00 | 42.60 | RNA1 | C |
| ATOM | 1584 | O4 | U | C | 1053 | 13.827 | -11.008 | 8.906 | 1.00 | 44.05 | RNA1 | O |
| ATOM | 1585 | C5 | U | C | 1053 | 13.666 | -13.253 | 8.157 | 1.00 | 39.63 | RNA1 | C |
| ATOM | 1586 | C6 | U | C | 1053 | 13.032 | -14.415 | 8.336 | 1.00 | 51.41 | RNA1 | C |
| ATOM | 1587 | P | G | C | 1054 | 8.426 | -16.576 | 5.682 | 1.00 | 62.77 | RNA1 | P |
| ATOM | 1588 | O1P | G | C | 1054 | 9.391 | -15.966 | 4.732 | 1.00 | 48.23 | RNA1 | O |
| ATOM | 1589 | O2P | G | C | 1054 | 7.391 | -17.524 | 5.177 | 1.00 | 63.46 | RNA1 | O |
| ATOM | 1590 | O5* | G | C | 1054 | 7.673 | -15.417 | 6.482 | 1.00 | 57.93 | RNA1 | O |
| ATOM | 1591 | C5* | G | C | 1054 | 6.589 | -15.737 | 7.376 | 1.00 | 58.01 | RNA1 | C |
| ATOM | 1592 | C4* | G | C | 1054 | 6.160 | -14.521 | 8.162 | 1.00 | 54.61 | RNA1 | C |
| ATOM | 1593 | O4* | G | C | 1054 | 7.279 | -14.019 | 8.937 | 1.00 | 57.89 | RNA1 | O |
| ATOM | 1594 | C3* | G | C | 1054 | 5.693 | -13.296 | 7.392 | 1.00 | 56.27 | RNA1 | C |
| ATOM | 1595 | O3* | G | C | 1054 | 4.352 | -13.378 | 6.946 | 1.00 | 61.66 | RNA1 | O |
| ATOM | 1596 | C2* | G | C | 1054 | 5.851 | -12.189 | 8.425 | 1.00 | 52.95 | RNA1 | C |
| ATOM | 1597 | O2* | G | C | 1054 | 4.779 | -12.130 | 9.346 | 1.00 | 49.43 | RNA1 | O |
| ATOM | 1598 | C1* | G | C | 1054 | 7.119 | -12.626 | 9.148 | 1.00 | 47.41 | RNA1 | C |
| ATOM | 1599 | N9 | G | C | 1054 | 8.274 | -11.911 | 8.616 | 1.00 | 41.21 | RNA1 | N |
| ATOM | 1600 | C8 | G | C | 1054 | 9.205 | -12.347 | 7.703 | 1.00 | 35.70 | RNA1 | C |
| ATOM | 1601 | N7 | G | C | 1054 | 10.100 | -11.440 | 7.414 | 1.00 | 39.32 | RNA1 | N |
| ATOM | 1602 | C5 | G | C | 1054 | 9.741 | -10.342 | 8.190 | 1.00 | 34.83 | RNA1 | C |
| ATOM | 1603 | C6 | G | C | 1054 | 10.333 | -9.051 | 8.304 | 1.00 | 30.48 | RNA1 | C |
| ATOM | 1604 | O6 | G | C | 1054 | 11.333 | -8.604 | 7.728 | 1.00 | 27.46 | RNA1 | O |
| ATOM | 1605 | N1 | G | C | 1054 | 9.635 | -8.245 | 9.199 | 1.00 | 30.56 | RNA1 | N |
| ATOM | 1606 | C2 | G | C | 1054 | 8.511 | -8.623 | 9.898 | 1.00 | 43.91 | RNA1 | C |
| ATOM | 1607 | N2 | G | C | 1054 | 7.967 | -7.703 | 10.717 | 1.00 | 37.62 | RNA1 | N |
| ATOM | 1608 | N3 | G | C | 1054 | 7.957 | -9.818 | 9.803 | 1.00 | 43.41 | RNA1 | N |
| ATOM | 1609 | C4 | G | C | 1054 | 8.619 | -10.620 | 8.938 | 1.00 | 41.38 | RNA1 | C |
| ATOM | 1610 | P | G | C | 1055 | 3.878 | -12.469 | 5.704 | 1.00 | 66.88 | RNA1 | P |
| ATOM | 1611 | O1P | G | C | 1055 | 4.889 | -12.575 | 4.612 | 1.00 | 48.03 | RNA1 | O |
| ATOM | 1612 | O2P | G | C | 1055 | 2.452 | -12.820 | 5.440 | 1.00 | 64.70 | RNA1 | O |
| ATOM | 1613 | O5* | G | C | 1055 | 3.943 | -10.971 | 6.248 | 1.00 | 63.61 | RNA1 | O |
| ATOM | 1614 | C5* | G | C | 1055 | 3.012 | -10.512 | 7.237 | 1.00 | 53.95 | RNA1 | C |
| ATOM | 1615 | C4* | G | C | 1055 | 3.371 | -9.125 | 7.706 | 1.00 | 46.33 | RNA1 | C |
| ATOM | 1616 | O4* | G | C | 1055 | 4.737 | -9.107 | 8.201 | 1.00 | 45.69 | RNA1 | O |
| ATOM | 1617 | C3* | G | C | 1055 | 3.363 | -8.001 | 6.687 | 1.00 | 40.52 | RNA1 | C |
| ATOM | 1618 | O3* | G | C | 1055 | 2.066 | -7.500 | 6.421 | 1.00 | 47.06 | RNA1 | O |
| ATOM | 1619 | C2* | G | C | 1055 | 4.212 | -6.943 | 7.377 | 1.00 | 42.04 | RNA1 | C |
| ATOM | 1620 | O2* | G | C | 1055 | 3.475 | -6.224 | 8.348 | 1.00 | 43.70 | RNA1 | O |
| ATOM | 1621 | C1* | G | C | 1055 | 5.264 | -7.798 | 8.076 | 1.00 | 31.41 | RNA1 | C |
| ATOM | 1622 | N9 | G | C | 1055 | 6.501 | -7.839 | 7.307 | 1.00 | 24.39 | RNA1 | N |
| ATOM | 1623 | C8 | G | C | 1055 | 7.026 | -8.888 | 6.592 | 1.00 | 29.37 | RNA1 | C |
| ATOM | 1624 | N7 | G | C | 1055 | 8.158 | -8.591 | 6.005 | 1.00 | 32.88 | RNA1 | N |
| ATOM | 1625 | C5 | G | C | 1055 | 8.388 | -7.266 | 6.352 | 1.00 | 23.47 | RNA1 | C |
| ATOM | 1626 | C6 | G | C | 1055 | 9.458 | -6.393 | 6.013 | 1.00 | 28.67 | RNA1 | C |
| ATOM | 1627 | O6 | G | C | 1055 | 10.450 | -6.622 | 5.314 | 1.00 | 27.35 | RNA1 | O |
| ATOM | 1628 | N1 | G | C | 1055 | 9.292 | -5.136 | 6.584 | 1.00 | 24.95 | RNA1 | N |
| ATOM | 1629 | C2 | G | C | 1055 | 8.235 | -4.763 | 7.377 | 1.00 | 26.92 | RNA1 | C |
| ATOM | 1630 | N2 | G | C | 1055 | 8.255 | -3.513 | 7.838 | 1.00 | 28.71 | RNA1 | N |
| ATOM | 1631 | N3 | G | C | 1055 | 7.234 | -5.561 | 7.696 | 1.00 | 22.90 | RNA1 | N |
| ATOM | 1632 | C4 | G | C | 1055 | 7.375 | -6.789 | 7.155 | 1.00 | 29.13 | RNA1 | C |
| ATOM | 1633 | P | G | C | 1056 | 1.758 | -6.834 | 4.989 | 1.00 | 49.25 | RNA1 | P |
| ATOM | 1634 | O1P | G | C | 1056 | 1.991 | -7.883 | 3.963 | 1.00 | 42.81 | RNA1 | O |
| ATOM | 1635 | O2P | G | C | 1056 | 0.428 | -6.158 | 5.065 | 1.00 | 37.09 | RNA1 | O |

TABLE II-continued

| | | | | | | | | | | | |
|---|---|---|---|---|---|---|---|---|---|---|---|
| ATOM | 1636 | O5* | G | C | 1056 | 2.899 | −5.734 | 4.819 | 1.00 | 32.92 | RNA1 | O |
| ATOM | 1637 | C5* | G | C | 1056 | 2.796 | −4.457 | 5.476 | 1.00 | 35.07 | RNA1 | C |
| ATOM | 1638 | C4* | G | C | 1056 | 3.939 | −3.563 | 5.065 | 1.00 | 31.58 | RNA1 | C |
| ATOM | 1639 | O4* | G | C | 1056 | 5.187 | −4.183 | 5.457 | 1.00 | 35.44 | RNA1 | O |
| ATOM | 1640 | C3* | G | C | 1056 | 4.089 | −3.329 | 3.575 | 1.00 | 34.14 | RNA1 | C |
| ATOM | 1641 | O3* | G | C | 1056 | 3.270 | −2.275 | 3.113 | 1.00 | 39.89 | RNA1 | O |
| ATOM | 1642 | C2* | G | C | 1056 | 5.567 | −3.005 | 3.429 | 1.00 | 33.87 | RNA1 | C |
| ATOM | 1643 | O2* | G | C | 1056 | 5.865 | −1.651 | 3.704 | 1.00 | 36.26 | RNA1 | O |
| ATOM | 1644 | C1* | G | C | 1056 | 6.184 | −3.915 | 4.489 | 1.00 | 31.52 | RNA1 | C |
| ATOM | 1645 | N9 | G | C | 1056 | 6.611 | −5.191 | 3.922 | 1.00 | 35.38 | RNA1 | N |
| ATOM | 1646 | C8 | G | C | 1056 | 5.874 | −6.350 | 3.845 | 1.00 | 33.57 | RNA1 | C |
| ATOM | 1647 | N7 | G | C | 1056 | 6.516 | −7.326 | 3.265 | 1.00 | 40.73 | RNA1 | N |
| ATOM | 1648 | C5 | G | C | 1056 | 7.752 | −6.782 | 2.941 | 1.00 | 37.74 | RNA1 | C |
| ATOM | 1649 | C6 | G | C | 1056 | 8.875 | −7.367 | 2.290 | 1.00 | 41.95 | RNA1 | C |
| ATOM | 1650 | O6 | G | C | 1056 | 8.999 | −8.519 | 1.852 | 1.00 | 52.67 | RNA1 | O |
| ATOM | 1651 | N1 | G | C | 1056 | 9.925 | −6.460 | 2.169 | 1.00 | 34.10 | RNA1 | N |
| ATOM | 1652 | C2 | G | C | 1056 | 9.899 | −5.160 | 2.611 | 1.00 | 28.22 | RNA1 | C |
| ATOM | 1653 | N2 | G | C | 1056 | 11.011 | −4.444 | 2.407 | 1.00 | 29.23 | RNA1 | N |
| ATOM | 1654 | N3 | G | C | 1056 | 8.860 | −4.603 | 3.211 | 1.00 | 30.05 | RNA1 | N |
| ATOM | 1655 | C4 | G | C | 1056 | 7.829 | −5.466 | 3.344 | 1.00 | 33.38 | RNA1 | C |
| ATOM | 1656 | P | A | C | 1057 | 2.647 | −2.350 | 1.636 | 1.00 | 36.51 | RNA1 | P |
| ATOM | 1657 | O1P | A | C | 1057 | 2.944 | −1.053 | 0.973 | 1.00 | 50.45 | RNA1 | O |
| ATOM | 1658 | O2P | A | C | 1057 | 3.064 | −3.614 | 0.988 | 1.00 | 31.54 | RNA1 | O |
| ATOM | 1659 | O5* | A | C | 1057 | 1.085 | −2.420 | 1.900 | 1.00 | 24.51 | RNA1 | O |
| ATOM | 1660 | C5* | A | C | 1057 | 0.516 | −3.490 | 2.659 | 1.00 | 23.76 | RNA1 | C |
| ATOM | 1661 | C4* | A | C | 1057 | −0.421 | −2.936 | 3.703 | 1.00 | 25.17 | RNA1 | C |
| ATOM | 1662 | O4* | A | C | 1057 | 0.346 | −2.384 | 4.802 | 1.00 | 26.26 | RNA1 | O |
| ATOM | 1663 | C3* | A | C | 1057 | −1.282 | −1.776 | 3.240 | 1.00 | 26.38 | RNA1 | C |
| ATOM | 1664 | O3* | A | C | 1057 | −2.429 | −2.174 | 2.517 | 1.00 | 39.01 | RNA1 | O |
| ATOM | 1665 | C2* | A | C | 1057 | −1.612 | −1.068 | 4.542 | 1.00 | 23.04 | RNA1 | C |
| ATOM | 1666 | O2* | A | C | 1057 | −2.658 | −1.705 | 5.241 | 1.00 | 26.68 | RNA1 | O |
| ATOM | 1667 | C1* | A | C | 1057 | −0.304 | −1.230 | 5.310 | 1.00 | 20.72 | RNA1 | C |
| ATOM | 1668 | N9 | A | C | 1057 | 0.587 | −0.081 | 5.125 | 1.00 | 25.31 | RNA1 | N |
| ATOM | 1669 | C8 | A | C | 1057 | 1.840 | −0.055 | 4.550 | 1.00 | 24.58 | RNA1 | C |
| ATOM | 1670 | N7 | A | C | 1057 | 2.393 | 1.135 | 4.537 | 1.00 | 16.48 | RNA1 | N |
| ATOM | 1671 | C5 | A | C | 1057 | 1.445 | 1.949 | 5.143 | 1.00 | 18.96 | RNA1 | C |
| ATOM | 1672 | C6 | A | C | 1057 | 1.428 | 3.322 | 5.438 | 1.00 | 21.91 | RNA1 | C |
| ATOM | 1673 | N6 | A | C | 1057 | 2.445 | 4.150 | 5.174 | 1.00 | 18.97 | RNA1 | N |
| ATOM | 1674 | N1 | A | C | 1057 | 0.322 | 3.824 | 6.029 | 1.00 | 28.79 | RNA1 | N |
| ATOM | 1675 | C2 | A | C | 1057 | −0.688 | 2.991 | 6.317 | 1.00 | 26.99 | RNA1 | C |
| ATOM | 1676 | N3 | A | C | 1057 | −0.786 | 1.681 | 6.104 | 1.00 | 27.54 | RNA1 | N |
| ATOM | 1677 | C4 | A | C | 1057 | 0.326 | 1.215 | 5.505 | 1.00 | 19.03 | RNA1 | C |
| ATOM | 1678 | P | U | C | 1058 | −2.943 | −1.256 | 1.300 | 1.00 | 33.80 | RNA1 | P |
| ATOM | 1679 | O1P | U | C | 1058 | −1.733 | −0.731 | 0.608 | 1.00 | 32.34 | RNA1 | O |
| ATOM | 1680 | O2P | U | C | 1058 | −3.967 | −1.996 | 0.524 | 1.00 | 30.00 | RNA1 | O |
| ATOM | 1681 | O5* | U | C | 1058 | −3.665 | −0.043 | 2.030 | 1.00 | 29.35 | RNA1 | O |
| ATOM | 1682 | C5* | U | C | 1058 | −4.955 | −0.218 | 2.627 | 1.00 | 31.01 | RNA1 | C |
| ATOM | 1683 | C4* | U | C | 1058 | −5.530 | 1.120 | 3.008 | 1.00 | 33.02 | RNA1 | C |
| ATOM | 1684 | O4* | U | C | 1058 | −4.686 | 1.734 | 4.018 | 1.00 | 32.59 | RNA1 | O |
| ATOM | 1685 | C3* | U | C | 1058 | −5.554 | 2.156 | 1.902 | 1.00 | 34.36 | RNA1 | C |
| ATOM | 1686 | O3* | U | C | 1058 | −6.626 | 2.018 | 0.993 | 1.00 | 36.65 | RNA1 | O |
| ATOM | 1687 | C2* | U | C | 1058 | −5.596 | 3.459 | 2.680 | 1.00 | 27.20 | RNA1 | C |
| ATOM | 1688 | O2* | U | C | 1058 | −6.886 | 3.727 | 3.188 | 1.00 | 26.74 | RNA1 | O |
| ATOM | 1689 | C1* | U | C | 1058 | −4.652 | 3.139 | 3.831 | 1.00 | 24.15 | RNA1 | C |
| ATOM | 1690 | N1 | U | C | 1058 | −3.267 | 3.546 | 3.532 | 1.00 | 18.02 | RNA1 | N |
| ATOM | 1691 | C2 | U | C | 1058 | −2.971 | 4.898 | 3.590 | 1.00 | 19.91 | RNA1 | C |
| ATOM | 1692 | O2 | U | C | 1058 | −3.802 | 5.750 | 3.879 | 1.00 | 30.16 | RNA1 | O |
| ATOM | 1693 | N3 | U | C | 1058 | −1.671 | 5.219 | 3.300 | 1.00 | 13.57 | RNA1 | N |
| ATOM | 1694 | C4 | U | C | 1058 | −0.655 | 4.353 | 2.965 | 1.00 | 20.26 | RNA1 | C |
| ATOM | 1695 | O4 | U | C | 1058 | 0.470 | 4.801 | 2.729 | 1.00 | 30.19 | RNA1 | O |
| ATOM | 1696 | C5 | U | C | 1058 | −1.035 | 2.981 | 2.926 | 1.00 | 12.30 | RNA1 | C |
| ATOM | 1697 | C6 | U | C | 1058 | −2.296 | 2.631 | 3.205 | 1.00 | 13.08 | RNA1 | C |
| ATOM | 1698 | P | G | C | 1059 | −6.470 | 2.631 | −0.484 | 1.00 | 30.00 | RNA1 | P |
| ATOM | 1699 | O1P | G | C | 1059 | −5.071 | 2.397 | −0.938 | 1.00 | 16.05 | RNA1 | O |
| ATOM | 1700 | O2P | G | C | 1059 | −7.607 | 2.157 | −1.311 | 1.00 | 33.73 | RNA1 | O |
| ATOM | 1701 | O5* | G | C | 1059 | −6.635 | 4.196 | −0.256 | 1.00 | 30.83 | RNA1 | O |
| ATOM | 1702 | C5* | G | C | 1059 | −7.854 | 4.731 | 0.279 | 1.00 | 22.74 | RNA1 | C |
| ATOM | 1703 | C4* | G | C | 1059 | −7.798 | 6.231 | 0.278 | 1.00 | 24.79 | RNA1 | C |
| ATOM | 1704 | O4* | G | C | 1059 | −6.727 | 6.667 | 1.149 | 1.00 | 28.49 | RNA1 | O |
| ATOM | 1705 | C3* | G | C | 1059 | −7.475 | 6.869 | −1.060 | 1.00 | 26.72 | RNA1 | C |
| ATOM | 1706 | O3* | G | C | 1059 | −8.642 | 7.007 | −1.857 | 1.00 | 34.13 | RNA1 | O |
| ATOM | 1707 | C2* | G | C | 1059 | −6.884 | 8.214 | −0.657 | 1.00 | 28.17 | RNA1 | C |
| ATOM | 1708 | O2* | G | C | 1059 | −7.880 | 9.178 | −0.371 | 1.00 | 38.10 | RNA1 | O |
| ATOM | 1709 | C1* | G | C | 1059 | −6.157 | 7.860 | 0.640 | 1.00 | 23.13 | RNA1 | C |
| ATOM | 1710 | N9 | G | C | 1059 | −4.721 | 7.665 | 0.480 | 1.00 | 15.04 | RNA1 | N |
| ATOM | 1711 | C8 | G | C | 1059 | −4.064 | 6.490 | 0.206 | 1.00 | 17.72 | RNA1 | C |
| ATOM | 1712 | N7 | G | C | 1059 | −2.766 | 6.634 | 0.130 | 1.00 | 21.45 | RNA1 | N |
| ATOM | 1713 | C5 | G | C | 1059 | −2.552 | 7.989 | 0.360 | 1.00 | 9.82 | RNA1 | C |
| ATOM | 1714 | C6 | G | C | 1059 | −1.344 | 8.740 | 0.392 | 1.00 | 23.72 | RNA1 | C |

TABLE II-continued

| | | | | | | | | | | | |
|---|---|---|---|---|---|---|---|---|---|---|---|
| ATOM | 1715 | O6 | G | C | 1059 | −0.177 | 8.344 | 0.216 | 1.00 | 19.54 | RNA1 | O |
| ATOM | 1716 | N1 | G | C | 1059 | −1.585 | 10.082 | 0.661 | 1.00 | 19.14 | RNA1 | N |
| ATOM | 1717 | C2 | G | C | 1059 | −2.822 | 10.638 | 0.874 | 1.00 | 19.08 | RNA1 | C |
| ATOM | 1718 | N2 | G | C | 1059 | −2.837 | 11.957 | 1.125 | 1.00 | 16.35 | RNA1 | N |
| ATOM | 1719 | N3 | G | C | 1059 | −3.955 | 9.953 | 0.844 | 1.00 | 20.08 | RNA1 | N |
| ATOM | 1720 | C4 | G | C | 1059 | −3.746 | 8.641 | 0.582 | 1.00 | 20.00 | RNA1 | C |
| ATOM | 1721 | P | U | C | 1060 | −8.509 | 7.045 | −3.456 | 1.00 | 31.42 | RNA1 | P |
| ATOM | 1722 | O1P | U | C | 1060 | −9.692 | 6.330 | −3.996 | 1.00 | 31.37 | RNA1 | O |
| ATOM | 1723 | O2P | U | C | 1060 | −8.243 | 8.446 | −3.872 | 1.00 | 36.54 | RNA1 | O |
| ATOM | 1724 | O5* | U | C | 1060 | −7.195 | 6.198 | −3.754 | 1.00 | 22.64 | RNA1 | O |
| ATOM | 1725 | C5* | U | C | 1060 | −7.016 | 5.523 | −5.009 | 1.00 | 22.76 | RNA1 | C |
| ATOM | 1726 | C4* | U | C | 1060 | −5.589 | 5.064 | −5.145 | 1.00 | 18.28 | RNA1 | C |
| ATOM | 1727 | O4* | U | C | 1060 | −4.739 | 6.232 | −5.160 | 1.00 | 20.83 | RNA1 | O |
| ATOM | 1728 | C3* | U | C | 1060 | −5.079 | 4.166 | −4.022 | 1.00 | 28.38 | RNA1 | C |
| ATOM | 1729 | O3* | U | C | 1060 | −4.142 | 3.234 | −4.559 | 1.00 | 34.99 | RNA1 | O |
| ATOM | 1730 | C2* | U | C | 1060 | −4.336 | 5.141 | −3.110 | 1.00 | 28.41 | RNA1 | C |
| ATOM | 1731 | O2* | U | C | 1060 | −3.277 | 4.523 | −2.401 | 1.00 | 41.53 | RNA1 | O |
| ATOM | 1732 | C1* | U | C | 1060 | −3.794 | 6.157 | −4.115 | 1.00 | 23.82 | RNA1 | C |
| ATOM | 1733 | N1 | U | C | 1060 | −3.613 | 7.518 | −3.587 | 1.00 | 15.63 | RNA1 | N |
| ATOM | 1734 | C2 | U | C | 1060 | −2.336 | 7.922 | −3.245 | 1.00 | 18.51 | RNA1 | C |
| ATOM | 1735 | O2 | U | C | 1060 | −1.353 | 7.193 | −3.325 | 1.00 | 21.06 | RNA1 | O |
| ATOM | 1736 | N3 | U | C | 1060 | −2.245 | 9.216 | −2.800 | 1.00 | 13.56 | RNA1 | N |
| ATOM | 1737 | C4 | U | C | 1060 | −3.271 | 10.129 | −2.661 | 1.00 | 21.90 | RNA1 | C |
| ATOM | 1738 | O4 | U | C | 1060 | −3.015 | 11.281 | −2.293 | 1.00 | 25.73 | RNA1 | O |
| ATOM | 1739 | C5 | U | C | 1060 | −4.559 | 9.632 | −3.018 | 1.00 | 7.65 | RNA1 | C |
| ATOM | 1740 | C6 | U | C | 1060 | −4.686 | 8.377 | −3.455 | 1.00 | 23.41 | RNA1 | C |
| ATOM | 1741 | P | U | C | 1061 | −4.622 | 2.136 | −5.633 | 1.00 | 28.90 | RNA1 | P |
| ATOM | 1742 | O1P | U | C | 1061 | −3.994 | 0.840 | −5.253 | 1.00 | 34.87 | RNA1 | O |
| ATOM | 1743 | O2P | U | C | 1061 | −6.093 | 2.222 | −5.792 | 1.00 | 16.57 | RNA1 | O |
| ATOM | 1744 | O5* | U | C | 1061 | −3.946 | 2.631 | −6.983 | 1.00 | 24.02 | RNA1 | O |
| ATOM | 1745 | C5* | U | C | 1061 | −2.514 | 2.667 | −7.117 | 1.00 | 25.58 | RNA1 | C |
| ATOM | 1746 | C4* | U | C | 1061 | −2.122 | 3.503 | −8.311 | 1.00 | 31.26 | RNA1 | C |
| ATOM | 1747 | O4* | U | C | 1061 | −2.694 | 2.914 | −9.507 | 1.00 | 36.66 | RNA1 | O |
| ATOM | 1748 | C3* | U | C | 1061 | −2.584 | 4.961 | −8.290 | 1.00 | 33.14 | RNA1 | C |
| ATOM | 1749 | O3* | U | C | 1061 | −1.601 | 5.740 | −8.967 | 1.00 | 23.50 | RNA1 | O |
| ATOM | 1750 | C2* | U | C | 1061 | −3.831 | 4.934 | −9.167 | 1.00 | 32.29 | RNA1 | C |
| ATOM | 1751 | O2* | U | C | 1061 | −4.100 | 6.183 | −9.775 | 1.00 | 33.30 | RNA1 | O |
| ATOM | 1752 | C1* | U | C | 1061 | −3.414 | 3.896 | −10.205 | 1.00 | 40.61 | RNA1 | C |
| ATOM | 1753 | N1 | U | C | 1061 | −4.461 | 3.257 | −11.015 | 1.00 | 50.51 | RNA1 | N |
| ATOM | 1754 | C2 | U | C | 1061 | −4.299 | 3.335 | −12.387 | 1.00 | 62.28 | RNA1 | C |
| ATOM | 1755 | O2 | U | C | 1061 | −3.330 | 3.880 | −12.914 | 1.00 | 62.30 | RNA1 | O |
| ATOM | 1756 | N3 | U | C | 1061 | −5.303 | 2.754 | −13.123 | 1.00 | 73.69 | RNA1 | N |
| ATOM | 1757 | C4 | U | C | 1061 | −6.427 | 2.110 | −12.641 | 1.00 | 67.10 | RNA1 | C |
| ATOM | 1758 | O4 | U | C | 1061 | −7.260 | 1.668 | −13.440 | 1.00 | 68.66 | RNA1 | O |
| ATOM | 1759 | C5 | U | C | 1061 | −6.515 | 2.056 | −11.210 | 1.00 | 54.52 | RNA1 | C |
| ATOM | 1760 | C6 | U | C | 1061 | −5.552 | 2.617 | −10.463 | 1.00 | 45.73 | RNA1 | C |
| ATOM | 1761 | P | G | C | 1062 | −0.570 | 6.637 | −8.138 | 1.00 | 27.54 | RNA1 | P |
| ATOM | 1762 | O1P | G | C | 1062 | −0.356 | 5.986 | −6.813 | 1.00 | 24.54 | RNA1 | O |
| ATOM | 1763 | O2P | G | C | 1062 | 0.600 | 6.908 | −9.017 | 1.00 | 15.00 | RNA1 | O |
| ATOM | 1764 | O5* | G | C | 1062 | −1.358 | 8.001 | −7.930 | 1.00 | 14.13 | RNA1 | O |
| ATOM | 1765 | C5* | G | C | 1062 | −2.396 | 8.125 | −6.939 | 1.00 | 22.88 | RNA1 | C |
| ATOM | 1766 | C4* | G | C | 1062 | −2.448 | 9.547 | −6.435 | 1.00 | 15.45 | RNA1 | C |
| ATOM | 1767 | O4* | G | C | 1062 | −1.246 | 9.824 | −5.677 | 1.00 | 24.75 | RNA1 | O |
| ATOM | 1768 | C3* | G | C | 1062 | −2.438 | 10.568 | −7.550 | 1.00 | 12.59 | RNA1 | C |
| ATOM | 1769 | O3* | G | C | 1062 | −3.742 | 10.823 | −8.006 | 1.00 | 33.25 | RNA1 | O |
| ATOM | 1770 | C2* | G | C | 1062 | −1.783 | 11.777 | −6.911 | 1.00 | 19.71 | RNA1 | C |
| ATOM | 1771 | O2* | G | C | 1062 | −2.709 | 12.520 | −6.141 | 1.00 | 23.78 | RNA1 | O |
| ATOM | 1772 | C1* | G | C | 1062 | −0.751 | 11.111 | −5.999 | 1.00 | 16.39 | RNA1 | C |
| ATOM | 1773 | N9 | G | C | 1062 | 0.564 | 10.927 | −6.611 | 1.00 | 14.13 | RNA1 | N |
| ATOM | 1774 | C8 | G | C | 1062 | 1.229 | 9.734 | −6.776 | 1.00 | 24.14 | RNA1 | C |
| ATOM | 1775 | N7 | G | C | 1062 | 2.388 | 9.866 | −7.361 | 1.00 | 25.47 | RNA1 | N |
| ATOM | 1776 | C5 | G | C | 1062 | 2.495 | 11.229 | −7.605 | 1.00 | 26.26 | RNA1 | C |
| ATOM | 1777 | C6 | G | C | 1062 | 3.527 | 11.966 | −8.235 | 1.00 | 31.66 | RNA1 | C |
| ATOM | 1778 | O6 | G | C | 1062 | 4.572 | 11.542 | −8.758 | 1.00 | 28.31 | RNA1 | O |
| ATOM | 1779 | N1 | G | C | 1062 | 3.246 | 13.328 | −8.243 | 1.00 | 23.22 | RNA1 | N |
| ATOM | 1780 | C2 | G | C | 1062 | 2.108 | 13.904 | −7.739 | 1.00 | 23.93 | RNA1 | C |
| ATOM | 1781 | N2 | G | C | 1062 | 2.025 | 15.238 | −7.844 | 1.00 | 18.71 | RNA1 | N |
| ATOM | 1782 | N3 | G | C | 1062 | 1.125 | 13.226 | −7.174 | 1.00 | 19.22 | RNA1 | N |
| ATOM | 1783 | C4 | G | C | 1062 | 1.384 | 11.902 | −7.137 | 1.00 | 21.18 | RNA1 | C |
| ATOM | 1784 | P | G | C | 1063 | −3.983 | 11.091 | −9.564 | 1.00 | 32.90 | RNA1 | P |
| ATOM | 1785 | O1P | G | C | 1063 | −3.162 | 10.105 | −10.324 | 1.00 | 29.07 | RNA1 | O |
| ATOM | 1786 | O2P | G | C | 1063 | −5.446 | 11.159 | −9.776 | 1.00 | 28.95 | RNA1 | O |
| ATOM | 1787 | O5* | G | C | 1063 | −3.361 | 12.534 | −9.798 | 1.00 | 32.11 | RNA1 | O |
| ATOM | 1788 | C5* | G | C | 1063 | −4.042 | 13.712 | −9.342 | 1.00 | 23.86 | RNA1 | C |
| ATOM | 1789 | C4* | G | C | 1063 | −3.302 | 14.944 | −9.798 | 1.00 | 22.38 | RNA1 | C |
| ATOM | 1790 | O4* | G | C | 1063 | −1.983 | 14.950 | −9.201 | 1.00 | 24.88 | RNA1 | O |
| ATOM | 1791 | C3* | G | C | 1063 | −3.019 | 15.022 | −11.287 | 1.00 | 26.89 | RNA1 | C |
| ATOM | 1792 | O3* | G | C | 1063 | −4.110 | 15.506 | −12.042 | 1.00 | 33.17 | RNA1 | O |
| ATOM | 1793 | C2* | G | C | 1063 | −1.806 | 15.936 | −11.343 | 1.00 | 25.82 | RNA1 | C |

TABLE II-continued

| | | | | | | | | | | | |
|---|---|---|---|---|---|---|---|---|---|---|---|
| ATOM | 1794 | O2* | G | C | 1063 | -2.149 | 17.294 | -11.168 | 1.00 | 34.75 | RNA1 | O |
| ATOM | 1795 | C1* | G | C | 1063 | -1.035 | 15.472 | -10.118 | 1.00 | 14.96 | RNA1 | C |
| ATOM | 1796 | N9 | G | C | 1063 | -0.093 | 14.412 | -10.461 | 1.00 | 16.28 | RNA1 | N |
| ATOM | 1797 | C8 | G | C | 1063 | -0.201 | 13.070 | -10.178 | 1.00 | 17.00 | RNA1 | C |
| ATOM | 1798 | N7 | G | C | 1063 | 0.820 | 12.373 | -10.602 | 1.00 | 23.95 | RNA1 | N |
| ATOM | 1799 | C5 | G | C | 1063 | 1.644 | 13.309 | -11.212 | 1.00 | 13.66 | RNA1 | C |
| ATOM | 1800 | C6 | G | C | 1063 | 2.898 | 13.151 | -11.857 | 1.00 | 19.46 | RNA1 | C |
| ATOM | 1801 | O6 | G | C | 1063 | 3.555 | 12.117 | -12.032 | 1.00 | 27.29 | RNA1 | O |
| ATOM | 1802 | N1 | G | C | 1063 | 3.385 | 14.363 | -12.326 | 1.00 | 19.82 | RNA1 | N |
| ATOM | 1803 | C2 | G | C | 1063 | 2.749 | 15.571 | -12.201 | 1.00 | 24.09 | RNA1 | C |
| ATOM | 1804 | N2 | G | C | 1063 | 3.385 | 16.631 | -12.718 | 1.00 | 33.27 | RNA1 | N |
| ATOM | 1805 | N3 | G | C | 1063 | 1.579 | 15.731 | -11.609 | 1.00 | 25.48 | RNA1 | N |
| ATOM | 1806 | C4 | G | C | 1063 | 1.091 | 14.569 | -11.137 | 1.00 | 16.05 | RNA1 | C |
| ATOM | 1807 | P | C | C | 1064 | -4.385 | 14.882 | -13.495 | 1.00 | 32.63 | RNA1 | P |
| ATOM | 1808 | O1P | C | C | 1064 | -4.311 | 13.399 | -13.376 | 1.00 | 34.14 | RNA1 | O |
| ATOM | 1809 | O2P | C | C | 1064 | -5.610 | 15.520 | -14.047 | 1.00 | 34.53 | RNA1 | O |
| ATOM | 1810 | O5* | C | C | 1064 | -3.124 | 15.351 | -14.340 | 1.00 | 25.39 | RNA1 | O |
| ATOM | 1811 | C5* | C | C | 1064 | -2.841 | 16.743 | -14.483 | 1.00 | 20.47 | RNA1 | C |
| ATOM | 1812 | C4* | C | C | 1064 | -1.510 | 16.945 | -15.158 | 1.00 | 22.15 | RNA1 | C |
| ATOM | 1813 | O4* | C | C | 1064 | -0.455 | 16.348 | -14.362 | 1.00 | 25.83 | RNA1 | O |
| ATOM | 1814 | C3* | C | C | 1064 | -1.320 | 16.321 | -16.528 | 1.00 | 29.48 | RNA1 | C |
| ATOM | 1815 | O3* | C | C | 1064 | -1.921 | 17.088 | -17.565 | 1.00 | 35.84 | RNA1 | O |
| ATOM | 1816 | C2* | C | C | 1064 | 0.199 | 16.267 | -16.648 | 1.00 | 29.04 | RNA1 | C |
| ATOM | 1817 | O2* | C | C | 1064 | 0.774 | 17.500 | -17.036 | 1.00 | 28.73 | RNA1 | O |
| ATOM | 1818 | C1* | C | C | 1064 | 0.611 | 15.958 | -15.212 | 1.00 | 21.28 | RNA1 | C |
| ATOM | 1819 | N1 | C | C | 1064 | 0.899 | 14.525 | -15.020 | 1.00 | 19.09 | RNA1 | N |
| ATOM | 1820 | C2 | C | C | 1064 | 2.155 | 14.044 | -15.409 | 1.00 | 27.83 | RNA1 | C |
| ATOM | 1821 | O2 | C | C | 1064 | 2.977 | 14.836 | -15.897 | 1.00 | 32.73 | RNA1 | O |
| ATOM | 1822 | N3 | C | C | 1064 | 2.442 | 12.734 | -15.247 | 1.00 | 23.67 | RNA1 | N |
| ATOM | 1823 | C4 | C | C | 1064 | 1.535 | 11.915 | -14.716 | 1.00 | 22.40 | RNA1 | C |
| ATOM | 1824 | N4 | C | C | 1064 | 1.871 | 10.635 | -14.564 | 1.00 | 29.03 | RNA1 | N |
| ATOM | 1825 | C5 | C | C | 1064 | 0.246 | 12.374 | -14.314 | 1.00 | 9.70 | RNA1 | C |
| ATOM | 1826 | C6 | C | C | 1064 | -0.027 | 13.674 | -14.482 | 1.00 | 20.34 | RNA1 | C |
| ATOM | 1827 | P | U | C | 1065 | -2.537 | 16.339 | -18.853 | 1.00 | 31.56 | RNA1 | P |
| ATOM | 1828 | O1P | U | C | 1065 | -3.488 | 15.293 | -18.407 | 1.00 | 29.35 | RNA1 | O |
| ATOM | 1829 | O2P | U | C | 1065 | -3.011 | 17.398 | -19.774 | 1.00 | 46.70 | RNA1 | O |
| ATOM | 1830 | O5* | U | C | 1065 | -1.266 | 15.617 | -19.495 | 1.00 | 22.04 | RNA1 | O |
| ATOM | 1831 | C5* | U | C | 1065 | -0.138 | 16.392 | -19.935 | 1.00 | 25.90 | RNA1 | C |
| ATOM | 1832 | C4* | U | C | 1065 | 1.022 | 15.492 | -20.286 | 1.00 | 32.86 | RNA1 | C |
| ATOM | 1833 | O4* | U | C | 1065 | 1.493 | 14.818 | -19.094 | 1.00 | 35.71 | RNA1 | O |
| ATOM | 1834 | C3* | U | C | 1065 | 0.721 | 14.374 | -21.270 | 1.00 | 35.55 | RNA1 | C |
| ATOM | 1835 | O3* | U | C | 1065 | 0.799 | 14.834 | -22.609 | 1.00 | 37.39 | RNA1 | O |
| ATOM | 1836 | C2* | U | C | 1065 | 1.793 | 13.340 | -20.939 | 1.00 | 36.11 | RNA1 | C |
| ATOM | 1837 | O2* | U | C | 1065 | 3.047 | 13.612 | -21.536 | 1.00 | 27.98 | RNA1 | O |
| ATOM | 1838 | C1* | U | C | 1065 | 1.917 | 13.505 | -19.423 | 1.00 | 33.40 | RNA1 | C |
| ATOM | 1839 | N1 | U | C | 1065 | 1.088 | 12.543 | -18.676 | 1.00 | 17.15 | RNA1 | N |
| ATOM | 1840 | C2 | U | C | 1065 | 1.653 | 11.323 | -18.364 | 1.00 | 21.75 | RNA1 | C |
| ATOM | 1841 | O2 | U | C | 1065 | 2.789 | 11.015 | -18.700 | 1.00 | 24.53 | RNA1 | O |
| ATOM | 1842 | N3 | U | C | 1065 | 0.841 | 10.472 | -17.652 | 1.00 | 12.86 | RNA1 | N |
| ATOM | 1843 | C4 | U | C | 1065 | -0.454 | 10.708 | -17.245 | 1.00 | 22.54 | RNA1 | C |
| ATOM | 1844 | O4 | U | C | 1065 | -1.068 | 9.829 | -16.631 | 1.00 | 33.30 | RNA1 | O |
| ATOM | 1845 | C5 | U | C | 1065 | -0.972 | 11.988 | -17.617 | 1.00 | 18.28 | RNA1 | C |
| ATOM | 1846 | C6 | U | C | 1065 | -0.202 | 12.840 | -18.300 | 1.00 | 12.72 | RNA1 | C |
| ATOM | 1847 | P | U | C | 1066 | -0.290 | 14.345 | -23.688 | 1.00 | 38.85 | RNA1 | P |
| ATOM | 1848 | O1P | U | C | 1066 | -1.664 | 14.499 | -23.126 | 1.00 | 18.29 | RNA1 | O |
| ATOM | 1849 | O2P | U | C | 1066 | 0.064 | 15.034 | -24.964 | 1.00 | 40.95 | RNA1 | O |
| ATOM | 1850 | O5* | U | C | 1066 | 0.014 | 12.790 | -23.851 | 1.00 | 36.40 | RNA1 | O |
| ATOM | 1851 | C5* | U | C | 1066 | 1.288 | 12.346 | -24.350 | 1.00 | 35.84 | RNA1 | C |
| ATOM | 1852 | C4* | U | C | 1066 | 1.461 | 10.870 | -24.107 | 1.00 | 38.35 | RNA1 | C |
| ATOM | 1853 | O4* | U | C | 1066 | 1.463 | 10.613 | -22.679 | 1.00 | 39.66 | RNA1 | O |
| ATOM | 1854 | C3* | U | C | 1066 | 0.359 | 9.974 | -24.652 | 1.00 | 44.84 | RNA1 | C |
| ATOM | 1855 | O3* | U | C | 1066 | 0.570 | 9.660 | -26.021 | 1.00 | 45.33 | RNA1 | O |
| ATOM | 1856 | C2* | U | C | 1066 | 0.473 | 8.739 | -23.769 | 1.00 | 44.55 | RNA1 | C |
| ATOM | 1857 | O2* | U | C | 1066 | 1.511 | 7.884 | -24.213 | 1.00 | 33.40 | RNA1 | O |
| ATOM | 1858 | C1* | U | C | 1066 | 0.859 | 9.357 | -22.421 | 1.00 | 39.47 | RNA1 | C |
| ATOM | 1859 | N1 | U | C | 1066 | -0.301 | 9.556 | -21.535 | 1.00 | 27.32 | RNA1 | N |
| ATOM | 1860 | C2 | U | C | 1066 | -0.598 | 8.548 | -20.630 | 1.00 | 27.94 | RNA1 | C |
| ATOM | 1861 | O2 | U | C | 1066 | 0.086 | 7.545 | -20.506 | 1.00 | 31.42 | RNA1 | O |
| ATOM | 1862 | N3 | U | C | 1066 | -1.722 | 8.759 | -19.869 | 1.00 | 19.18 | RNA1 | N |
| ATOM | 1863 | C4 | U | C | 1066 | -2.556 | 9.854 | -19.905 | 1.00 | 25.49 | RNA1 | C |
| ATOM | 1864 | O4 | U | C | 1066 | -3.565 | 9.870 | -19.194 | 1.00 | 36.42 | RNA1 | O |
| ATOM | 1865 | C5 | U | C | 1066 | -2.168 | 10.867 | -20.840 | 1.00 | 19.93 | RNA1 | C |
| ATOM | 1866 | C6 | U | C | 1066 | -1.082 | 10.689 | -21.604 | 1.00 | 23.45 | RNA1 | C |
| ATOM | 1867 | P | A | C | 1067 | -0.690 | 9.514 | -27.002 | 1.00 | 46.85 | RNA1 | P |
| ATOM | 1868 | O1P | A | C | 1067 | -1.666 | 10.598 | -26.712 | 1.00 | 36.17 | RNA1 | O |
| ATOM | 1869 | O2P | A | C | 1067 | -0.149 | 9.350 | -28.374 | 1.00 | 52.36 | RNA1 | O |
| ATOM | 1870 | O5* | A | C | 1067 | -1.379 | 8.151 | -26.562 | 1.00 | 45.01 | RNA1 | O |
| ATOM | 1871 | C5* | A | C | 1067 | -2.763 | 7.888 | -26.874 | 1.00 | 42.12 | RNA1 | C |
| ATOM | 1872 | C4* | A | C | 1067 | -3.108 | 6.464 | -26.511 | 1.00 | 37.93 | RNA1 | C |

TABLE II-continued

| ATOM | 1873 | O4* | A | C | 1067 | −2.272 | 5.567 | −27.279 | 1.00 | 37.30 | RNA1 | O |
|---|---|---|---|---|---|---|---|---|---|---|---|---|
| ATOM | 1874 | C3* | A | C | 1067 | −2.805 | 6.123 | −25.068 | 1.00 | 39.89 | RNA1 | C |
| ATOM | 1875 | O3* | A | C | 1067 | −3.905 | 6.462 | −24.244 | 1.00 | 44.47 | RNA1 | O |
| ATOM | 1876 | C2* | A | C | 1067 | −2.505 | 4.632 | −25.107 | 1.00 | 27.28 | RNA1 | C |
| ATOM | 1877 | O2* | A | C | 1067 | −3.664 | 3.829 | −25.084 | 1.00 | 44.22 | RNA1 | O |
| ATOM | 1878 | C1* | A | C | 1067 | −1.845 | 4.494 | −26.472 | 1.00 | 20.11 | RNA1 | C |
| ATOM | 1879 | N9 | A | C | 1067 | −0.389 | 4.519 | −26.443 | 1.00 | 16.55 | RNA1 | N |
| ATOM | 1880 | C8 | A | C | 1067 | 0.450 | 5.516 | −26.872 | 1.00 | 13.35 | RNA1 | C |
| ATOM | 1881 | N7 | A | C | 1067 | 1.722 | 5.206 | −26.785 | 1.00 | 21.36 | RNA1 | N |
| ATOM | 1882 | C5 | A | C | 1067 | 1.715 | 3.927 | −26.244 | 1.00 | 6.97 | RNA1 | C |
| ATOM | 1883 | C6 | A | C | 1067 | 2.746 | 3.037 | −25.917 | 1.00 | 18.48 | RNA1 | C |
| ATOM | 1884 | N6 | A | C | 1067 | 4.046 | 3.301 | −26.105 | 1.00 | 25.96 | RNA1 | N |
| ATOM | 1885 | N1 | A | C | 1067 | 2.400 | 1.845 | −25.391 | 1.00 | 13.59 | RNA1 | N |
| ATOM | 1886 | C2 | A | C | 1067 | 1.102 | 1.575 | −25.214 | 1.00 | 28.55 | RNA1 | C |
| ATOM | 1887 | N3 | A | C | 1067 | 0.041 | 2.326 | −25.488 | 1.00 | 23.97 | RNA1 | N |
| ATOM | 1888 | C4 | A | C | 1067 | 0.423 | 3.503 | −26.009 | 1.00 | 16.34 | RNA1 | C |
| ATOM | 1889 | P | G | C | 1068 | −3.632 | 7.060 | −22.783 | 1.00 | 39.02 | RNA1 | P |
| ATOM | 1890 | O1P | G | C | 1068 | −2.666 | 8.189 | −22.930 | 1.00 | 31.97 | RNA1 | O |
| ATOM | 1891 | O2P | G | C | 1068 | −4.955 | 7.282 | −22.122 | 1.00 | 23.85 | RNA1 | O |
| ATOM | 1892 | O5* | G | C | 1068 | −2.872 | 5.872 | −22.052 | 1.00 | 29.64 | RNA1 | O |
| ATOM | 1893 | C5* | G | C | 1068 | −3.560 | 4.650 | −21.753 | 1.00 | 26.14 | RNA1 | C |
| ATOM | 1894 | C4* | G | C | 1068 | −2.611 | 3.675 | −21.128 | 1.00 | 30.68 | RNA1 | C |
| ATOM | 1895 | O4* | G | C | 1068 | −1.612 | 3.299 | −22.105 | 1.00 | 33.92 | RNA1 | O |
| ATOM | 1896 | C3* | G | C | 1068 | −1.821 | 4.231 | −19.956 | 1.00 | 37.79 | RNA1 | C |
| ATOM | 1897 | O3* | G | C | 1068 | −2.586 | 4.140 | −18.752 | 1.00 | 40.54 | RNA1 | O |
| ATOM | 1898 | C2* | G | C | 1068 | −0.564 | 3.368 | −19.963 | 1.00 | 31.49 | RNA1 | C |
| ATOM | 1899 | O2* | G | C | 1068 | −0.774 | 2.123 | −19.322 | 1.00 | 38.55 | RNA1 | O |
| ATOM | 1900 | C1* | G | C | 1068 | −0.364 | 3.120 | −21.463 | 1.00 | 28.77 | RNA1 | C |
| ATOM | 1901 | N9 | G | C | 1068 | 0.605 | 3.989 | −22.123 | 1.00 | 18.63 | RNA1 | N |
| ATOM | 1902 | C8 | G | C | 1068 | 0.381 | 5.255 | −22.612 | 1.00 | 21.10 | RNA1 | C |
| ATOM | 1903 | N7 | G | C | 1068 | 1.437 | 5.779 | −23.177 | 1.00 | 18.47 | RNA1 | N |
| ATOM | 1904 | C5 | G | C | 1068 | 2.419 | 4.808 | −23.047 | 1.00 | 12.57 | RNA1 | C |
| ATOM | 1905 | C6 | G | C | 1068 | 3.776 | 4.807 | −23.476 | 1.00 | 23.53 | RNA1 | C |
| ATOM | 1906 | O6 | G | C | 1068 | 4.402 | 5.696 | −24.076 | 1.00 | 26.90 | RNA1 | O |
| ATOM | 1907 | N1 | G | C | 1068 | 4.417 | 3.616 | −23.140 | 1.00 | 26.41 | RNA1 | N |
| ATOM | 1908 | C2 | G | C | 1068 | 3.831 | 2.561 | −22.479 | 1.00 | 23.88 | RNA1 | C |
| ATOM | 1909 | N2 | G | C | 1068 | 4.625 | 1.500 | −22.232 | 1.00 | 22.10 | RNA1 | N |
| ATOM | 1910 | N3 | G | C | 1068 | 2.564 | 2.546 | −22.085 | 1.00 | 17.30 | RNA1 | N |
| ATOM | 1911 | C4 | G | C | 1068 | 1.924 | 3.695 | −22.396 | 1.00 | 15.61 | RNA1 | C |
| ATOM | 1912 | P | A | C | 1069 | −2.674 | 5.408 | −17.758 | 1.00 | 35.85 | RNA1 | P |
| ATOM | 1913 | O1P | A | C | 1069 | −2.982 | 6.639 | −18.536 | 1.00 | 34.22 | RNA1 | O |
| ATOM | 1914 | O2P | A | C | 1069 | −3.551 | 5.029 | −16.625 | 1.00 | 34.69 | RNA1 | O |
| ATOM | 1915 | O5* | A | C | 1069 | −1.186 | 5.532 | −17.220 | 1.00 | 22.83 | RNA1 | O |
| ATOM | 1916 | C5* | A | C | 1069 | −0.570 | 4.437 | −16.545 | 1.00 | 16.26 | RNA1 | C |
| ATOM | 1917 | C4* | A | C | 1069 | 0.859 | 4.768 | −16.237 | 1.00 | 21.94 | RNA1 | C |
| ATOM | 1918 | O4* | A | C | 1069 | 1.694 | 4.585 | −17.417 | 1.00 | 35.64 | RNA1 | O |
| ATOM | 1919 | C3* | A | C | 1069 | 1.093 | 6.209 | −15.768 | 1.00 | 37.69 | RNA1 | C |
| ATOM | 1920 | O3* | A | C | 1069 | 2.058 | 6.196 | −14.714 | 1.00 | 40.68 | RNA1 | O |
| ATOM | 1921 | C2* | A | C | 1069 | 1.737 | 6.855 | −16.996 | 1.00 | 39.67 | RNA1 | C |
| ATOM | 1922 | O2* | A | C | 1069 | 2.583 | 7.960 | −16.731 | 1.00 | 43.60 | RNA1 | O |
| ATOM | 1923 | C1* | A | C | 1069 | 2.567 | 5.680 | −17.491 | 1.00 | 37.65 | RNA1 | C |
| ATOM | 1924 | N9 | A | C | 1069 | 3.223 | 5.772 | −18.793 | 1.00 | 33.82 | RNA1 | N |
| ATOM | 1925 | C8 | A | C | 1069 | 2.972 | 6.600 | −19.858 | 1.00 | 28.66 | RNA1 | C |
| ATOM | 1926 | N7 | A | C | 1069 | 3.878 | 6.527 | −20.805 | 1.00 | 37.91 | RNA1 | N |
| ATOM | 1927 | C5 | A | C | 1069 | 4.758 | 5.554 | −20.349 | 1.00 | 34.14 | RNA1 | C |
| ATOM | 1928 | C6 | A | C | 1069 | 5.949 | 5.022 | −20.886 | 1.00 | 38.86 | RNA1 | C |
| ATOM | 1929 | N6 | A | C | 1069 | 6.490 | 5.420 | −22.038 | 1.00 | 44.62 | RNA1 | N |
| ATOM | 1930 | N1 | A | C | 1069 | 6.577 | 4.054 | −20.180 | 1.00 | 40.40 | RNA1 | N |
| ATOM | 1931 | C2 | A | C | 1069 | 6.041 | 3.661 | −19.017 | 1.00 | 35.55 | RNA1 | C |
| ATOM | 1932 | N3 | A | C | 1069 | 4.939 | 4.093 | −18.408 | 1.00 | 28.51 | RNA1 | N |
| ATOM | 1933 | C4 | A | C | 1069 | 4.342 | 5.053 | −19.133 | 1.00 | 31.82 | RNA1 | C |
| ATOM | 1934 | P | A | C | 1070 | 1.715 | 6.875 | −13.302 | 1.00 | 33.11 | RNA1 | P |
| ATOM | 1935 | O1P | A | C | 1070 | 3.039 | 7.134 | −12.680 | 1.00 | 18.08 | RNA1 | O |
| ATOM | 1936 | O2P | A | C | 1070 | 0.734 | 7.989 | −13.469 | 1.00 | 18.52 | RNA1 | O |
| ATOM | 1937 | O5* | A | C | 1070 | 0.968 | 5.723 | −12.497 | 1.00 | 30.46 | RNA1 | O |
| ATOM | 1938 | C5* | A | C | 1070 | 1.690 | 4.589 | −11.998 | 1.00 | 21.05 | RNA1 | C |
| ATOM | 1939 | C4* | A | C | 1070 | 0.844 | 3.851 | −11.000 | 1.00 | 30.01 | RNA1 | C |
| ATOM | 1940 | O4* | A | C | 1070 | −0.391 | 3.424 | −11.634 | 1.00 | 25.30 | RNA1 | O |
| ATOM | 1941 | C3* | A | C | 1070 | 1.479 | 2.612 | −10.390 | 1.00 | 36.56 | RNA1 | C |
| ATOM | 1942 | O3* | A | C | 1070 | 1.078 | 2.564 | −9.026 | 1.00 | 37.18 | RNA1 | O |
| ATOM | 1943 | C2* | A | C | 1070 | 0.847 | 1.469 | −11.185 | 1.00 | 37.06 | RNA1 | C |
| ATOM | 1944 | O2* | A | C | 1070 | 0.739 | 0.256 | −10.463 | 1.00 | 48.87 | RNA1 | O |
| ATOM | 1945 | C1* | A | C | 1070 | −0.539 | 2.028 | −11.495 | 1.00 | 32.98 | RNA1 | C |
| ATOM | 1946 | N9 | A | C | 1070 | −1.107 | 1.501 | −12.735 | 1.00 | 42.72 | RNA1 | N |
| ATOM | 1947 | C8 | A | C | 1070 | −0.659 | 1.702 | −14.019 | 1.00 | 49.93 | RNA1 | C |
| ATOM | 1948 | N7 | A | C | 1070 | −1.380 | 1.098 | −14.929 | 1.00 | 50.90 | RNA1 | N |
| ATOM | 1949 | C5 | A | C | 1070 | −2.366 | 0.452 | −14.198 | 1.00 | 55.33 | RNA1 | C |
| ATOM | 1950 | C6 | A | C | 1070 | −3.435 | −0.367 | −14.582 | 1.00 | 59.78 | RNA1 | C |
| ATOM | 1951 | N6 | A | C | 1070 | −3.697 | −0.683 | −15.850 | 1.00 | 68.95 | RNA1 | N |

TABLE II-continued

| ATOM | 1952 | N1 | A | C | 1070 | −4.235 | −0.857 | −13.608 | 1.00 | 56.29 | RNA1 | N |
|---|---|---|---|---|---|---|---|---|---|---|---|---|
| ATOM | 1953 | C2 | A | C | 1070 | −3.965 | −0.536 | −12.340 | 1.00 | 41.79 | RNA1 | C |
| ATOM | 1954 | N3 | A | C | 1070 | −2.987 | 0.222 | −11.854 | 1.00 | 44.24 | RNA1 | N |
| ATOM | 1955 | C4 | A | C | 1070 | −2.212 | 0.692 | −12.847 | 1.00 | 46.56 | RNA1 | C |
| ATOM | 1956 | P | G | C | 1071 | 2.022 | 1.866 | −7.940 | 1.00 | 29.75 | RNA1 | P |
| ATOM | 1957 | O1P | G | C | 1071 | 1.299 | 1.985 | −6.653 | 1.00 | 39.09 | RNA1 | O |
| ATOM | 1958 | O2P | G | C | 1071 | 2.436 | 0.526 | −8.435 | 1.00 | 39.01 | RNA1 | O |
| ATOM | 1959 | O5* | G | C | 1071 | 3.325 | 2.769 | −7.901 | 1.00 | 19.92 | RNA1 | O |
| ATOM | 1960 | C5* | G | C | 1071 | 3.295 | 4.113 | −7.406 | 1.00 | 16.74 | RNA1 | C |
| ATOM | 1961 | C4* | G | C | 1071 | 4.704 | 4.562 | −7.133 | 1.00 | 23.89 | RNA1 | C |
| ATOM | 1962 | O4* | G | C | 1071 | 5.222 | 3.769 | −6.044 | 1.00 | 22.65 | RNA1 | O |
| ATOM | 1963 | C3* | G | C | 1071 | 5.633 | 4.285 | −8.302 | 1.00 | 25.19 | RNA1 | C |
| ATOM | 1964 | O3* | G | C | 1071 | 5.646 | 5.390 | −9.187 | 1.00 | 38.67 | RNA1 | O |
| ATOM | 1965 | C2* | G | C | 1071 | 6.974 | 4.006 | −7.639 | 1.00 | 21.49 | RNA1 | C |
| ATOM | 1966 | O2* | G | C | 1071 | 7.729 | 5.164 | −7.347 | 1.00 | 30.27 | RNA1 | O |
| ATOM | 1967 | C1* | G | C | 1071 | 6.533 | 3.335 | −6.340 | 1.00 | 18.58 | RNA1 | C |
| ATOM | 1968 | N9 | G | C | 1071 | 6.500 | 1.878 | −6.393 | 1.00 | 22.64 | RNA1 | N |
| ATOM | 1969 | C8 | G | C | 1071 | 5.389 | 1.076 | −6.272 | 1.00 | 20.39 | RNA1 | C |
| ATOM | 1970 | N7 | G | C | 1071 | 5.672 | −0.196 | −6.315 | 1.00 | 31.29 | RNA1 | N |
| ATOM | 1971 | C5 | G | C | 1071 | 7.048 | −0.236 | −6.482 | 1.00 | 14.55 | RNA1 | C |
| ATOM | 1972 | C6 | G | C | 1071 | 7.922 | −1.342 | −6.582 | 1.00 | 28.22 | RNA1 | C |
| ATOM | 1973 | O6 | G | C | 1071 | 7.647 | −2.549 | −6.512 | 1.00 | 31.85 | RNA1 | O |
| ATOM | 1974 | N1 | G | C | 1071 | 9.239 | −0.934 | −6.762 | 1.00 | 15.53 | RNA1 | N |
| ATOM | 1975 | C2 | G | C | 1071 | 9.660 | 0.371 | −6.818 | 1.00 | 20.27 | RNA1 | C |
| ATOM | 1976 | N2 | G | C | 1071 | 10.977 | 0.567 | −6.997 | 1.00 | 25.10 | RNA1 | N |
| ATOM | 1977 | N3 | G | C | 1071 | 8.853 | 1.411 | −6.707 | 1.00 | 19.36 | RNA1 | N |
| ATOM | 1978 | C4 | G | C | 1071 | 7.570 | 1.035 | −6.546 | 1.00 | 11.18 | RNA1 | C |
| ATOM | 1979 | P | C | C | 1072 | 5.597 | 5.137 | −10.767 | 1.00 | 27.21 | RNA1 | P |
| ATOM | 1980 | O1P | C | C | 1072 | 4.563 | 4.110 | −11.043 | 1.00 | 30.50 | RNA1 | O |
| ATOM | 1981 | O2P | C | C | 1072 | 5.512 | 6.459 | −11.426 | 1.00 | 25.77 | RNA1 | O |
| ATOM | 1982 | O5* | C | C | 1072 | 7.022 | 4.506 | −11.073 | 1.00 | 15.96 | RNA1 | O |
| ATOM | 1983 | C5* | C | C | 1072 | 8.198 | 5.315 | −11.019 | 1.00 | 23.11 | RNA1 | C |
| ATOM | 1984 | C4* | C | C | 1072 | 9.419 | 4.471 | −11.280 | 1.00 | 32.01 | RNA1 | C |
| ATOM | 1985 | O4* | C | C | 1072 | 9.601 | 3.533 | −10.192 | 1.00 | 36.03 | RNA1 | O |
| ATOM | 1986 | C3* | C | C | 1072 | 9.365 | 3.597 | −12.522 | 1.00 | 30.99 | RNA1 | C |
| ATOM | 1987 | O3* | C | C | 1072 | 9.711 | 4.326 | −13.688 | 1.00 | 33.23 | RNA1 | O |
| ATOM | 1988 | C2* | C | C | 1072 | 10.362 | 2.496 | −12.188 | 1.00 | 29.75 | RNA1 | C |
| ATOM | 1989 | O2* | C | C | 1072 | 11.703 | 2.904 | −12.371 | 1.00 | 34.64 | RNA1 | O |
| ATOM | 1990 | C1* | C | C | 1072 | 10.121 | 2.314 | −10.692 | 1.00 | 29.06 | RNA1 | C |
| ATOM | 1991 | N1 | C | C | 1072 | 9.151 | 1.242 | −10.401 | 1.00 | 21.88 | RNA1 | N |
| ATOM | 1992 | C2 | C | C | 1072 | 9.623 | −0.062 | −10.229 | 1.00 | 22.42 | RNA1 | C |
| ATOM | 1993 | O2 | C | C | 1072 | 10.852 | −0.281 | −10.328 | 1.00 | 27.87 | RNA1 | O |
| ATOM | 1994 | N3 | C | C | 1072 | 8.735 | −1.053 | −9.964 | 1.00 | 9.91 | RNA1 | N |
| ATOM | 1995 | C4 | C | C | 1072 | 7.430 | −0.780 | −9.883 | 1.00 | 19.29 | RNA1 | C |
| ATOM | 1996 | N4 | C | C | 1072 | 6.591 | −1.789 | −9.644 | 1.00 | 23.91 | RNA1 | N |
| ATOM | 1997 | C5 | C | C | 1072 | 6.925 | 0.538 | −10.048 | 1.00 | 13.70 | RNA1 | C |
| ATOM | 1998 | C6 | C | C | 1072 | 7.812 | 1.510 | −10.304 | 1.00 | 24.95 | RNA1 | C |
| ATOM | 1999 | P | A | C | 1073 | 8.702 | 4.336 | −14.936 | 1.00 | 33.99 | RNA1 | P |
| ATOM | 2000 | O1P | A | C | 1073 | 8.504 | 2.919 | −15.333 | 1.00 | 35.83 | RNA1 | O |
| ATOM | 2001 | O2P | A | C | 1073 | 7.512 | 5.181 | −14.614 | 1.00 | 22.96 | RNA1 | O |
| ATOM | 2002 | O5* | A | C | 1073 | 9.551 | 5.050 | −16.074 | 1.00 | 31.36 | RNA1 | O |
| ATOM | 2003 | C5* | A | C | 1073 | 10.772 | 4.462 | −16.571 | 1.00 | 35.37 | RNA1 | C |
| ATOM | 2004 | C4* | A | C | 1073 | 11.245 | 5.227 | −17.781 | 1.00 | 39.45 | RNA1 | C |
| ATOM | 2005 | O4* | A | C | 1073 | 10.229 | 5.143 | −18.815 | 1.00 | 39.78 | RNA1 | O |
| ATOM | 2006 | C3* | A | C | 1073 | 11.400 | 6.713 | −17.522 | 1.00 | 40.87 | RNA1 | C |
| ATOM | 2007 | O3* | A | C | 1073 | 12.673 | 7.017 | −16.987 | 1.00 | 44.46 | RNA1 | O |
| ATOM | 2008 | C2* | A | C | 1073 | 11.147 | 7.327 | −18.890 | 1.00 | 38.57 | RNA1 | C |
| ATOM | 2009 | O2* | A | C | 1073 | 12.279 | 7.252 | −19.738 | 1.00 | 41.89 | RNA1 | O |
| ATOM | 2010 | C1* | A | C | 1073 | 10.054 | 6.409 | −19.426 | 1.00 | 27.18 | RNA1 | C |
| ATOM | 2011 | N9 | A | C | 1073 | 8.713 | 6.872 | −19.081 | 1.00 | 23.78 | RNA1 | N |
| ATOM | 2012 | C8 | A | C | 1073 | 7.835 | 6.282 | −18.209 | 1.00 | 31.10 | RNA1 | C |
| ATOM | 2013 | N7 | A | C | 1073 | 6.685 | 6.903 | −18.112 | 1.00 | 30.54 | RNA1 | N |
| ATOM | 2014 | C5 | A | C | 1073 | 6.819 | 7.979 | −18.974 | 1.00 | 22.89 | RNA1 | C |
| ATOM | 2015 | C6 | A | C | 1073 | 5.948 | 9.015 | −19.319 | 1.00 | 24.05 | RNA1 | C |
| ATOM | 2016 | N6 | A | C | 1073 | 4.711 | 9.130 | −18.836 | 1.00 | 24.67 | RNA1 | N |
| ATOM | 2017 | N1 | A | C | 1073 | 6.391 | 9.940 | −20.193 | 1.00 | 27.06 | RNA1 | N |
| ATOM | 2018 | C2 | A | C | 1073 | 7.627 | 9.815 | −20.684 | 1.00 | 28.92 | RNA1 | C |
| ATOM | 2019 | N3 | A | C | 1073 | 8.539 | 8.879 | −20.442 | 1.00 | 33.22 | RNA1 | N |
| ATOM | 2020 | C4 | A | C | 1073 | 8.066 | 7.979 | −19.568 | 1.00 | 24.70 | RNA1 | C |
| ATOM | 2021 | P | G | C | 1074 | 12.790 | 8.131 | −15.846 | 1.00 | 37.49 | RNA1 | P |
| ATOM | 2022 | O1P | G | C | 1074 | 11.994 | 7.638 | −14.698 | 1.00 | 42.76 | RNA1 | O |
| ATOM | 2023 | O2P | G | C | 1074 | 14.226 | 8.458 | −15.661 | 1.00 | 37.27 | RNA1 | O |
| ATOM | 2024 | O5* | G | C | 1074 | 12.052 | 9.389 | −16.488 | 1.00 | 32.12 | RNA1 | O |
| ATOM | 2025 | C5* | G | C | 1074 | 12.636 | 10.074 | −17.611 | 1.00 | 30.38 | RNA1 | C |
| ATOM | 2026 | C4* | G | C | 1074 | 11.776 | 11.239 | −18.042 | 1.00 | 29.26 | RNA1 | C |
| ATOM | 2027 | O4* | G | C | 1074 | 10.505 | 10.762 | −18.552 | 1.00 | 28.39 | RNA1 | O |
| ATOM | 2028 | C3* | G | C | 1074 | 11.393 | 12.245 | −16.972 | 1.00 | 30.49 | RNA1 | C |
| ATOM | 2029 | O3* | G | C | 1074 | 12.431 | 13.170 | −16.697 | 1.00 | 40.29 | RNA1 | O |
| ATOM | 2030 | C2* | G | C | 1074 | 10.152 | 12.899 | −17.566 | 1.00 | 32.10 | RNA1 | C |

TABLE II-continued

| ATOM | 2031 | O2* | G | C | 1074 | 10.452 | 13.891 | −18.528 | 1.00 | 36.08 | RNA1 | O |
|---|---|---|---|---|---|---|---|---|---|---|---|---|
| ATOM | 2032 | C1* | G | C | 1074 | 9.491 | 11.714 | −18.268 | 1.00 | 26.45 | RNA1 | C |
| ATOM | 2033 | N9 | G | C | 1074 | 8.479 | 11.075 | −17.435 | 1.00 | 22.10 | RNA1 | N |
| ATOM | 2034 | C8 | G | C | 1074 | 8.576 | 9.862 | −16.794 | 1.00 | 21.18 | RNA1 | C |
| ATOM | 2035 | N7 | G | C | 1074 | 7.490 | 9.539 | −16.145 | 1.00 | 28.77 | RNA1 | N |
| ATOM | 2036 | C5 | G | C | 1074 | 6.628 | 10.604 | −16.362 | 1.00 | 15.54 | RNA1 | C |
| ATOM | 2037 | C6 | G | C | 1074 | 5.300 | 10.815 | −15.917 | 1.00 | 22.89 | RNA1 | C |
| ATOM | 2038 | O6 | G | C | 1074 | 4.589 | 10.071 | −15.240 | 1.00 | 28.81 | RNA1 | O |
| ATOM | 2039 | N1 | G | C | 1074 | 4.802 | 12.038 | −16.351 | 1.00 | 26.73 | RNA1 | N |
| ATOM | 2040 | C2 | G | C | 1074 | 5.487 | 12.937 | −17.126 | 1.00 | 24.75 | RNA1 | C |
| ATOM | 2041 | N2 | G | C | 1074 | 4.828 | 14.058 | −17.440 | 1.00 | 20.91 | RNA1 | N |
| ATOM | 2042 | N3 | G | C | 1074 | 6.724 | 12.748 | −17.560 | 1.00 | 19.40 | RNA1 | N |
| ATOM | 2043 | C4 | G | C | 1074 | 7.228 | 11.568 | −17.144 | 1.00 | 19.49 | RNA1 | C |
| ATOM | 2044 | P | C | C | 1075 | 12.535 | 13.826 | −15.232 | 1.00 | 35.74 | RNA1 | P |
| ATOM | 2045 | O1P | C | C | 1075 | 12.251 | 12.757 | −14.239 | 1.00 | 37.48 | RNA1 | O |
| ATOM | 2046 | O2P | C | C | 1075 | 13.814 | 14.574 | −15.147 | 1.00 | 35.45 | RNA1 | O |
| ATOM | 2047 | O5* | C | C | 1075 | 11.326 | 14.864 | −15.223 | 1.00 | 29.10 | RNA1 | O |
| ATOM | 2048 | C5* | C | C | 1075 | 11.373 | 16.035 | −16.052 | 1.00 | 20.72 | RNA1 | C |
| ATOM | 2049 | C4* | C | C | 1075 | 10.144 | 16.884 | −15.848 | 1.00 | 27.73 | RNA1 | C |
| ATOM | 2050 | O4* | C | C | 1075 | 8.980 | 16.162 | −16.316 | 1.00 | 25.49 | RNA1 | O |
| ATOM | 2051 | C3* | C | C | 1075 | 9.804 | 17.254 | −14.413 | 1.00 | 29.84 | RNA1 | C |
| ATOM | 2052 | O3* | C | C | 1075 | 10.548 | 18.355 | −13.924 | 1.00 | 32.76 | RNA1 | O |
| ATOM | 2053 | C2* | C | C | 1075 | 8.311 | 17.537 | −14.490 | 1.00 | 32.29 | RNA1 | C |
| ATOM | 2054 | O2* | C | C | 1075 | 8.018 | 18.838 | −14.963 | 1.00 | 33.04 | RNA1 | O |
| ATOM | 2055 | C1* | C | C | 1075 | 7.860 | 16.488 | −15.508 | 1.00 | 30.74 | RNA1 | C |
| ATOM | 2056 | N1 | C | C | 1075 | 7.407 | 15.259 | −14.836 | 1.00 | 23.00 | RNA1 | N |
| ATOM | 2057 | C2 | C | C | 1075 | 6.083 | 15.178 | −14.407 | 1.00 | 25.39 | RNA1 | C |
| ATOM | 2058 | O2 | C | C | 1075 | 5.320 | 16.133 | −14.627 | 1.00 | 27.71 | RNA1 | O |
| ATOM | 2059 | N3 | C | C | 1075 | 5.666 | 14.063 | −13.764 | 1.00 | 20.56 | RNA1 | N |
| ATOM | 2060 | C4 | C | C | 1075 | 6.518 | 13.054 | −13.553 | 1.00 | 24.69 | RNA1 | C |
| ATOM | 2061 | N4 | C | C | 1075 | 6.067 | 11.975 | −12.911 | 1.00 | 22.56 | RNA1 | N |
| ATOM | 2062 | C5 | C | C | 1075 | 7.870 | 13.108 | −13.991 | 1.00 | 16.20 | RNA1 | C |
| ATOM | 2063 | C6 | C | C | 1075 | 8.269 | 14.217 | −14.622 | 1.00 | 23.77 | RNA1 | C |
| ATOM | 2064 | P | C | C | 1076 | 10.912 | 18.423 | −12.358 | 1.00 | 42.91 | RNA1 | P |
| ATOM | 2065 | O1P | C | C | 1076 | 11.372 | 17.085 | −11.911 | 1.00 | 24.52 | RNA1 | O |
| ATOM | 2066 | O2P | C | C | 1076 | 11.781 | 19.612 | −12.113 | 1.00 | 41.73 | RNA1 | O |
| ATOM | 2067 | O5* | C | C | 1076 | 9.491 | 18.679 | −11.696 | 1.00 | 32.86 | RNA1 | O |
| ATOM | 2068 | C5* | C | C | 1076 | 8.768 | 19.870 | −11.997 | 1.00 | 27.46 | RNA1 | C |
| ATOM | 2069 | C4* | C | C | 1076 | 7.458 | 19.893 | −11.255 | 1.00 | 30.86 | RNA1 | C |
| ATOM | 2070 | O4* | C | C | 1076 | 6.570 | 18.885 | −11.798 | 1.00 | 34.77 | RNA1 | O |
| ATOM | 2071 | C3* | C | C | 1076 | 7.500 | 19.581 | −9.769 | 1.00 | 26.66 | RNA1 | C |
| ATOM | 2072 | O3* | C | C | 1076 | 7.913 | 20.668 | −8.961 | 1.00 | 36.57 | RNA1 | O |
| ATOM | 2073 | C2* | C | C | 1076 | 6.062 | 19.172 | −9.499 | 1.00 | 32.47 | RNA1 | C |
| ATOM | 2074 | O2* | C | C | 1076 | 5.198 | 20.290 | −9.410 | 1.00 | 32.97 | RNA1 | O |
| ATOM | 2075 | C1* | C | C | 1076 | 5.735 | 18.385 | −10.765 | 1.00 | 34.29 | RNA1 | C |
| ATOM | 2076 | N1 | C | C | 1076 | 6.012 | 16.945 | −10.577 | 1.00 | 22.34 | RNA1 | N |
| ATOM | 2077 | C2 | C | C | 1076 | 5.036 | 16.150 | −9.959 | 1.00 | 24.18 | RNA1 | C |
| ATOM | 2078 | O2 | C | C | 1076 | 3.977 | 16.680 | −9.577 | 1.00 | 25.15 | RNA1 | O |
| ATOM | 2079 | N3 | C | C | 1076 | 5.271 | 14.825 | −9.784 | 1.00 | 20.85 | RNA1 | N |
| ATOM | 2080 | C4 | C | C | 1076 | 6.428 | 14.295 | −10.185 | 1.00 | 21.45 | RNA1 | C |
| ATOM | 2081 | N4 | C | C | 1076 | 6.611 | 12.987 | −9.994 | 1.00 | 19.48 | RNA1 | N |
| ATOM | 2082 | C5 | C | C | 1076 | 7.446 | 15.083 | −10.805 | 1.00 | 18.25 | RNA1 | C |
| ATOM | 2083 | C6 | C | C | 1076 | 7.196 | 16.389 | −10.984 | 1.00 | 25.90 | RNA1 | C |
| ATOM | 2084 | P | A | C | 1077 | 8.725 | 20.374 | −7.602 | 1.00 | 34.53 | RNA1 | P |
| ATOM | 2085 | O1P | A | C | 1077 | 9.776 | 19.366 | −7.891 | 1.00 | 32.29 | RNA1 | O |
| ATOM | 2086 | O2P | A | C | 1077 | 9.115 | 21.689 | −7.025 | 1.00 | 55.02 | RNA1 | O |
| ATOM | 2087 | O5* | A | C | 1077 | 7.641 | 19.691 | −6.652 | 1.00 | 22.72 | RNA1 | O |
| ATOM | 2088 | C5* | A | C | 1077 | 6.447 | 20.399 | −6.283 | 1.00 | 17.11 | RNA1 | C |
| ATOM | 2089 | C4* | A | C | 1077 | 5.461 | 19.477 | −5.601 | 1.00 | 26.56 | RNA1 | C |
| ATOM | 2090 | O4* | A | C | 1077 | 5.058 | 18.423 | −6.514 | 1.00 | 34.54 | RNA1 | O |
| ATOM | 2091 | C3* | A | C | 1077 | 5.916 | 18.724 | −4.357 | 1.00 | 32.85 | RNA1 | C |
| ATOM | 2092 | O3* | A | C | 1077 | 5.872 | 19.511 | −3.175 | 1.00 | 37.36 | RNA1 | O |
| ATOM | 2093 | C2* | A | C | 1077 | 4.913 | 17.576 | −4.297 | 1.00 | 36.94 | RNA1 | C |
| ATOM | 2094 | O2* | A | C | 1077 | 3.661 | 17.943 | −3.748 | 1.00 | 32.73 | RNA1 | O |
| ATOM | 2095 | C1* | A | C | 1077 | 4.723 | 17.255 | −5.778 | 1.00 | 32.51 | RNA1 | C |
| ATOM | 2096 | N9 | A | C | 1077 | 5.612 | 16.160 | −6.172 | 1.00 | 27.14 | RNA1 | N |
| ATOM | 2097 | C8 | A | C | 1077 | 6.830 | 16.224 | −6.802 | 1.00 | 22.59 | RNA1 | C |
| ATOM | 2098 | N7 | A | C | 1077 | 7.406 | 15.054 | −6.959 | 1.00 | 28.95 | RNA1 | N |
| ATOM | 2099 | C5 | A | C | 1077 | 6.500 | 14.158 | −6.405 | 1.00 | 23.18 | RNA1 | C |
| ATOM | 2100 | C6 | A | C | 1077 | 6.524 | 12.758 | −6.252 | 1.00 | 29.03 | RNA1 | C |
| ATOM | 2101 | N6 | A | C | 1077 | 7.543 | 11.984 | −6.643 | 1.00 | 32.89 | RNA1 | N |
| ATOM | 2102 | N1 | A | C | 1077 | 5.454 | 12.174 | −5.669 | 1.00 | 23.42 | RNA1 | N |
| ATOM | 2103 | C2 | A | C | 1077 | 4.443 | 12.948 | −5.259 | 1.00 | 10.65 | RNA1 | C |
| ATOM | 2104 | N3 | A | C | 1077 | 4.309 | 14.266 | −5.338 | 1.00 | 26.74 | RNA1 | N |
| ATOM | 2105 | C4 | A | C | 1077 | 5.385 | 14.821 | −5.930 | 1.00 | 26.08 | RNA1 | C |
| ATOM | 2106 | P | U | C | 1078 | 6.978 | 19.284 | −2.026 | 1.00 | 29.17 | RNA1 | P |
| ATOM | 2107 | O1P | U | C | 1078 | 8.330 | 19.420 | −2.616 | 1.00 | 22.94 | RNA1 | O |
| ATOM | 2108 | O2P | U | C | 1078 | 6.586 | 20.141 | −0.877 | 1.00 | 41.57 | RNA1 | O |
| ATOM | 2109 | O5* | U | C | 1078 | 6.828 | 17.754 | −1.608 | 1.00 | 29.90 | RNA1 | O |

TABLE II-continued

| ATOM | 2110 | C5* | U | C | 1078 | 5.706 | 17.287 | −0.830 | 1.00 | 21.78 | RNA1 | C |
|---|---|---|---|---|---|---|---|---|---|---|---|---|
| ATOM | 2111 | C4* | U | C | 1078 | 5.789 | 15.785 | −0.649 | 1.00 | 21.19 | RNA1 | C |
| ATOM | 2112 | O4* | U | C | 1078 | 5.732 | 15.157 | −1.957 | 1.00 | 29.99 | RNA1 | O |
| ATOM | 2113 | C3* | U | C | 1078 | 7.075 | 15.241 | −0.031 | 1.00 | 27.77 | RNA1 | C |
| ATOM | 2114 | O3* | U | C | 1078 | 7.057 | 15.184 | 1.390 | 1.00 | 36.77 | RNA1 | O |
| ATOM | 2115 | C2* | U | C | 1078 | 7.094 | 13.812 | −0.554 | 1.00 | 34.85 | RNA1 | C |
| ATOM | 2116 | O2* | U | C | 1078 | 6.229 | 12.972 | 0.191 | 1.00 | 32.65 | RNA1 | O |
| ATOM | 2117 | C1* | U | C | 1078 | 6.532 | 13.986 | −1.963 | 1.00 | 28.35 | RNA1 | C |
| ATOM | 2118 | N1 | U | C | 1078 | 7.611 | 14.137 | −2.955 | 1.00 | 21.70 | RNA1 | N |
| ATOM | 2119 | C2 | U | C | 1078 | 8.275 | 12.987 | −3.352 | 1.00 | 27.00 | RNA1 | C |
| ATOM | 2120 | O2 | U | C | 1078 | 7.975 | 11.872 | −2.946 | 1.00 | 29.58 | RNA1 | O |
| ATOM | 2121 | N3 | U | C | 1078 | 9.305 | 13.189 | −4.238 | 1.00 | 24.66 | RNA1 | N |
| ATOM | 2122 | C4 | U | C | 1078 | 9.728 | 14.393 | −4.760 | 1.00 | 26.71 | RNA1 | C |
| ATOM | 2123 | O4 | U | C | 1078 | 10.714 | 14.417 | −5.504 | 1.00 | 44.05 | RNA1 | O |
| ATOM | 2124 | C5 | U | C | 1078 | 8.978 | 15.530 | −4.320 | 1.00 | 18.54 | RNA1 | C |
| ATOM | 2125 | C6 | U | C | 1078 | 7.970 | 15.368 | −3.459 | 1.00 | 19.12 | RNA1 | C |
| ATOM | 2126 | P | C | C | 1079 | 7.168 | 16.527 | 2.260 | 1.00 | 28.61 | RNA1 | P |
| ATOM | 2127 | O1P | C | C | 1079 | 7.780 | 16.107 | 3.544 | 1.00 | 34.30 | RNA1 | O |
| ATOM | 2128 | O2P | C | C | 1079 | 7.770 | 17.644 | 1.487 | 1.00 | 31.33 | RNA1 | O |
| ATOM | 2129 | O5* | C | C | 1079 | 5.641 | 16.867 | 2.520 | 1.00 | 13.04 | RNA1 | O |
| ATOM | 2130 | C5* | C | C | 1079 | 4.851 | 15.965 | 3.271 | 1.00 | 17.43 | RNA1 | C |
| ATOM | 2131 | C4* | C | C | 1079 | 3.398 | 16.246 | 3.064 | 1.00 | 19.74 | RNA1 | C |
| ATOM | 2132 | O4* | C | C | 1079 | 2.954 | 15.688 | 1.803 | 1.00 | 26.36 | RNA1 | O |
| ATOM | 2133 | C3* | C | C | 1079 | 2.556 | 15.540 | 4.098 | 1.00 | 25.66 | RNA1 | C |
| ATOM | 2134 | O3* | C | C | 1079 | 2.525 | 16.312 | 5.278 | 1.00 | 37.56 | RNA1 | O |
| ATOM | 2135 | C2* | C | C | 1079 | 1.217 | 15.382 | 3.394 | 1.00 | 27.27 | RNA1 | C |
| ATOM | 2136 | O2* | C | C | 1079 | 0.452 | 16.573 | 3.416 | 1.00 | 25.00 | RNA1 | O |
| ATOM | 2137 | C1* | C | C | 1079 | 1.672 | 15.091 | 1.963 | 1.00 | 17.88 | RNA1 | C |
| ATOM | 2138 | N1 | C | C | 1079 | 1.795 | 13.641 | 1.677 | 1.00 | 17.52 | RNA1 | N |
| ATOM | 2139 | C2 | C | C | 1079 | 0.629 | 12.878 | 1.441 | 1.00 | 19.34 | RNA1 | C |
| ATOM | 2140 | O2 | C | C | 1079 | −0.488 | 13.427 | 1.500 | 1.00 | 24.52 | RNA1 | O |
| ATOM | 2141 | N3 | C | C | 1079 | 0.748 | 11.561 | 1.159 | 1.00 | 15.18 | RNA1 | N |
| ATOM | 2142 | C4 | C | C | 1079 | 1.955 | 10.994 | 1.111 | 1.00 | 20.12 | RNA1 | C |
| ATOM | 2143 | N4 | C | C | 1079 | 2.018 | 9.691 | 0.814 | 1.00 | 14.62 | RNA1 | N |
| ATOM | 2144 | C5 | C | C | 1079 | 3.150 | 11.734 | 1.359 | 1.00 | 16.35 | RNA1 | C |
| ATOM | 2145 | C6 | C | C | 1079 | 3.025 | 13.040 | 1.635 | 1.00 | 14.99 | RNA1 | C |
| ATOM | 2146 | P | A | C | 1080 | 2.747 | 15.593 | 6.692 | 1.00 | 32.18 | RNA1 | P |
| ATOM | 2147 | O1P | A | C | 1080 | 3.901 | 14.668 | 6.598 | 1.00 | 27.65 | RNA1 | O |
| ATOM | 2148 | O2P | A | C | 1080 | 2.748 | 16.674 | 7.711 | 1.00 | 42.21 | RNA1 | O |
| ATOM | 2149 | O5* | A | C | 1080 | 1.413 | 14.745 | 6.853 | 1.00 | 24.30 | RNA1 | O |
| ATOM | 2150 | C5* | A | C | 1080 | 0.157 | 15.421 | 6.836 | 1.00 | 25.92 | RNA1 | C |
| ATOM | 2151 | C4* | A | C | 1080 | −0.967 | 14.459 | 6.593 | 1.00 | 27.37 | RNA1 | C |
| ATOM | 2152 | O4* | A | C | 1080 | −0.902 | 13.924 | 5.248 | 1.00 | 35.15 | RNA1 | O |
| ATOM | 2153 | C3* | A | C | 1080 | −1.028 | 13.223 | 7.462 | 1.00 | 26.09 | RNA1 | C |
| ATOM | 2154 | O3* | A | C | 1080 | −1.528 | 13.489 | 8.759 | 1.00 | 36.10 | RNA1 | O |
| ATOM | 2155 | C2* | A | C | 1080 | −1.956 | 12.331 | 6.651 | 1.00 | 33.11 | RNA1 | C |
| ATOM | 2156 | O2* | A | C | 1080 | −3.309 | 12.717 | 6.787 | 1.00 | 32.80 | RNA1 | O |
| ATOM | 2157 | C1* | A | C | 1080 | −1.510 | 12.643 | 5.223 | 1.00 | 26.83 | RNA1 | C |
| ATOM | 2158 | N9 | A | C | 1080 | −0.538 | 11.650 | 4.767 | 1.00 | 16.76 | RNA1 | N |
| ATOM | 2159 | C8 | A | C | 1080 | 0.838 | 11.722 | 4.719 | 1.00 | 20.21 | RNA1 | C |
| ATOM | 2160 | N7 | A | C | 1080 | 1.411 | 10.609 | 4.319 | 1.00 | 8.53 | RNA1 | N |
| ATOM | 2161 | C5 | A | C | 1080 | 0.340 | 9.754 | 4.073 | 1.00 | 7.38 | RNA1 | C |
| ATOM | 2162 | C6 | A | C | 1080 | 0.273 | 8.414 | 3.649 | 1.00 | 15.76 | RNA1 | C |
| ATOM | 2163 | N6 | A | C | 1080 | 1.348 | 7.660 | 3.376 | 1.00 | 25.46 | RNA1 | N |
| ATOM | 2164 | N1 | A | C | 1080 | −0.952 | 7.859 | 3.514 | 1.00 | 17.62 | RNA1 | N |
| ATOM | 2165 | C2 | A | C | 1080 | −2.029 | 8.606 | 3.785 | 1.00 | 16.21 | RNA1 | C |
| ATOM | 2166 | N3 | A | C | 1080 | −2.095 | 9.868 | 4.192 | 1.00 | 17.28 | RNA1 | N |
| ATOM | 2167 | C4 | A | C | 1080 | −0.861 | 10.389 | 4.323 | 1.00 | 7.47 | RNA1 | C |
| ATOM | 2168 | P | U | C | 1081 | −1.136 | 12.505 | 9.973 | 1.00 | 29.01 | RNA1 | P |
| ATOM | 2169 | O1P | U | C | 1081 | 0.273 | 12.088 | 9.807 | 1.00 | 19.32 | RNA1 | O |
| ATOM | 2170 | O2P | U | C | 1081 | −1.558 | 13.151 | 11.237 | 1.00 | 36.17 | RNA1 | O |
| ATOM | 2171 | O5* | U | C | 1081 | −2.072 | 11.248 | 9.708 | 1.00 | 27.53 | RNA1 | O |
| ATOM | 2172 | C5* | U | C | 1081 | −3.469 | 11.439 | 9.421 | 1.00 | 34.97 | RNA1 | C |
| ATOM | 2173 | C4* | U | C | 1081 | −4.093 | 10.146 | 8.967 | 1.00 | 39.34 | RNA1 | C |
| ATOM | 2174 | O4* | U | C | 1081 | −3.488 | 9.719 | 7.725 | 1.00 | 36.64 | RNA1 | O |
| ATOM | 2175 | C3* | U | C | 1081 | −3.908 | 8.982 | 9.922 | 1.00 | 36.77 | RNA1 | C |
| ATOM | 2176 | O3* | U | C | 1081 | −4.954 | 9.001 | 10.888 | 1.00 | 49.64 | RNA1 | O |
| ATOM | 2177 | C2* | U | C | 1081 | −4.001 | 7.774 | 9.001 | 1.00 | 31.27 | RNA1 | C |
| ATOM | 2178 | O2* | U | C | 1081 | −5.344 | 7.418 | 8.739 | 1.00 | 35.76 | RNA1 | O |
| ATOM | 2179 | C1* | U | C | 1081 | −3.375 | 8.311 | 7.713 | 1.00 | 27.99 | RNA1 | C |
| ATOM | 2180 | N1 | U | C | 1081 | −1.959 | 7.966 | 7.513 | 1.00 | 16.45 | RNA1 | N |
| ATOM | 2181 | C2 | U | C | 1081 | −1.659 | 6.684 | 7.082 | 1.00 | 15.53 | RNA1 | C |
| ATOM | 2182 | O2 | U | C | 1081 | −2.511 | 5.822 | 6.912 | 1.00 | 24.70 | RNA1 | O |
| ATOM | 2183 | N3 | U | C | 1081 | −0.328 | 6.446 | 6.856 | 1.00 | 6.42 | RNA1 | N |
| ATOM | 2184 | C4 | U | C | 1081 | 0.717 | 7.335 | 7.015 | 1.00 | 17.75 | RNA1 | C |
| ATOM | 2185 | O4 | U | C | 1081 | 1.850 | 7.005 | 6.656 | 1.00 | 12.74 | RNA1 | O |
| ATOM | 2186 | C5 | U | C | 1081 | 0.332 | 8.627 | 7.495 | 1.00 | 15.50 | RNA1 | C |
| ATOM | 2187 | C6 | U | C | 1081 | −0.961 | 8.890 | 7.724 | 1.00 | 17.69 | RNA1 | C |
| ATOM | 2188 | P | U | C | 1082 | −4.709 | 8.375 | 12.348 | 1.00 | 43.16 | RNA1 | P |

TABLE II-continued

| | | | | | | | | | | | |
|---|---|---|---|---|---|---|---|---|---|---|---|
| ATOM | 2189 | O1P | U | C | 1082 | −3.513 | 9.034 | 12.942 | 1.00 | 33.87 | RNA1 O |
| ATOM | 2190 | O2P | U | C | 1082 | −6.019 | 8.423 | 13.060 | 1.00 | 35.46 | RNA1 O |
| ATOM | 2191 | O5* | U | C | 1082 | −4.357 | 6.855 | 12.050 | 1.00 | 39.66 | RNA1 O |
| ATOM | 2192 | C5* | U | C | 1082 | −5.388 | 5.949 | 11.643 | 1.00 | 36.85 | RNA1 C |
| ATOM | 2193 | C4* | U | C | 1082 | −4.834 | 4.563 | 11.500 | 1.00 | 35.35 | RNA1 C |
| ATOM | 2194 | O4* | U | C | 1082 | −4.024 | 4.471 | 10.301 | 1.00 | 27.83 | RNA1 O |
| ATOM | 2195 | C3* | U | C | 1082 | −3.895 | 4.106 | 12.600 | 1.00 | 42.67 | RNA1 C |
| ATOM | 2196 | O3* | U | C | 1082 | −4.544 | 3.677 | 13.786 | 1.00 | 48.43 | RNA1 O |
| ATOM | 2197 | C2* | U | C | 1082 | −3.130 | 2.979 | 11.925 | 1.00 | 41.00 | RNA1 C |
| ATOM | 2198 | O2* | U | C | 1082 | −3.847 | 1.757 | 11.941 | 1.00 | 43.11 | RNA1 O |
| ATOM | 2199 | C1* | U | C | 1082 | −3.000 | 3.510 | 10.496 | 1.00 | 29.73 | RNA1 C |
| ATOM | 2200 | N1 | U | C | 1082 | −1.691 | 4.146 | 10.281 | 1.00 | 21.48 | RNA1 N |
| ATOM | 2201 | C2 | U | C | 1082 | −0.650 | 3.342 | 9.826 | 1.00 | 24.74 | RNA1 C |
| ATOM | 2202 | O2 | U | C | 1082 | −0.781 | 2.155 | 9.573 | 1.00 | 35.44 | RNA1 O |
| ATOM | 2203 | N3 | U | C | 1082 | 0.552 | 3.980 | 9.678 | 1.00 | 16.73 | RNA1 N |
| ATOM | 2204 | C4 | U | C | 1082 | 0.825 | 5.303 | 9.921 | 1.00 | 20.16 | RNA1 C |
| ATOM | 2205 | O4 | U | C | 1082 | 1.963 | 5.730 | 9.715 | 1.00 | 29.48 | RNA1 O |
| ATOM | 2206 | C5 | U | C | 1082 | −0.293 | 6.069 | 10.378 | 1.00 | 15.77 | RNA1 C |
| ATOM | 2207 | C6 | U | C | 1082 | −1.485 | 5.479 | 10.536 | 1.00 | 20.32 | RNA1 C |
| ATOM | 2208 | P | U | C | 1083 | −3.685 | 3.548 | 15.138 | 1.00 | 44.11 | RNA1 P |
| ATOM | 2209 | O1P | U | C | 1083 | −3.013 | 4.855 | 15.416 | 1.00 | 33.72 | RNA1 O |
| ATOM | 2210 | O2P | U | C | 1083 | −4.550 | 2.923 | 16.170 | 1.00 | 44.56 | RNA1 O |
| ATOM | 2211 | O5* | U | C | 1083 | −2.554 | 2.515 | 14.732 | 1.00 | 26.53 | RNA1 O |
| ATOM | 2212 | C5* | U | C | 1083 | −1.204 | 2.710 | 15.133 | 1.00 | 27.01 | RNA1 C |
| ATOM | 2213 | C4* | U | C | 1083 | −0.310 | 1.810 | 14.328 | 1.00 | 35.50 | RNA1 C |
| ATOM | 2214 | O4* | U | C | 1083 | 0.049 | 2.450 | 13.077 | 1.00 | 37.83 | RNA1 O |
| ATOM | 2215 | C3* | U | C | 1083 | 1.014 | 1.490 | 14.985 | 1.00 | 42.54 | RNA1 C |
| ATOM | 2216 | O3* | U | C | 1083 | 0.829 | 0.394 | 15.868 | 1.00 | 53.77 | RNA1 O |
| ATOM | 2217 | C2* | U | C | 1083 | 1.899 | 1.142 | 13.797 | 1.00 | 40.40 | RNA1 C |
| ATOM | 2218 | O2* | U | C | 1083 | 1.676 | −0.184 | 13.354 | 1.00 | 50.14 | RNA1 O |
| ATOM | 2219 | C1* | U | C | 1083 | 1.383 | 2.112 | 12.733 | 1.00 | 31.81 | RNA1 C |
| ATOM | 2220 | N1 | U | C | 1083 | 2.176 | 3.350 | 12.641 | 1.00 | 27.07 | RNA1 N |
| ATOM | 2221 | C2 | U | C | 1083 | 3.403 | 3.291 | 11.995 | 1.00 | 27.98 | RNA1 C |
| ATOM | 2222 | O2 | U | C | 1083 | 3.842 | 2.278 | 11.491 | 1.00 | 38.26 | RNA1 O |
| ATOM | 2223 | N3 | U | C | 1083 | 4.101 | 4.471 | 11.959 | 1.00 | 27.06 | RNA1 N |
| ATOM | 2224 | C4 | U | C | 1083 | 3.711 | 5.686 | 12.480 | 1.00 | 29.89 | RNA1 C |
| ATOM | 2225 | O4 | U | C | 1083 | 4.463 | 6.660 | 12.376 | 1.00 | 35.97 | RNA1 O |
| ATOM | 2226 | C5 | U | C | 1083 | 2.432 | 5.676 | 13.120 | 1.00 | 28.35 | RNA1 C |
| ATOM | 2227 | C6 | U | C | 1083 | 1.726 | 4.538 | 13.180 | 1.00 | 34.18 | RNA1 C |
| ATOM | 2228 | P | A | C | 1084 | 1.531 | 0.409 | 17.308 | 1.00 | 46.22 | RNA1 P |
| ATOM | 2229 | O1P | A | C | 1084 | 1.502 | 1.811 | 17.819 | 1.00 | 47.82 | RNA1 O |
| ATOM | 2230 | O2P | A | C | 1084 | 0.915 | −0.683 | 18.102 | 1.00 | 45.99 | RNA1 O |
| ATOM | 2231 | O5* | A | C | 1084 | 3.037 | 0.024 | 16.984 | 1.00 | 32.44 | RNA1 O |
| ATOM | 2232 | C5* | A | C | 1084 | 4.103 | 0.403 | 17.854 | 1.00 | 26.01 | RNA1 C |
| ATOM | 2233 | C4* | A | C | 1084 | 5.395 | −0.104 | 17.293 | 1.00 | 30.31 | RNA1 C |
| ATOM | 2234 | O4* | A | C | 1084 | 5.314 | −1.544 | 17.185 | 1.00 | 39.98 | RNA1 O |
| ATOM | 2235 | C3* | A | C | 1084 | 5.631 | 0.378 | 15.881 | 1.00 | 31.04 | RNA1 C |
| ATOM | 2236 | O3* | A | C | 1084 | 6.308 | 1.611 | 15.926 | 1.00 | 35.76 | RNA1 O |
| ATOM | 2237 | C2* | A | C | 1084 | 6.448 | −0.741 | 15.252 | 1.00 | 34.39 | RNA1 C |
| ATOM | 2238 | O2* | A | C | 1084 | 7.825 | −0.635 | 15.548 | 1.00 | 29.53 | RNA1 O |
| ATOM | 2239 | C1* | A | C | 1084 | 5.872 | −1.970 | 15.956 | 1.00 | 36.40 | RNA1 C |
| ATOM | 2240 | N9 | A | C | 1084 | 4.827 | −2.698 | 15.230 | 1.00 | 38.88 | RNA1 N |
| ATOM | 2241 | C8 | A | C | 1084 | 3.464 | −2.577 | 15.388 | 1.00 | 38.21 | RNA1 C |
| ATOM | 2242 | N7 | A | C | 1084 | 2.770 | −3.432 | 14.677 | 1.00 | 33.92 | RNA1 N |
| ATOM | 2243 | C5 | A | C | 1084 | 3.737 | −4.151 | 13.984 | 1.00 | 35.92 | RNA1 C |
| ATOM | 2244 | C6 | A | C | 1084 | 3.648 | −5.222 | 13.069 | 1.00 | 34.35 | RNA1 C |
| ATOM | 2245 | N6 | A | C | 1084 | 2.493 | −5.781 | 12.695 | 1.00 | 38.02 | RNA1 N |
| ATOM | 2246 | N1 | A | C | 1084 | 4.802 | −5.704 | 12.551 | 1.00 | 36.24 | RNA1 N |
| ATOM | 2247 | C2 | A | C | 1084 | 5.960 | −5.145 | 12.935 | 1.00 | 38.72 | RNA1 C |
| ATOM | 2248 | N3 | A | C | 1084 | 6.173 | −4.143 | 13.790 | 1.00 | 34.15 | RNA1 N |
| ATOM | 2249 | C4 | A | C | 1084 | 5.007 | −3.689 | 14.291 | 1.00 | 36.93 | RNA1 C |
| ATOM | 2250 | P | A | C | 1085 | 5.839 | 2.793 | 14.965 | 1.00 | 32.91 | RNA1 P |
| ATOM | 2251 | O1P | A | C | 1085 | 4.351 | 2.768 | 14.939 | 1.00 | 23.95 | RNA1 O |
| ATOM | 2252 | O2P | A | C | 1085 | 6.554 | 4.030 | 15.366 | 1.00 | 36.15 | RNA1 O |
| ATOM | 2253 | O5* | A | C | 1085 | 6.414 | 2.342 | 13.557 | 1.00 | 34.02 | RNA1 O |
| ATOM | 2254 | C5* | A | C | 1085 | 7.826 | 2.172 | 13.384 | 1.00 | 35.68 | RNA1 C |
| ATOM | 2255 | C4* | A | C | 1085 | 8.100 | 1.383 | 12.136 | 1.00 | 40.49 | RNA1 C |
| ATOM | 2256 | O4* | A | C | 1085 | 7.592 | 0.035 | 12.283 | 1.00 | 46.64 | RNA1 O |
| ATOM | 2257 | C3* | A | C | 1085 | 7.426 | 1.921 | 10.889 | 1.00 | 37.28 | RNA1 C |
| ATOM | 2258 | O3* | A | C | 1085 | 8.249 | 2.933 | 10.322 | 1.00 | 38.08 | RNA1 O |
| ATOM | 2259 | C2* | A | C | 1085 | 7.311 | 0.685 | 10.002 | 1.00 | 36.45 | RNA1 C |
| ATOM | 2260 | O2* | A | C | 1085 | 8.496 | 0.425 | 9.278 | 1.00 | 44.66 | RNA1 O |
| ATOM | 2261 | C1* | A | C | 1085 | 7.122 | −0.432 | 11.032 | 1.00 | 36.77 | RNA1 C |
| ATOM | 2262 | N9 | A | C | 1085 | 5.743 | −0.875 | 11.198 | 1.00 | 24.80 | RNA1 N |
| ATOM | 2263 | C8 | A | C | 1085 | 4.754 | −0.265 | 11.923 | 1.00 | 28.92 | RNA1 C |
| ATOM | 2264 | N7 | A | C | 1085 | 3.606 | −0.896 | 11.888 | 1.00 | 28.93 | RNA1 N |
| ATOM | 2265 | C5 | A | C | 1085 | 3.857 | −2.000 | 11.087 | 1.00 | 22.34 | RNA1 C |
| ATOM | 2266 | C6 | A | C | 1085 | 3.040 | −3.060 | 10.664 | 1.00 | 26.52 | RNA1 C |
| ATOM | 2267 | N6 | A | C | 1085 | 1.749 | −3.175 | 11.000 | 1.00 | 26.24 | RNA1 N |

TABLE II-continued

| | | | | | | | | | | | |
|---|---|---|---|---|---|---|---|---|---|---|---|
| ATOM | 2268 | N1 | A | C | 1085 | 3.596 | −4.006 | 9.874 | 1.00 | 25.01 | RNA1 N |
| ATOM | 2269 | C2 | A | C | 1085 | 4.889 | −3.875 | 9.532 | 1.00 | 27.90 | RNA1 C |
| ATOM | 2270 | N3 | A | C | 1085 | 5.758 | −2.920 | 9.864 | 1.00 | 23.94 | RNA1 N |
| ATOM | 2271 | C4 | A | C | 1085 | 5.171 | −2.002 | 10.654 | 1.00 | 23.81 | RNA1 C |
| ATOM | 2272 | P | A | C | 1086 | 7.578 | 4.220 | 9.636 | 1.00 | 38.44 | RNA1 P |
| ATOM | 2273 | O1P | A | C | 1086 | 6.238 | 4.440 | 10.244 | 1.00 | 21.00 | RNA1 O |
| ATOM | 2274 | O2P | A | C | 1086 | 8.578 | 5.315 | 9.641 | 1.00 | 32.04 | RNA1 O |
| ATOM | 2275 | O5* | A | C | 1086 | 7.359 | 3.750 | 8.133 | 1.00 | 44.64 | RNA1 O |
| ATOM | 2276 | C5* | A | C | 1086 | 8.465 | 3.286 | 7.337 | 1.00 | 27.97 | RNA1 C |
| ATOM | 2277 | C4* | A | C | 1086 | 7.965 | 2.407 | 6.217 | 1.00 | 34.03 | RNA1 C |
| ATOM | 2278 | O4* | A | C | 1086 | 7.509 | 1.138 | 6.753 | 1.00 | 34.69 | RNA1 O |
| ATOM | 2279 | C3* | A | C | 1086 | 6.759 | 2.929 | 5.455 | 1.00 | 38.31 | RNA1 C |
| ATOM | 2280 | O3* | A | C | 1086 | 7.095 | 3.913 | 4.484 | 1.00 | 30.65 | RNA1 O |
| ATOM | 2281 | C2* | A | C | 1086 | 6.166 | 1.659 | 4.850 | 1.00 | 40.89 | RNA1 C |
| ATOM | 2282 | O2* | A | C | 1086 | 6.734 | 1.284 | 3.610 | 1.00 | 37.38 | RNA1 O |
| ATOM | 2283 | C1* | A | C | 1086 | 6.488 | 0.616 | 5.925 | 1.00 | 29.88 | RNA1 C |
| ATOM | 2284 | N9 | A | C | 1086 | 5.326 | 0.253 | 6.739 | 1.00 | 26.28 | RNA1 N |
| ATOM | 2285 | C8 | A | C | 1086 | 4.885 | −1.015 | 7.018 | 1.00 | 26.71 | RNA1 C |
| ATOM | 2286 | N7 | A | C | 1086 | 3.748 | −1.049 | 7.675 | 1.00 | 32.50 | RNA1 N |
| ATOM | 2287 | C5 | A | C | 1086 | 3.437 | 0.289 | 7.869 | 1.00 | 23.83 | RNA1 C |
| ATOM | 2288 | C6 | A | C | 1086 | 2.346 | 0.926 | 8.486 | 1.00 | 32.24 | RNA1 C |
| ATOM | 2289 | N6 | A | C | 1086 | 1.320 | 0.274 | 9.042 | 1.00 | 40.46 | RNA1 N |
| ATOM | 2290 | N1 | A | C | 1086 | 2.340 | 2.275 | 8.508 | 1.00 | 27.06 | RNA1 N |
| ATOM | 2291 | C2 | A | C | 1086 | 3.359 | 2.928 | 7.943 | 1.00 | 26.31 | RNA1 C |
| ATOM | 2292 | N3 | A | C | 1086 | 4.435 | 2.444 | 7.329 | 1.00 | 27.72 | RNA1 N |
| ATOM | 2293 | C4 | A | C | 1086 | 4.413 | 1.102 | 7.323 | 1.00 | 23.09 | RNA1 C |
| ATOM | 2294 | P | G | C | 1087 | 6.254 | 5.281 | 4.430 | 1.00 | 30.97 | RNA1 P |
| ATOM | 2295 | O1P | G | C | 1087 | 4.896 | 4.969 | 3.921 | 1.00 | 19.34 | RNA1 O |
| ATOM | 2296 | O2P | G | C | 1087 | 6.402 | 5.980 | 5.734 | 1.00 | 46.09 | RNA1 O |
| ATOM | 2297 | O5* | G | C | 1087 | 7.006 | 6.141 | 3.329 | 1.00 | 29.62 | RNA1 O |
| ATOM | 2298 | C5* | G | C | 1087 | 8.108 | 6.998 | 3.667 | 1.00 | 28.45 | RNA1 C |
| ATOM | 2299 | C4* | G | C | 1087 | 8.911 | 7.283 | 2.428 | 1.00 | 31.27 | RNA1 C |
| ATOM | 2300 | O4* | G | C | 1087 | 9.604 | 6.075 | 2.060 | 1.00 | 35.33 | RNA1 O |
| ATOM | 2301 | C3* | G | C | 1087 | 8.034 | 7.656 | 1.244 | 1.00 | 31.37 | RNA1 C |
| ATOM | 2302 | O3* | G | C | 1087 | 7.978 | 9.077 | 1.163 | 1.00 | 19.46 | RNA1 O |
| ATOM | 2303 | C2* | G | C | 1087 | 8.776 | 7.064 | 0.049 | 1.00 | 32.80 | RNA1 C |
| ATOM | 2304 | O2* | G | C | 1087 | 9.745 | 7.961 | −0.462 | 1.00 | 29.59 | RNA1 O |
| ATOM | 2305 | C1* | G | C | 1087 | 9.484 | 5.854 | 0.674 | 1.00 | 27.32 | RNA1 C |
| ATOM | 2306 | N9 | G | C | 1087 | 8.899 | 4.525 | 0.520 | 1.00 | 19.62 | RNA1 N |
| ATOM | 2307 | C8 | G | C | 1087 | 7.596 | 4.129 | 0.735 | 1.00 | 23.90 | RNA1 C |
| ATOM | 2308 | N7 | G | C | 1087 | 7.429 | 2.836 | 0.618 | 1.00 | 9.45 | RNA1 N |
| ATOM | 2309 | C5 | G | C | 1087 | 8.685 | 2.359 | 0.273 | 1.00 | 16.55 | RNA1 C |
| ATOM | 2310 | C6 | G | C | 1087 | 9.128 | 1.036 | 0.007 | 1.00 | 25.58 | RNA1 C |
| ATOM | 2311 | O6 | G | C | 1087 | 8.476 | −0.016 | 0.029 | 1.00 | 25.76 | RNA1 O |
| ATOM | 2312 | N1 | G | C | 1087 | 10.483 | 1.004 | −0.307 | 1.00 | 13.38 | RNA1 N |
| ATOM | 2313 | C2 | G | C | 1087 | 11.309 | 2.103 | −0.354 | 1.00 | 25.58 | RNA1 C |
| ATOM | 2314 | N2 | G | C | 1087 | 12.595 | 1.870 | −0.653 | 1.00 | 21.09 | RNA1 N |
| ATOM | 2315 | N3 | G | C | 1087 | 10.906 | 3.341 | −0.116 | 1.00 | 22.18 | RNA1 N |
| ATOM | 2316 | C4 | G | C | 1087 | 9.596 | 3.394 | 0.191 | 1.00 | 16.33 | RNA1 C |
| ATOM | 2317 | P | A | C | 1088 | 6.677 | 9.862 | 1.669 | 1.00 | 23.48 | RNA1 P |
| ATOM | 2318 | O1P | A | C | 1088 | 6.035 | 9.121 | 2.788 | 1.00 | 34.67 | RNA1 O |
| ATOM | 2319 | O2P | A | C | 1088 | 7.106 | 11.267 | 1.858 | 1.00 | 30.75 | RNA1 O |
| ATOM | 2320 | O5* | A | C | 1088 | 5.683 | 9.810 | 0.434 | 1.00 | 34.79 | RNA1 O |
| ATOM | 2321 | C5* | A | C | 1088 | 6.166 | 10.084 | −0.886 | 1.00 | 33.74 | RNA1 C |
| ATOM | 2322 | C4* | A | C | 1088 | 5.808 | 8.952 | −1.804 | 1.00 | 29.37 | RNA1 C |
| ATOM | 2323 | O4* | A | C | 1088 | 4.376 | 8.744 | −1.752 | 1.00 | 30.18 | RNA1 O |
| ATOM | 2324 | C3* | A | C | 1088 | 6.153 | 9.200 | −3.261 | 1.00 | 27.75 | RNA1 C |
| ATOM | 2325 | O3* | A | C | 1088 | 6.465 | 7.951 | −3.847 | 1.00 | 19.39 | RNA1 O |
| ATOM | 2326 | C2* | A | C | 1088 | 4.848 | 9.717 | −3.842 | 1.00 | 20.69 | RNA1 C |
| ATOM | 2327 | O2* | A | C | 1088 | 4.730 | 9.462 | −5.224 | 1.00 | 39.54 | RNA1 O |
| ATOM | 2328 | C1* | A | C | 1088 | 3.821 | 8.926 | −3.035 | 1.00 | 19.38 | RNA1 C |
| ATOM | 2329 | N9 | A | C | 1088 | 2.553 | 9.623 | −2.868 | 1.00 | 12.67 | RNA1 N |
| ATOM | 2330 | C8 | A | C | 1088 | 1.291 | 9.132 | −3.089 | 1.00 | 19.49 | RNA1 C |
| ATOM | 2331 | N7 | A | C | 1088 | 0.338 | 9.996 | −2.842 | 1.00 | 19.80 | RNA1 N |
| ATOM | 2332 | C5 | A | C | 1088 | 1.019 | 11.134 | −2.432 | 1.00 | 11.03 | RNA1 C |
| ATOM | 2333 | C6 | A | C | 1088 | 0.578 | 12.406 | −2.033 | 1.00 | 14.84 | RNA1 C |
| ATOM | 2334 | N6 | A | C | 1088 | −0.708 | 12.768 | −1.988 | 1.00 | 13.38 | RNA1 N |
| ATOM | 2335 | N1 | A | C | 1088 | 1.517 | 13.309 | −1.680 | 1.00 | 16.35 | RNA1 N |
| ATOM | 2336 | C2 | A | C | 1088 | 2.807 | 12.952 | −1.736 | 1.00 | 16.68 | RNA1 C |
| ATOM | 2337 | N3 | A | C | 1088 | 3.343 | 11.792 | −2.099 | 1.00 | 19.47 | RNA1 N |
| ATOM | 2338 | C4 | A | C | 1088 | 2.383 | 10.917 | −2.440 | 1.00 | 11.60 | RNA1 C |
| ATOM | 2339 | P | G | C | 1089 | 7.282 | 7.896 | −5.216 | 1.00 | 26.48 | RNA1 P |
| ATOM | 2340 | O1P | G | C | 1089 | 7.768 | 9.270 | −5.525 | 1.00 | 30.79 | RNA1 O |
| ATOM | 2341 | O2P | G | C | 1089 | 6.437 | 7.171 | −6.198 | 1.00 | 18.45 | RNA1 O |
| ATOM | 2342 | O5* | G | C | 1089 | 8.548 | 7.011 | −4.853 | 1.00 | 14.93 | RNA1 O |
| ATOM | 2343 | C5* | G | C | 1089 | 9.568 | 7.515 | −3.971 | 1.00 | 29.50 | RNA1 C |
| ATOM | 2344 | C4* | G | C | 1089 | 10.362 | 6.367 | −3.400 | 1.00 | 26.25 | RNA1 C |
| ATOM | 2345 | O4* | G | C | 1089 | 9.469 | 5.554 | −2.600 | 1.00 | 34.26 | RNA1 O |
| ATOM | 2346 | C3* | G | C | 1089 | 10.981 | 5.439 | −4.439 | 1.00 | 20.63 | RNA1 C |

TABLE II-continued

| | | | | | | | | | | | |
|---|---|---|---|---|---|---|---|---|---|---|---|
| ATOM | 2347 | O3* | G | C | 1089 | 12.197 | 4.922 | −3.925 | 1.00 | 28.79 | RNA1 O |
| ATOM | 2348 | C2* | G | C | 1089 | 9.965 | 4.305 | −4.531 | 1.00 | 28.82 | RNA1 C |
| ATOM | 2349 | O2* | G | C | 1089 | 10.543 | 3.072 | −4.908 | 1.00 | 40.76 | RNA1 O |
| ATOM | 2350 | C1* | G | C | 1089 | 9.439 | 4.238 | −3.099 | 1.00 | 19.76 | RNA1 C |
| ATOM | 2351 | N9 | G | C | 1089 | 8.069 | 3.749 | −2.988 | 1.00 | 15.09 | RNA1 N |
| ATOM | 2352 | C8 | G | C | 1089 | 6.930 | 4.499 | −2.817 | 1.00 | 17.24 | RNA1 C |
| ATOM | 2353 | N7 | G | C | 1089 | 5.848 | 3.773 | −2.729 | 1.00 | 20.25 | RNA1 N |
| ATOM | 2354 | C5 | G | C | 1089 | 6.301 | 2.466 | −2.857 | 1.00 | 14.36 | RNA1 C |
| ATOM | 2355 | C6 | G | C | 1089 | 5.590 | 1.243 | −2.839 | 1.00 | 23.53 | RNA1 C |
| ATOM | 2356 | O6 | G | C | 1089 | 4.368 | 1.060 | −2.704 | 1.00 | 38.04 | RNA1 O |
| ATOM | 2357 | N1 | G | C | 1089 | 6.442 | 0.156 | −2.998 | 1.00 | 10.56 | RNA1 N |
| ATOM | 2358 | C2 | G | C | 1089 | 7.801 | 0.235 | −3.159 | 1.00 | 16.75 | RNA1 C |
| ATOM | 2359 | N2 | G | C | 1089 | 8.456 | −0.931 | −3.305 | 1.00 | 18.05 | RNA1 N |
| ATOM | 2360 | N3 | G | C | 1089 | 8.475 | 1.369 | −3.178 | 1.00 | 14.70 | RNA1 N |
| ATOM | 2361 | C4 | G | C | 1089 | 7.668 | 2.437 | −3.022 | 1.00 | 10.92 | RNA1 C |
| ATOM | 2362 | P | U | C | 1090 | 13.585 | 5.675 | −4.221 | 1.00 | 43.14 | RNA1 P |
| ATOM | 2363 | O1P | U | C | 1090 | 13.436 | 6.453 | −5.476 | 1.00 | 42.35 | RNA1 O |
| ATOM | 2364 | O2P | U | C | 1090 | 14.010 | 6.371 | −2.971 | 1.00 | 42.92 | RNA1 O |
| ATOM | 2365 | O5* | U | C | 1090 | 14.587 | 4.467 | −4.490 | 1.00 | 39.62 | RNA1 O |
| ATOM | 2366 | C5* | U | C | 1090 | 15.989 | 4.585 | −4.207 | 1.00 | 45.78 | RNA1 C |
| ATOM | 2367 | C4* | U | C | 1090 | 16.693 | 3.275 | −4.492 | 1.00 | 55.27 | RNA1 C |
| ATOM | 2368 | O4* | U | C | 1090 | 16.237 | 2.246 | −3.570 | 1.00 | 55.21 | RNA1 O |
| ATOM | 2369 | C3* | U | C | 1090 | 16.455 | 2.661 | −5.862 | 1.00 | 53.66 | RNA1 C |
| ATOM | 2370 | O3* | U | C | 1090 | 17.267 | 3.222 | −6.875 | 1.00 | 51.89 | RNA1 O |
| ATOM | 2371 | C2* | U | C | 1090 | 16.781 | 1.194 | −5.637 | 1.00 | 48.18 | RNA1 C |
| ATOM | 2372 | O2* | U | C | 1090 | 18.172 | 0.949 | −5.690 | 1.00 | 54.31 | RNA1 O |
| ATOM | 2373 | C1* | U | C | 1090 | 16.271 | 0.979 | −4.213 | 1.00 | 41.15 | RNA1 C |
| ATOM | 2374 | N1 | U | C | 1090 | 14.922 | 0.387 | −4.190 | 1.00 | 41.07 | RNA1 N |
| ATOM | 2375 | C2 | U | C | 1090 | 14.823 | −0.998 | −4.283 | 1.00 | 36.51 | RNA1 C |
| ATOM | 2376 | O2 | U | C | 1090 | 15.792 | −1.730 | −4.388 | 1.00 | 37.99 | RNA1 O |
| ATOM | 2377 | N3 | U | C | 1090 | 13.542 | −1.493 | −4.256 | 1.00 | 24.06 | RNA1 N |
| ATOM | 2378 | C4 | U | C | 1090 | 12.374 | −0.772 | −4.150 | 1.00 | 29.36 | RNA1 C |
| ATOM | 2379 | O4 | U | C | 1090 | 11.297 | −1.373 | −4.078 | 1.00 | 32.44 | RNA1 O |
| ATOM | 2380 | C5 | U | C | 1090 | 12.554 | 0.649 | −4.068 | 1.00 | 27.73 | RNA1 C |
| ATOM | 2381 | C6 | U | C | 1090 | 13.788 | 1.167 | −4.087 | 1.00 | 33.24 | RNA1 C |
| ATOM | 2382 | P | G | C | 1091 | 16.725 | 3.245 | −8.383 | 1.00 | 58.06 | RNA1 P |
| ATOM | 2383 | O1P | G | C | 1091 | 15.277 | 3.599 | −8.351 | 1.00 | 49.18 | RNA1 O |
| ATOM | 2384 | O2P | G | C | 1091 | 17.668 | 4.074 | −9.177 | 1.00 | 62.85 | RNA1 O |
| ATOM | 2385 | O5* | G | C | 1091 | 16.838 | 1.724 | −8.851 | 1.00 | 59.36 | RNA1 O |
| ATOM | 2386 | C5* | G | C | 1091 | 18.123 | 1.141 | −9.135 | 1.00 | 62.76 | RNA1 C |
| ATOM | 2387 | C4* | G | C | 1091 | 18.029 | −0.370 | −9.212 | 1.00 | 62.76 | RNA1 C |
| ATOM | 2388 | O4* | G | C | 1091 | 17.448 | −0.882 | −7.980 | 1.00 | 57.83 | RNA1 O |
| ATOM | 2389 | C3* | G | C | 1091 | 17.168 | −0.998 | −10.302 | 1.00 | 67.15 | RNA1 C |
| ATOM | 2390 | O3* | G | C | 1091 | 17.800 | −1.073 | −11.581 | 1.00 | 73.47 | RNA1 O |
| ATOM | 2391 | C2* | G | C | 1091 | 16.911 | −2.391 | −9.736 | 1.00 | 63.68 | RNA1 C |
| ATOM | 2392 | O2* | G | C | 1091 | 17.997 | −3.276 | −9.939 | 1.00 | 66.38 | RNA1 O |
| ATOM | 2393 | C1* | G | C | 1091 | 16.766 | −2.098 | −8.243 | 1.00 | 52.76 | RNA1 C |
| ATOM | 2394 | N9 | G | C | 1091 | 15.354 | −1.954 | −7.902 | 1.00 | 42.68 | RNA1 N |
| ATOM | 2395 | C8 | G | C | 1091 | 14.638 | −0.795 | −7.717 | 1.00 | 43.79 | RNA1 C |
| ATOM | 2396 | N7 | G | C | 1091 | 13.368 | −1.009 | −7.490 | 1.00 | 42.36 | RNA1 N |
| ATOM | 2397 | C5 | G | C | 1091 | 13.243 | −2.392 | −7.512 | 1.00 | 31.07 | RNA1 C |
| ATOM | 2398 | C6 | G | C | 1091 | 12.100 | −3.220 | −7.342 | 1.00 | 32.80 | RNA1 C |
| ATOM | 2399 | O6 | G | C | 1091 | 10.926 | −2.886 | −7.133 | 1.00 | 29.29 | RNA1 O |
| ATOM | 2400 | N1 | G | C | 1091 | 12.427 | −4.567 | −7.442 | 1.00 | 27.53 | RNA1 N |
| ATOM | 2401 | C2 | G | C | 1091 | 13.687 | −5.057 | −7.676 | 1.00 | 37.58 | RNA1 C |
| ATOM | 2402 | N2 | G | C | 1091 | 13.806 | −6.387 | −7.734 | 1.00 | 43.37 | RNA1 N |
| ATOM | 2403 | N3 | G | C | 1091 | 14.754 | −4.300 | −7.840 | 1.00 | 37.83 | RNA1 N |
| ATOM | 2404 | C4 | G | C | 1091 | 14.461 | −2.989 | −7.748 | 1.00 | 34.74 | RNA1 C |
| ATOM | 2405 | P | C | C | 1092 | 16.901 | −1.334 | −12.902 | 1.00 | 78.16 | RNA1 P |
| ATOM | 2406 | O1P | C | C | 1092 | 15.717 | −0.429 | −12.869 | 1.00 | 76.90 | RNA1 O |
| ATOM | 2407 | O2P | C | C | 1092 | 17.813 | −1.307 | −14.079 | 1.00 | 77.44 | RNA1 O |
| ATOM | 2408 | O5* | C | C | 1092 | 16.360 | −2.822 | −12.721 | 1.00 | 69.64 | RNA1 O |
| ATOM | 2409 | C5* | C | C | 1092 | 17.277 | −3.929 | −12.693 | 1.00 | 63.11 | RNA1 C |
| ATOM | 2410 | C4* | C | C | 1092 | 16.536 | −5.243 | −12.604 | 1.00 | 59.28 | RNA1 C |
| ATOM | 2411 | O4* | C | C | 1092 | 15.859 | −5.364 | −11.322 | 1.00 | 50.31 | RNA1 O |
| ATOM | 2412 | C3* | C | C | 1092 | 15.433 | −5.487 | −13.621 | 1.00 | 60.54 | RNA1 C |
| ATOM | 2413 | O3* | C | C | 1092 | 15.910 | −5.898 | −14.893 | 1.00 | 61.03 | RNA1 O |
| ATOM | 2414 | C2* | C | C | 1092 | 14.614 | −6.580 | −12.949 | 1.00 | 56.00 | RNA1 C |
| ATOM | 2415 | O2* | C | C | 1092 | 15.155 | −7.875 | −13.128 | 1.00 | 59.60 | RNA1 O |
| ATOM | 2416 | C1* | C | C | 1092 | 14.704 | −6.175 | −11.477 | 1.00 | 46.68 | RNA1 C |
| ATOM | 2417 | N1 | C | C | 1092 | 13.500 | −5.411 | −11.103 | 1.00 | 45.69 | RNA1 N |
| ATOM | 2418 | C2 | C | C | 1092 | 12.311 | −6.125 | −10.845 | 1.00 | 48.75 | RNA1 C |
| ATOM | 2419 | O2 | C | C | 1092 | 12.334 | −7.367 | −10.877 | 1.00 | 35.22 | RNA1 O |
| ATOM | 2420 | N3 | C | C | 1092 | 11.175 | −5.443 | −10.568 | 1.00 | 40.06 | RNA1 N |
| ATOM | 2421 | C4 | C | C | 1092 | 11.191 | −4.109 | −10.529 | 1.00 | 43.65 | RNA1 C |
| ATOM | 2422 | N4 | C | C | 1092 | 10.043 | −3.483 | −10.269 | 1.00 | 38.14 | RNA1 N |
| ATOM | 2423 | C5 | C | C | 1092 | 12.386 | −3.357 | −10.759 | 1.00 | 43.83 | RNA1 C |
| ATOM | 2424 | C6 | C | C | 1092 | 13.508 | −4.043 | −11.036 | 1.00 | 48.70 | RNA1 C |
| ATOM | 2425 | P | G | C | 1093 | 15.082 | −5.497 | −16.210 | 1.00 | 59.69 | RNA1 P |

TABLE II-continued

| | | | | | | | | | | | |
|---|---|---|---|---|---|---|---|---|---|---|---|
| ATOM | 2426 | O1P | G | C | 1093 | 14.954 | −4.014 | −16.213 | 1.00 | 64.26 | RNA1 | O |
| ATOM | 2427 | O2P | G | C | 1093 | 15.706 | −6.182 | −17.376 | 1.00 | 68.36 | RNA1 | O |
| ATOM | 2428 | O5* | G | C | 1093 | 13.629 | −6.109 | −15.961 | 1.00 | 39.18 | RNA1 | O |
| ATOM | 2429 | C5* | G | C | 1093 | 13.440 | −7.525 | −15.810 | 1.00 | 34.94 | RNA1 | C |
| ATOM | 2430 | C4* | G | C | 1093 | 12.017 | −7.828 | −15.395 | 1.00 | 40.12 | RNA1 | C |
| ATOM | 2431 | O4* | G | C | 1093 | 11.737 | −7.199 | −14.117 | 1.00 | 45.67 | RNA1 | O |
| ATOM | 2432 | C3* | G | C | 1093 | 10.929 | −7.304 | −16.315 | 1.00 | 43.53 | RNA1 | C |
| ATOM | 2433 | O3* | G | C | 1093 | 10.687 | −8.168 | −17.410 | 1.00 | 48.03 | RNA1 | O |
| ATOM | 2434 | C2* | G | C | 1093 | 9.720 | −7.183 | −15.391 | 1.00 | 41.69 | RNA1 | C |
| ATOM | 2435 | O2* | G | C | 1093 | 8.996 | −8.389 | −15.229 | 1.00 | 27.92 | RNA1 | O |
| ATOM | 2436 | C1* | G | C | 1093 | 10.381 | −6.769 | −14.075 | 1.00 | 38.16 | RNA1 | C |
| ATOM | 2437 | N9 | G | C | 1093 | 10.350 | −5.318 | −13.870 | 1.00 | 36.77 | RNA1 | N |
| ATOM | 2438 | C8 | G | C | 1093 | 11.401 | −4.431 | −13.970 | 1.00 | 34.83 | RNA1 | C |
| ATOM | 2439 | N7 | G | C | 1093 | 11.048 | −3.190 | −13.762 | 1.00 | 32.06 | RNA1 | N |
| ATOM | 2440 | C5 | G | C | 1093 | 9.685 | −3.259 | −13.505 | 1.00 | 27.72 | RNA1 | C |
| ATOM | 2441 | C6 | G | C | 1093 | 8.752 | −2.231 | −13.223 | 1.00 | 27.54 | RNA1 | C |
| ATOM | 2442 | O6 | G | C | 1093 | 8.947 | −1.013 | −13.160 | 1.00 | 34.45 | RNA1 | O |
| ATOM | 2443 | N1 | G | C | 1093 | 7.475 | −2.743 | −13.014 | 1.00 | 19.53 | RNA1 | N |
| ATOM | 2444 | C2 | G | C | 1093 | 7.136 | −4.075 | −13.075 | 1.00 | 19.64 | RNA1 | C |
| ATOM | 2445 | N2 | G | C | 1093 | 5.851 | −4.382 | −12.830 | 1.00 | 17.24 | RNA1 | N |
| ATOM | 2446 | N3 | G | C | 1093 | 7.993 | −5.040 | −13.352 | 1.00 | 21.92 | RNA1 | N |
| ATOM | 2447 | C4 | G | C | 1093 | 9.241 | −4.566 | −13.554 | 1.00 | 25.99 | RNA1 | C |
| ATOM | 2448 | P | U | C | 1094 | 10.214 | −7.545 | −18.808 | 1.00 | 48.86 | RNA1 | P |
| ATOM | 2449 | O1P | U | C | 1094 | 11.019 | −6.314 | −19.033 | 1.00 | 51.40 | RNA1 | O |
| ATOM | 2450 | O2P | U | C | 1094 | 10.225 | −8.631 | −19.820 | 1.00 | 62.99 | RNA1 | O |
| ATOM | 2451 | O5* | U | C | 1094 | 8.700 | −7.137 | −18.549 | 1.00 | 35.14 | RNA1 | O |
| ATOM | 2452 | C5* | U | C | 1094 | 7.726 | −8.151 | −18.319 | 1.00 | 39.65 | RNA1 | C |
| ATOM | 2453 | C4* | U | C | 1094 | 6.342 | −7.561 | −18.289 | 1.00 | 45.60 | RNA1 | C |
| ATOM | 2454 | O4* | U | C | 1094 | 6.086 | −6.907 | −17.022 | 1.00 | 47.84 | RNA1 | O |
| ATOM | 2455 | C3* | U | C | 1094 | 6.030 | −6.503 | −19.328 | 1.00 | 46.03 | RNA1 | C |
| ATOM | 2456 | O3* | U | C | 1094 | 5.775 | −7.078 | −20.601 | 1.00 | 56.79 | RNA1 | O |
| ATOM | 2457 | C2* | U | C | 1094 | 4.829 | −5.786 | −18.713 | 1.00 | 44.04 | RNA1 | C |
| ATOM | 2458 | O2* | U | C | 1094 | 3.588 | −6.431 | −18.943 | 1.00 | 37.76 | RNA1 | O |
| ATOM | 2459 | C1* | U | C | 1094 | 5.168 | −5.844 | −17.219 | 1.00 | 44.47 | RNA1 | C |
| ATOM | 2460 | N1 | U | C | 1094 | 5.770 | −4.589 | −16.742 | 1.00 | 26.87 | RNA1 | N |
| ATOM | 2461 | C2 | U | C | 1094 | 4.909 | −3.585 | −16.329 | 1.00 | 22.09 | RNA1 | C |
| ATOM | 2462 | O2 | U | C | 1094 | 3.691 | −3.719 | −16.288 | 1.00 | 25.93 | RNA1 | O |
| ATOM | 2463 | N3 | U | C | 1094 | 5.519 | −2.419 | −15.962 | 1.00 | 13.38 | RNA1 | N |
| ATOM | 2464 | C4 | U | C | 1094 | 6.869 | −2.159 | −15.947 | 1.00 | 36.16 | RNA1 | C |
| ATOM | 2465 | O4 | U | C | 1094 | 7.263 | −1.036 | −15.621 | 1.00 | 36.16 | RNA1 | O |
| ATOM | 2466 | C5 | U | C | 1094 | 7.696 | −3.256 | −16.357 | 1.00 | 27.39 | RNA1 | C |
| ATOM | 2467 | C6 | U | C | 1094 | 7.131 | −4.404 | −16.729 | 1.00 | 19.00 | RNA1 | C |
| ATOM | 2468 | P | A | C | 1095 | 6.404 | −6.394 | −21.913 | 1.00 | 56.22 | RNA1 | P |
| ATOM | 2469 | O1P | A | C | 1095 | 7.761 | −5.866 | −21.571 | 1.00 | 36.24 | RNA1 | O |
| ATOM | 2470 | O2P | A | C | 1095 | 6.257 | −7.345 | −23.045 | 1.00 | 62.45 | RNA1 | O |
| ATOM | 2471 | O5* | A | C | 1095 | 5.420 | −5.169 | −22.156 | 1.00 | 37.34 | RNA1 | O |
| ATOM | 2472 | C5* | A | C | 1095 | 5.858 | −3.993 | −22.836 | 1.00 | 26.88 | RNA1 | C |
| ATOM | 2473 | C4* | A | C | 1095 | 4.732 | −3.002 | −22.897 | 1.00 | 25.01 | RNA1 | C |
| ATOM | 2474 | O4* | A | C | 1095 | 3.576 | −3.668 | −23.451 | 1.00 | 31.13 | RNA1 | O |
| ATOM | 2475 | C3* | A | C | 1095 | 4.254 | −2.489 | −21.555 | 1.00 | 30.12 | RNA1 | C |
| ATOM | 2476 | O3* | A | C | 1095 | 5.068 | −1.403 | −21.134 | 1.00 | 47.22 | RNA1 | O |
| ATOM | 2477 | C2* | A | C | 1095 | 2.797 | −2.116 | −21.824 | 1.00 | 32.85 | RNA1 | C |
| ATOM | 2478 | O2* | A | C | 1095 | 2.630 | −0.839 | −22.418 | 1.00 | 29.79 | RNA1 | O |
| ATOM | 2479 | C1* | A | C | 1095 | 2.395 | −3.179 | −22.845 | 1.00 | 21.93 | RNA1 | C |
| ATOM | 2480 | N9 | A | C | 1095 | 1.649 | −4.328 | −22.333 | 1.00 | 17.01 | RNA1 | N |
| ATOM | 2481 | C8 | A | C | 1095 | 2.142 | −5.568 | −21.985 | 1.00 | 21.36 | RNA1 | C |
| ATOM | 2482 | N7 | A | C | 1095 | 1.211 | −6.424 | −21.627 | 1.00 | 21.32 | RNA1 | N |
| ATOM | 2483 | C5 | A | C | 1095 | 0.031 | −5.696 | −21.729 | 1.00 | 10.86 | RNA1 | C |
| ATOM | 2484 | C6 | A | C | 1095 | −1.315 | −6.037 | −21.498 | 1.00 | 23.82 | RNA1 | C |
| ATOM | 2485 | N6 | A | C | 1095 | −1.717 | −7.254 | −21.118 | 1.00 | 35.80 | RNA1 | N |
| ATOM | 2486 | N1 | A | C | 1095 | −2.249 | −5.076 | −21.679 | 1.00 | 30.20 | RNA1 | N |
| ATOM | 2487 | C2 | A | C | 1095 | −1.844 | −3.861 | −22.076 | 1.00 | 23.15 | RNA1 | C |
| ATOM | 2488 | N3 | A | C | 1095 | −0.610 | −3.423 | −22.337 | 1.00 | 20.47 | RNA1 | N |
| ATOM | 2489 | C4 | A | C | 1095 | 0.289 | −4.399 | −22.143 | 1.00 | 9.00 | RNA1 | C |
| ATOM | 2490 | P | A | C | 1096 | 5.554 | −1.325 | −19.607 | 1.00 | 33.71 | RNA1 | P |
| ATOM | 2491 | O1P | A | C | 1096 | 5.985 | −2.689 | −19.209 | 1.00 | 38.06 | RNA1 | O |
| ATOM | 2492 | O2P | A | C | 1096 | 6.505 | −0.198 | −19.472 | 1.00 | 30.42 | RNA1 | O |
| ATOM | 2493 | O5* | A | C | 1096 | 4.203 | −0.950 | −18.856 | 1.00 | 19.71 | RNA1 | O |
| ATOM | 2494 | C5* | A | C | 1096 | 3.610 | 0.332 | −19.065 | 1.00 | 17.59 | RNA1 | C |
| ATOM | 2495 | C4* | A | C | 1096 | 2.176 | 0.335 | −18.609 | 1.00 | 25.20 | RNA1 | C |
| ATOM | 2496 | O4* | A | C | 1096 | 1.399 | −0.548 | −19.452 | 1.00 | 36.18 | RNA1 | O |
| ATOM | 2497 | C3* | A | C | 1096 | 1.916 | −0.155 | −17.197 | 1.00 | 31.52 | RNA1 | C |
| ATOM | 2498 | O3* | A | C | 1096 | 2.158 | 0.858 | −16.224 | 1.00 | 40.13 | RNA1 | O |
| ATOM | 2499 | C2* | A | C | 1096 | 0.458 | −0.589 | −17.277 | 1.00 | 29.94 | RNA1 | C |
| ATOM | 2500 | O2* | A | C | 1096 | −0.436 | 0.497 | −17.220 | 1.00 | 33.53 | RNA1 | O |
| ATOM | 2501 | C1* | A | C | 1096 | 0.392 | −1.181 | −18.684 | 1.00 | 28.76 | RNA1 | C |
| ATOM | 2502 | N9 | A | C | 1096 | 0.682 | −2.615 | −18.662 | 1.00 | 29.57 | RNA1 | N |
| ATOM | 2503 | C8 | A | C | 1096 | 1.915 | −3.230 | −18.760 | 1.00 | 20.07 | RNA1 | C |
| ATOM | 2504 | N7 | A | C | 1096 | 1.862 | −4.536 | −18.673 | 1.00 | 16.60 | RNA1 | N |

TABLE II-continued

| | | | | | | | | | | | |
|---|---|---|---|---|---|---|---|---|---|---|---|
| ATOM | 2505 | C5 | A | C | 1096 | 0.506 | −4.803 | −18.515 | 1.00 | 21.73 | RNA1 | C |
| ATOM | 2506 | C6 | A | C | 1096 | −0.207 | −6.004 | −18.372 | 1.00 | 21.62 | RNA1 | C |
| ATOM | 2507 | N6 | A | C | 1096 | 0.376 | −7.207 | −18.386 | 1.00 | 30.29 | RNA1 | N |
| ATOM | 2508 | N1 | A | C | 1096 | −1.551 | −5.928 | −18.222 | 1.00 | 19.53 | RNA1 | N |
| ATOM | 2509 | C2 | A | C | 1096 | −2.130 | −4.715 | −18.234 | 1.00 | 19.83 | RNA1 | C |
| ATOM | 2510 | N3 | A | C | 1096 | −1.565 | −3.512 | −18.377 | 1.00 | 21.31 | RNA1 | N |
| ATOM | 2511 | C4 | A | C | 1096 | −0.231 | −3.630 | −18.511 | 1.00 | 13.07 | RNA1 | C |
| ATOM | 2512 | P | C | C | 1097 | 2.770 | 0.451 | −14.795 | 1.00 | 34.58 | RNA1 | P |
| ATOM | 2513 | O1P | C | C | 1097 | 3.901 | −0.488 | −15.013 | 1.00 | 24.95 | RNA1 | O |
| ATOM | 2514 | O2P | C | C | 1097 | 3.010 | 1.716 | −14.062 | 1.00 | 42.37 | RNA1 | O |
| ATOM | 2515 | O5* | C | C | 1097 | 1.558 | −0.333 | −14.115 | 1.00 | 33.44 | RNA1 | O |
| ATOM | 2516 | C5* | C | C | 1097 | 1.711 | −1.664 | −13.564 | 1.00 | 27.30 | RNA1 | C |
| ATOM | 2517 | C4* | C | C | 1097 | 0.347 | −2.298 | −13.386 | 1.00 | 34.16 | RNA1 | C |
| ATOM | 2518 | O4* | C | C | 1097 | −0.067 | −2.943 | −14.625 | 1.00 | 37.39 | RNA1 | O |
| ATOM | 2519 | C3* | C | C | 1097 | 0.219 | −3.406 | −12.354 | 1.00 | 33.88 | RNA1 | C |
| ATOM | 2520 | O3* | C | C | 1097 | 0.093 | −2.924 | −11.025 | 1.00 | 36.37 | RNA1 | O |
| ATOM | 2521 | C2* | C | C | 1097 | −1.041 | −4.120 | −12.816 | 1.00 | 36.19 | RNA1 | C |
| ATOM | 2522 | O2* | C | C | 1097 | −2.214 | −3.415 | −12.457 | 1.00 | 31.86 | RNA1 | O |
| ATOM | 2523 | C1* | C | C | 1097 | −0.865 | −4.089 | −14.334 | 1.00 | 35.36 | RNA1 | C |
| ATOM | 2524 | N1 | C | C | 1097 | −0.146 | −5.311 | −14.780 | 1.00 | 29.78 | RNA1 | N |
| ATOM | 2525 | C2 | C | C | 1097 | −0.859 | −6.537 | −14.895 | 1.00 | 31.29 | RNA1 | C |
| ATOM | 2526 | O2 | C | C | 1097 | −2.097 | −6.552 | −14.732 | 1.00 | 30.74 | RNA1 | O |
| ATOM | 2527 | N3 | C | C | 1097 | −0.175 | −7.667 | −15.188 | 1.00 | 27.52 | RNA1 | N |
| ATOM | 2528 | C4 | C | C | 1097 | 1.146 | −7.616 | −15.390 | 1.00 | 35.55 | RNA1 | C |
| ATOM | 2529 | N4 | C | C | 1097 | 1.788 | −8.764 | −15.640 | 1.00 | 38.53 | RNA1 | N |
| ATOM | 2530 | C5 | C | C | 1097 | 1.874 | −6.389 | −15.338 | 1.00 | 27.77 | RNA1 | C |
| ATOM | 2531 | C6 | C | C | 1097 | 1.197 | −5.275 | −15.036 | 1.00 | 24.47 | RNA1 | C |
| ATOM | 2532 | P | A | C | 1098 | 1.072 | −3.493 | −9.886 | 1.00 | 38.47 | RNA1 | P |
| ATOM | 2533 | O1P | A | C | 1098 | 2.477 | −3.131 | −10.212 | 1.00 | 22.01 | RNA1 | O |
| ATOM | 2534 | O2P | A | C | 1098 | 0.484 | −3.068 | −8.588 | 1.00 | 56.40 | RNA1 | O |
| ATOM | 2535 | O5* | A | C | 1098 | 0.959 | −5.079 | −10.023 | 1.00 | 40.54 | RNA1 | O |
| ATOM | 2536 | C5* | A | C | 1098 | −0.328 | −5.740 | −9.972 | 1.00 | 47.03 | RNA1 | C |
| ATOM | 2537 | C4* | A | C | 1098 | −0.192 | −7.201 | −10.348 | 1.00 | 50.05 | RNA1 | C |
| ATOM | 2538 | O4* | A | C | 1098 | 0.276 | −7.310 | −11.720 | 1.00 | 43.04 | RNA1 | O |
| ATOM | 2539 | C3* | A | C | 1098 | 0.819 | −8.007 | −9.544 | 1.00 | 59.35 | RNA1 | C |
| ATOM | 2540 | O3* | A | C | 1098 | 0.289 | −8.467 | −8.305 | 1.00 | 57.94 | RNA1 | O |
| ATOM | 2541 | C2* | A | C | 1098 | 1.170 | −9.146 | −10.496 | 1.00 | 54.42 | RNA1 | C |
| ATOM | 2542 | O2* | A | C | 1098 | 0.229 | −10.203 | −10.479 | 1.00 | 63.88 | RNA1 | O |
| ATOM | 2543 | C1* | A | C | 1098 | 1.125 | −8.440 | −11.851 | 1.00 | 42.41 | RNA1 | C |
| ATOM | 2544 | N9 | A | C | 1098 | 2.456 | −7.982 | −12.247 | 1.00 | 29.98 | RNA1 | N |
| ATOM | 2545 | C8 | A | C | 1098 | 2.967 | −6.709 | −12.213 | 1.00 | 32.72 | RNA1 | C |
| ATOM | 2546 | N7 | A | C | 1098 | 4.222 | −6.633 | −12.588 | 1.00 | 34.32 | RNA1 | N |
| ATOM | 2547 | C5 | A | C | 1098 | 4.557 | −7.942 | −12.902 | 1.00 | 34.44 | RNA1 | C |
| ATOM | 2548 | C6 | A | C | 1098 | 5.751 | −8.533 | −13.363 | 1.00 | 43.55 | RNA1 | C |
| ATOM | 2549 | N6 | A | C | 1098 | 6.879 | −7.852 | −13.597 | 1.00 | 39.58 | RNA1 | N |
| ATOM | 2550 | N1 | A | C | 1098 | 5.746 | −9.866 | −13.579 | 1.00 | 48.91 | RNA1 | N |
| ATOM | 2551 | C2 | A | C | 1098 | 4.615 | −10.549 | −13.348 | 1.00 | 42.95 | RNA1 | C |
| ATOM | 2552 | N3 | A | C | 1098 | 3.435 | −10.108 | −12.916 | 1.00 | 35.82 | RNA1 | N |
| ATOM | 2553 | C4 | A | C | 1098 | 3.474 | −8.782 | −12.708 | 1.00 | 35.65 | RNA1 | C |
| ATOM | 2554 | P | G | C | 1099 | 1.238 | −8.516 | −7.006 | 1.00 | 52.26 | RNA1 | P |
| ATOM | 2555 | O1P | G | C | 1099 | 1.696 | −7.137 | −6.706 | 1.00 | 52.99 | RNA1 | O |
| ATOM | 2556 | O2P | G | C | 1099 | 0.511 | −9.287 | −5.970 | 1.00 | 54.62 | RNA1 | O |
| ATOM | 2557 | O5* | G | C | 1099 | 2.513 | −9.346 | −7.481 | 1.00 | 43.47 | RNA1 | O |
| ATOM | 2558 | C5* | G | C | 1099 | 2.413 | −10.749 | −7.772 | 1.00 | 41.68 | RNA1 | C |
| ATOM | 2559 | C4* | G | C | 1099 | 3.735 | −11.273 | −8.271 | 1.00 | 42.05 | RNA1 | C |
| ATOM | 2560 | O4* | G | C | 1099 | 4.033 | −10.671 | −9.554 | 1.00 | 43.83 | RNA1 | O |
| ATOM | 2561 | C3* | G | C | 1099 | 4.938 | −10.934 | −7.409 | 1.00 | 48.09 | RNA1 | C |
| ATOM | 2562 | O3* | G | C | 1099 | 5.100 | −11.821 | −6.317 | 1.00 | 58.27 | RNA1 | O |
| ATOM | 2563 | C2* | G | C | 1099 | 6.089 | −10.992 | −8.402 | 1.00 | 50.43 | RNA1 | C |
| ATOM | 2564 | O2* | G | C | 1099 | 6.588 | −12.296 | −8.639 | 1.00 | 57.02 | RNA1 | O |
| ATOM | 2565 | C1* | G | C | 1099 | 5.426 | −10.432 | −9.660 | 1.00 | 44.89 | RNA1 | C |
| ATOM | 2566 | N9 | G | C | 1099 | 5.639 | −8.989 | −9.729 | 1.00 | 45.65 | RNA1 | N |
| ATOM | 2567 | C8 | G | C | 1099 | 4.714 | −7.993 | −9.515 | 1.00 | 38.56 | RNA1 | C |
| ATOM | 2568 | N7 | G | C | 1099 | 5.228 | −6.796 | −9.584 | 1.00 | 41.94 | RNA1 | N |
| ATOM | 2569 | C5 | G | C | 1099 | 6.569 | −7.014 | −9.873 | 1.00 | 34.92 | RNA1 | C |
| ATOM | 2570 | C6 | G | C | 1099 | 7.631 | −6.094 | −10.053 | 1.00 | 42.48 | RNA1 | C |
| ATOM | 2571 | O6 | G | C | 1099 | 7.601 | −4.857 | −9.985 | 1.00 | 44.46 | RNA1 | O |
| ATOM | 2572 | N1 | G | C | 1099 | 8.829 | −6.746 | −10.336 | 1.00 | 41.82 | RNA1 | N |
| ATOM | 2573 | C2 | G | C | 1099 | 8.982 | −8.108 | −10.437 | 1.00 | 42.77 | RNA1 | C |
| ATOM | 2574 | N2 | G | C | 1099 | 10.211 | −8.548 | −10.736 | 1.00 | 31.50 | RNA1 | N |
| ATOM | 2575 | N3 | G | C | 1099 | 8.001 | −8.974 | −10.262 | 1.00 | 31.12 | RNA1 | N |
| ATOM | 2576 | C4 | G | C | 1099 | 6.832 | −8.362 | −9.984 | 1.00 | 33.36 | RNA1 | C |
| ATOM | 2577 | P | C | C | 1100 | 5.772 | −11.286 | −4.956 | 1.00 | 62.31 | RNA1 | P |
| ATOM | 2578 | O1P | C | C | 1100 | 5.270 | −9.914 | −4.687 | 1.00 | 56.23 | RNA1 | O |
| ATOM | 2579 | O2P | C | C | 1100 | 5.583 | −12.348 | −3.934 | 1.00 | 65.10 | RNA1 | O |
| ATOM | 2580 | O5* | C | C | 1100 | 7.320 | −11.188 | −5.316 | 1.00 | 45.54 | RNA1 | O |
| ATOM | 2581 | C5* | C | C | 1100 | 8.052 | −12.366 | −5.670 | 1.00 | 43.72 | RNA1 | C |
| ATOM | 2582 | C4* | C | C | 1100 | 9.458 | −12.015 | −6.069 | 1.00 | 40.97 | RNA1 | C |
| ATOM | 2583 | O4* | C | C | 1100 | 9.429 | −11.213 | −7.276 | 1.00 | 44.70 | RNA1 | O |

TABLE II-continued

| | | | | | | | | | | | |
|---|---|---|---|---|---|---|---|---|---|---|---|
| ATOM | 2584 | C3* | C | C | 1100 | 10.249 | −11.173 | −5.087 | 1.00 | 43.30 | RNA1 | C |
| ATOM | 2585 | O3* | C | C | 1100 | 10.817 | −11.913 | −4.022 | 1.00 | 57.32 | RNA1 | O |
| ATOM | 2586 | C2* | C | C | 1100 | 11.306 | −10.543 | −5.980 | 1.00 | 45.40 | RNA1 | C |
| ATOM | 2587 | O2* | C | C | 1100 | 12.407 | −11.390 | −6.236 | 1.00 | 41.08 | RNA1 | O |
| ATOM | 2588 | C1* | C | C | 1100 | 10.508 | −10.293 | −7.258 | 1.00 | 40.42 | RNA1 | C |
| ATOM | 2589 | N1 | C | C | 1100 | 9.968 | −8.923 | −7.239 | 1.00 | 34.22 | RNA1 | N |
| ATOM | 2590 | C2 | C | C | 1100 | 10.851 | −7.860 | −7.450 | 1.00 | 34.09 | RNA1 | C |
| ATOM | 2591 | O2 | C | C | 1100 | 12.043 | −8.112 | −7.698 | 1.00 | 30.44 | RNA1 | O |
| ATOM | 2592 | N3 | C | C | 1100 | 10.390 | −6.595 | −7.377 | 1.00 | 32.20 | RNA1 | N |
| ATOM | 2593 | C4 | C | C | 1100 | 9.102 | −6.369 | −7.112 | 1.00 | 36.06 | RNA1 | C |
| ATOM | 2594 | N4 | C | C | 1100 | 8.695 | −5.101 | −7.023 | 1.00 | 42.37 | RNA1 | N |
| ATOM | 2595 | C5 | C | C | 1100 | 8.173 | −7.432 | −6.920 | 1.00 | 31.00 | RNA1 | C |
| ATOM | 2596 | C6 | C | C | 1100 | 8.643 | −8.681 | −6.995 | 1.00 | 29.98 | RNA1 | C |
| ATOM | 2597 | P | U | C | 1101 | 11.026 | −11.199 | −2.592 | 1.00 | 60.70 | RNA1 | P |
| ATOM | 2598 | O1P | U | C | 1101 | 9.727 | −10.588 | −2.196 | 1.00 | 50.26 | RNA1 | O |
| ATOM | 2599 | O2P | U | C | 1101 | 11.694 | −12.160 | −1.673 | 1.00 | 70.90 | RNA1 | O |
| ATOM | 2600 | O5* | U | C | 1101 | 12.055 | −10.024 | −2.904 | 1.00 | 44.87 | RNA1 | O |
| ATOM | 2601 | C5* | U | C | 1101 | 13.364 | −10.316 | −3.411 | 1.00 | 39.54 | RNA1 | C |
| ATOM | 2602 | C4* | U | C | 1101 | 14.139 | −9.041 | −3.619 | 1.00 | 45.93 | RNA1 | C |
| ATOM | 2603 | O4* | U | C | 1101 | 13.487 | −8.234 | −4.635 | 1.00 | 53.56 | RNA1 | O |
| ATOM | 2604 | C3* | U | C | 1101 | 14.232 | −8.111 | −2.424 | 1.00 | 45.04 | RNA1 | C |
| ATOM | 2605 | O3* | U | C | 1101 | 15.241 | −8.491 | −1.503 | 1.00 | 55.35 | RNA1 | O |
| ATOM | 2606 | C2* | U | C | 1101 | 14.519 | −6.767 | −3.078 | 1.00 | 45.97 | RNA1 | C |
| ATOM | 2607 | O2* | U | C | 1101 | 15.875 | −6.620 | −3.450 | 1.00 | 43.86 | RNA1 | O |
| ATOM | 2608 | C1* | U | C | 1101 | 13.668 | −6.856 | −4.341 | 1.00 | 43.43 | RNA1 | C |
| ATOM | 2609 | N1 | U | C | 1101 | 12.349 | −6.220 | −4.172 | 1.00 | 40.87 | RNA1 | N |
| ATOM | 2610 | C2 | U | C | 1101 | 12.289 | −4.831 | −4.234 | 1.00 | 35.67 | RNA1 | C |
| ATOM | 2611 | O2 | U | C | 1101 | 13.277 | −4.130 | −4.420 | 1.00 | 34.43 | RNA1 | O |
| ATOM | 2612 | N3 | U | C | 1101 | 11.032 | −4.294 | −4.067 | 1.00 | 27.89 | RNA1 | N |
| ATOM | 2613 | C4 | U | C | 1101 | 9.851 | −4.983 | −3.852 | 1.00 | 38.34 | RNA1 | C |
| ATOM | 2614 | O4 | U | C | 1101 | 8.792 | −4.355 | −3.727 | 1.00 | 30.79 | RNA1 | O |
| ATOM | 2615 | C5 | U | C | 1101 | 9.993 | −6.408 | −3.801 | 1.00 | 38.67 | RNA1 | C |
| ATOM | 2616 | C6 | U | C | 1101 | 11.204 | −6.965 | −3.959 | 1.00 | 40.99 | RNA1 | C |
| ATOM | 2617 | P | C | C | 1102 | 15.110 | −8.040 | 0.038 | 1.00 | 56.93 | RNA1 | P |
| ATOM | 2618 | O1P | C | C | 1102 | 13.690 | −8.220 | 0.458 | 1.00 | 45.32 | RNA1 | O |
| ATOM | 2619 | O2P | C | C | 1102 | 16.195 | −8.697 | 0.810 | 1.00 | 59.07 | RNA1 | O |
| ATOM | 2620 | O5* | C | C | 1102 | 15.415 | −6.479 | 0.002 | 1.00 | 47.10 | RNA1 | O |
| ATOM | 2621 | C5* | C | C | 1102 | 16.687 | −6.002 | −0.447 | 1.00 | 40.92 | RNA1 | C |
| ATOM | 2622 | C4* | C | C | 1102 | 16.706 | −4.495 | −0.480 | 1.00 | 41.54 | RNA1 | C |
| ATOM | 2623 | O4* | C | C | 1102 | 15.809 | −4.001 | −1.511 | 1.00 | 45.86 | RNA1 | O |
| ATOM | 2624 | C3* | C | C | 1102 | 16.235 | −3.772 | 0.769 | 1.00 | 43.22 | RNA1 | C |
| ATOM | 2625 | O3* | C | C | 1102 | 17.189 | −3.732 | 1.814 | 1.00 | 49.70 | RNA1 | O |
| ATOM | 2626 | C2* | C | C | 1102 | 15.910 | −2.389 | 0.227 | 1.00 | 45.44 | RNA1 | C |
| ATOM | 2627 | O2* | C | C | 1102 | 17.061 | −1.587 | 0.031 | 1.00 | 39.52 | RNA1 | O |
| ATOM | 2628 | C1* | C | C | 1102 | 15.294 | −2.733 | −1.125 | 1.00 | 41.32 | RNA1 | C |
| ATOM | 2629 | N1 | C | C | 1102 | 13.822 | −2.807 | −1.006 | 1.00 | 35.07 | RNA1 | N |
| ATOM | 2630 | C2 | C | C | 1102 | 13.091 | −1.607 | −0.999 | 1.00 | 35.73 | RNA1 | C |
| ATOM | 2631 | O2 | C | C | 1102 | 13.700 | −0.530 | −1.134 | 1.00 | 40.70 | RNA1 | O |
| ATOM | 2632 | N3 | C | C | 1102 | 11.748 | −1.649 | −0.843 | 1.00 | 24.21 | RNA1 | N |
| ATOM | 2633 | C4 | C | C | 1102 | 11.131 | −2.821 | −0.703 | 1.00 | 25.56 | RNA1 | C |
| ATOM | 2634 | N4 | C | C | 1102 | 9.805 | −2.813 | −0.534 | 1.00 | 27.04 | RNA1 | N |
| ATOM | 2635 | C5 | C | C | 1102 | 11.844 | −4.056 | −0.726 | 1.00 | 25.22 | RNA1 | C |
| ATOM | 2636 | C6 | C | C | 1102 | 13.175 | −4.004 | −0.880 | 1.00 | 29.24 | RNA1 | C |
| ATOM | 2637 | P | A | C | 1103 | 16.678 | −3.598 | 3.336 | 1.00 | 46.37 | RNA1 | P |
| ATOM | 2638 | O1P | A | C | 1103 | 15.453 | −4.431 | 3.507 | 1.00 | 34.79 | RNA1 | O |
| ATOM | 2639 | O2P | A | C | 1103 | 17.841 | −3.806 | 4.238 | 1.00 | 53.23 | RNA1 | O |
| ATOM | 2640 | O5* | A | C | 1103 | 16.223 | −2.077 | 3.443 | 1.00 | 50.88 | RNA1 | O |
| ATOM | 2641 | C5* | A | C | 1103 | 17.095 | −1.012 | 3.017 | 1.00 | 45.92 | RNA1 | C |
| ATOM | 2642 | C4* | A | C | 1103 | 16.368 | 0.307 | 3.082 | 1.00 | 42.03 | RNA1 | C |
| ATOM | 2643 | O4* | A | C | 1103 | 15.249 | 0.282 | 2.164 | 1.00 | 42.45 | RNA1 | O |
| ATOM | 2644 | C3* | A | C | 1103 | 15.748 | 0.629 | 4.431 | 1.00 | 46.34 | RNA1 | C |
| ATOM | 2645 | O3* | A | C | 1103 | 16.697 | 1.231 | 5.297 | 1.00 | 50.61 | RNA1 | O |
| ATOM | 2646 | C2* | A | C | 1103 | 14.604 | 1.568 | 4.068 | 1.00 | 40.60 | RNA1 | C |
| ATOM | 2647 | O2* | A | C | 1103 | 15.018 | 2.911 | 3.913 | 1.00 | 43.99 | RNA1 | O |
| ATOM | 2648 | C1* | A | C | 1103 | 14.163 | 1.007 | 2.714 | 1.00 | 35.23 | RNA1 | C |
| ATOM | 2649 | N9 | A | C | 1103 | 13.007 | 0.114 | 2.815 | 1.00 | 24.56 | RNA1 | N |
| ATOM | 2650 | C8 | A | C | 1103 | 12.964 | −1.259 | 2.771 | 1.00 | 12.09 | RNA1 | C |
| ATOM | 2651 | N7 | A | C | 1103 | 11.755 | −1.754 | 2.912 | 1.00 | 21.27 | RNA1 | N |
| ATOM | 2652 | C5 | A | C | 1103 | 10.949 | −0.629 | 3.052 | 1.00 | 11.33 | RNA1 | C |
| ATOM | 2653 | C6 | A | C | 1103 | 9.566 | −0.469 | 3.247 | 1.00 | 17.54 | RNA1 | C |
| ATOM | 2654 | N6 | A | C | 1103 | 8.699 | −1.485 | 3.341 | 1.00 | 18.44 | RNA1 | N |
| ATOM | 2655 | N1 | A | C | 1103 | 9.091 | 0.792 | 3.351 | 1.00 | 23.77 | RNA1 | N |
| ATOM | 2656 | C2 | A | C | 1103 | 9.947 | 1.810 | 3.270 | 1.00 | 20.47 | RNA1 | C |
| ATOM | 2657 | N3 | A | C | 1103 | 11.262 | 1.789 | 3.093 | 1.00 | 25.40 | RNA1 | N |
| ATOM | 2658 | C4 | A | C | 1103 | 11.706 | 0.525 | 2.990 | 1.00 | 22.14 | RNA1 | C |
| ATOM | 2659 | P | C | C | 1104 | 16.907 | 0.637 | 6.771 | 1.00 | 47.34 | RNA1 | P |
| ATOM | 2660 | O1P | C | C | 1104 | 17.274 | −0.801 | 6.656 | 1.00 | 47.39 | RNA1 | O |
| ATOM | 2661 | O2P | C | C | 1104 | 17.809 | 1.572 | 7.493 | 1.00 | 49.59 | RNA1 | O |
| ATOM | 2662 | O5* | C | C | 1104 | 15.454 | 0.717 | 7.410 | 1.00 | 32.80 | RNA1 | O |

TABLE II-continued

| ATOM | 2663 | C5* | C | C | 1104 | 14.847 | 1.985 | 7.660 | 1.00 | 32.89 | RNA1 | C |
|---|---|---|---|---|---|---|---|---|---|---|---|---|
| ATOM | 2664 | C4* | C | C | 1104 | 13.409 | 1.804 | 8.055 | 1.00 | 33.67 | RNA1 | C |
| ATOM | 2665 | O4* | C | C | 1104 | 12.654 | 1.301 | 6.924 | 1.00 | 36.61 | RNA1 | O |
| ATOM | 2666 | C3* | C | C | 1104 | 13.151 | 0.793 | 9.157 | 1.00 | 44.60 | RNA1 | C |
| ATOM | 2667 | O3* | C | C | 1104 | 13.379 | 1.321 | 10.455 | 1.00 | 47.83 | RNA1 | O |
| ATOM | 2668 | C2* | C | C | 1104 | 11.699 | 0.409 | 8.912 | 1.00 | 41.50 | RNA1 | C |
| ATOM | 2669 | O2* | C | C | 1104 | 10.802 | 1.363 | 9.443 | 1.00 | 39.51 | RNA1 | O |
| ATOM | 2670 | C1* | C | C | 1104 | 11.635 | 0.426 | 7.382 | 1.00 | 35.38 | RNA1 | C |
| ATOM | 2671 | N1 | C | C | 1104 | 11.881 | −0.915 | 6.818 | 1.00 | 26.79 | RNA1 | N |
| ATOM | 2672 | C2 | C | C | 1104 | 10.807 | −1.804 | 6.699 | 1.00 | 30.49 | RNA1 | C |
| ATOM | 2673 | O2 | C | C | 1104 | 9.672 | −1.426 | 7.039 | 1.00 | 25.17 | RNA1 | O |
| ATOM | 2674 | N3 | C | C | 1104 | 11.031 | −3.049 | 6.216 | 1.00 | 35.06 | RNA1 | N |
| ATOM | 2675 | C4 | C | C | 1104 | 12.264 | −3.412 | 5.850 | 1.00 | 35.48 | RNA1 | C |
| ATOM | 2676 | N4 | C | C | 1104 | 12.440 | −4.649 | 5.381 | 1.00 | 39.73 | RNA1 | N |
| ATOM | 2677 | C5 | C | C | 1104 | 13.370 | −2.524 | 5.948 | 1.00 | 26.28 | RNA1 | C |
| ATOM | 2678 | C6 | C | C | 1104 | 13.137 | −1.298 | 6.432 | 1.00 | 26.38 | RNA1 | C |
| ATOM | 2679 | P | C | C | 1105 | 13.943 | 0.357 | 11.610 | 1.00 | 45.15 | RNA1 | P |
| ATOM | 2680 | O1P | C | C | 1105 | 14.937 | −0.579 | 11.008 | 1.00 | 37.59 | RNA1 | O |
| ATOM | 2681 | O2P | C | C | 1105 | 14.345 | 1.217 | 12.749 | 1.00 | 50.66 | RNA1 | O |
| ATOM | 2682 | O5* | C | C | 1105 | 12.669 | −0.496 | 12.036 | 1.00 | 27.84 | RNA1 | O |
| ATOM | 2683 | C5* | C | C | 1105 | 11.541 | 0.141 | 12.636 | 1.00 | 26.44 | RNA1 | C |
| ATOM | 2684 | C4* | C | C | 1105 | 10.431 | −0.855 | 12.852 | 1.00 | 36.80 | RNA1 | C |
| ATOM | 2685 | O4* | C | C | 1105 | 9.967 | −1.354 | 11.569 | 1.00 | 46.02 | RNA1 | O |
| ATOM | 2686 | C3* | C | C | 1105 | 10.793 | −2.111 | 13.623 | 1.00 | 39.57 | RNA1 | C |
| ATOM | 2687 | O3* | C | C | 1105 | 10.794 | −1.905 | 15.026 | 1.00 | 48.60 | RNA1 | O |
| ATOM | 2688 | C2* | C | C | 1105 | 9.713 | −3.084 | 13.169 | 1.00 | 42.79 | RNA1 | C |
| ATOM | 2689 | O2* | C | C | 1105 | 8.473 | −2.848 | 13.811 | 1.00 | 36.52 | RNA1 | O |
| ATOM | 2690 | C1* | C | C | 1105 | 9.576 | −2.714 | 11.693 | 1.00 | 39.01 | RNA1 | C |
| ATOM | 2691 | N1 | C | C | 1105 | 10.448 | −3.539 | 10.827 | 1.00 | 31.92 | RNA1 | N |
| ATOM | 2692 | C2 | C | C | 1105 | 10.029 | −4.832 | 10.461 | 1.00 | 29.04 | RNA1 | C |
| ATOM | 2693 | O2 | C | C | 1105 | 8.934 | −5.259 | 10.875 | 1.00 | 27.41 | RNA1 | O |
| ATOM | 2694 | N3 | C | C | 1105 | 10.831 | −5.584 | 9.672 | 1.00 | 26.50 | RNA1 | N |
| ATOM | 2695 | C4 | C | C | 1105 | 12.005 | −5.100 | 9.255 | 1.00 | 26.95 | RNA1 | C |
| ATOM | 2696 | N4 | C | C | 1105 | 12.768 | −5.879 | 8.473 | 1.00 | 32.01 | RNA1 | N |
| ATOM | 2697 | C5 | C | C | 1105 | 12.453 | −3.798 | 9.614 | 1.00 | 31.44 | RNA1 | C |
| ATOM | 2698 | C6 | C | C | 1105 | 11.652 | −3.059 | 10.389 | 1.00 | 27.18 | RNA1 | C |
| ATOM | 2699 | P | A | C | 1106 | 11.685 | −2.860 | 15.964 | 1.00 | 49.11 | RNA1 | P |
| ATOM | 2700 | O1P | A | C | 1106 | 12.987 | −3.106 | 15.282 | 1.00 | 36.36 | RNA1 | O |
| ATOM | 2701 | O2P | A | C | 1106 | 11.676 | −2.277 | 17.331 | 1.00 | 55.01 | RNA1 | O |
| ATOM | 2702 | O5* | A | C | 1106 | 10.861 | −4.222 | 15.988 | 1.00 | 33.45 | RNA1 | O |
| ATOM | 2703 | C5* | A | C | 1106 | 9.507 | −4.255 | 16.482 | 1.00 | 40.30 | RNA1 | C |
| ATOM | 2704 | C4* | A | C | 1106 | 8.910 | −5.628 | 16.280 | 1.00 | 55.66 | RNA1 | C |
| ATOM | 2705 | O4* | A | C | 1106 | 8.774 | −5.892 | 14.859 | 1.00 | 57.89 | RNA1 | O |
| ATOM | 2706 | C3* | A | C | 1106 | 9.747 | −6.785 | 16.804 | 1.00 | 61.21 | RNA1 | C |
| ATOM | 2707 | O3* | A | C | 1106 | 9.552 | −7.004 | 18.196 | 1.00 | 63.93 | RNA1 | O |
| ATOM | 2708 | C2* | A | C | 1106 | 9.287 | −7.945 | 15.928 | 1.00 | 60.31 | RNA1 | C |
| ATOM | 2709 | O2* | A | C | 1106 | 8.040 | −8.478 | 16.344 | 1.00 | 54.72 | RNA1 | O |
| ATOM | 2710 | C1* | A | C | 1106 | 9.104 | −7.244 | 14.582 | 1.00 | 50.43 | RNA1 | C |
| ATOM | 2711 | N9 | A | C | 1106 | 10.327 | −7.245 | 13.772 | 1.00 | 40.12 | RNA1 | N |
| ATOM | 2712 | C8 | A | C | 1106 | 11.297 | −6.265 | 13.730 | 1.00 | 43.18 | RNA1 | C |
| ATOM | 2713 | N7 | A | C | 1106 | 12.279 | −6.522 | 12.899 | 1.00 | 35.92 | RNA1 | N |
| ATOM | 2714 | C5 | A | C | 1106 | 11.940 | −7.754 | 12.356 | 1.00 | 35.80 | RNA1 | C |
| ATOM | 2715 | C6 | A | C | 1106 | 12.574 | −8.570 | 11.401 | 1.00 | 32.97 | RNA1 | C |
| ATOM | 2716 | N6 | A | C | 1106 | 13.721 | −8.242 | 10.791 | 1.00 | 42.58 | RNA1 | N |
| ATOM | 2717 | N1 | A | C | 1106 | 11.984 | −9.744 | 11.088 | 1.00 | 28.98 | RNA1 | N |
| ATOM | 2718 | C2 | A | C | 1106 | 10.831 | −10.065 | 11.694 | 1.00 | 37.34 | RNA1 | C |
| ATOM | 2719 | N3 | A | C | 1106 | 10.132 | −9.379 | 12.601 | 1.00 | 37.05 | RNA1 | N |
| ATOM | 2720 | C4 | A | C | 1106 | 10.746 | −8.218 | 12.893 | 1.00 | 37.35 | RNA1 | C |
| ATOM | 2721 | P | G | C | 1107 | 10.770 | −7.554 | 19.093 | 1.00 | 58.93 | RNA1 | P |
| ATOM | 2722 | O1P | G | C | 1107 | 12.057 | −7.023 | 18.562 | 1.00 | 36.85 | RNA1 | O |
| ATOM | 2723 | O2P | G | C | 1107 | 10.406 | −7.307 | 20.512 | 1.00 | 61.45 | RNA1 | O |
| ATOM | 2724 | O5* | G | C | 1107 | 10.741 | −9.124 | 18.823 | 1.00 | 57.72 | RNA1 | O |
| ATOM | 2725 | C5* | G | C | 1107 | 9.559 | −9.898 | 19.117 | 1.00 | 58.74 | RNA1 | C |
| ATOM | 2726 | C4* | G | C | 1107 | 9.678 | −11.278 | 18.520 | 1.00 | 65.40 | RNA1 | C |
| ATOM | 2727 | O4* | G | C | 1107 | 9.633 | −11.183 | 17.073 | 1.00 | 61.43 | RNA1 | O |
| ATOM | 2728 | C3* | G | C | 1107 | 10.983 | −11.999 | 18.818 | 1.00 | 66.79 | RNA1 | C |
| ATOM | 2729 | O3* | G | C | 1107 | 10.969 | −12.653 | 20.079 | 1.00 | 66.96 | RNA1 | O |
| ATOM | 2730 | C2* | G | C | 1107 | 11.110 | −12.966 | 17.647 | 1.00 | 65.40 | RNA1 | C |
| ATOM | 2731 | O2* | G | C | 1107 | 10.392 | −14.174 | 17.833 | 1.00 | 59.25 | RNA1 | O |
| ATOM | 2732 | C1* | G | C | 1107 | 10.509 | −12.142 | 16.504 | 1.00 | 56.87 | RNA1 | C |
| ATOM | 2733 | N9 | G | C | 1107 | 11.541 | −11.428 | 15.759 | 1.00 | 46.90 | RNA1 | N |
| ATOM | 2734 | C8 | G | C | 1107 | 11.980 | −10.140 | 15.964 | 1.00 | 49.14 | RNA1 | C |
| ATOM | 2735 | N7 | G | C | 1107 | 12.952 | −9.797 | 15.163 | 1.00 | 45.19 | RNA1 | N |
| ATOM | 2736 | C5 | G | C | 1107 | 13.159 | −10.921 | 14.374 | 1.00 | 43.33 | RNA1 | C |
| ATOM | 2737 | C6 | G | C | 1107 | 14.092 | −11.155 | 13.326 | 1.00 | 44.94 | RNA1 | C |
| ATOM | 2738 | O6 | G | C | 1107 | 14.953 | −10.387 | 12.869 | 1.00 | 41.91 | RNA1 | O |
| ATOM | 2739 | N1 | G | C | 1107 | 13.958 | −12.437 | 12.803 | 1.00 | 44.05 | RNA1 | N |
| ATOM | 2740 | C2 | G | C | 1107 | 13.048 | −13.374 | 13.227 | 1.00 | 48.45 | RNA1 | C |
| ATOM | 2741 | N2 | G | C | 1107 | 13.071 | −14.553 | 12.597 | 1.00 | 49.02 | RNA1 | N |

TABLE II-continued

| | | | | | | | | | | | |
|---|---|---|---|---|---|---|---|---|---|---|---|
| ATOM | 2742 | N3 | G | C | 1107 | 12.177 | −13.169 | 14.198 | 1.00 | 48.55 | RNA1 | N |
| ATOM | 2743 | C4 | G | C | 1107 | 12.289 | −11.932 | 14.725 | 1.00 | 47.37 | RNA1 | C |
| ATOM | 2744 | P | C | C | 1108 | 12.345 | −12.840 | 20.886 | 1.00 | 71.15 | RNA1 | P |
| ATOM | 2745 | O1P | C | C | 1108 | 13.100 | −11.558 | 20.849 | 1.00 | 59.46 | RNA1 | O |
| ATOM | 2746 | O2P | C | C | 1108 | 12.015 | −13.463 | 22.194 | 1.00 | 75.00 | RNA1 | O |
| ATOM | 2747 | O5* | C | C | 1108 | 13.155 | −13.893 | 20.010 | 1.00 | 72.84 | RNA1 | O |
| ATOM | 2748 | C5* | C | C | 1108 | 12.697 | −15.251 | 19.876 | 1.00 | 75.04 | RNA1 | C |
| ATOM | 2749 | C4* | C | C | 1108 | 13.581 | −16.004 | 18.914 | 1.00 | 76.03 | RNA1 | C |
| ATOM | 2750 | O4* | C | C | 1108 | 13.459 | −15.420 | 17.592 | 1.00 | 73.82 | RNA1 | O |
| ATOM | 2751 | C3* | C | C | 1108 | 15.073 | −15.954 | 19.208 | 1.00 | 77.22 | RNA1 | C |
| ATOM | 2752 | O3* | C | C | 1108 | 15.576 | −16.622 | 20.377 | 1.00 | 76.14 | RNA1 | O |
| ATOM | 2753 | C2* | C | C | 1108 | 15.696 | −16.220 | 17.844 | 1.00 | 77.82 | RNA1 | C |
| ATOM | 2754 | O2* | C | C | 1108 | 15.731 | −17.593 | 17.507 | 1.00 | 80.53 | RNA1 | O |
| ATOM | 2755 | C1* | C | C | 1108 | 14.705 | −15.511 | 16.916 | 1.00 | 74.18 | RNA1 | C |
| ATOM | 2756 | N1 | C | C | 1108 | 15.147 | −14.151 | 16.545 | 1.00 | 69.37 | RNA1 | N |
| ATOM | 2757 | C2 | C | C | 1108 | 15.946 | −13.987 | 15.400 | 1.00 | 64.11 | RNA1 | C |
| ATOM | 2758 | O2 | C | C | 1108 | 16.232 | −14.979 | 14.713 | 1.00 | 63.69 | RNA1 | O |
| ATOM | 2759 | N3 | C | C | 1108 | 16.383 | −12.750 | 15.074 | 1.00 | 59.38 | RNA1 | N |
| ATOM | 2760 | C4 | C | C | 1108 | 16.047 | −11.702 | 15.829 | 1.00 | 57.06 | RNA1 | C |
| ATOM | 2761 | N4 | C | C | 1108 | 16.508 | −10.503 | 15.472 | 1.00 | 58.03 | RNA1 | N |
| ATOM | 2762 | C5 | C | C | 1108 | 15.224 | −11.837 | 16.984 | 1.00 | 61.31 | RNA1 | C |
| ATOM | 2763 | C6 | C | C | 1108 | 14.801 | −13.066 | 17.303 | 1.00 | 67.15 | RNA1 | C |
| TER | 2764 | | C | C | 1108 | | | | | | | |
| ATOM | 2765 | O5* | G | D | 1051 | 13.368 | 11.108 | −58.535 | 1.00 | 55.60 | RNA2 | O |
| ATOM | 2766 | C5* | G | D | 1051 | 14.100 | 12.302 | −58.210 | 1.00 | 63.32 | RNA2 | C |
| ATOM | 2767 | C4* | G | D | 1051 | 13.550 | 13.505 | −58.939 | 1.00 | 61.69 | RNA2 | C |
| ATOM | 2768 | O4* | G | D | 1051 | 13.809 | 13.364 | −60.359 | 1.00 | 66.02 | RNA2 | O |
| ATOM | 2769 | C3* | G | D | 1051 | 12.043 | 13.659 | −58.835 | 1.00 | 59.67 | RNA2 | C |
| ATOM | 2770 | O3* | G | D | 1051 | 11.661 | 14.349 | −57.659 | 1.00 | 53.26 | RNA2 | O |
| ATOM | 2771 | C2* | G | D | 1051 | 11.684 | 14.404 | −60.113 | 1.00 | 58.82 | RNA2 | C |
| ATOM | 2772 | O2* | G | D | 1051 | 11.873 | 15.801 | −60.015 | 1.00 | 62.26 | RNA2 | O |
| ATOM | 2773 | C1* | G | D | 1051 | 12.691 | 13.815 | −61.102 | 1.00 | 58.27 | RNA2 | C |
| ATOM | 2774 | N9 | G | D | 1051 | 12.147 | 12.672 | −61.833 | 1.00 | 55.11 | RNA2 | N |
| ATOM | 2775 | C8 | G | D | 1051 | 12.505 | 11.352 | −61.693 | 1.00 | 57.64 | RNA2 | C |
| ATOM | 2776 | N7 | G | D | 1051 | 11.830 | 10.552 | −62.472 | 1.00 | 63.74 | RNA2 | N |
| ATOM | 2777 | C5 | G | D | 1051 | 10.976 | 11.393 | −63.171 | 1.00 | 59.62 | RNA2 | C |
| ATOM | 2778 | C6 | G | D | 1051 | 10.002 | 11.100 | −64.162 | 1.00 | 54.61 | RNA2 | C |
| ATOM | 2779 | O6 | G | D | 1051 | 9.687 | 9.999 | −64.634 | 1.00 | 56.94 | RNA2 | O |
| ATOM | 2780 | N1 | G | D | 1051 | 9.366 | 12.254 | −64.606 | 1.00 | 52.85 | RNA2 | N |
| ATOM | 2781 | C2 | G | D | 1051 | 9.629 | 13.525 | −64.157 | 1.00 | 48.26 | RNA2 | C |
| ATOM | 2782 | N2 | G | D | 1051 | 8.910 | 14.509 | −64.707 | 1.00 | 49.20 | RNA2 | N |
| ATOM | 2783 | N3 | G | D | 1051 | 10.531 | 13.811 | −63.237 | 1.00 | 51.58 | RNA2 | N |
| ATOM | 2784 | C4 | G | D | 1051 | 11.163 | 12.707 | −62.791 | 1.00 | 56.30 | RNA2 | C |
| ATOM | 2785 | P | C | D | 1052 | 10.243 | 14.024 | −56.983 | 1.00 | 59.48 | RNA2 | P |
| ATOM | 2786 | O1P | C | D | 1052 | 10.050 | 12.549 | −57.013 | 1.00 | 61.66 | RNA2 | O |
| ATOM | 2787 | O2P | C | D | 1052 | 10.183 | 14.741 | −55.688 | 1.00 | 73.92 | RNA2 | O |
| ATOM | 2788 | O5* | C | D | 1052 | 9.194 | 14.690 | −57.976 | 1.00 | 41.41 | RNA2 | O |
| ATOM | 2789 | C5* | C | D | 1052 | 9.295 | 16.081 | −58.307 | 1.00 | 47.28 | RNA2 | C |
| ATOM | 2790 | C4* | C | D | 1052 | 8.298 | 16.442 | −59.376 | 1.00 | 45.31 | RNA2 | C |
| ATOM | 2791 | O4* | C | D | 1052 | 8.683 | 15.855 | −60.645 | 1.00 | 50.63 | RNA2 | O |
| ATOM | 2792 | C3* | C | D | 1052 | 6.892 | 15.933 | −59.137 | 1.00 | 47.61 | RNA2 | C |
| ATOM | 2793 | O3* | C | D | 1052 | 6.174 | 16.759 | −58.247 | 1.00 | 56.07 | RNA2 | O |
| ATOM | 2794 | C2* | C | D | 1052 | 6.301 | 15.896 | −60.540 | 1.00 | 49.42 | RNA2 | C |
| ATOM | 2795 | O2* | C | D | 1052 | 5.816 | 17.144 | −60.990 | 1.00 | 40.34 | RNA2 | O |
| ATOM | 2796 | C1* | C | D | 1052 | 7.518 | 15.487 | −61.371 | 1.00 | 50.98 | RNA2 | C |
| ATOM | 2797 | N1 | C | D | 1052 | 7.546 | 14.031 | −61.621 | 1.00 | 53.95 | RNA2 | N |
| ATOM | 2798 | C2 | C | D | 1052 | 6.704 | 13.502 | −62.611 | 1.00 | 53.59 | RNA2 | C |
| ATOM | 2799 | O2 | C | D | 1052 | 5.974 | 14.271 | −63.253 | 1.00 | 52.10 | RNA2 | O |
| ATOM | 2800 | N3 | C | D | 1052 | 6.705 | 12.169 | −62.838 | 1.00 | 59.04 | RNA2 | N |
| ATOM | 2801 | C4 | C | D | 1052 | 7.499 | 11.370 | −62.120 | 1.00 | 65.70 | RNA2 | C |
| ATOM | 2802 | N4 | C | D | 1052 | 7.459 | 10.056 | −62.374 | 1.00 | 66.17 | RNA2 | N |
| ATOM | 2803 | C5 | C | D | 1052 | 8.369 | 11.880 | −61.110 | 1.00 | 59.37 | RNA2 | C |
| ATOM | 2804 | C6 | C | D | 1052 | 8.363 | 13.202 | −60.898 | 1.00 | 55.97 | RNA2 | C |
| ATOM | 2805 | P | U | D | 1053 | 5.067 | 16.101 | −57.298 | 1.00 | 63.43 | RNA2 | P |
| ATOM | 2806 | O1P | U | D | 1053 | 5.641 | 14.831 | −56.780 | 1.00 | 62.31 | RNA2 | O |
| ATOM | 2807 | O2P | U | D | 1053 | 4.576 | 17.128 | −56.343 | 1.00 | 74.13 | RNA2 | O |
| ATOM | 2808 | O5* | U | D | 1053 | 3.889 | 15.763 | −58.312 | 1.00 | 57.11 | RNA2 | O |
| ATOM | 2809 | C5* | U | D | 1053 | 3.199 | 16.820 | −58.990 | 1.00 | 48.12 | RNA2 | C |
| ATOM | 2810 | C4* | U | D | 1053 | 2.185 | 16.257 | −59.953 | 1.00 | 50.31 | RNA2 | C |
| ATOM | 2811 | O4* | U | D | 1053 | 2.860 | 15.628 | −61.074 | 1.00 | 49.75 | RNA2 | O |
| ATOM | 2812 | C3* | U | D | 1053 | 1.277 | 15.164 | −59.421 | 1.00 | 50.89 | RNA2 | C |
| ATOM | 2813 | O3* | U | D | 1053 | 0.202 | 15.634 | −58.629 | 1.00 | 56.33 | RNA2 | O |
| ATOM | 2814 | C2* | U | D | 1053 | 0.818 | 14.477 | −60.698 | 1.00 | 50.72 | RNA2 | C |
| ATOM | 2815 | O2* | U | D | 1053 | −0.225 | 15.175 | −61.357 | 1.00 | 48.82 | RNA2 | O |
| ATOM | 2816 | C1* | U | D | 1053 | 2.091 | 14.528 | −61.540 | 1.00 | 43.49 | RNA2 | C |
| ATOM | 2817 | N1 | U | D | 1053 | 2.881 | 13.292 | −61.391 | 1.00 | 42.34 | RNA2 | N |
| ATOM | 2818 | C2 | U | D | 1053 | 2.501 | 12.182 | −62.141 | 1.00 | 40.65 | RNA2 | C |
| ATOM | 2819 | O2 | U | D | 1053 | 1.564 | 12.193 | −62.926 | 1.00 | 43.48 | RNA2 | O |
| ATOM | 2820 | N3 | U | D | 1053 | 3.258 | 11.057 | −61.935 | 1.00 | 32.60 | RNA2 | N |

TABLE II-continued

| ATOM | 2821 | C4 | U | D | 1053 | 4.329 | 10.920 | −61.079 | 1.00 | 48.03 | RNA2 | C |
|---|---|---|---|---|---|---|---|---|---|---|---|---|
| ATOM | 2822 | O4 | U | D | 1053 | 4.880 | 9.822 | −60.973 | 1.00 | 58.30 | RNA2 | O |
| ATOM | 2823 | C5 | U | D | 1053 | 4.670 | 12.106 | −60.352 | 1.00 | 43.77 | RNA2 | C |
| ATOM | 2824 | C6 | U | D | 1053 | 3.954 | 13.222 | −60.528 | 1.00 | 44.26 | RNA2 | C |
| ATOM | 2825 | P | G | D | 1054 | −0.300 | 14.738 | −57.393 | 1.00 | 63.07 | RNA2 | P |
| ATOM | 2826 | O1P | G | D | 1054 | 0.909 | 14.253 | −56.659 | 1.00 | 56.57 | RNA2 | O |
| ATOM | 2827 | O2P | G | D | 1054 | −1.342 | 15.504 | −56.670 | 1.00 | 55.48 | RNA2 | O |
| ATOM | 2828 | O5* | G | D | 1054 | −0.993 | 13.484 | −58.088 | 1.00 | 55.82 | RNA2 | O |
| ATOM | 2829 | C5* | G | D | 1054 | −2.203 | 13.659 | −58.842 | 1.00 | 63.34 | RNA2 | C |
| ATOM | 2830 | C4* | G | D | 1054 | −2.607 | 12.376 | −59.540 | 1.00 | 61.66 | RNA2 | C |
| ATOM | 2831 | O4* | G | D | 1054 | −1.612 | 11.993 | −60.529 | 1.00 | 57.48 | RNA2 | O |
| ATOM | 2832 | C3* | G | D | 1054 | −2.785 | 11.116 | −58.707 | 1.00 | 58.52 | RNA2 | C |
| ATOM | 2833 | O3* | G | D | 1054 | −4.027 | 11.063 | −58.021 | 1.00 | 50.20 | RNA2 | O |
| ATOM | 2834 | C2* | G | D | 1054 | −2.702 | 10.021 | −59.766 | 1.00 | 54.72 | RNA2 | C |
| ATOM | 2835 | O2* | G | D | 1054 | −3.915 | 9.849 | −60.469 | 1.00 | 57.84 | RNA2 | O |
| ATOM | 2836 | C1* | G | D | 1054 | −1.657 | 10.588 | −60.723 | 1.00 | 42.15 | RNA2 | C |
| ATOM | 2837 | N9 | G | D | 1054 | −0.347 | 10.004 | −60.453 | 1.00 | 43.98 | RNA2 | N |
| ATOM | 2838 | C8 | G | D | 1054 | 0.686 | 10.525 | −59.707 | 1.00 | 48.29 | RNA2 | C |
| ATOM | 2839 | N7 | G | D | 1054 | 1.715 | 9.721 | −59.624 | 1.00 | 48.90 | RNA2 | N |
| ATOM | 2840 | C5 | G | D | 1054 | 1.340 | 8.607 | −60.367 | 1.00 | 43.87 | RNA2 | C |
| ATOM | 2841 | C6 | G | D | 1054 | 2.037 | 7.396 | −60.634 | 1.00 | 37.83 | RNA2 | C |
| ATOM | 2842 | O6 | G | D | 1054 | 3.167 | 7.050 | −60.252 | 1.00 | 35.95 | RNA2 | O |
| ATOM | 2843 | N1 | G | D | 1054 | 1.279 | 6.539 | −61.428 | 1.00 | 42.56 | RNA2 | N |
| ATOM | 2844 | C2 | G | D | 1054 | 0.013 | 6.807 | −61.901 | 1.00 | 45.28 | RNA2 | C |
| ATOM | 2845 | N2 | G | D | 1054 | −0.567 | 5.854 | −62.647 | 1.00 | 42.14 | RNA2 | N |
| ATOM | 2846 | N3 | G | D | 1054 | −0.642 | 7.925 | −61.659 | 1.00 | 40.97 | RNA2 | N |
| ATOM | 2847 | C4 | G | D | 1054 | 0.074 | 8.774 | −60.892 | 1.00 | 45.06 | RNA2 | C |
| ATOM | 2848 | P | G | D | 1055 | −4.174 | 10.115 | −56.729 | 1.00 | 60.11 | RNA2 | P |
| ATOM | 2849 | O1P | G | D | 1055 | −3.012 | 10.347 | −55.817 | 1.00 | 52.31 | RNA2 | O |
| ATOM | 2850 | O2P | G | D | 1055 | −5.562 | 10.287 | −56.226 | 1.00 | 45.31 | RNA2 | O |
| ATOM | 2851 | O5* | G | D | 1055 | −4.016 | 8.633 | −57.297 | 1.00 | 61.25 | RNA2 | O |
| ATOM | 2852 | C5* | G | D | 1055 | −5.060 | 8.044 | −58.084 | 1.00 | 49.39 | RNA2 | C |
| ATOM | 2853 | C4* | G | D | 1055 | −4.631 | 6.705 | −58.643 | 1.00 | 46.06 | RNA2 | C |
| ATOM | 2854 | O4* | G | D | 1055 | −3.395 | 6.848 | −59.392 | 1.00 | 46.04 | RNA2 | O |
| ATOM | 2855 | C3* | G | D | 1055 | −4.322 | 5.571 | −57.678 | 1.00 | 46.58 | RNA2 | C |
| ATOM | 2856 | O3* | G | D | 1055 | −5.478 | 4.904 | −57.197 | 1.00 | 44.61 | RNA2 | O |
| ATOM | 2857 | C2* | G | D | 1055 | −3.512 | 4.627 | −58.556 | 1.00 | 50.61 | RNA2 | C |
| ATOM | 2858 | O2* | G | D | 1055 | −4.337 | 3.844 | −59.397 | 1.00 | 57.17 | RNA2 | O |
| ATOM | 2859 | C1* | G | D | 1055 | −2.719 | 5.604 | −59.419 | 1.00 | 37.93 | RNA2 | C |
| ATOM | 2860 | N9 | G | D | 1055 | −1.364 | 5.764 | −58.905 | 1.00 | 28.75 | RNA2 | N |
| ATOM | 2861 | C8 | G | D | 1055 | −0.813 | 6.849 | −58.266 | 1.00 | 28.74 | RNA2 | C |
| ATOM | 2862 | N7 | G | D | 1055 | 0.437 | 6.662 | −57.928 | 1.00 | 31.82 | RNA2 | N |
| ATOM | 2863 | C5 | G | D | 1055 | 0.725 | 5.377 | −58.371 | 1.00 | 24.53 | RNA2 | C |
| ATOM | 2864 | C6 | G | D | 1055 | 1.924 | 4.619 | −58.293 | 1.00 | 28.90 | RNA2 | C |
| ATOM | 2865 | O6 | G | D | 1055 | 3.010 | 4.943 | −57.807 | 1.00 | 32.85 | RNA2 | O |
| ATOM | 2866 | N1 | G | D | 1055 | 1.771 | 3.360 | −58.862 | 1.00 | 26.15 | RNA2 | N |
| ATOM | 2867 | C2 | G | D | 1055 | 0.615 | 2.884 | −59.432 | 1.00 | 32.58 | RNA2 | C |
| ATOM | 2868 | N2 | G | D | 1055 | 0.658 | 1.635 | −59.922 | 1.00 | 28.69 | RNA2 | N |
| ATOM | 2869 | N3 | G | D | 1055 | −0.505 | 3.580 | −59.514 | 1.00 | 26.67 | RNA2 | N |
| ATOM | 2870 | C4 | G | D | 1055 | −0.377 | 4.809 | −58.971 | 1.00 | 28.85 | RNA2 | C |
| ATOM | 2871 | P | G | D | 1056 | −5.427 | 4.178 | −55.764 | 1.00 | 41.37 | RNA2 | P |
| ATOM | 2872 | O1P | G | D | 1056 | −5.088 | 5.212 | −54.752 | 1.00 | 49.91 | RNA2 | O |
| ATOM | 2873 | O2P | G | D | 1056 | −6.660 | 3.370 | −55.603 | 1.00 | 41.24 | RNA2 | O |
| ATOM | 2874 | O5* | G | D | 1056 | −4.173 | 3.205 | −55.857 | 1.00 | 31.72 | RNA2 | O |
| ATOM | 2875 | C5* | G | D | 1056 | −4.288 | 1.915 | −56.458 | 1.00 | 26.06 | RNA2 | C |
| ATOM | 2876 | C4* | G | D | 1056 | −2.992 | 1.163 | −56.310 | 1.00 | 30.23 | RNA2 | C |
| ATOM | 2877 | O4* | G | D | 1056 | −1.926 | 1.929 | −56.923 | 1.00 | 33.12 | RNA2 | O |
| ATOM | 2878 | C3* | G | D | 1056 | −2.520 | 0.944 | −54.886 | 1.00 | 25.25 | RNA2 | C |
| ATOM | 2879 | O3* | G | D | 1056 | −3.091 | −0.214 | −54.323 | 1.00 | 32.82 | RNA2 | O |
| ATOM | 2880 | C2* | G | D | 1056 | −1.015 | 0.792 | −55.044 | 1.00 | 30.19 | RNA2 | C |
| ATOM | 2881 | O2* | G | D | 1056 | −0.631 | −0.515 | −55.418 | 1.00 | 28.72 | RNA2 | O |
| ATOM | 2882 | C1* | G | D | 1056 | −0.728 | 1.769 | −56.181 | 1.00 | 29.85 | RNA2 | C |
| ATOM | 2883 | N9 | G | D | 1056 | −0.326 | 3.081 | −55.682 | 1.00 | 33.20 | RNA2 | N |
| ATOM | 2884 | C8 | G | D | 1056 | −1.142 | 4.165 | −55.453 | 1.00 | 31.51 | RNA2 | C |
| ATOM | 2885 | N7 | G | D | 1056 | −0.496 | 5.205 | −55.003 | 1.00 | 40.50 | RNA2 | N |
| ATOM | 2886 | C5 | G | D | 1056 | 0.825 | 4.784 | −54.926 | 1.00 | 37.25 | RNA2 | C |
| ATOM | 2887 | C6 | G | D | 1056 | 1.985 | 5.481 | −54.505 | 1.00 | 45.50 | RNA2 | C |
| ATOM | 2888 | O6 | G | D | 1056 | 2.078 | 6.654 | −54.106 | 1.00 | 54.00 | RNA2 | O |
| ATOM | 2889 | N1 | G | D | 1056 | 3.122 | 4.677 | −54.584 | 1.00 | 42.27 | RNA2 | N |
| ATOM | 2890 | C2 | G | D | 1056 | 3.138 | 3.372 | −55.020 | 1.00 | 38.28 | RNA2 | C |
| ATOM | 2891 | N2 | G | D | 1056 | 4.337 | 2.765 | −55.040 | 1.00 | 33.41 | RNA2 | N |
| ATOM | 2892 | N3 | G | D | 1056 | 2.060 | 2.712 | −55.413 | 1.00 | 35.91 | RNA2 | N |
| ATOM | 2893 | C4 | G | D | 1056 | 0.947 | 3.474 | −55.341 | 1.00 | 31.74 | RNA2 | C |
| ATOM | 2894 | P | A | D | 1057 | −3.445 | −0.241 | −52.765 | 1.00 | 34.80 | RNA2 | P |
| ATOM | 2895 | O1P | A | D | 1057 | −2.899 | −1.503 | −52.213 | 1.00 | 40.31 | RNA2 | O |
| ATOM | 2896 | O2P | A | D | 1057 | −3.058 | 1.055 | −52.152 | 1.00 | 39.35 | RNA2 | O |
| ATOM | 2897 | O5* | A | D | 1057 | −5.027 | −0.331 | −52.754 | 1.00 | 19.58 | RNA2 | O |
| ATOM | 2898 | C5* | A | D | 1057 | −5.823 | 0.724 | −53.304 | 1.00 | 24.68 | RNA2 | C |
| ATOM | 2899 | C4* | A | D | 1057 | −6.915 | 0.144 | −54.161 | 1.00 | 26.68 | RNA2 | C |

TABLE II-continued

| | | | | | | | | | | | |
|---|---|---|---|---|---|---|---|---|---|---|---|
| ATOM | 2900 | O4* | A | D | 1057 | −6.359 | −0.301 | −55.425 | 1.00 | 40.11 | RNA2 | O |
| ATOM | 2901 | C3* | A | D | 1057 | −7.560 | −1.100 | −53.585 | 1.00 | 30.27 | RNA2 | C |
| ATOM | 2902 | O3* | A | D | 1057 | −8.559 | −0.816 | −52.635 | 1.00 | 35.52 | RNA2 | O |
| ATOM | 2903 | C2* | A | D | 1057 | −8.090 | −1.811 | −54.820 | 1.00 | 30.75 | RNA2 | C |
| ATOM | 2904 | O2* | A | D | 1057 | −9.317 | −1.270 | −55.268 | 1.00 | 24.78 | RNA2 | O |
| ATOM | 2905 | C1* | A | D | 1057 | −6.991 | −1.506 | −55.834 | 1.00 | 16.37 | RNA2 | C |
| ATOM | 2906 | N9 | A | D | 1057 | −5.973 | −2.559 | −55.883 | 1.00 | 21.50 | RNA2 | N |
| ATOM | 2907 | C8 | A | D | 1057 | −4.626 | −2.445 | −55.613 | 1.00 | 18.28 | RNA2 | C |
| ATOM | 2908 | N7 | A | D | 1057 | −3.962 | −3.566 | −55.754 | 1.00 | 23.67 | RNA2 | N |
| ATOM | 2909 | C5 | A | D | 1057 | −4.935 | −4.484 | −56.140 | 1.00 | 21.49 | RNA2 | C |
| ATOM | 2910 | C6 | A | D | 1057 | −4.872 | −5.852 | −56.447 | 1.00 | 17.73 | RNA2 | C |
| ATOM | 2911 | N6 | A | D | 1057 | −3.748 | −6.569 | −56.412 | 1.00 | 22.33 | RNA2 | N |
| ATOM | 2912 | N1 | A | D | 1057 | −6.019 | −6.470 | −56.797 | 1.00 | 29.29 | RNA2 | N |
| ATOM | 2913 | C2 | A | D | 1057 | −7.150 | −5.753 | −56.829 | 1.00 | 30.01 | RNA2 | C |
| ATOM | 2914 | N3 | A | D | 1057 | −7.337 | −4.465 | −56.559 | 1.00 | 24.69 | RNA2 | N |
| ATOM | 2915 | C4 | A | D | 1057 | −6.177 | −3.879 | −56.219 | 1.00 | 18.45 | RNA2 | C |
| ATOM | 2916 | P | U | D | 1058 | −8.746 | −1.807 | −51.399 | 1.00 | 30.93 | RNA2 | P |
| ATOM | 2917 | O1P | U | D | 1058 | −7.361 | −2.213 | −50.993 | 1.00 | 24.94 | RNA2 | O |
| ATOM | 2918 | O2P | U | D | 1058 | −9.669 | −1.203 | −50.402 | 1.00 | 29.08 | RNA2 | O |
| ATOM | 2919 | O5* | U | D | 1058 | −9.464 | −3.068 | −52.042 | 1.00 | 30.31 | RNA2 | O |
| ATOM | 2920 | C5* | U | D | 1058 | −10.859 | −3.043 | −52.331 | 1.00 | 28.81 | RNA2 | C |
| ATOM | 2921 | C4* | U | D | 1058 | −11.349 | −4.440 | −52.592 | 1.00 | 31.83 | RNA2 | C |
| ATOM | 2922 | O4* | U | D | 1058 | −10.668 | −4.953 | −53.765 | 1.00 | 33.24 | RNA2 | O |
| ATOM | 2923 | C3* | U | D | 1058 | −11.031 | −5.471 | −51.520 | 1.00 | 33.13 | RNA2 | C |
| ATOM | 2924 | O3* | U | D | 1058 | −11.925 | −5.479 | −50.425 | 1.00 | 32.98 | RNA2 | O |
| ATOM | 2925 | C2* | U | D | 1058 | −11.084 | −6.772 | −52.299 | 1.00 | 29.12 | RNA2 | C |
| ATOM | 2926 | O2* | U | D | 1058 | −12.414 | −7.204 | −52.513 | 1.00 | 29.74 | RNA2 | O |
| ATOM | 2927 | C1* | U | D | 1058 | −10.455 | −6.348 | −53.622 | 1.00 | 26.32 | RNA2 | C |
| ATOM | 2928 | N1 | U | D | 1058 | −9.008 | −6.614 | −53.638 | 1.00 | 21.34 | RNA2 | N |
| ATOM | 2929 | C2 | U | D | 1058 | −8.608 | −7.932 | −53.803 | 1.00 | 24.87 | RNA2 | C |
| ATOM | 2930 | O2 | U | D | 1058 | −9.402 | −8.853 | −53.938 | 1.00 | 31.94 | RNA2 | O |
| ATOM | 2931 | N3 | U | D | 1058 | −7.253 | −8.136 | −53.799 | 1.00 | 8.92 | RNA2 | N |
| ATOM | 2932 | C4 | U | D | 1058 | −6.273 | −7.188 | −53.647 | 1.00 | 22.44 | RNA2 | C |
| ATOM | 2933 | O4 | U | D | 1058 | −5.088 | −7.533 | −53.685 | 1.00 | 18.08 | RNA2 | O |
| ATOM | 2934 | C5 | U | D | 1058 | −6.759 | −5.848 | −53.482 | 1.00 | 22.73 | RNA2 | C |
| ATOM | 2935 | C6 | U | D | 1058 | −8.080 | −5.614 | −53.488 | 1.00 | 18.95 | RNA2 | C |
| ATOM | 2936 | P | G | D | 1059 | −11.432 | −6.089 | −49.022 | 1.00 | 29.43 | RNA2 | P |
| ATOM | 2937 | O1P | G | D | 1059 | −9.995 | −5.757 | −48.812 | 1.00 | 18.78 | RNA2 | O |
| ATOM | 2938 | O2P | G | D | 1059 | −12.431 | −5.724 | −47.993 | 1.00 | 38.92 | RNA2 | O |
| ATOM | 2939 | O5* | G | D | 1059 | −11.490 | −7.659 | −49.247 | 1.00 | 34.42 | RNA2 | O |
| ATOM | 2940 | C5* | G | D | 1059 | −12.729 | −8.312 | −49.534 | 1.00 | 29.33 | RNA2 | C |
| ATOM | 2941 | C4* | G | D | 1059 | −12.525 | −9.801 | −49.573 | 1.00 | 27.67 | RNA2 | C |
| ATOM | 2942 | O4* | G | D | 1059 | −11.608 | −10.126 | −50.645 | 1.00 | 28.30 | RNA2 | O |
| ATOM | 2943 | C3* | G | D | 1059 | −11.883 | −10.411 | −48.339 | 1.00 | 32.02 | RNA2 | C |
| ATOM | 2944 | O3* | G | D | 1059 | −12.840 | −10.666 | −47.314 | 1.00 | 37.54 | RNA2 | O |
| ATOM | 2945 | C2* | G | D | 1059 | −11.260 | −11.691 | −48.887 | 1.00 | 27.34 | RNA2 | C |
| ATOM | 2946 | O2* | G | D | 1059 | −12.207 | −12.736 | −48.993 | 1.00 | 21.26 | RNA2 | O |
| ATOM | 2947 | C1* | G | D | 1059 | −10.838 | −11.258 | −50.289 | 1.00 | 18.26 | RNA2 | C |
| ATOM | 2948 | N9 | G | D | 1059 | −9.425 | −10.920 | −50.414 | 1.00 | 11.76 | RNA2 | N |
| ATOM | 2949 | C8 | G | D | 1059 | −8.846 | −9.686 | −50.262 | 1.00 | 10.37 | RNA2 | C |
| ATOM | 2950 | N7 | G | D | 1059 | −7.552 | −9.700 | −50.455 | 1.00 | 15.12 | RNA2 | N |
| ATOM | 2951 | C5 | G | D | 1059 | −7.260 | −11.026 | −50.747 | 1.00 | 5.51 | RNA2 | C |
| ATOM | 2952 | C6 | G | D | 1059 | −6.022 | −11.652 | −51.055 | 1.00 | 15.78 | RNA2 | C |
| ATOM | 2953 | O6 | G | D | 1059 | −4.892 | −11.145 | −51.124 | 1.00 | 17.40 | RNA2 | O |
| ATOM | 2954 | N1 | G | D | 1059 | −6.184 | −13.009 | −51.300 | 1.00 | 12.54 | RNA2 | N |
| ATOM | 2955 | C2 | G | D | 1059 | −7.377 | −13.685 | −51.256 | 1.00 | 23.87 | RNA2 | C |
| ATOM | 2956 | N2 | G | D | 1059 | −7.326 | −14.997 | −51.540 | 1.00 | 21.07 | RNA2 | N |
| ATOM | 2957 | N3 | G | D | 1059 | −8.536 | −13.119 | −50.962 | 1.00 | 20.56 | RNA2 | N |
| ATOM | 2958 | C4 | G | D | 1059 | −8.404 | −11.794 | −50.723 | 1.00 | 17.53 | RNA2 | C |
| ATOM | 2959 | P | U | D | 1060 | −12.363 | −10.713 | −45.780 | 1.00 | 31.30 | RNA2 | P |
| ATOM | 2960 | O1P | U | D | 1060 | −13.473 | −10.167 | −44.963 | 1.00 | 29.83 | RNA2 | O |
| ATOM | 2961 | O2P | U | D | 1060 | −11.840 | −12.074 | −45.484 | 1.00 | 37.29 | RNA2 | O |
| ATOM | 2962 | O5* | U | D | 1060 | −11.129 | −9.708 | −45.745 | 1.00 | 25.29 | RNA2 | O |
| ATOM | 2963 | C5* | U | D | 1060 | −10.735 | −9.064 | −44.527 | 1.00 | 22.54 | RNA2 | C |
| ATOM | 2964 | C4* | U | D | 1060 | −9.378 | −8.435 | −44.692 | 1.00 | 22.65 | RNA2 | C |
| ATOM | 2965 | O4* | U | D | 1060 | −8.401 | −9.481 | −44.882 | 1.00 | 24.56 | RNA2 | O |
| ATOM | 2966 | C3* | U | D | 1060 | −9.238 | −7.481 | −45.870 | 1.00 | 26.03 | RNA2 | C |
| ATOM | 2967 | O3* | U | D | 1060 | −8.303 | −6.454 | −45.522 | 1.00 | 41.53 | RNA2 | O |
| ATOM | 2968 | C2* | U | D | 1060 | −8.608 | −8.361 | −46.946 | 1.00 | 31.11 | RNA2 | C |
| ATOM | 2969 | O2* | U | D | 1060 | −7.808 | −7.616 | −47.841 | 1.00 | 45.38 | RNA2 | O |
| ATOM | 2970 | C1* | U | D | 1060 | −7.735 | −9.299 | −46.110 | 1.00 | 26.61 | RNA2 | C |
| ATOM | 2971 | N1 | U | D | 1060 | −7.519 | −10.632 | −46.690 | 1.00 | 21.85 | RNA2 | N |
| ATOM | 2972 | C2 | U | D | 1060 | −6.291 | −10.898 | −47.261 | 1.00 | 23.55 | RNA2 | C |
| ATOM | 2973 | O2 | U | D | 1060 | −5.402 | −10.063 | −47.355 | 1.00 | 21.48 | RNA2 | O |
| ATOM | 2974 | N3 | U | D | 1060 | −6.141 | −12.182 | −47.726 | 1.00 | 25.97 | RNA2 | N |
| ATOM | 2975 | C4 | U | D | 1060 | −7.076 | −13.199 | −47.691 | 1.00 | 28.32 | RNA2 | C |
| ATOM | 2976 | O4 | U | D | 1060 | −6.778 | −14.311 | −48.139 | 1.00 | 27.53 | RNA2 | O |
| ATOM | 2977 | C5 | U | D | 1060 | −8.329 | −12.837 | −47.107 | 1.00 | 18.41 | RNA2 | C |
| ATOM | 2978 | C6 | U | D | 1060 | −8.507 | −11.600 | −46.642 | 1.00 | 21.87 | RNA2 | C |

TABLE II-continued

| | | | | | | | | | | | | |
|---|---|---|---|---|---|---|---|---|---|---|---|---|
| ATOM | 2979 | P    | U | D | 1061 | −8.630  | −5.419  | −44.325 | 1.00 | 28.91 | RNA2 | P |
| ATOM | 2980 | O1P  | U | D | 1061 | −8.173  | −4.091  | −44.810 | 1.00 | 33.68 | RNA2 | O |
| ATOM | 2981 | O2P  | U | D | 1061 | −10.037 | −5.590  | −43.863 | 1.00 | 15.62 | RNA2 | O |
| ATOM | 2982 | O5*  | U | D | 1061 | −7.649  | −5.888  | −43.161 | 1.00 | 19.70 | RNA2 | O |
| ATOM | 2983 | C5*  | U | D | 1061 | −6.225  | −5.745  | −43.301 | 1.00 | 18.21 | RNA2 | C |
| ATOM | 2984 | C4*  | U | D | 1061 | −5.514  | −6.526  | −42.225 | 1.00 | 27.99 | RNA2 | C |
| ATOM | 2985 | O4*  | U | D | 1061 | −5.894  | −5.996  | −40.927 | 1.00 | 36.85 | RNA2 | O |
| ATOM | 2986 | C3*  | U | D | 1061 | −5.800  | −8.028  | −42.181 | 1.00 | 29.80 | RNA2 | C |
| ATOM | 2987 | O3*  | U | D | 1061 | −4.608  | −8.696  | −41.772 | 1.00 | 33.59 | RNA2 | O |
| ATOM | 2988 | C2*  | U | D | 1061 | −6.812  | −8.151  | −41.043 | 1.00 | 33.22 | RNA2 | C |
| ATOM | 2989 | O2*  | U | D | 1061 | −6.748  | −9.417  | −40.415 | 1.00 | 27.78 | RNA2 | O |
| ATOM | 2990 | C1*  | U | D | 1061 | −6.313  | −7.055  | −40.102 | 1.00 | 42.74 | RNA2 | C |
| ATOM | 2991 | N1   | U | D | 1061 | −7.205  | −6.543  | −39.046 | 1.00 | 44.96 | RNA2 | N |
| ATOM | 2992 | C2   | U | D | 1061 | −6.737  | −6.649  | −37.742 | 1.00 | 53.51 | RNA2 | C |
| ATOM | 2993 | O2   | U | D | 1061 | −5.650  | −7.143  | −37.464 | 1.00 | 44.65 | RNA2 | O |
| ATOM | 2994 | N3   | U | D | 1061 | −7.579  | −6.157  | −36.776 | 1.00 | 60.76 | RNA2 | N |
| ATOM | 2995 | C4   | U | D | 1061 | −8.811  | −5.585  | −36.961 | 1.00 | 51.80 | RNA2 | C |
| ATOM | 2996 | O4   | U | D | 1061 | −9.435  | −5.195  | −35.977 | 1.00 | 48.61 | RNA2 | O |
| ATOM | 2997 | C5   | U | D | 1061 | −9.240  | −5.508  | −38.333 | 1.00 | 40.80 | RNA2 | C |
| ATOM | 2998 | C6   | U | D | 1061 | −8.440  | −5.979  | −39.307 | 1.00 | 43.37 | RNA2 | C |
| ATOM | 2999 | P    | G | D | 1062 | −3.700  | −9.466  | −42.848 | 1.00 | 33.56 | RNA2 | P |
| ATOM | 3000 | O1P  | G | D | 1062 | −3.835  | −8.777  | −44.158 | 1.00 | 35.31 | RNA2 | O |
| ATOM | 3001 | O2P  | G | D | 1062 | −2.353  | −9.644  | −42.252 | 1.00 | 21.04 | RNA2 | O |
| ATOM | 3002 | O5*  | G | D | 1062 | −4.367  | −10.905 | −42.956 | 1.00 | 30.74 | RNA2 | O |
| ATOM | 3003 | C5*  | G | D | 1062 | −5.563  | −11.128 | −43.737 | 1.00 | 36.95 | RNA2 | C |
| ATOM | 3004 | C4*  | G | D | 1062 | −5.583  | −12.554 | −44.235 | 1.00 | 30.45 | RNA2 | C |
| ATOM | 3005 | O4*  | G | D | 1062 | −4.531  | −12.739 | −45.222 | 1.00 | 26.47 | RNA2 | O |
| ATOM | 3006 | C3*  | G | D | 1062 | −5.264  | −13.550 | −43.139 | 1.00 | 20.89 | RNA2 | C |
| ATOM | 3007 | O3*  | G | D | 1062 | −6.428  | −13.905 | −42.431 | 1.00 | 31.67 | RNA2 | O |
| ATOM | 3008 | C2*  | G | D | 1062 | −4.625  | −14.707 | −43.894 | 1.00 | 23.56 | RNA2 | C |
| ATOM | 3009 | O2*  | G | D | 1062 | −5.589  | −15.567 | −44.466 | 1.00 | 18.76 | RNA2 | O |
| ATOM | 3010 | C1*  | G | D | 1062 | −3.854  | −13.963 | −44.988 | 1.00 | 16.90 | RNA2 | C |
| ATOM | 3011 | N9   | G | D | 1062 | −2.473  | −13.642 | −44.620 | 1.00 | 13.03 | RNA2 | N |
| ATOM | 3012 | C8   | G | D | 1062 | −1.919  | −12.387 | −44.523 | 1.00 | 19.49 | RNA2 | C |
| ATOM | 3013 | N7   | G | D | 1062 | −0.660  | −12.404 | −44.173 | 1.00 | 13.70 | RNA2 | N |
| ATOM | 3014 | C5   | G | D | 1062 | −0.362  | −13.749 | −44.024 | 1.00 | 14.04 | RNA2 | C |
| ATOM | 3015 | C6   | G | D | 1062 |  0.850  | −14.379 | −43.651 | 1.00 | 24.18 | RNA2 | C |
| ATOM | 3016 | O6   | G | D | 1062 |  1.933  | −13.852 | −43.356 | 1.00 | 29.04 | RNA2 | O |
| ATOM | 3017 | N1   | G | D | 1062 |  0.723  | −15.765 | −43.634 | 1.00 | 22.87 | RNA2 | N |
| ATOM | 3018 | C2   | G | D | 1062 | −0.427  | −16.456 | −43.927 | 1.00 | 30.15 | RNA2 | C |
| ATOM | 3019 | N2   | G | D | 1062 | −0.349  | −17.795 | −43.849 | 1.00 | 24.93 | RNA2 | N |
| ATOM | 3020 | N3   | G | D | 1062 | −1.570  | −15.878 | −44.269 | 1.00 | 30.88 | RNA2 | N |
| ATOM | 3021 | C4   | G | D | 1062 | −1.466  | −14.531 | −44.300 | 1.00 | 16.88 | RNA2 | C |
| ATOM | 3022 | P    | G | D | 1063 | −6.322  | −14.242 | −40.874 | 1.00 | 28.41 | RNA2 | P |
| ATOM | 3023 | O1P  | G | D | 1063 | −5.463  | −13.199 | −40.266 | 1.00 | 27.32 | RNA2 | O |
| ATOM | 3024 | O2P  | G | D | 1063 | −7.701  | −14.468 | −40.367 | 1.00 | 29.73 | RNA2 | O |
| ATOM | 3025 | O5*  | G | D | 1063 | −5.523  | −15.617 | −40.821 | 1.00 | 30.17 | RNA2 | O |
| ATOM | 3026 | C5*  | G | D | 1063 | −6.184  | −16.864 | −41.087 | 1.00 | 24.95 | RNA2 | C |
| ATOM | 3027 | C4*  | G | D | 1063 | −5.241  | −18.011 | −40.832 | 1.00 | 20.87 | RNA2 | C |
| ATOM | 3028 | O4*  | G | D | 1063 | −4.075  | −17.850 | −41.677 | 1.00 | 27.19 | RNA2 | O |
| ATOM | 3029 | C3*  | G | D | 1063 | −4.659  | −18.092 | −39.434 | 1.00 | 26.89 | RNA2 | C |
| ATOM | 3030 | O3*  | G | D | 1063 | −5.539  | −18.706 | −38.508 | 1.00 | 40.50 | RNA2 | O |
| ATOM | 3031 | C2*  | G | D | 1063 | −3.373  | −18.869 | −39.659 | 1.00 | 23.40 | RNA2 | C |
| ATOM | 3032 | O2*  | G | D | 1063 | −3.601  | −20.256 | −39.810 | 1.00 | 29.18 | RNA2 | O |
| ATOM | 3033 | C1*  | G | D | 1063 | −2.919  | −18.297 | −40.994 | 1.00 | 21.30 | RNA2 | C |
| ATOM | 3034 | N9   | G | D | 1063 | −2.022  | −17.158 | −40.820 | 1.00 | 18.48 | RNA2 | N |
| ATOM | 3035 | C8   | G | D | 1063 | −2.309  | −15.827 | −41.016 | 1.00 | 13.94 | RNA2 | C |
| ATOM | 3036 | N7   | G | D | 1063 | −1.283  | −15.044 | −40.798 | 1.00 | 19.66 | RNA2 | N |
| ATOM | 3037 | C5   | G | D | 1063 | −0.260  | −15.909 | −40.428 | 1.00 | 17.05 | RNA2 | C |
| ATOM | 3038 | C6   | G | D | 1063 |  1.093  | −15.646 | −40.066 | 1.00 | 24.81 | RNA2 | C |
| ATOM | 3039 | O6   | G | D | 1063 |  1.680  | −14.559 | −39.999 | 1.00 | 27.63 | RNA2 | O |
| ATOM | 3040 | N1   | G | D | 1063 |  1.776  | −16.819 | −39.756 | 1.00 | 29.06 | RNA2 | N |
| ATOM | 3041 | C2   | G | D | 1063 |  1.234  | −18.080 | −39.781 | 1.00 | 24.76 | RNA2 | C |
| ATOM | 3042 | N2   | G | D | 1063 |  2.051  | −19.081 | −39.433 | 1.00 | 26.32 | RNA2 | N |
| ATOM | 3043 | N3   | G | D | 1063 | −0.018  | −18.340 | −40.119 | 1.00 | 25.89 | RNA2 | N |
| ATOM | 3044 | C4   | G | D | 1063 | −0.702  | −17.217 | −40.429 | 1.00 | 24.85 | RNA2 | C |
| ATOM | 3045 | P    | C | D | 1064 | −5.606  | −18.145 | −37.003 | 1.00 | 33.12 | RNA2 | P |
| ATOM | 3046 | O1P  | C | D | 1064 | −5.740  | −16.669 | −37.090 | 1.00 | 33.72 | RNA2 | O |
| ATOM | 3047 | O2P  | C | D | 1064 | −6.628  | −18.934 | −36.261 | 1.00 | 34.10 | RNA2 | O |
| ATOM | 3048 | O5*  | C | D | 1064 | −4.159  | −18.476 | −36.424 | 1.00 | 27.13 | RNA2 | O |
| ATOM | 3049 | C5*  | C | D | 1064 | −3.695  | −19.826 | −36.395 | 1.00 | 16.79 | RNA2 | C |
| ATOM | 3050 | C4*  | C | D | 1064 | −2.235  | −19.884 | −36.032 | 1.00 | 25.70 | RNA2 | C |
| ATOM | 3051 | O4*  | C | D | 1064 | −1.436  | −19.190 | −37.022 | 1.00 | 29.89 | RNA2 | O |
| ATOM | 3052 | C3*  | C | D | 1064 | −1.813  | −19.250 | −34.720 | 1.00 | 29.70 | RNA2 | C |
| ATOM | 3053 | O3*  | C | D | 1064 | −2.095  | −20.085 | −33.611 | 1.00 | 37.04 | RNA2 | O |
| ATOM | 3054 | C2*  | C | D | 1064 | −0.315  | −19.047 | −34.923 | 1.00 | 30.06 | RNA2 | C |
| ATOM | 3055 | O2*  | C | D | 1064 |  0.445  | −20.216 | −34.696 | 1.00 | 28.38 | RNA2 | O |
| ATOM | 3056 | C1*  | C | D | 1064 | −0.251  | −18.704 | −36.409 | 1.00 | 30.33 | RNA2 | C |
| ATOM | 3057 | N1   | C | D | 1064 | −0.140  | −17.251 | −36.627 | 1.00 | 20.71 | RNA2 | N |

TABLE II-continued

| | | | | | | | | | | | |
|---|---|---|---|---|---|---|---|---|---|---|---|
| ATOM | 3058 | C2 | C | D | 1064 | 1.114 | −16.655 | −36.474 | 1.00 | 24.44 | RNA2 C |
| ATOM | 3059 | O2 | C | D | 1064 | 2.086 | −17.365 | −36.175 | 1.00 | 30.49 | RNA2 O |
| ATOM | 3060 | N3 | C | D | 1064 | 1.237 | −15.325 | −36.654 | 1.00 | 26.69 | RNA2 N |
| ATOM | 3061 | C4 | C | D | 1064 | 0.170 | −14.591 | −36.976 | 1.00 | 20.50 | RNA2 C |
| ATOM | 3062 | N4 | C | D | 1064 | 0.347 | −13.279 | −37.141 | 1.00 | 22.60 | RNA2 N |
| ATOM | 3063 | C5 | C | D | 1064 | −1.120 | −15.169 | −37.143 | 1.00 | 10.11 | RNA2 C |
| ATOM | 3064 | C6 | C | D | 1064 | −1.229 | −16.492 | −36.962 | 1.00 | 23.85 | RNA2 C |
| ATOM | 3065 | P | U | D | 1065 | −2.513 | −19.420 | −32.214 | 1.00 | 35.56 | RNA2 P |
| ATOM | 3066 | O1P | U | D | 1065 | −3.615 | −18.460 | −32.467 | 1.00 | 26.06 | RNA2 O |
| ATOM | 3067 | O2P | U | D | 1065 | −2.716 | −20.527 | −31.248 | 1.00 | 43.50 | RNA2 O |
| ATOM | 3068 | O5* | U | D | 1065 | −1.209 | −18.600 | −31.807 | 1.00 | 27.70 | RNA2 O |
| ATOM | 3069 | C5* | U | D | 1065 | 0.044 | −19.282 | −31.609 | 1.00 | 30.92 | RNA2 C |
| ATOM | 3070 | C4* | U | D | 1065 | 1.168 | −18.287 | −31.469 | 1.00 | 30.67 | RNA2 C |
| ATOM | 3071 | O4* | U | D | 1065 | 1.332 | −17.559 | −32.713 | 1.00 | 39.57 | RNA2 O |
| ATOM | 3072 | C3* | U | D | 1065 | 0.951 | −17.209 | −30.423 | 1.00 | 36.18 | RNA2 C |
| ATOM | 3073 | O3* | U | D | 1065 | 1.285 | −17.667 | −29.123 | 1.00 | 36.24 | RNA2 O |
| ATOM | 3074 | C2* | U | D | 1065 | 1.843 | −16.076 | −30.921 | 1.00 | 38.21 | RNA2 C |
| ATOM | 3075 | O2* | U | D | 1065 | 3.207 | −16.224 | −30.578 | 1.00 | 34.14 | RNA2 O |
| ATOM | 3076 | C1* | U | D | 1065 | 1.692 | −16.216 | −32.437 | 1.00 | 34.96 | RNA2 C |
| ATOM | 3077 | N1 | U | D | 1065 | 0.645 | −15.327 | −32.968 | 1.00 | 22.93 | RNA2 N |
| ATOM | 3078 | C2 | U | D | 1065 | 1.028 | −14.066 | −33.377 | 1.00 | 24.04 | RNA2 C |
| ATOM | 3079 | O2 | U | D | 1065 | 2.187 | −13.674 | −33.325 | 1.00 | 20.47 | RNA2 O |
| ATOM | 3080 | N3 | U | D | 1065 | 0.008 | −13.276 | −33.849 | 1.00 | 17.91 | RNA2 N |
| ATOM | 3081 | C4 | U | D | 1065 | −1.325 | −13.612 | −33.954 | 1.00 | 25.02 | RNA2 C |
| ATOM | 3082 | O4 | U | D | 1065 | −2.125 | −12.793 | −34.424 | 1.00 | 30.88 | RNA2 O |
| ATOM | 3083 | C5 | U | D | 1065 | −1.640 | −14.934 | −33.511 | 1.00 | 26.71 | RNA2 C |
| ATOM | 3084 | C6 | U | D | 1065 | −0.670 | −15.727 | −33.046 | 1.00 | 28.23 | RNA2 C |
| ATOM | 3085 | P | U | D | 1066 | 0.342 | −17.279 | −27.876 | 1.00 | 35.54 | RNA2 P |
| ATOM | 3086 | O1P | U | D | 1066 | −1.089 | −17.498 | −28.212 | 1.00 | 19.51 | RNA2 O |
| ATOM | 3087 | O2P | U | D | 1066 | 0.927 | −17.960 | −26.692 | 1.00 | 43.24 | RNA2 O |
| ATOM | 3088 | O5* | U | D | 1066 | 0.552 | −15.708 | −27.728 | 1.00 | 32.79 | RNA2 O |
| ATOM | 3089 | C5* | U | D | 1066 | 1.867 | −15.163 | −27.509 | 1.00 | 39.57 | RNA2 C |
| ATOM | 3090 | C4* | U | D | 1066 | 1.853 | −13.664 | −27.695 | 1.00 | 41.26 | RNA2 C |
| ATOM | 3091 | O4* | U | D | 1066 | 1.606 | −13.339 | −29.088 | 1.00 | 50.01 | RNA2 O |
| ATOM | 3092 | C3* | U | D | 1066 | 0.773 | −12.909 | −26.935 | 1.00 | 46.81 | RNA2 C |
| ATOM | 3093 | O3* | U | D | 1066 | 1.137 | −12.653 | −25.587 | 1.00 | 47.16 | RNA2 O |
| ATOM | 3094 | C2* | U | D | 1066 | 0.645 | −11.626 | −27.743 | 1.00 | 45.38 | RNA2 C |
| ATOM | 3095 | O2* | U | D | 1066 | 1.671 | −10.702 | −27.422 | 1.00 | 47.24 | RNA2 O |
| ATOM | 3096 | C1* | U | D | 1066 | 0.848 | −12.142 | −29.168 | 1.00 | 44.66 | RNA2 C |
| ATOM | 3097 | N1 | U | D | 1066 | −0.437 | −12.423 | −29.835 | 1.00 | 36.02 | RNA2 N |
| ATOM | 3098 | C2 | U | D | 1066 | −1.001 | −11.401 | −30.583 | 1.00 | 31.01 | RNA2 C |
| ATOM | 3099 | O2 | U | D | 1066 | −0.450 | −10.325 | −30.752 | 1.00 | 24.12 | RNA2 O |
| ATOM | 3100 | N3 | U | D | 1066 | −2.231 | −11.687 | −31.131 | 1.00 | 26.04 | RNA2 N |
| ATOM | 3101 | C4 | U | D | 1066 | −2.939 | −12.872 | −31.028 | 1.00 | 32.10 | RNA2 C |
| ATOM | 3102 | O4 | U | D | 1066 | −4.082 | −12.941 | −31.501 | 1.00 | 32.26 | RNA2 O |
| ATOM | 3103 | C5 | U | D | 1066 | −2.276 | −13.895 | −30.271 | 1.00 | 27.27 | RNA2 C |
| ATOM | 3104 | C6 | U | D | 1066 | −1.080 | −13.644 | −29.712 | 1.00 | 35.51 | RNA2 C |
| ATOM | 3105 | P | A | D | 1067 | 0.011 | −12.695 | −24.442 | 1.00 | 41.56 | RNA2 P |
| ATOM | 3106 | O1P | A | D | 1067 | −0.869 | −13.868 | −24.667 | 1.00 | 35.90 | RNA2 O |
| ATOM | 3107 | O2P | A | D | 1067 | 0.710 | −12.532 | −23.138 | 1.00 | 61.37 | RNA2 O |
| ATOM | 3108 | O5* | A | D | 1067 | −0.877 | −11.403 | −24.702 | 1.00 | 37.80 | RNA2 O |
| ATOM | 3109 | C5* | A | D | 1067 | −2.175 | −11.275 | −24.099 | 1.00 | 33.78 | RNA2 C |
| ATOM | 3110 | C4* | A | D | 1067 | −2.689 | −9.870 | −24.284 | 1.00 | 40.27 | RNA2 C |
| ATOM | 3111 | O4* | A | D | 1067 | −1.791 | −8.952 | −23.617 | 1.00 | 40.68 | RNA2 O |
| ATOM | 3112 | C3* | A | D | 1067 | −2.714 | −9.402 | −25.727 | 1.00 | 40.11 | RNA2 C |
| ATOM | 3113 | O3* | A | D | 1067 | −3.918 | −9.794 | −26.362 | 1.00 | 46.79 | RNA2 O |
| ATOM | 3114 | C2* | A | D | 1067 | −2.560 | −7.892 | −25.606 | 1.00 | 33.18 | RNA2 C |
| ATOM | 3115 | O2* | A | D | 1067 | −3.785 | −7.245 | −25.315 | 1.00 | 34.55 | RNA2 O |
| ATOM | 3116 | C1* | A | D | 1067 | −1.637 | −7.782 | −24.394 | 1.00 | 30.38 | RNA2 C |
| ATOM | 3117 | N9 | A | D | 1067 | −0.216 | −7.636 | −24.699 | 1.00 | 18.52 | RNA2 N |
| ATOM | 3118 | C8 | A | D | 1067 | 0.791 | −8.539 | −24.462 | 1.00 | 19.03 | RNA2 C |
| ATOM | 3119 | N7 | A | D | 1067 | 1.987 | −8.090 | −24.769 | 1.00 | 23.17 | RNA2 N |
| ATOM | 3120 | C5 | A | D | 1067 | 1.748 | −6.814 | −25.262 | 1.00 | 12.64 | RNA2 C |
| ATOM | 3121 | C6 | A | D | 1067 | 2.605 | −5.811 | −25.748 | 1.00 | 16.33 | RNA2 C |
| ATOM | 3122 | N6 | A | D | 1067 | 3.934 | −5.945 | −25.831 | 1.00 | 21.10 | RNA2 N |
| ATOM | 3123 | N1 | A | D | 1067 | 2.046 | −4.651 | −26.154 | 1.00 | 17.93 | RNA2 N |
| ATOM | 3124 | C2 | A | D | 1067 | 0.714 | −4.518 | −26.077 | 1.00 | 24.51 | RNA2 C |
| ATOM | 3125 | N3 | A | D | 1067 | −0.197 | −5.388 | −25.642 | 1.00 | 23.41 | RNA2 N |
| ATOM | 3126 | C4 | A | D | 1067 | 0.393 | −6.528 | −25.240 | 1.00 | 22.32 | RNA2 C |
| ATOM | 3127 | P | G | D | 1068 | −3.863 | −10.352 | −27.861 | 1.00 | 37.45 | RNA2 P |
| ATOM | 3128 | O1P | G | D | 1068 | −2.775 | −11.365 | −27.915 | 1.00 | 32.87 | RNA2 O |
| ATOM | 3129 | O2P | G | D | 1068 | −5.247 | −10.719 | −28.265 | 1.00 | 30.61 | RNA2 O |
| ATOM | 3130 | O5* | G | D | 1068 | −3.399 | −9.084 | −28.697 | 1.00 | 34.59 | RNA2 O |
| ATOM | 3131 | C5* | G | D | 1068 | −4.254 | −7.938 | −28.794 | 1.00 | 32.91 | RNA2 C |
| ATOM | 3132 | C4* | G | D | 1068 | −3.550 | −6.828 | −29.521 | 1.00 | 39.65 | RNA2 C |
| ATOM | 3133 | O4* | G | D | 1068 | −2.460 | −6.334 | −28.708 | 1.00 | 34.36 | RNA2 O |
| ATOM | 3134 | C3* | G | D | 1068 | −2.908 | −7.218 | −30.840 | 1.00 | 41.96 | RNA2 C |
| ATOM | 3135 | O3* | G | D | 1068 | −3.874 | −7.194 | −31.893 | 1.00 | 38.73 | RNA2 O |
| ATOM | 3136 | C2* | G | D | 1068 | −1.811 | −6.168 | −30.989 | 1.00 | 37.55 | RNA2 C |

TABLE II-continued

| | | | | | | | | | | |
|---|---|---|---|---|---|---|---|---|---|---|
| ATOM | 3137 | O2* | G | D | 1068 | −2.315 | −4.944 | −31.487 | 1.00 | 54.39 | RNA2 | O |
| ATOM | 3138 | C1* | G | D | 1068 | −1.382 | −5.951 | −29.535 | 1.00 | 22.83 | RNA2 | C |
| ATOM | 3139 | N9 | G | D | 1068 | −0.226 | −6.739 | −29.134 | 1.00 | 20.42 | RNA2 | N |
| ATOM | 3140 | C8 | G | D | 1068 | −0.246 | −8.011 | −28.616 | 1.00 | 22.08 | RNA2 | C |
| ATOM | 3141 | N7 | G | D | 1068 | 0.944 | −8.464 | −28.328 | 1.00 | 22.50 | RNA2 | N |
| ATOM | 3142 | C5 | G | D | 1068 | 1.803 | −7.433 | −28.683 | 1.00 | 10.90 | RNA2 | C |
| ATOM | 3143 | C6 | G | D | 1068 | 3.211 | −7.347 | −28.595 | 1.00 | 18.64 | RNA2 | C |
| ATOM | 3144 | O6 | G | D | 1068 | 4.011 | −8.196 | −28.176 | 1.00 | 32.91 | RNA2 | O |
| ATOM | 3145 | N1 | G | D | 1068 | 3.679 | −6.123 | −29.060 | 1.00 | 12.16 | RNA2 | N |
| ATOM | 3146 | C2 | G | D | 1068 | 2.894 | −5.115 | −29.547 | 1.00 | 13.74 | RNA2 | C |
| ATOM | 3147 | N2 | G | D | 1068 | 3.543 | −4.013 | −29.960 | 1.00 | 20.53 | RNA2 | N |
| ATOM | 3148 | N3 | G | D | 1068 | 1.575 | −5.179 | −29.629 | 1.00 | 16.63 | RNA2 | N |
| ATOM | 3149 | C4 | G | D | 1068 | 1.100 | −6.360 | −29.184 | 1.00 | 16.14 | RNA2 | C |
| ATOM | 3150 | P | A | D | 1069 | −3.995 | −8.447 | −32.902 | 1.00 | 27.21 | RNA2 | P |
| ATOM | 3151 | O1P | A | D | 1069 | −4.082 | −9.718 | −32.124 | 1.00 | 34.28 | RNA2 | O |
| ATOM | 3152 | O2P | A | D | 1069 | −5.070 | −8.102 | −33.864 | 1.00 | 29.02 | RNA2 | O |
| ATOM | 3153 | O5* | A | D | 1069 | −2.601 | −8.445 | −33.661 | 1.00 | 13.61 | RNA2 | O |
| ATOM | 3154 | C5* | A | D | 1069 | −2.231 | −7.337 | −34.472 | 1.00 | 12.04 | RNA2 | C |
| ATOM | 3155 | C4* | A | D | 1069 | −0.867 | −7.557 | −35.055 | 1.00 | 21.87 | RNA2 | C |
| ATOM | 3156 | O4* | A | D | 1069 | 0.149 | −7.322 | −34.046 | 1.00 | 32.63 | RNA2 | O |
| ATOM | 3157 | C3* | A | D | 1069 | −0.590 | −8.954 | −35.628 | 1.00 | 35.90 | RNA2 | C |
| ATOM | 3158 | O3* | A | D | 1069 | 0.162 | −8.819 | −36.833 | 1.00 | 43.63 | RNA2 | O |
| ATOM | 3159 | C2* | A | D | 1069 | 0.352 | −9.560 | −34.592 | 1.00 | 35.57 | RNA2 | C |
| ATOM | 3160 | O2* | A | D | 1069 | 1.241 | −10.526 | −35.127 | 1.00 | 44.23 | RNA2 | O |
| ATOM | 3161 | C1* | A | D | 1069 | 1.127 | −8.311 | −34.199 | 1.00 | 42.00 | RNA2 | C |
| ATOM | 3162 | N9 | A | D | 1069 | 2.031 | −8.358 | −33.054 | 1.00 | 38.32 | RNA2 | N |
| ATOM | 3163 | C8 | A | D | 1069 | 2.071 | −9.207 | −31.976 | 1.00 | 30.76 | RNA2 | C |
| ATOM | 3164 | N7 | A | D | 1069 | 3.141 | −9.059 | −31.233 | 1.00 | 35.91 | RNA2 | N |
| ATOM | 3165 | C5 | A | D | 1069 | 3.827 | −8.017 | −31.841 | 1.00 | 33.30 | RNA2 | C |
| ATOM | 3166 | C6 | A | D | 1069 | 5.053 | −7.392 | −31.552 | 1.00 | 39.74 | RNA2 | C |
| ATOM | 3167 | N6 | A | D | 1069 | 5.850 | −7.751 | −30.540 | 1.00 | 50.68 | RNA2 | N |
| ATOM | 3168 | N1 | A | D | 1069 | 5.443 | −6.375 | −32.353 | 1.00 | 41.06 | RNA2 | N |
| ATOM | 3169 | C2 | A | D | 1069 | 4.649 | −6.022 | −33.371 | 1.00 | 43.25 | RNA2 | C |
| ATOM | 3170 | N3 | A | D | 1069 | 3.483 | −6.540 | −33.747 | 1.00 | 36.03 | RNA2 | N |
| ATOM | 3171 | C4 | A | D | 1069 | 3.131 | −7.548 | −32.935 | 1.00 | 31.57 | RNA2 | C |
| ATOM | 3172 | P | A | D | 1070 | −0.353 | −9.514 | −38.183 | 1.00 | 39.29 | RNA2 | P |
| ATOM | 3173 | O1P | A | D | 1070 | 0.847 | −9.589 | −39.057 | 1.00 | 23.58 | RNA2 | O |
| ATOM | 3174 | O2P | A | D | 1070 | −1.128 | −10.747 | −37.873 | 1.00 | 27.46 | RNA2 | O |
| ATOM | 3175 | O5* | A | D | 1070 | −1.376 | −8.452 | −38.783 | 1.00 | 32.87 | RNA2 | O |
| ATOM | 3176 | C5* | A | D | 1070 | −0.906 | −7.233 | −39.388 | 1.00 | 32.49 | RNA2 | C |
| ATOM | 3177 | C4* | A | D | 1070 | −2.018 | −6.594 | −40.179 | 1.00 | 35.94 | RNA2 | C |
| ATOM | 3178 | O4* | A | D | 1070 | −3.134 | −6.304 | −39.296 | 1.00 | 34.73 | RNA2 | O |
| ATOM | 3179 | C3* | A | D | 1070 | −1.665 | −5.292 | −40.885 | 1.00 | 39.27 | RNA2 | C |
| ATOM | 3180 | O3* | A | D | 1070 | −2.329 | −5.275 | −42.147 | 1.00 | 42.75 | RNA2 | O |
| ATOM | 3181 | C2* | A | D | 1070 | −2.248 | −4.225 | −39.960 | 1.00 | 39.48 | RNA2 | C |
| ATOM | 3182 | O2* | A | D | 1070 | −2.656 | −3.052 | −40.635 | 1.00 | 46.91 | RNA2 | O |
| ATOM | 3183 | C1* | A | D | 1070 | −3.468 | −4.935 | −39.379 | 1.00 | 38.47 | RNA2 | C |
| ATOM | 3184 | N9 | A | D | 1070 | −3.821 | −4.467 | −38.038 | 1.00 | 42.60 | RNA2 | N |
| ATOM | 3185 | C8 | A | D | 1070 | −3.112 | −4.646 | −36.878 | 1.00 | 43.81 | RNA2 | C |
| ATOM | 3186 | N7 | A | D | 1070 | −3.690 | −4.133 | −35.822 | 1.00 | 45.93 | RNA2 | N |
| ATOM | 3187 | C5 | A | D | 1070 | −4.854 | −3.570 | −36.318 | 1.00 | 44.50 | RNA2 | C |
| ATOM | 3188 | C6 | A | D | 1070 | −5.898 | −2.873 | −35.697 | 1.00 | 50.91 | RNA2 | C |
| ATOM | 3189 | N6 | A | D | 1070 | −5.936 | −2.617 | −34.390 | 1.00 | 62.29 | RNA2 | N |
| ATOM | 3190 | N1 | A | D | 1070 | −6.915 | −2.441 | −36.474 | 1.00 | 49.05 | RNA2 | N |
| ATOM | 3191 | C2 | A | D | 1070 | −6.870 | −2.698 | −37.783 | 1.00 | 37.67 | RNA2 | C |
| ATOM | 3192 | N3 | A | D | 1070 | −5.940 | −3.344 | −38.485 | 1.00 | 40.26 | RNA2 | N |
| ATOM | 3193 | C4 | A | D | 1070 | −4.946 | −3.761 | −37.683 | 1.00 | 42.22 | RNA2 | C |
| ATOM | 3194 | P | G | D | 1071 | −1.684 | −4.476 | −43.382 | 1.00 | 30.55 | RNA2 | P |
| ATOM | 3195 | O1P | G | D | 1071 | −2.623 | −4.642 | −44.520 | 1.00 | 33.24 | RNA2 | O |
| ATOM | 3196 | O2P | G | D | 1071 | −1.310 | −3.114 | −42.932 | 1.00 | 42.96 | RNA2 | O |
| ATOM | 3197 | O5* | G | D | 1071 | −0.331 | −5.246 | −43.697 | 1.00 | 21.65 | RNA2 | O |
| ATOM | 3198 | C5* | G | D | 1071 | −0.333 | −6.592 | −44.214 | 1.00 | 29.38 | RNA2 | C |
| ATOM | 3199 | C4* | G | D | 1071 | 1.026 | −6.907 | −44.779 | 1.00 | 23.80 | RNA2 | C |
| ATOM | 3200 | O4* | G | D | 1071 | 1.238 | −6.061 | −45.928 | 1.00 | 28.20 | RNA2 | O |
| ATOM | 3201 | C3* | G | D | 1071 | 2.141 | −6.557 | −43.811 | 1.00 | 30.81 | RNA2 | C |
| ATOM | 3202 | O3* | G | D | 1071 | 2.441 | −7.666 | −42.979 | 1.00 | 41.31 | RNA2 | O |
| ATOM | 3203 | C2* | G | D | 1071 | 3.288 | −6.132 | −44.719 | 1.00 | 22.22 | RNA2 | C |
| ATOM | 3204 | O2* | G | D | 1071 | 4.080 | −7.199 | −45.191 | 1.00 | 28.60 | RNA2 | O |
| ATOM | 3205 | C1* | G | D | 1071 | 2.532 | −5.498 | −45.883 | 1.00 | 21.88 | RNA2 | C |
| ATOM | 3206 | N9 | G | D | 1071 | 2.369 | −4.053 | −45.773 | 1.00 | 20.68 | RNA2 | N |
| ATOM | 3207 | C8 | G | D | 1071 | 1.186 | −3.366 | −45.636 | 1.00 | 17.70 | RNA2 | C |
| ATOM | 3208 | N7 | G | D | 1071 | 1.347 | −2.072 | −45.623 | 1.00 | 24.21 | RNA2 | N |
| ATOM | 3209 | C5 | G | D | 1071 | 2.716 | −1.895 | −45.742 | 1.00 | 13.42 | RNA2 | C |
| ATOM | 3210 | C6 | G | D | 1071 | 3.478 | −0.710 | −45.794 | 1.00 | 24.45 | RNA2 | C |
| ATOM | 3211 | O6 | G | D | 1071 | 3.078 | 0.460 | −45.758 | 1.00 | 34.15 | RNA2 | O |
| ATOM | 3212 | N1 | G | D | 1071 | 4.841 | −0.981 | −45.904 | 1.00 | 15.33 | RNA2 | N |
| ATOM | 3213 | C2 | G | D | 1071 | 5.395 | −2.241 | −45.961 | 1.00 | 23.28 | RNA2 | C |
| ATOM | 3214 | N2 | G | D | 1071 | 6.734 | −2.306 | −46.052 | 1.00 | 12.46 | RNA2 | N |
| ATOM | 3215 | N3 | G | D | 1071 | 4.686 | −3.356 | −45.925 | 1.00 | 19.68 | RNA2 | N |

TABLE II-continued

| | | | | | | | | | | | |
|---|---|---|---|---|---|---|---|---|---|---|---|
| ATOM | 3216 | C4 | G | D | 1071 | 3.363 | −3.109 | −45.817 | 1.00 | 12.68 | RNA2 C |
| ATOM | 3217 | P | C | D | 1072 | 2.695 | −7.430 | −41.419 | 1.00 | 33.36 | RNA2 P |
| ATOM | 3218 | O1P | C | D | 1072 | 1.653 | −6.490 | −40.920 | 1.00 | 33.81 | RNA2 O |
| ATOM | 3219 | O2P | C | D | 1072 | 2.864 | −8.759 | −40.777 | 1.00 | 35.75 | RNA2 O |
| ATOM | 3220 | O5* | C | D | 1072 | 4.090 | −6.677 | −41.393 | 1.00 | 20.85 | RNA2 O |
| ATOM | 3221 | C5* | C | D | 1072 | 5.294 | −7.370 | −41.724 | 1.00 | 18.04 | RNA2 C |
| ATOM | 3222 | C4* | C | D | 1072 | 6.458 | −6.420 | −41.676 | 1.00 | 27.13 | RNA2 C |
| ATOM | 3223 | O4* | C | D | 1072 | 6.309 | −5.437 | −42.729 | 1.00 | 37.39 | RNA2 O |
| ATOM | 3224 | C3* | C | D | 1072 | 6.577 | −5.591 | −40.408 | 1.00 | 33.89 | RNA2 C |
| ATOM | 3225 | O3* | C | D | 1072 | 7.216 | −6.295 | −39.352 | 1.00 | 27.21 | RNA2 O |
| ATOM | 3226 | C2* | C | D | 1072 | 7.364 | −4.376 | −40.882 | 1.00 | 36.24 | RNA2 C |
| ATOM | 3227 | O2* | C | D | 1072 | 8.753 | −4.637 | −40.967 | 1.00 | 40.82 | RNA2 O |
| ATOM | 3228 | C1* | C | D | 1072 | 6.803 | −4.182 | −42.291 | 1.00 | 32.40 | RNA2 C |
| ATOM | 3229 | N1 | C | D | 1072 | 5.704 | −3.196 | −42.347 | 1.00 | 21.10 | RNA2 N |
| ATOM | 3230 | C2 | C | D | 1072 | 6.015 | −1.860 | −42.594 | 1.00 | 22.51 | RNA2 C |
| ATOM | 3231 | O2 | C | D | 1072 | 7.206 | −1.541 | −42.755 | 1.00 | 32.30 | RNA2 O |
| ATOM | 3232 | N3 | C | D | 1072 | 5.016 | −0.947 | −42.647 | 1.00 | 18.99 | RNA2 N |
| ATOM | 3233 | C4 | C | D | 1072 | 3.750 | −1.327 | −42.456 | 1.00 | 23.03 | RNA2 C |
| ATOM | 3234 | N4 | C | D | 1072 | 2.795 | −0.389 | −42.506 | 1.00 | 21.64 | RNA2 N |
| ATOM | 3235 | C5 | C | D | 1072 | 3.405 | −2.681 | −42.204 | 1.00 | 18.92 | RNA2 C |
| ATOM | 3236 | C6 | C | D | 1072 | 4.404 | −3.575 | −42.160 | 1.00 | 22.99 | RNA2 C |
| ATOM | 3237 | P | A | D | 1073 | 6.502 | −6.360 | −37.915 | 1.00 | 37.37 | RNA2 P |
| ATOM | 3238 | O1P | A | D | 1073 | 6.300 | −4.954 | −37.487 | 1.00 | 30.80 | RNA2 O |
| ATOM | 3239 | O2P | A | D | 1073 | 5.328 | −7.287 | −37.972 | 1.00 | 26.29 | RNA2 O |
| ATOM | 3240 | O5* | A | D | 1073 | 7.614 | −6.996 | −36.980 | 1.00 | 33.33 | RNA2 O |
| ATOM | 3241 | C5* | A | D | 1073 | 8.842 | −6.293 | −36.711 | 1.00 | 45.87 | RNA2 C |
| ATOM | 3242 | C4* | A | D | 1073 | 9.614 | −7.024 | −35.651 | 1.00 | 39.23 | RNA2 C |
| ATOM | 3243 | O4* | A | D | 1073 | 8.804 | −7.060 | −34.451 | 1.00 | 42.33 | RNA2 O |
| ATOM | 3244 | C3* | A | D | 1073 | 9.847 | −8.484 | −35.996 | 1.00 | 42.31 | RNA2 C |
| ATOM | 3245 | O3* | A | D | 1073 | 11.022 | −8.666 | −36.753 | 1.00 | 46.57 | RNA2 O |
| ATOM | 3246 | C2* | A | D | 1073 | 9.902 | −9.161 | −34.638 | 1.00 | 40.15 | RNA2 C |
| ATOM | 3247 | O2* | A | D | 1073 | 11.169 | −9.047 | −34.018 | 1.00 | 50.42 | RNA2 O |
| ATOM | 3248 | C1* | A | D | 1073 | 8.866 | −8.350 | −33.866 | 1.00 | 29.91 | RNA2 C |
| ATOM | 3249 | N9 | A | D | 1073 | 7.532 | −8.935 | −33.963 | 1.00 | 24.96 | RNA2 N |
| ATOM | 3250 | C8 | A | D | 1073 | 6.453 | −8.438 | −34.648 | 1.00 | 25.01 | RNA2 C |
| ATOM | 3251 | N7 | A | D | 1073 | 5.373 | −9.170 | −34.534 | 1.00 | 31.09 | RNA2 N |
| ATOM | 3252 | C5 | A | D | 1073 | 5.770 | −10.224 | −33.727 | 1.00 | 16.48 | RNA2 C |
| ATOM | 3253 | C6 | A | D | 1073 | 5.085 | −11.338 | −33.237 | 1.00 | 25.59 | RNA2 C |
| ATOM | 3254 | N6 | A | D | 1073 | 3.804 | −11.589 | −33.504 | 1.00 | 28.23 | RNA2 N |
| ATOM | 3255 | N1 | A | D | 1073 | 5.765 | −12.201 | −32.456 | 1.00 | 25.23 | RNA2 N |
| ATOM | 3256 | C2 | A | D | 1073 | 7.053 | −11.951 | −32.200 | 1.00 | 27.30 | RNA2 C |
| ATOM | 3257 | N3 | A | D | 1073 | 7.811 | −10.937 | −32.608 | 1.00 | 31.09 | RNA2 N |
| ATOM | 3258 | C4 | A | D | 1073 | 7.099 | −10.097 | −33.375 | 1.00 | 27.01 | RNA2 C |
| ATOM | 3259 | P | G | D | 1074 | 11.030 | −9.753 | −37.924 | 1.00 | 43.98 | RNA2 P |
| ATOM | 3260 | O1P | G | D | 1074 | 9.978 | −9.343 | −38.892 | 1.00 | 47.14 | RNA2 O |
| ATOM | 3261 | O2P | G | D | 1074 | 12.435 | −9.917 | −38.384 | 1.00 | 36.10 | RNA2 O |
| ATOM | 3262 | O5* | G | D | 1074 | 10.556 | −11.084 | −37.192 | 1.00 | 30.43 | RNA2 O |
| ATOM | 3263 | C5* | G | D | 1074 | 11.408 | −11.715 | −36.230 | 1.00 | 29.08 | RNA2 C |
| ATOM | 3264 | C4* | G | D | 1074 | 10.753 | −12.951 | −35.675 | 1.00 | 27.13 | RNA2 C |
| ATOM | 3265 | O4* | G | D | 1074 | 9.559 | −12.586 | −34.940 | 1.00 | 25.79 | RNA2 O |
| ATOM | 3266 | C3* | G | D | 1074 | 10.260 | −13.964 | −36.689 | 1.00 | 34.21 | RNA2 C |
| ATOM | 3267 | O3* | G | D | 1074 | 11.289 | −14.803 | −37.175 | 1.00 | 42.20 | RNA2 O |
| ATOM | 3268 | C2* | G | D | 1074 | 9.202 | −14.730 | −35.908 | 1.00 | 33.31 | RNA2 C |
| ATOM | 3269 | O2* | G | D | 1074 | 9.747 | −15.738 | −35.080 | 1.00 | 37.22 | RNA2 O |
| ATOM | 3270 | C1* | G | D | 1074 | 8.598 | −13.621 | −35.049 | 1.00 | 21.21 | RNA2 C |
| ATOM | 3271 | N9 | G | D | 1074 | 7.387 | −13.070 | −35.648 | 1.00 | 27.34 | RNA2 N |
| ATOM | 3272 | C8 | G | D | 1074 | 7.235 | −11.852 | −36.268 | 1.00 | 27.08 | RNA2 C |
| ATOM | 3273 | N7 | G | D | 1074 | 6.017 | −11.640 | −36.688 | 1.00 | 25.47 | RNA2 N |
| ATOM | 3274 | C5 | G | D | 1074 | 5.325 | −12.787 | −36.327 | 1.00 | 19.99 | RNA2 C |
| ATOM | 3275 | C6 | G | D | 1074 | 3.966 | −13.130 | −36.504 | 1.00 | 30.58 | RNA2 C |
| ATOM | 3276 | O6 | G | D | 1074 | 3.063 | −12.460 | −37.021 | 1.00 | 35.90 | RNA2 O |
| ATOM | 3277 | N1 | G | D | 1074 | 3.687 | −14.396 | −35.992 | 1.00 | 36.16 | RNA2 N |
| ATOM | 3278 | C2 | G | D | 1074 | 4.597 | −15.219 | −35.379 | 1.00 | 34.56 | RNA2 C |
| ATOM | 3279 | N2 | G | D | 1074 | 4.134 | −16.400 | −34.936 | 1.00 | 34.63 | RNA2 N |
| ATOM | 3280 | N3 | G | D | 1074 | 5.868 | −14.906 | −35.205 | 1.00 | 31.20 | RNA2 N |
| ATOM | 3281 | C4 | G | D | 1074 | 6.159 | −13.683 | −35.695 | 1.00 | 23.24 | RNA2 C |
| ATOM | 3282 | P | C | D | 1075 | 11.130 | −15.471 | −38.624 | 1.00 | 45.43 | RNA2 P |
| ATOM | 3283 | O1P | C | D | 1075 | 10.527 | −14.447 | −39.520 | 1.00 | 54.78 | RNA2 O |
| ATOM | 3284 | O2P | C | D | 1075 | 12.430 | −16.096 | −38.995 | 1.00 | 41.18 | RNA2 O |
| ATOM | 3285 | O5* | C | D | 1075 | 10.046 | −16.607 | −38.379 | 1.00 | 33.77 | RNA2 O |
| ATOM | 3286 | C5* | C | D | 1075 | 10.384 | −17.767 | −37.609 | 1.00 | 31.73 | RNA2 C |
| ATOM | 3287 | C4* | C | D | 1075 | 9.233 | −18.737 | −37.587 | 1.00 | 31.50 | RNA2 C |
| ATOM | 3288 | O4* | C | D | 1075 | 8.122 | −18.137 | −36.879 | 1.00 | 31.95 | RNA2 O |
| ATOM | 3289 | C3* | C | D | 1075 | 8.653 | −19.112 | −38.940 | 1.00 | 34.59 | RNA2 C |
| ATOM | 3290 | O3* | C | D | 1075 | 9.390 | −20.130 | −39.596 | 1.00 | 42.98 | RNA2 O |
| ATOM | 3291 | C2* | C | D | 1075 | 7.239 | −19.539 | −38.581 | 1.00 | 30.88 | RNA2 C |
| ATOM | 3292 | O2* | C | D | 1075 | 7.175 | −20.852 | −38.064 | 1.00 | 24.97 | RNA2 O |
| ATOM | 3293 | C1* | C | D | 1075 | 6.902 | −18.546 | −37.472 | 1.00 | 31.01 | RNA2 C |
| ATOM | 3294 | N1 | C | D | 1075 | 6.223 | −17.355 | −38.013 | 1.00 | 26.90 | RNA2 N |

TABLE II-continued

| | | | | | | | | | | | |
|---|---|---|---|---|---|---|---|---|---|---|---|
| ATOM | 3295 | C2 | C | D | 1075 | 4.831 | −17.388 | −38.173 | 1.00 | 32.07 | RNA2 C |
| ATOM | 3296 | O2 | C | D | 1075 | 4.206 | −18.407 | −37.825 | 1.00 | 31.32 | RNA2 O |
| ATOM | 3297 | N3 | C | D | 1075 | 4.204 | −16.313 | −38.700 | 1.00 | 31.52 | RNA2 N |
| ATOM | 3298 | C4 | C | D | 1075 | 4.908 | −15.237 | −39.059 | 1.00 | 24.70 | RNA2 C |
| ATOM | 3299 | N4 | C | D | 1075 | 4.246 | −14.208 | −39.592 | 1.00 | 23.21 | RNA2 N |
| ATOM | 3300 | C5 | C | D | 1075 | 6.320 | −15.169 | −38.892 | 1.00 | 20.78 | RNA2 C |
| ATOM | 3301 | C6 | C | D | 1075 | 6.932 | −16.239 | −38.370 | 1.00 | 26.55 | RNA2 C |
| ATOM | 3302 | P | C | D | 1076 | 9.458 | −20.140 | −41.200 | 1.00 | 41.54 | RNA2 P |
| ATOM | 3303 | O1P | C | D | 1076 | 9.719 | −18.749 | −41.663 | 1.00 | 42.90 | RNA2 O |
| ATOM | 3304 | O2P | C | D | 1076 | 10.363 | −21.241 | −41.628 | 1.00 | 43.49 | RNA2 O |
| ATOM | 3305 | O5* | C | D | 1076 | 7.973 | −20.524 | −41.614 | 1.00 | 36.12 | RNA2 O |
| ATOM | 3306 | C5* | C | D | 1076 | 7.448 | −21.808 | −41.272 | 1.00 | 35.93 | RNA2 C |
| ATOM | 3307 | C4* | C | D | 1076 | 6.024 | −21.941 | −41.742 | 1.00 | 36.70 | RNA2 C |
| ATOM | 3308 | O4* | C | D | 1076 | 5.179 | −21.022 | −41.003 | 1.00 | 41.67 | RNA2 O |
| ATOM | 3309 | C3* | C | D | 1076 | 5.735 | −21.611 | −43.198 | 1.00 | 33.47 | RNA2 C |
| ATOM | 3310 | O3* | C | D | 1076 | 6.076 | −22.654 | −44.099 | 1.00 | 41.74 | RNA2 O |
| ATOM | 3311 | C2* | C | D | 1076 | 4.240 | −21.334 | −43.160 | 1.00 | 38.53 | RNA2 C |
| ATOM | 3312 | O2* | C | D | 1076 | 3.483 | −22.530 | −43.103 | 1.00 | 31.60 | RNA2 O |
| ATOM | 3313 | C1* | C | D | 1076 | 4.107 | −20.590 | −41.831 | 1.00 | 39.34 | RNA2 C |
| ATOM | 3314 | N1 | C | D | 1076 | 4.199 | −19.124 | −42.018 | 1.00 | 25.11 | RNA2 N |
| ATOM | 3315 | C2 | C | D | 1076 | 3.048 | −18.421 | −42.397 | 1.00 | 28.28 | RNA2 C |
| ATOM | 3316 | O2 | C | D | 1076 | 1.978 | −19.045 | −42.536 | 1.00 | 22.07 | RNA2 O |
| ATOM | 3317 | N3 | C | D | 1076 | 3.127 | −17.083 | −42.605 | 1.00 | 27.17 | RNA2 N |
| ATOM | 3318 | C4 | C | D | 1076 | 4.293 | −16.452 | −42.451 | 1.00 | 27.03 | RNA2 C |
| ATOM | 3319 | N4 | C | D | 1076 | 4.330 | −15.136 | −42.681 | 1.00 | 24.90 | RNA2 N |
| ATOM | 3320 | C5 | C | D | 1076 | 5.475 | −17.140 | −42.056 | 1.00 | 21.98 | RNA2 C |
| ATOM | 3321 | C6 | C | D | 1076 | 5.384 | −18.460 | −41.849 | 1.00 | 26.59 | RNA2 C |
| ATOM | 3322 | P | A | D | 1077 | 6.603 | −22.281 | −45.575 | 1.00 | 39.40 | RNA2 P |
| ATOM | 3323 | O1P | A | D | 1077 | 7.618 | −21.198 | −45.455 | 1.00 | 25.39 | RNA2 O |
| ATOM | 3324 | O2P | A | D | 1077 | 6.965 | −23.549 | −46.255 | 1.00 | 45.75 | RNA2 O |
| ATOM | 3325 | O5* | A | D | 1077 | 5.308 | −21.688 | −46.290 | 1.00 | 35.32 | RNA2 O |
| ATOM | 3326 | C5* | A | D | 1077 | 4.132 | −22.496 | −46.434 | 1.00 | 30.36 | RNA2 C |
| ATOM | 3327 | C4* | A | D | 1077 | 2.948 | −21.659 | −46.863 | 1.00 | 39.87 | RNA2 C |
| ATOM | 3328 | O4* | A | D | 1077 | 2.657 | −20.660 | −45.852 | 1.00 | 36.52 | RNA2 O |
| ATOM | 3329 | C3* | A | D | 1077 | 3.067 | −20.856 | −48.149 | 1.00 | 35.06 | RNA2 C |
| ATOM | 3330 | O3* | A | D | 1077 | 2.842 | −21.640 | −49.313 | 1.00 | 33.77 | RNA2 O |
| ATOM | 3331 | C2* | A | D | 1077 | 1.981 | −19.801 | −47.965 | 1.00 | 41.16 | RNA2 C |
| ATOM | 3332 | O2* | A | D | 1077 | 0.677 | −20.271 | −48.264 | 1.00 | 33.46 | RNA2 O |
| ATOM | 3333 | C1* | A | D | 1077 | 2.078 | −19.520 | −46.466 | 1.00 | 37.76 | RNA2 C |
| ATOM | 3334 | N9 | A | D | 1077 | 2.924 | −18.352 | −46.211 | 1.00 | 25.78 | RNA2 N |
| ATOM | 3335 | C8 | A | D | 1077 | 4.243 | −18.300 | −45.836 | 1.00 | 18.19 | RNA2 C |
| ATOM | 3336 | N7 | A | D | 1077 | 4.722 | −17.081 | −45.756 | 1.00 | 17.18 | RNA2 N |
| ATOM | 3337 | C5 | A | D | 1077 | 3.639 | −16.275 | −46.087 | 1.00 | 18.35 | RNA2 C |
| ATOM | 3338 | C6 | A | D | 1077 | 3.492 | −14.874 | −46.208 | 1.00 | 24.31 | RNA2 C |
| ATOM | 3339 | N6 | A | D | 1077 | 4.486 | −13.996 | −46.008 | 1.00 | 25.10 | RNA2 N |
| ATOM | 3340 | N1 | A | D | 1077 | 2.277 | −14.401 | −46.558 | 1.00 | 22.28 | RNA2 N |
| ATOM | 3341 | C2 | A | D | 1077 | 1.285 | −15.278 | −46.776 | 1.00 | 17.11 | RNA2 C |
| ATOM | 3342 | N3 | A | D | 1077 | 1.302 | −16.604 | −46.702 | 1.00 | 22.31 | RNA2 N |
| ATOM | 3343 | C4 | A | D | 1077 | 2.522 | −17.044 | −46.352 | 1.00 | 17.88 | RNA2 C |
| ATOM | 3344 | P | U | D | 1078 | 3.650 | −21.306 | −50.662 | 1.00 | 27.11 | RNA2 P |
| ATOM | 3345 | O1P | U | D | 1078 | 5.104 | −21.343 | −50.374 | 1.00 | 20.77 | RNA2 O |
| ATOM | 3346 | O2P | U | D | 1078 | 3.091 | −22.176 | −51.728 | 1.00 | 43.45 | RNA2 O |
| ATOM | 3347 | O5* | U | D | 1078 | 3.288 | −19.785 | −50.981 | 1.00 | 30.32 | RNA2 O |
| ATOM | 3348 | C5* | U | D | 1078 | 1.985 | −19.408 | −51.478 | 1.00 | 30.56 | RNA2 C |
| ATOM | 3349 | C4* | U | D | 1078 | 1.896 | −17.901 | −51.631 | 1.00 | 32.53 | RNA2 C |
| ATOM | 3350 | O4* | U | D | 1078 | 2.062 | −17.283 | −50.329 | 1.00 | 27.97 | RNA2 O |
| ATOM | 3351 | C3* | U | D | 1078 | 2.967 | −17.244 | −52.497 | 1.00 | 36.01 | RNA2 C |
| ATOM | 3352 | O3* | U | D | 1078 | 2.620 | −17.183 | −53.871 | 1.00 | 42.75 | RNA2 O |
| ATOM | 3353 | C2* | U | D | 1078 | 2.990 | −15.821 | −51.961 | 1.00 | 36.74 | RNA2 C |
| ATOM | 3354 | O2* | U | D | 1078 | 1.935 | −15.045 | −52.493 | 1.00 | 40.26 | RNA2 O |
| ATOM | 3355 | C1* | U | D | 1078 | 2.744 | −16.048 | −50.472 | 1.00 | 35.91 | RNA2 C |
| ATOM | 3356 | N1 | U | D | 1078 | 4.015 | −16.102 | −49.729 | 1.00 | 25.89 | RNA2 N |
| ATOM | 3357 | C2 | U | D | 1078 | 4.637 | −14.892 | −49.423 | 1.00 | 35.33 | RNA2 C |
| ATOM | 3358 | O2 | U | D | 1078 | 4.167 | −13.800 | −49.730 | 1.00 | 30.93 | RNA2 O |
| ATOM | 3359 | N3 | U | D | 1078 | 5.830 | −15.008 | −48.749 | 1.00 | 28.65 | RNA2 N |
| ATOM | 3360 | C4 | U | D | 1078 | 6.455 | −16.177 | −48.357 | 1.00 | 30.34 | RNA2 C |
| ATOM | 3361 | O4 | U | D | 1078 | 7.555 | −16.119 | −47.795 | 1.00 | 39.15 | RNA2 O |
| ATOM | 3362 | C5 | U | D | 1078 | 5.749 | −17.376 | −48.699 | 1.00 | 25.89 | RNA2 C |
| ATOM | 3363 | C6 | U | D | 1078 | 4.584 | −17.300 | −49.355 | 1.00 | 28.67 | RNA2 C |
| ATOM | 3364 | P | C | D | 1079 | 2.674 | −18.503 | −54.775 | 1.00 | 37.89 | RNA2 P |
| ATOM | 3365 | O1P | C | D | 1079 | 2.944 | −18.013 | −56.153 | 1.00 | 39.80 | RNA2 O |
| ATOM | 3366 | O2P | C | D | 1079 | 3.558 | −19.539 | −54.176 | 1.00 | 37.02 | RNA2 O |
| ATOM | 3367 | O5* | C | D | 1079 | 1.167 | −18.996 | −54.704 | 1.00 | 15.08 | RNA2 O |
| ATOM | 3368 | C5* | C | D | 1079 | 0.145 | −18.192 | −55.288 | 1.00 | 23.37 | RNA2 C |
| ATOM | 3369 | C4* | C | D | 1079 | −1.208 | −18.608 | −54.795 | 1.00 | 19.59 | RNA2 C |
| ATOM | 3370 | O4* | C | D | 1079 | −1.438 | −18.079 | −53.467 | 1.00 | 27.26 | RNA2 O |
| ATOM | 3371 | C3* | C | D | 1079 | −2.308 | −17.995 | −55.628 | 1.00 | 31.62 | RNA2 C |
| ATOM | 3372 | O3* | C | D | 1079 | −2.525 | −18.767 | −56.789 | 1.00 | 35.58 | RNA2 O |
| ATOM | 3373 | C2* | C | D | 1079 | −3.484 | −17.941 | −54.667 | 1.00 | 27.16 | RNA2 C |

TABLE II-continued

| ATOM | 3374 | O2* | C | D | 1079 | -4.148 | -19.180 | -54.551 | 1.00 | 30.55 | RNA2 | O |
|---|---|---|---|---|---|---|---|---|---|---|---|---|
| ATOM | 3375 | C1* | C | D | 1079 | -2.774 | -17.609 | -53.357 | 1.00 | 19.20 | RNA2 | C |
| ATOM | 3376 | N1 | C | D | 1079 | -2.738 | -16.155 | -53.087 | 1.00 | 15.42 | RNA2 | N |
| ATOM | 3377 | C2 | C | D | 1079 | -3.891 | -15.525 | -52.594 | 1.00 | 14.73 | RNA2 | C |
| ATOM | 3378 | O2 | C | D | 1079 | -4.922 | -16.196 | -52.423 | 1.00 | 22.43 | RNA2 | O |
| ATOM | 3379 | N3 | C | D | 1079 | -3.853 | -14.203 | -52.319 | 1.00 | 15.70 | RNA2 | N |
| ATOM | 3380 | C4 | C | D | 1079 | -2.730 | -13.512 | -52.513 | 1.00 | 19.14 | RNA2 | C |
| ATOM | 3381 | N4 | C | D | 1079 | -2.733 | -12.219 | -52.194 | 1.00 | 18.52 | RNA2 | N |
| ATOM | 3382 | C5 | C | D | 1079 | -1.550 | -14.119 | -53.033 | 1.00 | 14.27 | RNA2 | C |
| ATOM | 3383 | C6 | C | D | 1079 | -1.598 | -15.430 | -53.303 | 1.00 | 9.72 | RNA2 | C |
| ATOM | 3384 | P | A | D | 1080 | -2.665 | -18.025 | -58.200 | 1.00 | 33.84 | RNA2 | P |
| ATOM | 3385 | O1P | A | D | 1080 | -1.604 | -16.982 | -58.302 | 1.00 | 29.98 | RNA2 | O |
| ATOM | 3386 | O2P | A | D | 1080 | -2.762 | -19.085 | -59.240 | 1.00 | 51.18 | RNA2 | O |
| ATOM | 3387 | O5* | A | D | 1080 | -4.078 | -17.315 | -58.069 | 1.00 | 18.89 | RNA2 | O |
| ATOM | 3388 | C5* | A | D | 1080 | -5.228 | -18.109 | -57.802 | 1.00 | 23.14 | RNA2 | C |
| ATOM | 3389 | C4* | A | D | 1080 | -6.362 | -17.256 | -57.316 | 1.00 | 29.15 | RNA2 | C |
| ATOM | 3390 | O4* | A | D | 1080 | -6.077 | -16.724 | -55.997 | 1.00 | 31.88 | RNA2 | O |
| ATOM | 3391 | C3* | A | D | 1080 | -6.704 | -16.028 | -58.131 | 1.00 | 27.12 | RNA2 | C |
| ATOM | 3392 | O3* | A | D | 1080 | -7.427 | -16.344 | -59.312 | 1.00 | 35.45 | RNA2 | O |
| ATOM | 3393 | C2* | A | D | 1080 | -7.520 | -15.221 | -57.129 | 1.00 | 24.68 | RNA2 | C |
| ATOM | 3394 | O2* | A | D | 1080 | -8.839 | -15.710 | -57.002 | 1.00 | 23.19 | RNA2 | O |
| ATOM | 3395 | C1* | A | D | 1080 | -6.774 | -15.502 | -55.826 | 1.00 | 22.08 | RNA2 | C |
| ATOM | 3396 | N9 | A | D | 1080 | -5.817 | -14.431 | -55.545 | 1.00 | 19.19 | RNA2 | N |
| ATOM | 3397 | C8 | A | D | 1080 | -4.460 | -14.391 | -55.773 | 1.00 | 21.24 | RNA2 | C |
| ATOM | 3398 | N7 | A | D | 1080 | -3.911 | -13.232 | -55.485 | 1.00 | 17.04 | RNA2 | N |
| ATOM | 3399 | C5 | A | D | 1080 | -4.974 | -12.465 | -55.021 | 1.00 | 10.07 | RNA2 | C |
| ATOM | 3400 | C6 | A | D | 1080 | -5.061 | -11.132 | -54.578 | 1.00 | 15.82 | RNA2 | C |
| ATOM | 3401 | N6 | A | D | 1080 | -4.019 | -10.295 | -54.529 | 1.00 | 19.09 | RNA2 | N |
| ATOM | 3402 | N1 | A | D | 1080 | -6.271 | -10.680 | -54.183 | 1.00 | 20.36 | RNA2 | N |
| ATOM | 3403 | C2 | A | D | 1080 | -7.317 | -11.517 | -54.229 | 1.00 | 15.92 | RNA2 | C |
| ATOM | 3404 | N3 | A | D | 1080 | -7.362 | -12.783 | -54.626 | 1.00 | 14.17 | RNA2 | N |
| ATOM | 3405 | C4 | A | D | 1080 | -6.145 | -13.200 | -55.023 | 1.00 | 9.63 | RNA2 | C |
| ATOM | 3406 | P | U | D | 1081 | -7.413 | -15.312 | -60.548 | 1.00 | 31.28 | RNA2 | P |
| ATOM | 3407 | O1P | U | D | 1081 | -6.027 | -14.791 | -60.717 | 1.00 | 8.76 | RNA2 | O |
| ATOM | 3408 | O2P | U | D | 1081 | -8.089 | -15.971 | -61.696 | 1.00 | 35.73 | RNA2 | O |
| ATOM | 3409 | O5* | U | D | 1081 | -8.356 | -14.144 | -60.021 | 1.00 | 18.56 | RNA2 | O |
| ATOM | 3410 | C5* | U | D | 1081 | -9.643 | -14.457 | -59.459 | 1.00 | 22.44 | RNA2 | C |
| ATOM | 3411 | C4* | U | D | 1081 | -10.276 | -13.222 | -58.867 | 1.00 | 34.63 | RNA2 | C |
| ATOM | 3412 | O4* | U | D | 1081 | -9.471 | -12.728 | -57.771 | 1.00 | 31.00 | RNA2 | O |
| ATOM | 3413 | C3* | U | D | 1081 | -10.406 | -12.045 | -59.817 | 1.00 | 37.02 | RNA2 | C |
| ATOM | 3414 | O3* | U | D | 1081 | -11.605 | -12.172 | -60.569 | 1.00 | 43.64 | RNA2 | O |
| ATOM | 3415 | C2* | U | D | 1081 | -10.429 | -10.844 | -58.874 | 1.00 | 32.75 | RNA2 | C |
| ATOM | 3416 | O2* | U | D | 1081 | -11.714 | -10.603 | -58.330 | 1.00 | 30.48 | RNA2 | O |
| ATOM | 3417 | C1* | U | D | 1081 | -9.499 | -11.311 | -57.756 | 1.00 | 21.25 | RNA2 | C |
| ATOM | 3418 | N1 | U | D | 1081 | -8.115 | -10.826 | -57.857 | 1.00 | 8.85 | RNA2 | N |
| ATOM | 3419 | C2 | U | D | 1081 | -7.839 | -9.537 | -57.429 | 1.00 | 18.01 | RNA2 | C |
| ATOM | 3420 | O2 | U | D | 1081 | -8.706 | -8.754 | -57.039 | 1.00 | 20.38 | RNA2 | O |
| ATOM | 3421 | N3 | U | D | 1081 | -6.515 | -9.190 | -57.477 | 1.00 | 4.56 | RNA2 | N |
| ATOM | 3422 | C4 | U | D | 1081 | -5.463 | -9.977 | -57.902 | 1.00 | 19.29 | RNA2 | C |
| ATOM | 3423 | O4 | U | D | 1081 | -4.306 | -9.560 | -57.785 | 1.00 | 17.28 | RNA2 | O |
| ATOM | 3424 | C5 | U | D | 1081 | -5.838 | -11.273 | -58.364 | 1.00 | 8.37 | RNA2 | C |
| ATOM | 3425 | C6 | U | D | 1081 | -7.118 | -11.640 | -58.331 | 1.00 | 9.01 | RNA2 | C |
| ATOM | 3426 | P | U | D | 1082 | -11.700 | -11.511 | -62.026 | 1.00 | 37.21 | RNA2 | P |
| ATOM | 3427 | O1P | U | D | 1082 | -10.555 | -11.984 | -62.849 | 1.00 | 30.04 | RNA2 | O |
| ATOM | 3428 | O2P | U | D | 1082 | -13.101 | -11.726 | -62.489 | 1.00 | 36.07 | RNA2 | O |
| ATOM | 3429 | O5* | U | D | 1082 | -11.463 | -9.962 | -61.755 | 1.00 | 48.61 | RNA2 | O |
| ATOM | 3430 | C5* | U | D | 1082 | -12.470 | -9.172 | -61.107 | 1.00 | 49.13 | RNA2 | C |
| ATOM | 3431 | C4* | U | D | 1082 | -12.043 | -7.729 | -61.052 | 1.00 | 45.78 | RNA2 | C |
| ATOM | 3432 | O4* | U | D | 1082 | -11.006 | -7.553 | -60.054 | 1.00 | 41.16 | RNA2 | O |
| ATOM | 3433 | C3* | U | D | 1082 | -11.417 | -7.176 | -62.317 | 1.00 | 45.00 | RNA2 | C |
| ATOM | 3434 | O3* | U | D | 1082 | -12.349 | -6.822 | -63.321 | 1.00 | 44.91 | RNA2 | O |
| ATOM | 3435 | C2* | U | D | 1082 | -10.633 | -5.979 | -61.801 | 1.00 | 41.47 | RNA2 | C |
| ATOM | 3436 | O2* | U | D | 1082 | -11.449 | -4.837 | -61.628 | 1.00 | 38.13 | RNA2 | O |
| ATOM | 3437 | C1* | U | D | 1082 | -10.147 | -6.497 | -60.448 | 1.00 | 34.17 | RNA2 | C |
| ATOM | 3438 | N1 | U | D | 1082 | -8.767 | -6.998 | -60.524 | 1.00 | 21.76 | RNA2 | N |
| ATOM | 3439 | C2 | U | D | 1082 | -7.752 | -6.093 | -60.271 | 1.00 | 27.58 | RNA2 | C |
| ATOM | 3440 | O2 | U | D | 1082 | -7.961 | -4.925 | -59.983 | 1.00 | 39.33 | RNA2 | O |
| ATOM | 3441 | N3 | U | D | 1082 | -6.482 | -6.599 | -60.370 | 1.00 | 17.32 | RNA2 | N |
| ATOM | 3442 | C4 | U | D | 1082 | -6.125 | -7.886 | -60.687 | 1.00 | 19.81 | RNA2 | C |
| ATOM | 3443 | O4 | U | D | 1082 | -4.925 | -8.184 | -60.736 | 1.00 | 21.01 | RNA2 | O |
| ATOM | 3444 | C5 | U | D | 1082 | -7.228 | -8.767 | -60.933 | 1.00 | 16.38 | RNA2 | C |
| ATOM | 3445 | C6 | U | D | 1082 | -8.483 | -8.304 | -60.843 | 1.00 | 16.69 | RNA2 | C |
| ATOM | 3446 | P | U | D | 1083 | -11.820 | -6.597 | -64.817 | 1.00 | 43.63 | RNA2 | P |
| ATOM | 3447 | O1P | U | D | 1083 | -11.131 | -7.845 | -65.255 | 1.00 | 40.26 | RNA2 | O |
| ATOM | 3448 | O2P | U | D | 1083 | -12.950 | -6.055 | -65.619 | 1.00 | 45.21 | RNA2 | O |
| ATOM | 3449 | O5* | U | D | 1083 | -10.714 | -5.466 | -64.618 | 1.00 | 33.40 | RNA2 | O |
| ATOM | 3450 | C5* | U | D | 1083 | -9.461 | -5.509 | -65.306 | 1.00 | 21.92 | RNA2 | C |
| ATOM | 3451 | C4* | U | D | 1083 | -8.508 | -4.519 | -64.689 | 1.00 | 33.84 | RNA2 | C |
| ATOM | 3452 | O4* | U | D | 1083 | -7.824 | -5.125 | -63.563 | 1.00 | 30.68 | RNA2 | O |

TABLE II-continued

| | | | | | | | | | | | |
|---|---|---|---|---|---|---|---|---|---|---|---|
| ATOM | 3453 | C3* | U | D | 1083 | −7.392 | −4.060 | −65.607 | 1.00 | 39.61 | RNA2 C |
| ATOM | 3454 | O3* | U | D | 1083 | −7.851 | −2.983 | −66.405 | 1.00 | 47.78 | RNA2 O |
| ATOM | 3455 | C2* | U | D | 1083 | −6.301 | −3.633 | −64.635 | 1.00 | 38.07 | RNA2 C |
| ATOM | 3456 | O2* | U | D | 1083 | −6.517 | −2.326 | −64.141 | 1.00 | 48.19 | RNA2 O |
| ATOM | 3457 | C1* | U | D | 1083 | −6.486 | −4.647 | −63.504 | 1.00 | 32.72 | RNA2 C |
| ATOM | 3458 | N1 | U | D | 1083 | −5.568 | −5.793 | −63.608 | 1.00 | 23.49 | RNA2 N |
| ATOM | 3459 | C2 | U | D | 1083 | −4.251 | −5.604 | −63.225 | 1.00 | 27.40 | RNA2 C |
| ATOM | 3460 | O2 | U | D | 1083 | −3.823 | −4.541 | −62.823 | 1.00 | 42.53 | RNA2 O |
| ATOM | 3461 | N3 | U | D | 1083 | −3.447 | −6.710 | −63.335 | 1.00 | 31.74 | RNA2 N |
| ATOM | 3462 | C4 | U | D | 1083 | −3.809 | −7.963 | −63.784 | 1.00 | 30.45 | RNA2 C |
| ATOM | 3463 | O4 | U | D | 1083 | −2.962 | −8.863 | −63.823 | 1.00 | 30.78 | RNA2 O |
| ATOM | 3464 | C5 | U | D | 1083 | −5.183 | −8.081 | −64.168 | 1.00 | 19.97 | RNA2 C |
| ATOM | 3465 | C6 | U | D | 1083 | −5.995 | −7.019 | −64.069 | 1.00 | 27.83 | RNA2 C |
| ATOM | 3466 | P | A | D | 1084 | −7.438 | −2.912 | −67.949 | 1.00 | 45.35 | RNA2 P |
| ATOM | 3467 | O1P | A | D | 1084 | −7.390 | −4.295 | −68.485 | 1.00 | 47.07 | RNA2 O |
| ATOM | 3468 | O2P | A | D | 1084 | −8.323 | −1.906 | −68.587 | 1.00 | 48.86 | RNA2 O |
| ATOM | 3469 | O5* | A | D | 1084 | −5.952 | −2.353 | −67.903 | 1.00 | 30.12 | RNA2 O |
| ATOM | 3470 | C5* | A | D | 1084 | −5.051 | −2.560 | −68.990 | 1.00 | 25.41 | RNA2 C |
| ATOM | 3471 | C4* | A | D | 1084 | −3.717 | −1.960 | −68.652 | 1.00 | 29.72 | RNA2 C |
| ATOM | 3472 | O4* | A | D | 1084 | −3.876 | −0.534 | −68.496 | 1.00 | 39.52 | RNA2 O |
| ATOM | 3473 | C3* | A | D | 1084 | −3.174 | −2.444 | −67.326 | 1.00 | 26.49 | RNA2 C |
| ATOM | 3474 | O3* | A | D | 1084 | −2.405 | −3.601 | −67.544 | 1.00 | 36.34 | RNA2 O |
| ATOM | 3475 | C2* | A | D | 1084 | −2.346 | −1.271 | −66.828 | 1.00 | 33.86 | RNA2 C |
| ATOM | 3476 | O2* | A | D | 1084 | −1.043 | −1.267 | −67.373 | 1.00 | 28.54 | RNA2 O |
| ATOM | 3477 | C1* | A | D | 1084 | −3.138 | −0.086 | −67.379 | 1.00 | 30.15 | RNA2 C |
| ATOM | 3478 | N9 | A | D | 1084 | −4.093 | 0.522 | −66.459 | 1.00 | 28.36 | RNA2 N |
| ATOM | 3479 | C8 | A | D | 1084 | −5.439 | 0.258 | −66.342 | 1.00 | 28.20 | RNA2 C |
| ATOM | 3480 | N7 | A | D | 1084 | −6.058 | 1.041 | −65.494 | 1.00 | 25.56 | RNA2 N |
| ATOM | 3481 | C5 | A | D | 1084 | −5.050 | 1.861 | −65.004 | 1.00 | 22.38 | RNA2 C |
| ATOM | 3482 | C6 | A | D | 1084 | −5.061 | 2.922 | −64.088 | 1.00 | 27.67 | RNA2 C |
| ATOM | 3483 | N6 | A | D | 1084 | −6.165 | 3.359 | −63.482 | 1.00 | 38.68 | RNA2 N |
| ATOM | 3484 | N1 | A | D | 1084 | −3.884 | 3.530 | −63.815 | 1.00 | 34.84 | RNA2 N |
| ATOM | 3485 | C2 | A | D | 1084 | −2.776 | 3.091 | −64.434 | 1.00 | 37.58 | RNA2 C |
| ATOM | 3486 | N3 | A | D | 1084 | −2.641 | 2.106 | −65.322 | 1.00 | 27.16 | RNA2 N |
| ATOM | 3487 | C4 | A | D | 1084 | −3.830 | 1.530 | −65.569 | 1.00 | 29.13 | RNA2 C |
| ATOM | 3488 | P | A | D | 1085 | −2.533 | −4.824 | −66.531 | 1.00 | 33.05 | RNA2 P |
| ATOM | 3489 | O1P | A | D | 1085 | −3.976 | −4.945 | −66.187 | 1.00 | 26.54 | RNA2 O |
| ATOM | 3490 | O2P | A | D | 1085 | −1.809 | −5.987 | −67.103 | 1.00 | 37.42 | RNA2 O |
| ATOM | 3491 | O5* | A | D | 1085 | −1.708 | −4.311 | −65.275 | 1.00 | 37.64 | RNA2 O |
| ATOM | 3492 | C5* | A | D | 1085 | −0.321 | −3.983 | −65.415 | 1.00 | 34.30 | RNA2 C |
| ATOM | 3493 | C4* | A | D | 1085 | 0.137 | −3.193 | −64.225 | 1.00 | 40.98 | RNA2 C |
| ATOM | 3494 | O4* | A | D | 1085 | −0.509 | −1.900 | −64.217 | 1.00 | 45.08 | RNA2 O |
| ATOM | 3495 | C3* | A | D | 1085 | −0.209 | −3.817 | −62.888 | 1.00 | 33.48 | RNA2 C |
| ATOM | 3496 | O3* | A | D | 1085 | 0.816 | −4.734 | −62.538 | 1.00 | 33.50 | RNA2 O |
| ATOM | 3497 | C2* | A | D | 1085 | −0.260 | −2.614 | −61.955 | 1.00 | 33.78 | RNA2 C |
| ATOM | 3498 | O2* | A | D | 1085 | 1.022 | −2.252 | −61.488 | 1.00 | 36.97 | RNA2 O |
| ATOM | 3499 | C1* | A | D | 1085 | −0.762 | −1.506 | −62.885 | 1.00 | 29.69 | RNA2 C |
| ATOM | 3500 | N9 | A | D | 1085 | −2.183 | −1.205 | −62.769 | 1.00 | 20.61 | RNA2 N |
| ATOM | 3501 | C8 | A | D | 1085 | −3.232 | −1.910 | −63.299 | 1.00 | 32.48 | RNA2 C |
| ATOM | 3502 | N7 | A | D | 1085 | −4.406 | −1.388 | −63.038 | 1.00 | 31.65 | RNA2 N |
| ATOM | 3503 | C5 | A | D | 1085 | −4.110 | −0.263 | −62.285 | 1.00 | 23.98 | RNA2 C |
| ATOM | 3504 | C6 | A | D | 1085 | −4.922 | 0.724 | −61.710 | 1.00 | 27.87 | RNA2 C |
| ATOM | 3505 | N6 | A | D | 1085 | −6.253 | 0.732 | −61.813 | 1.00 | 35.25 | RNA2 N |
| ATOM | 3506 | N1 | A | D | 1085 | −4.315 | 1.716 | −61.023 | 1.00 | 23.17 | RNA2 N |
| ATOM | 3507 | C2 | A | D | 1085 | −2.975 | 1.709 | −60.936 | 1.00 | 28.66 | RNA2 C |
| ATOM | 3508 | N3 | A | D | 1085 | −2.102 | 0.838 | −61.439 | 1.00 | 29.00 | RNA2 N |
| ATOM | 3509 | C4 | A | D | 1085 | −2.742 | −0.137 | −62.110 | 1.00 | 24.43 | RNA2 C |
| ATOM | 3510 | P | A | D | 1086 | 0.438 | −6.094 | −61.782 | 1.00 | 32.76 | RNA2 P |
| ATOM | 3511 | O1P | A | D | 1086 | −0.961 | −6.454 | −62.137 | 1.00 | 17.94 | RNA2 O |
| ATOM | 3512 | O2P | A | D | 1086 | 1.532 | −7.068 | −62.001 | 1.00 | 30.14 | RNA2 O |
| ATOM | 3513 | O5* | A | D | 1086 | 0.451 | −5.671 | −60.253 | 1.00 | 42.21 | RNA2 O |
| ATOM | 3514 | C5* | A | D | 1086 | 1.644 | −5.155 | −59.645 | 1.00 | 32.88 | RNA2 C |
| ATOM | 3515 | C4* | A | D | 1086 | 1.288 | −4.326 | −58.440 | 1.00 | 36.41 | RNA2 C |
| ATOM | 3516 | O4* | A | D | 1086 | 0.612 | −3.114 | −58.860 | 1.00 | 29.39 | RNA2 O |
| ATOM | 3517 | C3* | A | D | 1086 | 0.303 | −4.967 | −57.481 | 1.00 | 36.90 | RNA2 C |
| ATOM | 3518 | O3* | A | D | 1086 | 0.922 | −5.900 | −56.613 | 1.00 | 33.24 | RNA2 O |
| ATOM | 3519 | C2* | A | D | 1086 | −0.287 | −3.768 | −56.748 | 1.00 | 42.63 | RNA2 C |
| ATOM | 3520 | O2* | A | D | 1086 | 0.470 | −3.347 | −55.630 | 1.00 | 53.18 | RNA2 O |
| ATOM | 3521 | C1* | A | D | 1086 | −0.267 | −2.692 | −57.839 | 1.00 | 38.42 | RNA2 C |
| ATOM | 3522 | N9 | A | D | 1086 | −1.590 | −2.432 | −58.407 | 1.00 | 27.17 | RNA2 N |
| ATOM | 3523 | C8 | A | D | 1086 | −2.195 | −1.210 | −58.569 | 1.00 | 27.28 | RNA2 C |
| ATOM | 3524 | N7 | A | D | 1086 | −3.431 | −1.285 | −59.001 | 1.00 | 32.05 | RNA2 N |
| ATOM | 3525 | C5 | A | D | 1086 | −3.644 | −2.647 | −59.160 | 1.00 | 25.72 | RNA2 C |
| ATOM | 3526 | C6 | A | D | 1086 | −4.765 | −3.385 | −59.572 | 1.00 | 30.69 | RNA2 C |
| ATOM | 3527 | N6 | A | D | 1086 | −5.930 | −2.832 | −59.910 | 1.00 | 37.15 | RNA2 N |
| ATOM | 3528 | N1 | A | D | 1086 | −4.650 | −4.731 | −59.619 | 1.00 | 26.67 | RNA2 N |
| ATOM | 3529 | C2 | A | D | 1086 | −3.484 | −5.284 | −59.271 | 1.00 | 27.74 | RNA2 C |
| ATOM | 3530 | N3 | A | D | 1086 | −2.360 | −4.697 | −58.860 | 1.00 | 32.46 | RNA2 N |
| ATOM | 3531 | C4 | A | D | 1086 | −2.510 | −3.363 | −58.824 | 1.00 | 28.26 | RNA2 C |

TABLE II-continued

| | | | | | | | | | | | |
|---|---|---|---|---|---|---|---|---|---|---|---|
| ATOM | 3532 | P    | G | D | 1087 | 0.286   | −7.364  | −56.455 | 1.00 | 31.77 | RNA2 P |
| ATOM | 3533 | O1P  | G | D | 1087 | −0.973  | −7.249  | −55.682 | 1.00 | 28.82 | RNA2 O |
| ATOM | 3534 | O2P  | G | D | 1087 | 0.266   | −8.020  | −57.788 | 1.00 | 46.35 | RNA2 O |
| ATOM | 3535 | O5*  | G | D | 1087 | 1.337   | −8.122  | −55.545 | 1.00 | 32.87 | RNA2 O |
| ATOM | 3536 | C5*  | G | D | 1087 | 2.401   | −8.899  | −56.109 | 1.00 | 29.23 | RNA2 C |
| ATOM | 3537 | C4*  | G | D | 1087 | 3.449   | −9.109  | −55.061 | 1.00 | 33.39 | RNA2 C |
| ATOM | 3538 | O4*  | G | D | 1087 | 4.062   | −7.829  | −54.802 | 1.00 | 39.61 | RNA2 O |
| ATOM | 3539 | C3*  | G | D | 1087 | 2.847   | −9.568  | −53.742 | 1.00 | 26.85 | RNA2 C |
| ATOM | 3540 | O3*  | G | D | 1087 | 2.937   | −10.985 | −53.689 | 1.00 | 26.33 | RNA2 O |
| ATOM | 3541 | C2*  | G | D | 1087 | 3.745   | −8.914  | −52.696 | 1.00 | 29.63 | RNA2 C |
| ATOM | 3542 | O2*  | G | D | 1087 | 4.887   | −9.702  | −52.418 | 1.00 | 30.88 | RNA2 O |
| ATOM | 3543 | C1*  | G | D | 1087 | 4.196   | −7.635  | −53.412 | 1.00 | 31.58 | RNA2 C |
| ATOM | 3544 | N9   | G | D | 1087 | 3.534   | −6.370  | −53.099 | 1.00 | 24.38 | RNA2 N |
| ATOM | 3545 | C8   | G | D | 1087 | 2.184   | −6.105  | −53.015 | 1.00 | 13.22 | RNA2 C |
| ATOM | 3546 | N7   | G | D | 1087 | 1.926   | −4.837  | −52.821 | 1.00 | 6.56  | RNA2 N |
| ATOM | 3547 | C5   | G | D | 1087 | 3.176   | −4.240  | −52.743 | 1.00 | 11.78 | RNA2 C |
| ATOM | 3548 | C6   | G | D | 1087 | 3.536   | −2.887  | −52.546 | 1.00 | 26.38 | RNA2 C |
| ATOM | 3549 | O6   | G | D | 1087 | 2.796   | −1.905  | −52.394 | 1.00 | 28.30 | RNA2 O |
| ATOM | 3550 | N1   | G | D | 1087 | 4.919   | −2.723  | −52.537 | 1.00 | 19.38 | RNA2 N |
| ATOM | 3551 | C2   | G | D | 1087 | 5.836   | −3.736  | −52.697 | 1.00 | 26.46 | RNA2 C |
| ATOM | 3552 | N2   | G | D | 1087 | 7.138   | −3.390  | −52.661 | 1.00 | 19.48 | RNA2 N |
| ATOM | 3553 | N3   | G | D | 1087 | 5.509   | −4.997  | −52.881 | 1.00 | 20.61 | RNA2 N |
| ATOM | 3554 | C4   | G | D | 1087 | 4.176   | −5.176  | −52.894 | 1.00 | 16.45 | RNA2 C |
| ATOM | 3555 | P    | A | D | 1088 | 1.639   | −11.888 | −53.962 | 1.00 | 30.91 | RNA2 P |
| ATOM | 3556 | O1P  | A | D | 1088 | 0.713   | −11.203 | −54.900 | 1.00 | 35.03 | RNA2 O |
| ATOM | 3557 | O2P  | A | D | 1088 | 2.152   | −13.234 | −54.286 | 1.00 | 39.93 | RNA2 O |
| ATOM | 3558 | O5*  | A | D | 1088 | 0.937   | −11.965 | −52.543 | 1.00 | 35.70 | RNA2 O |
| ATOM | 3559 | C5*  | A | D | 1088 | 1.728   | −12.195 | −51.367 | 1.00 | 40.71 | RNA2 C |
| ATOM | 3560 | C4*  | A | D | 1088 | 1.473   | −11.114 | −50.352 | 1.00 | 31.86 | RNA2 C |
| ATOM | 3561 | O4*  | A | D | 1088 | 0.051   | −11.035 | −50.098 | 1.00 | 31.43 | RNA2 O |
| ATOM | 3562 | C3*  | A | D | 1088 | 2.134   | −11.354 | −49.008 | 1.00 | 28.62 | RNA2 C |
| ATOM | 3563 | O3*  | A | D | 1088 | 2.454   | −10.092 | −48.453 | 1.00 | 22.01 | RNA2 O |
| ATOM | 3564 | C2*  | A | D | 1088 | 1.032   | −12.007 | −48.192 | 1.00 | 19.87 | RNA2 C |
| ATOM | 3565 | O2*  | A | D | 1088 | 1.196   | −11.783 | −46.811 | 1.00 | 35.87 | RNA2 O |
| ATOM | 3566 | C1*  | A | D | 1088 | −0.209  | −11.301 | −48.739 | 1.00 | 17.80 | RNA2 C |
| ATOM | 3567 | N9   | A | D | 1088 | −1.421  | −12.106 | −48.687 | 1.00 | 8.11  | RNA2 N |
| ATOM | 3568 | C8   | A | D | 1088 | −2.654  | −11.733 | −48.221 | 1.00 | 11.14 | RNA2 C |
| ATOM | 3569 | N7   | A | D | 1088 | −3.559  | −12.675 | −48.317 | 1.00 | 26.75 | RNA2 N |
| ATOM | 3570 | C5   | A | D | 1088 | −2.873  | −13.743 | −48.883 | 1.00 | 15.31 | RNA2 C |
| ATOM | 3571 | C6   | A | D | 1088 | −3.272  | −15.045 | −49.241 | 1.00 | 15.70 | RNA2 C |
| ATOM | 3572 | N6   | A | D | 1088 | −4.511  | −15.516 | −49.067 | 1.00 | 17.72 | RNA2 N |
| ATOM | 3573 | N1   | A | D | 1088 | −2.343  | −15.856 | −49.789 | 1.00 | 9.16  | RNA2 N |
| ATOM | 3574 | C2   | A | D | 1088 | −1.099  | −15.388 | −49.957 | 1.00 | 14.79 | RNA2 C |
| ATOM | 3575 | N3   | A | D | 1088 | −0.603  | −14.189 | −49.657 | 1.00 | 18.20 | RNA2 N |
| ATOM | 3576 | C4   | A | D | 1088 | −1.555  | −13.405 | −49.117 | 1.00 | 14.12 | RNA2 C |
| ATOM | 3577 | P    | G | D | 1089 | 3.501   | −9.994  | −47.248 | 1.00 | 27.70 | RNA2 P |
| ATOM | 3578 | O1P  | G | D | 1089 | 4.147   | −11.322 | −47.068 | 1.00 | 28.27 | RNA2 O |
| ATOM | 3579 | O2P  | G | D | 1089 | 2.776   | −9.361  | −46.117 | 1.00 | 25.52 | RNA2 O |
| ATOM | 3580 | O5*  | G | D | 1089 | 4.606   | −8.988  | −47.785 | 1.00 | 22.53 | RNA2 O |
| ATOM | 3581 | C5*  | G | D | 1089 | 5.471   | −9.357  | −48.871 | 1.00 | 30.86 | RNA2 C |
| ATOM | 3582 | C4*  | G | D | 1089 | 5.959   | −8.118  | −49.573 | 1.00 | 24.73 | RNA2 C |
| ATOM | 3583 | O4*  | G | D | 1089 | 4.810   | −7.428  | −50.122 | 1.00 | 31.53 | RNA2 O |
| ATOM | 3584 | C3*  | G | D | 1089 | 6.676   | −7.119  | −48.676 | 1.00 | 23.96 | RNA2 C |
| ATOM | 3585 | O3*  | G | D | 1089 | 7.692   | −6.491  | −49.437 | 1.00 | 35.59 | RNA2 O |
| ATOM | 3586 | C2*  | G | D | 1089 | 5.581   | −6.109  | −48.333 | 1.00 | 26.26 | RNA2 C |
| ATOM | 3587 | O2*  | G | D | 1089 | 6.055   | −4.799  | −48.099 | 1.00 | 39.73 | RNA2 O |
| ATOM | 3588 | C1*  | G | D | 1089 | 4.742   | −6.120  | −49.602 | 1.00 | 26.61 | RNA2 C |
| ATOM | 3589 | N9   | G | D | 1089 | 3.339   | −5.773  | −49.400 | 1.00 | 22.30 | RNA2 N |
| ATOM | 3590 | C8   | G | D | 1089 | 2.265   | −6.629  | −49.311 | 1.00 | 19.61 | RNA2 C |
| ATOM | 3591 | N7   | G | D | 1089 | 1.123   | −6.007  | −49.184 | 1.00 | 20.16 | RNA2 N |
| ATOM | 3592 | C5   | G | D | 1089 | 1.468   | −4.661  | −49.171 | 1.00 | 20.55 | RNA2 C |
| ATOM | 3593 | C6   | G | D | 1089 | 0.653   | −3.505  | −49.059 | 1.00 | 26.65 | RNA2 C |
| ATOM | 3594 | O6   | G | D | 1089 | −0.582  | −3.435  | −48.934 | 1.00 | 34.44 | RNA2 O |
| ATOM | 3595 | N1   | G | D | 1089 | 1.415   | −2.339  | −49.098 | 1.00 | 18.23 | RNA2 N |
| ATOM | 3596 | C2   | G | D | 1089 | 2.782   | −2.292  | −49.218 | 1.00 | 22.47 | RNA2 C |
| ATOM | 3597 | N2   | G | D | 1089 | 3.341   | −1.065  | −49.215 | 1.00 | 23.99 | RNA2 N |
| ATOM | 3598 | N3   | G | D | 1089 | 3.551   | −3.365  | −49.325 | 1.00 | 21.65 | RNA2 N |
| ATOM | 3599 | C4   | G | D | 1089 | 2.832   | −4.504  | −49.293 | 1.00 | 15.76 | RNA2 C |
| ATOM | 3600 | P    | U | D | 1090 | 9.177   | −7.107  | −49.459 | 1.00 | 46.88 | RNA2 P |
| ATOM | 3601 | O1P  | U | D | 1090 | 9.375   | −7.944  | −48.246 | 1.00 | 47.63 | RNA2 O |
| ATOM | 3602 | O2P  | U | D | 1090 | 9.376   | −7.711  | −50.800 | 1.00 | 46.50 | RNA2 O |
| ATOM | 3603 | O5*  | U | D | 1090 | 10.098  | −5.811  | −49.333 | 1.00 | 47.06 | RNA2 O |
| ATOM | 3604 | C5*  | U | D | 1090 | 11.428  | −5.782  | −49.876 | 1.00 | 48.58 | RNA2 C |
| ATOM | 3605 | C4*  | U | D | 1090 | 12.040  | −4.407  | −49.703 | 1.00 | 55.86 | RNA2 C |
| ATOM | 3606 | O4*  | U | D | 1090 | 11.307  | −3.422  | −50.482 | 1.00 | 58.42 | RNA2 O |
| ATOM | 3607 | C3*  | U | D | 1090 | 12.027  | −3.835  | −48.296 | 1.00 | 57.85 | RNA2 C |
| ATOM | 3608 | O3*  | U | D | 1090 | 13.074  | −4.330  | −47.488 | 1.00 | 54.72 | RNA2 O |
| ATOM | 3609 | C2*  | U | D | 1090 | 12.152  | −2.336  | −48.538 | 1.00 | 56.90 | RNA2 C |
| ATOM | 3610 | O2*  | U | D | 1090 | 13.486  | −1.912  | −48.750 | 1.00 | 55.53 | RNA2 O |

TABLE II-continued

| ATOM | 3611 | C1* | U | D | 1090 | 11.345 | -2.164 | -49.823 | 1.00 | 47.41 | RNA2 | C |
|---|---|---|---|---|---|---|---|---|---|---|---|---|
| ATOM | 3612 | N1 | U | D | 1090 | 9.971 | -1.713 | -49.552 | 1.00 | 39.04 | RNA2 | N |
| ATOM | 3613 | C2 | U | D | 1090 | 9.769 | -0.350 | -49.369 | 1.00 | 41.49 | RNA2 | C |
| ATOM | 3614 | O2 | U | D | 1090 | 10.675 | 0.475 | -49.415 | 1.00 | 47.92 | RNA2 | O |
| ATOM | 3615 | N3 | U | D | 1090 | 8.468 | 0.014 | -49.123 | 1.00 | 33.29 | RNA2 | N |
| ATOM | 3616 | C4 | U | D | 1090 | 7.371 | -0.820 | -49.033 | 1.00 | 35.37 | RNA2 | C |
| ATOM | 3617 | O4 | U | D | 1090 | 6.255 | -0.333 | -48.820 | 1.00 | 43.33 | RNA2 | O |
| ATOM | 3618 | C5 | U | D | 1090 | 7.660 | -2.210 | -49.227 | 1.00 | 26.33 | RNA2 | C |
| ATOM | 3619 | C6 | U | D | 1090 | 8.916 | -2.599 | -49.476 | 1.00 | 31.79 | RNA2 | C |
| ATOM | 3620 | P | G | D | 1091 | 12.865 | -4.400 | -45.899 | 1.00 | 63.03 | RNA2 | P |
| ATOM | 3621 | O1P | G | D | 1091 | 11.489 | -4.915 | -45.629 | 1.00 | 48.47 | RNA2 | O |
| ATOM | 3622 | O2P | G | D | 1091 | 14.047 | -5.119 | -45.346 | 1.00 | 63.48 | RNA2 | O |
| ATOM | 3623 | O5* | G | D | 1091 | 12.909 | -2.874 | -45.434 | 1.00 | 53.82 | RNA2 | O |
| ATOM | 3624 | C5* | G | D | 1091 | 14.160 | -2.173 | -45.369 | 1.00 | 60.37 | RNA2 | C |
| ATOM | 3625 | C4* | G | D | 1091 | 13.939 | -0.687 | -45.231 | 1.00 | 57.35 | RNA2 | C |
| ATOM | 3626 | O4* | G | D | 1091 | 13.057 | -0.232 | -46.291 | 1.00 | 51.52 | RNA2 | O |
| ATOM | 3627 | C3* | G | D | 1091 | 13.275 | -0.168 | -43.964 | 1.00 | 64.14 | RNA2 | C |
| ATOM | 3628 | O3* | G | D | 1091 | 14.165 | -0.050 | -42.851 | 1.00 | 71.95 | RNA2 | O |
| ATOM | 3629 | C2* | G | D | 1091 | 12.766 | 1.197 | -44.414 | 1.00 | 59.80 | RNA2 | C |
| ATOM | 3630 | O2* | G | D | 1091 | 13.774 | 2.190 | -44.402 | 1.00 | 67.83 | RNA2 | O |
| ATOM | 3631 | C1* | G | D | 1091 | 12.345 | 0.913 | -45.854 | 1.00 | 48.17 | RNA2 | C |
| ATOM | 3632 | N9 | G | D | 1091 | 10.912 | 0.647 | -45.911 | 1.00 | 35.24 | RNA2 | N |
| ATOM | 3633 | C8 | G | D | 1091 | 10.281 | -0.571 | -45.991 | 1.00 | 35.20 | RNA2 | C |
| ATOM | 3634 | N7 | G | D | 1091 | 8.979 | -0.474 | -45.954 | 1.00 | 29.59 | RNA2 | N |
| ATOM | 3635 | C5 | G | D | 1091 | 8.739 | 0.890 | -45.858 | 1.00 | 21.43 | RNA2 | C |
| ATOM | 3636 | C6 | G | D | 1091 | 7.518 | 1.604 | -45.771 | 1.00 | 32.33 | RNA2 | C |
| ATOM | 3637 | O6 | G | D | 1091 | 6.364 | 1.159 | -45.749 | 1.00 | 43.19 | RNA2 | O |
| ATOM | 3638 | N1 | G | D | 1091 | 7.731 | 2.976 | -45.699 | 1.00 | 28.62 | RNA2 | N |
| ATOM | 3639 | C2 | G | D | 1091 | 8.961 | 3.582 | -45.701 | 1.00 | 39.37 | RNA2 | C |
| ATOM | 3640 | N2 | G | D | 1091 | 8.965 | 4.920 | -45.626 | 1.00 | 34.96 | RNA2 | N |
| ATOM | 3641 | N3 | G | D | 1091 | 10.107 | 2.925 | -45.772 | 1.00 | 32.50 | RNA2 | N |
| ATOM | 3642 | C4 | G | D | 1091 | 9.920 | 1.594 | -45.848 | 1.00 | 25.53 | RNA2 | C |
| ATOM | 3643 | P | C | D | 1092 | 13.560 | 0.093 | -41.358 | 1.00 | 80.57 | RNA2 | P |
| ATOM | 3644 | O1P | C | D | 1092 | 12.499 | -0.941 | -41.171 | 1.00 | 72.16 | RNA2 | O |
| ATOM | 3645 | O2P | C | D | 1092 | 14.702 | 0.146 | -40.409 | 1.00 | 77.36 | RNA2 | O |
| ATOM | 3646 | O5* | C | D | 1092 | 12.841 | 1.520 | -41.356 | 1.00 | 67.00 | RNA2 | O |
| ATOM | 3647 | C5* | C | D | 1092 | 13.608 | 2.728 | -41.517 | 1.00 | 47.50 | RNA2 | C |
| ATOM | 3648 | C4* | C | D | 1092 | 12.721 | 3.950 | -41.413 | 1.00 | 46.89 | RNA2 | C |
| ATOM | 3649 | O4* | C | D | 1092 | 11.785 | 3.999 | -42.524 | 1.00 | 47.64 | RNA2 | O |
| ATOM | 3650 | C3* | C | D | 1092 | 11.825 | 4.069 | -40.193 | 1.00 | 48.58 | RNA2 | C |
| ATOM | 3651 | O3* | C | D | 1092 | 12.485 | 4.523 | -39.029 | 1.00 | 50.53 | RNA2 | O |
| ATOM | 3652 | C2* | C | D | 1092 | 10.775 | 5.069 | -40.650 | 1.00 | 46.94 | RNA2 | C |
| ATOM | 3653 | O2* | C | D | 1092 | 11.196 | 6.411 | -40.524 | 1.00 | 56.76 | RNA2 | O |
| ATOM | 3654 | C1* | C | D | 1092 | 10.610 | 4.694 | -42.122 | 1.00 | 44.37 | RNA2 | C |
| ATOM | 3655 | N1 | C | D | 1092 | 9.429 | 3.823 | -42.282 | 1.00 | 40.91 | RNA2 | N |
| ATOM | 3656 | C2 | C | D | 1092 | 8.155 | 4.415 | -42.217 | 1.00 | 43.01 | RNA2 | C |
| ATOM | 3657 | O2 | C | D | 1092 | 8.072 | 5.647 | -42.083 | 1.00 | 41.14 | RNA2 | O |
| ATOM | 3658 | N3 | C | D | 1092 | 7.056 | 3.632 | -42.298 | 1.00 | 33.92 | RNA2 | N |
| ATOM | 3659 | C4 | C | D | 1092 | 7.188 | 2.312 | -42.444 | 1.00 | 39.14 | RNA2 | C |
| ATOM | 3660 | N4 | C | D | 1092 | 6.075 | 1.577 | -42.496 | 1.00 | 35.85 | RNA2 | N |
| ATOM | 3661 | C5 | C | D | 1092 | 8.469 | 1.685 | -42.538 | 1.00 | 31.59 | RNA2 | C |
| ATOM | 3662 | C6 | C | D | 1092 | 9.552 | 2.471 | -42.458 | 1.00 | 35.03 | RNA2 | C |
| ATOM | 3663 | P | G | D | 1093 | 11.977 | 4.012 | -37.593 | 1.00 | 51.96 | RNA2 | P |
| ATOM | 3664 | O1P | G | D | 1093 | 11.975 | 2.526 | -37.626 | 1.00 | 48.41 | RNA2 | O |
| ATOM | 3665 | O2P | G | D | 1093 | 12.764 | 4.724 | -36.553 | 1.00 | 64.77 | RNA2 | O |
| ATOM | 3666 | O5* | G | D | 1093 | 10.458 | 4.492 | -37.515 | 1.00 | 35.20 | RNA2 | O |
| ATOM | 3667 | C5* | G | D | 1093 | 10.122 | 5.886 | -37.581 | 1.00 | 24.69 | RNA2 | C |
| ATOM | 3668 | C4* | G | D | 1093 | 8.630 | 6.056 | -37.704 | 1.00 | 29.37 | RNA2 | C |
| ATOM | 3669 | O4* | G | D | 1093 | 8.164 | 5.435 | -38.930 | 1.00 | 34.30 | RNA2 | O |
| ATOM | 3670 | C3* | G | D | 1093 | 7.808 | 5.387 | -36.620 | 1.00 | 33.91 | RNA2 | C |
| ATOM | 3671 | O3* | G | D | 1093 | 7.738 | 6.175 | -35.452 | 1.00 | 53.14 | RNA2 | O |
| ATOM | 3672 | C2* | G | D | 1093 | 6.454 | 5.194 | -37.289 | 1.00 | 36.57 | RNA2 | C |
| ATOM | 3673 | O2* | G | D | 1093 | 5.628 | 6.344 | -37.254 | 1.00 | 23.38 | RNA2 | O |
| ATOM | 3674 | C1* | G | D | 1093 | 6.871 | 4.878 | -38.726 | 1.00 | 33.38 | RNA2 | C |
| ATOM | 3675 | N9 | G | D | 1093 | 6.940 | 3.436 | -38.961 | 1.00 | 31.32 | RNA2 | N |
| ATOM | 3676 | C8 | G | D | 1093 | 8.073 | 2.656 | -39.054 | 1.00 | 27.97 | RNA2 | C |
| ATOM | 3677 | N7 | G | D | 1093 | 7.812 | 1.389 | -39.243 | 1.00 | 30.70 | RNA2 | N |
| ATOM | 3678 | C5 | G | D | 1093 | 6.424 | 1.326 | -39.280 | 1.00 | 27.66 | RNA2 | C |
| ATOM | 3679 | C6 | G | D | 1093 | 5.563 | 0.215 | -39.451 | 1.00 | 30.04 | RNA2 | C |
| ATOM | 3680 | O6 | G | D | 1093 | 5.866 | -0.977 | -39.608 | 1.00 | 42.76 | RNA2 | O |
| ATOM | 3681 | N1 | G | D | 1093 | 4.222 | 0.596 | -39.422 | 1.00 | 21.84 | RNA2 | N |
| ATOM | 3682 | C2 | G | D | 1093 | 3.770 | 1.881 | -39.247 | 1.00 | 13.29 | RNA2 | C |
| ATOM | 3683 | N2 | G | D | 1093 | 2.437 | 2.046 | -39.237 | 1.00 | 19.33 | RNA2 | N |
| ATOM | 3684 | N3 | G | D | 1093 | 4.564 | 2.926 | -39.091 | 1.00 | 16.91 | RNA2 | N |
| ATOM | 3685 | C4 | G | D | 1093 | 5.869 | 2.579 | -39.115 | 1.00 | 23.30 | RNA2 | C |
| ATOM | 3686 | P | U | D | 1094 | 7.627 | 5.455 | -34.022 | 1.00 | 46.64 | RNA2 | P |
| ATOM | 3687 | O1P | U | D | 1094 | 8.556 | 4.303 | -34.026 | 1.00 | 32.38 | RNA2 | O |
| ATOM | 3688 | O2P | U | D | 1094 | 7.774 | 6.516 | -32.989 | 1.00 | 56.93 | RNA2 | O |
| ATOM | 3689 | O5* | U | D | 1094 | 6.124 | 4.934 | -33.989 | 1.00 | 26.86 | RNA2 | O |

TABLE II-continued

| | | | | | | | | | | | |
|---|---|---|---|---|---|---|---|---|---|---|---|
| ATOM | 3690 | C5* | U | D | 1094 | 5.051 | 5.877 | −33.932 | 1.00 | 35.20 | RNA2 C |
| ATOM | 3691 | C4* | U | D | 1094 | 3.735 | 5.172 | −33.742 | 1.00 | 45.98 | RNA2 C |
| ATOM | 3692 | O4* | U | D | 1094 | 3.308 | 4.545 | −34.978 | 1.00 | 50.88 | RNA2 O |
| ATOM | 3693 | C3* | U | D | 1094 | 3.692 | 4.055 | −32.717 | 1.00 | 39.85 | RNA2 C |
| ATOM | 3694 | O3* | U | D | 1094 | 3.600 | 4.551 | −31.387 | 1.00 | 48.03 | RNA2 O |
| ATOM | 3695 | C2* | U | D | 1094 | 2.457 | 3.270 | −33.154 | 1.00 | 40.06 | RNA2 C |
| ATOM | 3696 | O2* | U | D | 1094 | 1.243 | 3.843 | −32.701 | 1.00 | 44.52 | RNA2 O |
| ATOM | 3697 | C1* | U | D | 1094 | 2.527 | 3.400 | −34.678 | 1.00 | 45.26 | RNA2 C |
| ATOM | 3698 | N1 | U | D | 1094 | 3.134 | 2.217 | −35.313 | 1.00 | 38.99 | RNA2 N |
| ATOM | 3699 | C2 | U | D | 1094 | 2.294 | 1.148 | −35.606 | 1.00 | 29.79 | RNA2 C |
| ATOM | 3700 | O2 | U | D | 1094 | 1.083 | 1.180 | −35.422 | 1.00 | 31.88 | RNA2 O |
| ATOM | 3701 | N3 | U | D | 1094 | 2.920 | 0.043 | −36.124 | 1.00 | 17.61 | RNA2 N |
| ATOM | 3702 | C4 | U | D | 1094 | 4.262 | −0.105 | −36.384 | 1.00 | 31.42 | RNA2 C |
| ATOM | 3703 | O4 | U | D | 1094 | 4.679 | −1.193 | −36.785 | 1.00 | 23.03 | RNA2 O |
| ATOM | 3704 | C5 | U | D | 1094 | 5.062 | 1.053 | −36.093 | 1.00 | 28.82 | RNA2 C |
| ATOM | 3705 | C6 | U | D | 1094 | 4.485 | 2.147 | −35.584 | 1.00 | 23.80 | RNA2 C |
| ATOM | 3706 | P | A | D | 1095 | 4.523 | 3.907 | −30.234 | 1.00 | 43.63 | RNA2 P |
| ATOM | 3707 | O1P | A | D | 1095 | 5.870 | 3.607 | −30.802 | 1.00 | 36.61 | RNA2 O |
| ATOM | 3708 | O2P | A | D | 1095 | 4.416 | 4.772 | −29.033 | 1.00 | 64.56 | RNA2 O |
| ATOM | 3709 | O5* | A | D | 1095 | 3.794 | 2.535 | −29.896 | 1.00 | 28.91 | RNA2 O |
| ATOM | 3710 | C5* | A | D | 1095 | 4.511 | 1.451 | −29.281 | 1.00 | 29.01 | RNA2 C |
| ATOM | 3711 | C4* | A | D | 1095 | 3.579 | 0.291 | −29.049 | 1.00 | 27.64 | RNA2 C |
| ATOM | 3712 | O4* | A | D | 1095 | 2.506 | 0.741 | −28.191 | 1.00 | 38.10 | RNA2 O |
| ATOM | 3713 | C3* | A | D | 1095 | 2.890 | −0.216 | −30.302 | 1.00 | 32.19 | RNA2 C |
| ATOM | 3714 | O3* | A | D | 1095 | 3.698 | −1.186 | −30.964 | 1.00 | 40.82 | RNA2 O |
| ATOM | 3715 | C2* | A | D | 1095 | 1.575 | −0.772 | −29.769 | 1.00 | 37.08 | RNA2 C |
| ATOM | 3716 | O2* | A | D | 1095 | 1.705 | −2.077 | −29.240 | 1.00 | 37.59 | RNA2 O |
| ATOM | 3717 | C1* | A | D | 1095 | 1.278 | 0.195 | −28.623 | 1.00 | 27.61 | RNA2 C |
| ATOM | 3718 | N9 | A | D | 1095 | 0.397 | 1.313 | −28.956 | 1.00 | 26.65 | RNA2 N |
| ATOM | 3719 | C8 | A | D | 1095 | 0.753 | 2.601 | −29.290 | 1.00 | 20.45 | RNA2 C |
| ATOM | 3720 | N7 | A | D | 1095 | −0.273 | 3.404 | −29.463 | 1.00 | 27.16 | RNA2 N |
| ATOM | 3721 | C5 | A | D | 1095 | −1.376 | 2.587 | −29.246 | 1.00 | 16.61 | RNA2 C |
| ATOM | 3722 | C6 | A | D | 1095 | −2.765 | 2.837 | −29.271 | 1.00 | 25.70 | RNA2 C |
| ATOM | 3723 | N6 | A | D | 1095 | −3.303 | 4.034 | −29.520 | 1.00 | 29.59 | RNA2 N |
| ATOM | 3724 | N1 | A | D | 1095 | −3.596 | 1.799 | −29.023 | 1.00 | 28.34 | RNA2 N |
| ATOM | 3725 | C2 | A | D | 1095 | −3.060 | 0.599 | −28.761 | 1.00 | 25.38 | RNA2 C |
| ATOM | 3726 | N3 | A | D | 1095 | −1.775 | 0.240 | −28.702 | 1.00 | 28.20 | RNA2 N |
| ATOM | 3727 | C4 | A | D | 1095 | −0.977 | 1.292 | −28.955 | 1.00 | 21.18 | RNA2 C |
| ATOM | 3728 | P | A | D | 1096 | 3.829 | −1.151 | −32.569 | 1.00 | 34.70 | RNA2 P |
| ATOM | 3729 | O1P | A | D | 1096 | 4.017 | 0.256 | −32.992 | 1.00 | 37.33 | RNA2 O |
| ATOM | 3730 | O2P | A | D | 1096 | 4.838 | −2.167 | −32.962 | 1.00 | 24.34 | RNA2 O |
| ATOM | 3731 | O5* | A | D | 1096 | 2.383 | −1.617 | −33.047 | 1.00 | 20.77 | RNA2 O |
| ATOM | 3732 | C5* | A | D | 1096 | 1.913 | −2.930 | −32.724 | 1.00 | 19.81 | RNA2 C |
| ATOM | 3733 | C4* | A | D | 1096 | 0.421 | −3.021 | −32.910 | 1.00 | 22.36 | RNA2 C |
| ATOM | 3734 | O4* | A | D | 1096 | −0.262 | −2.200 | −31.934 | 1.00 | 23.18 | RNA2 O |
| ATOM | 3735 | C3* | A | D | 1096 | −0.119 | −2.546 | −34.243 | 1.00 | 23.44 | RNA2 C |
| ATOM | 3736 | O3* | A | D | 1096 | 0.028 | −3.536 | −35.249 | 1.00 | 37.12 | RNA2 O |
| ATOM | 3737 | C2* | A | D | 1096 | −1.575 | −2.237 | −33.914 | 1.00 | 26.79 | RNA2 C |
| ATOM | 3738 | O2* | A | D | 1096 | −2.392 | −3.387 | −33.889 | 1.00 | 29.84 | RNA2 O |
| ATOM | 3739 | C1* | A | D | 1096 | −1.458 | −1.686 | −32.493 | 1.00 | 23.36 | RNA2 C |
| ATOM | 3740 | N9 | A | D | 1096 | −1.373 | −0.228 | −32.496 | 1.00 | 24.90 | RNA2 N |
| ATOM | 3741 | C8 | A | D | 1096 | −0.240 | 0.551 | −32.560 | 1.00 | 30.09 | RNA2 C |
| ATOM | 3742 | N7 | A | D | 1096 | −0.485 | 1.838 | −32.573 | 1.00 | 29.53 | RNA2 N |
| ATOM | 3743 | C5 | A | D | 1096 | −1.870 | 1.914 | −32.507 | 1.00 | 21.47 | RNA2 C |
| ATOM | 3744 | C6 | A | D | 1096 | −2.751 | 3.005 | −32.479 | 1.00 | 23.47 | RNA2 C |
| ATOM | 3745 | N6 | A | D | 1096 | −2.348 | 4.281 | −32.511 | 1.00 | 30.56 | RNA2 N |
| ATOM | 3746 | N1 | A | D | 1096 | −4.075 | 2.741 | −32.411 | 1.00 | 23.77 | RNA2 N |
| ATOM | 3747 | C2 | A | D | 1096 | −4.471 | 1.460 | −32.368 | 1.00 | 24.81 | RNA2 C |
| ATOM | 3748 | N3 | A | D | 1096 | −3.736 | 0.349 | −32.383 | 1.00 | 22.60 | RNA2 N |
| ATOM | 3749 | C4 | A | D | 1096 | −2.429 | 0.650 | −32.454 | 1.00 | 13.49 | RNA2 C |
| ATOM | 3750 | P | C | D | 1097 | 0.158 | −3.087 | −36.781 | 1.00 | 28.43 | RNA2 P |
| ATOM | 3751 | O1P | C | D | 1097 | 1.274 | −2.107 | −36.889 | 1.00 | 25.96 | RNA2 O |
| ATOM | 3752 | O2P | C | D | 1097 | 0.208 | −4.341 | −37.575 | 1.00 | 39.67 | RNA2 O |
| ATOM | 3753 | O5* | C | D | 1097 | −1.234 | −2.357 | −37.037 | 1.00 | 17.23 | RNA2 O |
| ATOM | 3754 | C5* | C | D | 1097 | −1.317 | −1.078 | −37.691 | 1.00 | 20.94 | RNA2 C |
| ATOM | 3755 | C4* | C | D | 1097 | −2.742 | −0.584 | −37.636 | 1.00 | 29.32 | RNA2 C |
| ATOM | 3756 | O4* | C | D | 1097 | −3.029 | −0.045 | −36.315 | 1.00 | 40.36 | RNA2 O |
| ATOM | 3757 | C3* | C | D | 1097 | −3.106 | 0.550 | −38.569 | 1.00 | 29.37 | RNA2 C |
| ATOM | 3758 | O3* | C | D | 1097 | −3.388 | 0.082 | −39.870 | 1.00 | 44.58 | RNA2 O |
| ATOM | 3759 | C2* | C | D | 1097 | −4.341 | 1.126 | −37.895 | 1.00 | 33.92 | RNA2 C |
| ATOM | 3760 | O2* | C | D | 1097 | −5.487 | 0.330 | −38.113 | 1.00 | 32.32 | RNA2 O |
| ATOM | 3761 | C1* | C | D | 1097 | −3.945 | 1.037 | −36.423 | 1.00 | 34.10 | RNA2 C |
| ATOM | 3762 | N1 | C | D | 1097 | −3.265 | 2.289 | −36.012 | 1.00 | 31.44 | RNA2 N |
| ATOM | 3763 | C2 | C | D | 1097 | −4.047 | 3.417 | −35.683 | 1.00 | 27.94 | RNA2 C |
| ATOM | 3764 | O2 | C | D | 1097 | −5.285 | 3.313 | −35.669 | 1.00 | 29.21 | RNA2 O |
| ATOM | 3765 | N3 | C | D | 1097 | −3.427 | 4.588 | −35.390 | 1.00 | 30.98 | RNA2 N |
| ATOM | 3766 | C4 | C | D | 1097 | −2.090 | 4.658 | −35.404 | 1.00 | 44.95 | RNA2 C |
| ATOM | 3767 | N4 | C | D | 1097 | −1.519 | 5.838 | −35.133 | 1.00 | 50.64 | RNA2 N |
| ATOM | 3768 | C5 | C | D | 1097 | −1.275 | 3.522 | −35.698 | 1.00 | 39.09 | RNA2 C |

TABLE II-continued

| ATOM | 3769 | C6 | C | D | 1097 | −1.897 | 2.370 | −35.988 | 1.00 | 32.35 | RNA2 | C |
|---|---|---|---|---|---|---|---|---|---|---|---|---|
| ATOM | 3770 | P | A | D | 1098 | −2.688 | 0.785 | −41.132 | 1.00 | 43.71 | RNA2 | P |
| ATOM | 3771 | O1P | A | D | 1098 | −1.216 | 0.563 | −41.059 | 1.00 | 24.08 | RNA2 | O |
| ATOM | 3772 | O2P | A | D | 1098 | −3.449 | 0.343 | −42.334 | 1.00 | 56.53 | RNA2 | O |
| ATOM | 3773 | O5* | A | D | 1098 | −2.952 | 2.337 | −40.908 | 1.00 | 42.07 | RNA2 | O |
| ATOM | 3774 | C5* | A | D | 1098 | −4.281 | 2.842 | −40.702 | 1.00 | 41.90 | RNA2 | C |
| ATOM | 3775 | C4* | A | D | 1098 | −4.225 | 4.295 | −40.292 | 1.00 | 49.33 | RNA2 | C |
| ATOM | 3776 | O4* | A | D | 1098 | −3.523 | 4.414 | −39.025 | 1.00 | 47.73 | RNA2 | O |
| ATOM | 3777 | C3* | A | D | 1098 | −3.462 | 5.219 | −41.229 | 1.00 | 50.90 | RNA2 | C |
| ATOM | 3778 | O3* | A | D | 1098 | −4.263 | 5.645 | −42.324 | 1.00 | 54.47 | RNA2 | O |
| ATOM | 3779 | C2* | A | D | 1098 | −3.057 | 6.363 | −40.303 | 1.00 | 47.39 | RNA2 | C |
| ATOM | 3780 | O2* | A | D | 1098 | −4.104 | 7.289 | −40.085 | 1.00 | 53.57 | RNA2 | O |
| ATOM | 3781 | C1* | A | D | 1098 | −2.781 | 5.621 | −38.995 | 1.00 | 36.88 | RNA2 | C |
| ATOM | 3782 | N9 | A | D | 1098 | −1.365 | 5.289 | −38.851 | 1.00 | 28.68 | RNA2 | N |
| ATOM | 3783 | C8 | A | D | 1098 | −0.744 | 4.078 | −39.051 | 1.00 | 36.76 | RNA2 | C |
| ATOM | 3784 | N7 | A | D | 1098 | 0.560 | 4.120 | −38.906 | 1.00 | 27.01 | RNA2 | N |
| ATOM | 3785 | C5 | A | D | 1098 | 0.813 | 5.442 | −38.575 | 1.00 | 32.11 | RNA2 | C |
| ATOM | 3786 | C6 | A | D | 1098 | 2.004 | 6.136 | −38.311 | 1.00 | 39.08 | RNA2 | C |
| ATOM | 3787 | N6 | A | D | 1098 | 3.217 | 5.578 | −38.364 | 1.00 | 35.79 | RNA2 | N |
| ATOM | 3788 | N1 | A | D | 1098 | 1.907 | 7.447 | −37.996 | 1.00 | 37.08 | RNA2 | N |
| ATOM | 3789 | C2 | A | D | 1098 | 0.692 | 8.013 | −37.969 | 1.00 | 35.02 | RNA2 | C |
| ATOM | 3790 | N3 | A | D | 1098 | −0.498 | 7.470 | −38.214 | 1.00 | 31.17 | RNA2 | N |
| ATOM | 3791 | C4 | A | D | 1098 | −0.366 | 6.169 | −38.516 | 1.00 | 35.12 | RNA2 | C |
| ATOM | 3792 | P | G | D | 1099 | −3.598 | 5.799 | −43.783 | 1.00 | 57.31 | RNA2 | P |
| ATOM | 3793 | O1P | G | D | 1099 | −3.062 | 4.481 | −44.215 | 1.00 | 60.32 | RNA2 | O |
| ATOM | 3794 | O2P | G | D | 1099 | −4.589 | 6.508 | −44.640 | 1.00 | 60.85 | RNA2 | O |
| ATOM | 3795 | O5* | G | D | 1099 | −2.349 | 6.753 | −43.537 | 1.00 | 41.11 | RNA2 | O |
| ATOM | 3796 | C5* | G | D | 1099 | −2.543 | 8.130 | −43.169 | 1.00 | 50.07 | RNA2 | C |
| ATOM | 3797 | C4* | G | D | 1099 | −1.216 | 8.782 | −42.888 | 1.00 | 47.05 | RNA2 | C |
| ATOM | 3798 | O4* | G | D | 1099 | −0.626 | 8.173 | −41.712 | 1.00 | 46.92 | RNA2 | O |
| ATOM | 3799 | C3* | G | D | 1099 | −0.174 | 8.588 | −43.975 | 1.00 | 54.47 | RNA2 | C |
| ATOM | 3800 | O3* | G | D | 1099 | −0.305 | 9.517 | −45.036 | 1.00 | 55.05 | RNA2 | O |
| ATOM | 3801 | C2* | G | D | 1099 | 1.139 | 8.720 | −43.217 | 1.00 | 48.61 | RNA2 | C |
| ATOM | 3802 | O2* | G | D | 1099 | 1.553 | 10.057 | −43.029 | 1.00 | 55.32 | RNA2 | O |
| ATOM | 3803 | C1* | G | D | 1099 | 0.781 | 8.073 | −41.878 | 1.00 | 40.34 | RNA2 | C |
| ATOM | 3804 | N9 | G | D | 1099 | 1.140 | 6.659 | −41.891 | 1.00 | 34.55 | RNA2 | N |
| ATOM | 3805 | C8 | G | D | 1099 | 0.293 | 5.577 | −41.965 | 1.00 | 33.18 | RNA2 | C |
| ATOM | 3806 | N7 | G | D | 1099 | 0.926 | 4.437 | −42.047 | 1.00 | 37.87 | RNA2 | N |
| ATOM | 3807 | C5 | G | D | 1099 | 2.270 | 4.787 | −42.007 | 1.00 | 28.79 | RNA2 | C |
| ATOM | 3808 | C6 | G | D | 1099 | 3.437 | 3.978 | −42.083 | 1.00 | 36.73 | RNA2 | C |
| ATOM | 3809 | O6 | G | D | 1099 | 3.519 | 2.747 | −42.210 | 1.00 | 46.32 | RNA2 | O |
| ATOM | 3810 | N1 | G | D | 1099 | 4.596 | 4.744 | −42.006 | 1.00 | 30.92 | RNA2 | N |
| ATOM | 3811 | C2 | G | D | 1099 | 4.630 | 6.113 | −41.873 | 1.00 | 40.47 | RNA2 | C |
| ATOM | 3812 | N2 | G | D | 1099 | 5.847 | 6.678 | −41.812 | 1.00 | 23.42 | RNA2 | N |
| ATOM | 3813 | N3 | G | D | 1099 | 3.549 | 6.876 | −41.805 | 1.00 | 31.10 | RNA2 | N |
| ATOM | 3814 | C4 | G | D | 1099 | 2.415 | 6.152 | −41.883 | 1.00 | 28.17 | RNA2 | C |
| ATOM | 3815 | P | C | D | 1100 | 0.097 | 9.071 | −46.522 | 1.00 | 56.56 | RNA2 | P |
| ATOM | 3816 | O1P | C | D | 1100 | −0.323 | 7.657 | −46.716 | 1.00 | 63.87 | RNA2 | O |
| ATOM | 3817 | O2P | C | D | 1100 | −0.407 | 10.115 | −47.447 | 1.00 | 69.36 | RNA2 | O |
| ATOM | 3818 | O5* | C | D | 1100 | 1.688 | 9.106 | −46.507 | 1.00 | 39.12 | RNA2 | O |
| ATOM | 3819 | C5* | C | D | 1100 | 2.380 | 10.337 | −46.298 | 1.00 | 32.71 | RNA2 | C |
| ATOM | 3820 | C4* | C | D | 1100 | 3.863 | 10.098 | −46.207 | 1.00 | 40.37 | RNA2 | C |
| ATOM | 3821 | O4* | C | D | 1100 | 4.155 | 9.281 | −45.042 | 1.00 | 45.57 | RNA2 | O |
| ATOM | 3822 | C3* | C | D | 1100 | 4.502 | 9.335 | −47.356 | 1.00 | 48.34 | RNA2 | C |
| ATOM | 3823 | O3* | C | D | 1100 | 4.774 | 10.136 | −48.495 | 1.00 | 58.69 | RNA2 | O |
| ATOM | 3824 | C2* | C | D | 1100 | 5.771 | 8.784 | −46.718 | 1.00 | 42.72 | RNA2 | C |
| ATOM | 3825 | O2* | C | D | 1100 | 6.840 | 9.707 | −46.670 | 1.00 | 45.27 | RNA2 | O |
| ATOM | 3826 | C1* | C | D | 1100 | 5.289 | 8.466 | −45.303 | 1.00 | 36.28 | RNA2 | C |
| ATOM | 3827 | N1 | C | D | 1100 | 4.897 | 7.048 | −45.234 | 1.00 | 33.17 | RNA2 | N |
| ATOM | 3828 | C2 | C | D | 1100 | 5.910 | 6.083 | −45.177 | 1.00 | 37.72 | RNA2 | C |
| ATOM | 3829 | O2 | C | D | 1100 | 7.090 | 6.461 | −45.104 | 1.00 | 37.78 | RNA2 | O |
| ATOM | 3830 | N3 | C | D | 1100 | 5.582 | 4.772 | −45.201 | 1.00 | 34.10 | RNA2 | N |
| ATOM | 3831 | C4 | C | D | 1100 | 4.299 | 4.409 | −45.268 | 1.00 | 36.21 | RNA2 | C |
| ATOM | 3832 | N4 | C | D | 1100 | 4.024 | 3.103 | −45.330 | 1.00 | 35.52 | RNA2 | N |
| ATOM | 3833 | C5 | C | D | 1100 | 3.242 | 5.369 | −45.283 | 1.00 | 32.04 | RNA2 | C |
| ATOM | 3834 | C6 | C | D | 1100 | 3.583 | 6.665 | −45.263 | 1.00 | 33.05 | RNA2 | C |
| ATOM | 3835 | P | U | D | 1101 | 4.754 | 9.460 | −49.951 | 1.00 | 59.64 | RNA2 | P |
| ATOM | 3836 | O1P | U | D | 1101 | 3.464 | 8.731 | −50.077 | 1.00 | 53.79 | RNA2 | O |
| ATOM | 3837 | O2P | U | D | 1101 | 5.117 | 10.490 | −50.957 | 1.00 | 73.54 | RNA2 | O |
| ATOM | 3838 | O5* | U | D | 1101 | 5.931 | 8.390 | −49.894 | 1.00 | 44.03 | RNA2 | O |
| ATOM | 3839 | C5* | U | D | 1101 | 7.275 | 8.809 | −49.652 | 1.00 | 37.19 | RNA2 | C |
| ATOM | 3840 | C4* | U | D | 1101 | 8.197 | 7.620 | −49.625 | 1.00 | 44.44 | RNA2 | C |
| ATOM | 3841 | O4* | U | D | 1101 | 7.844 | 6.748 | −48.520 | 1.00 | 47.50 | RNA2 | O |
| ATOM | 3842 | C3* | U | D | 1101 | 8.140 | 6.710 | −50.836 | 1.00 | 49.53 | RNA2 | C |
| ATOM | 3843 | O3* | U | D | 1101 | 8.892 | 7.203 | −51.930 | 1.00 | 55.95 | RNA2 | O |
| ATOM | 3844 | C2* | U | D | 1101 | 8.681 | 5.396 | −50.286 | 1.00 | 46.03 | RNA2 | C |
| ATOM | 3845 | O2* | U | D | 1101 | 10.091 | 5.371 | −50.196 | 1.00 | 46.23 | RNA2 | O |
| ATOM | 3846 | C1* | U | D | 1101 | 8.097 | 5.396 | −48.875 | 1.00 | 41.37 | RNA2 | C |
| ATOM | 3847 | N1 | U | D | 1101 | 6.840 | 4.627 | −48.800 | 1.00 | 33.41 | RNA2 | N |

TABLE II-continued

| | | | | | | | | | | | |
|---|---|---|---|---|---|---|---|---|---|---|---|
| ATOM | 3848 | C2 | U | D | 1101 | 6.935 | 3.238 | −48.784 | 1.00 | 34.44 | RNA2 | C |
| ATOM | 3849 | O2 | U | D | 1101 | 8.011 | 2.640 | −48.812 | 1.00 | 33.60 | RNA2 | O |
| ATOM | 3850 | N3 | U | D | 1101 | 5.730 | 2.575 | −48.737 | 1.00 | 17.93 | RNA2 | N |
| ATOM | 3851 | C4 | U | D | 1101 | 4.466 | 3.143 | −48.705 | 1.00 | 36.01 | RNA2 | C |
| ATOM | 3852 | O4 | U | D | 1101 | 3.465 | 2.411 | −48.702 | 1.00 | 25.00 | RNA2 | O |
| ATOM | 3853 | C5 | U | D | 1101 | 4.457 | 4.577 | −48.714 | 1.00 | 24.85 | RNA2 | C |
| ATOM | 3854 | C6 | U | D | 1101 | 5.610 | 5.251 | −48.760 | 1.00 | 26.88 | RNA2 | C |
| ATOM | 3855 | P | C | D | 1102 | 8.485 | 6.763 | −53.418 | 1.00 | 41.89 | RNA2 | P |
| ATOM | 3856 | O1P | C | D | 1102 | 7.001 | 6.821 | −53.510 | 1.00 | 43.20 | RNA2 | O |
| ATOM | 3857 | O2P | C | D | 1102 | 9.312 | 7.542 | −54.372 | 1.00 | 53.94 | RNA2 | O |
| ATOM | 3858 | O5* | C | D | 1102 | 8.938 | 5.240 | −53.483 | 1.00 | 38.14 | RNA2 | O |
| ATOM | 3859 | C5* | C | D | 1102 | 10.317 | 4.889 | −53.306 | 1.00 | 37.05 | RNA2 | C |
| ATOM | 3860 | C4* | C | D | 1102 | 10.494 | 3.390 | −53.332 | 1.00 | 45.27 | RNA2 | C |
| ATOM | 3861 | O4* | C | D | 1102 | 9.855 | 2.793 | −52.168 | 1.00 | 52.28 | RNA2 | O |
| ATOM | 3862 | C3* | C | D | 1102 | 9.872 | 2.637 | −54.498 | 1.00 | 54.50 | RNA2 | C |
| ATOM | 3863 | O3* | C | D | 1102 | 10.597 | 2.706 | −55.716 | 1.00 | 57.12 | RNA2 | O |
| ATOM | 3864 | C2* | C | D | 1102 | 9.784 | 1.219 | −53.949 | 1.00 | 52.66 | RNA2 | C |
| ATOM | 3865 | O2* | C | D | 1102 | 11.017 | 0.522 | −54.000 | 1.00 | 56.57 | RNA2 | O |
| ATOM | 3866 | C1* | C | D | 1102 | 9.401 | 1.482 | −52.493 | 1.00 | 46.15 | RNA2 | C |
| ATOM | 3867 | N1 | C | D | 1102 | 7.932 | 1.399 | −52.330 | 1.00 | 28.20 | RNA2 | N |
| ATOM | 3868 | C2 | C | D | 1102 | 7.331 | 0.128 | −52.307 | 1.00 | 22.69 | RNA2 | C |
| ATOM | 3869 | O2 | C | D | 1102 | 8.053 | −0.881 | −52.366 | 1.00 | 35.31 | RNA2 | O |
| ATOM | 3870 | N3 | C | D | 1102 | 5.988 | 0.028 | −52.219 | 1.00 | 9.49 | RNA2 | N |
| ATOM | 3871 | C4 | C | D | 1102 | 5.246 | 1.129 | −52.135 | 1.00 | 16.43 | RNA2 | C |
| ATOM | 3872 | N4 | C | D | 1102 | 3.922 | 0.979 | −52.052 | 1.00 | 15.53 | RNA2 | N |
| ATOM | 3873 | C5 | C | D | 1102 | 5.825 | 2.433 | −52.133 | 1.00 | 15.77 | RNA2 | C |
| ATOM | 3874 | C6 | C | D | 1102 | 7.158 | 2.521 | −52.229 | 1.00 | 21.76 | RNA2 | C |
| ATOM | 3875 | P | A | D | 1103 | 9.806 | 2.525 | −57.105 | 1.00 | 47.42 | RNA2 | P |
| ATOM | 3876 | O1P | A | D | 1103 | 8.514 | 3.264 | −57.011 | 1.00 | 38.37 | RNA2 | O |
| ATOM | 3877 | O2P | A | D | 1103 | 10.747 | 2.818 | −58.216 | 1.00 | 57.18 | RNA2 | O |
| ATOM | 3878 | O5* | A | D | 1103 | 9.456 | 0.974 | −57.138 | 1.00 | 48.19 | RNA2 | O |
| ATOM | 3879 | C5* | A | D | 1103 | 10.493 | −0.015 | −56.995 | 1.00 | 51.39 | RNA2 | C |
| ATOM | 3880 | C4* | A | D | 1103 | 9.894 | −1.397 | −56.965 | 1.00 | 45.50 | RNA2 | C |
| ATOM | 3881 | O4* | A | D | 1103 | 8.978 | −1.488 | −55.847 | 1.00 | 45.01 | RNA2 | O |
| ATOM | 3882 | C3* | A | D | 1103 | 9.053 | −1.764 | −58.178 | 1.00 | 51.96 | RNA2 | C |
| ATOM | 3883 | O3* | A | D | 1103 | 9.867 | −2.246 | −59.243 | 1.00 | 53.83 | RNA2 | O |
| ATOM | 3884 | C2* | A | D | 1103 | 8.095 | −2.817 | −57.622 | 1.00 | 48.46 | RNA2 | C |
| ATOM | 3885 | O2* | A | D | 1103 | 8.635 | −4.125 | −57.578 | 1.00 | 47.52 | RNA2 | O |
| ATOM | 3886 | C1* | A | D | 1103 | 7.882 | −2.316 | −56.192 | 1.00 | 43.28 | RNA2 | C |
| ATOM | 3887 | N9 | A | D | 1103 | 6.646 | −1.549 | −56.032 | 1.00 | 30.89 | RNA2 | N |
| ATOM | 3888 | C8 | A | D | 1103 | 6.477 | −0.189 | −55.914 | 1.00 | 25.35 | RNA2 | C |
| ATOM | 3889 | N7 | A | D | 1103 | 5.222 | 0.179 | −55.797 | 1.00 | 26.03 | RNA2 | N |
| ATOM | 3890 | C5 | A | D | 1103 | 4.519 | −1.019 | −55.836 | 1.00 | 17.17 | RNA2 | C |
| ATOM | 3891 | C6 | A | D | 1103 | 3.149 | −1.314 | −55.759 | 1.00 | 19.87 | RNA2 | C |
| ATOM | 3892 | N6 | A | D | 1103 | 2.193 | −0.387 | −55.623 | 1.00 | 16.79 | RNA2 | N |
| ATOM | 3893 | N1 | A | D | 1103 | 2.784 | −2.616 | −55.828 | 1.00 | 26.16 | RNA2 | N |
| ATOM | 3894 | C2 | A | D | 1103 | 3.737 | −3.548 | −55.965 | 1.00 | 23.04 | RNA2 | C |
| ATOM | 3895 | N3 | A | D | 1103 | 5.055 | −3.394 | −56.049 | 1.00 | 30.58 | RNA2 | N |
| ATOM | 3896 | C4 | A | D | 1103 | 5.384 | −2.090 | −55.977 | 1.00 | 28.62 | RNA2 | C |
| ATOM | 3897 | P | C | D | 1104 | 9.699 | −1.627 | −60.718 | 1.00 | 44.57 | RNA2 | P |
| ATOM | 3898 | O1P | C | D | 1104 | 9.942 | −0.162 | −60.644 | 1.00 | 47.15 | RNA2 | O |
| ATOM | 3899 | O2P | C | D | 1104 | 10.506 | −2.463 | −61.648 | 1.00 | 47.11 | RNA2 | O |
| ATOM | 3900 | O5* | C | D | 1104 | 8.160 | −1.850 | −61.042 | 1.00 | 36.26 | RNA2 | O |
| ATOM | 3901 | C5* | C | D | 1104 | 7.642 | −3.172 | −61.211 | 1.00 | 34.08 | RNA2 | C |
| ATOM | 3902 | C4* | C | D | 1104 | 6.144 | −3.130 | −61.321 | 1.00 | 33.02 | RNA2 | C |
| ATOM | 3903 | O4* | C | D | 1104 | 5.569 | −2.739 | −60.048 | 1.00 | 35.45 | RNA2 | O |
| ATOM | 3904 | C3* | C | D | 1104 | 5.595 | −2.113 | −62.301 | 1.00 | 36.26 | RNA2 | C |
| ATOM | 3905 | O3* | C | D | 1104 | 5.633 | −2.561 | −63.643 | 1.00 | 42.96 | RNA2 | O |
| ATOM | 3906 | C2* | C | D | 1104 | 4.183 | −1.890 | −61.780 | 1.00 | 35.20 | RNA2 | C |
| ATOM | 3907 | O2* | C | D | 1104 | 3.297 | −2.916 | −62.185 | 1.00 | 38.85 | RNA2 | O |
| ATOM | 3908 | C1* | C | D | 1104 | 4.408 | −1.952 | −60.268 | 1.00 | 31.46 | RNA2 | C |
| ATOM | 3909 | N1 | C | D | 1104 | 4.636 | −0.606 | −59.702 | 1.00 | 26.13 | RNA2 | N |
| ATOM | 3910 | C2 | C | D | 1104 | 3.528 | 0.178 | −59.334 | 1.00 | 24.36 | RNA2 | C |
| ATOM | 3911 | O2 | C | D | 1104 | 2.386 | −0.295 | −59.447 | 1.00 | 21.42 | RNA2 | O |
| ATOM | 3912 | N3 | C | D | 1104 | 3.735 | 1.428 | −58.865 | 1.00 | 27.00 | RNA2 | N |
| ATOM | 3913 | C4 | C | D | 1104 | 4.981 | 1.900 | −58.745 | 1.00 | 31.66 | RNA2 | C |
| ATOM | 3914 | N4 | C | D | 1104 | 5.140 | 3.147 | −58.292 | 1.00 | 37.50 | RNA2 | N |
| ATOM | 3915 | C5 | C | D | 1104 | 6.120 | 1.119 | −59.087 | 1.00 | 19.85 | RNA2 | C |
| ATOM | 3916 | C6 | C | D | 1104 | 5.906 | −0.115 | −59.554 | 1.00 | 26.62 | RNA2 | C |
| ATOM | 3917 | P | C | D | 1105 | 5.825 | −1.489 | −64.826 | 1.00 | 42.78 | RNA2 | P |
| ATOM | 3918 | O1P | C | D | 1105 | 6.805 | −0.460 | −64.381 | 1.00 | 36.29 | RNA2 | O |
| ATOM | 3919 | O2P | C | D | 1105 | 6.074 | −2.246 | −66.084 | 1.00 | 51.04 | RNA2 | O |
| ATOM | 3920 | O5* | C | D | 1105 | 4.397 | −0.802 | −64.932 | 1.00 | 18.59 | RNA2 | O |
| ATOM | 3921 | C5* | C | D | 1105 | 3.253 | −1.574 | −65.316 | 1.00 | 29.02 | RNA2 | C |
| ATOM | 3922 | C4* | C | D | 1105 | 2.021 | −0.711 | −65.320 | 1.00 | 36.00 | RNA2 | C |
| ATOM | 3923 | O4* | C | D | 1105 | 1.741 | −0.275 | −63.965 | 1.00 | 45.01 | RNA2 | O |
| ATOM | 3924 | C3* | C | D | 1105 | 2.122 | 0.582 | −66.111 | 1.00 | 43.97 | RNA2 | C |
| ATOM | 3925 | O3* | C | D | 1105 | 1.919 | 0.405 | −67.505 | 1.00 | 50.57 | RNA2 | O |
| ATOM | 3926 | C2* | C | D | 1105 | 1.060 | 1.451 | −65.447 | 1.00 | 42.61 | RNA2 | C |

TABLE II-continued

| | | | | | | | | | | | |
|---|---|---|---|---|---|---|---|---|---|---|---|
| ATOM | 3927 | O2* | C | D | 1105 | −0.259 | 1.147 | −65.873 | 1.00 | 33.02 | RNA2 O |
| ATOM | 3928 | C1* | C | D | 1105 | 1.225 | 1.048 | −63.983 | 1.00 | 40.14 | RNA2 C |
| ATOM | 3929 | N1 | C | D | 1105 | 2.173 | 1.938 | −63.273 | 1.00 | 34.85 | RNA2 N |
| ATOM | 3930 | C2 | C | D | 1105 | 1.704 | 3.161 | −62.765 | 1.00 | 30.45 | RNA2 C |
| ATOM | 3931 | O2 | C | D | 1105 | 0.516 | 3.473 | −62.939 | 1.00 | 29.26 | RNA2 O |
| ATOM | 3932 | N3 | C | D | 1105 | 2.558 | 3.975 | −62.106 | 1.00 | 32.19 | RNA2 N |
| ATOM | 3933 | C4 | C | D | 1105 | 3.836 | 3.622 | −61.956 | 1.00 | 39.46 | RNA2 C |
| ATOM | 3934 | N4 | C | D | 1105 | 4.644 | 4.466 | −61.298 | 1.00 | 41.48 | RNA2 N |
| ATOM | 3935 | C5 | C | D | 1105 | 4.346 | 2.391 | −62.471 | 1.00 | 36.86 | RNA2 C |
| ATOM | 3936 | C6 | C | D | 1105 | 3.488 | 1.587 | −63.114 | 1.00 | 34.30 | RNA2 C |
| ATOM | 3937 | P | A | D | 1106 | 2.559 | 1.463 | −68.538 | 1.00 | 47.42 | RNA2 P |
| ATOM | 3938 | O1P | A | D | 1106 | 3.960 | 1.743 | −68.117 | 1.00 | 33.03 | RNA2 O |
| ATOM | 3939 | O2P | A | D | 1106 | 2.297 | 0.944 | −69.905 | 1.00 | 51.03 | RNA2 O |
| ATOM | 3940 | O5* | A | D | 1106 | 1.674 | 2.772 | −68.323 | 1.00 | 38.12 | RNA2 O |
| ATOM | 3941 | C5* | A | D | 1106 | 0.283 | 2.777 | −68.706 | 1.00 | 43.96 | RNA2 C |
| ATOM | 3942 | C4* | A | D | 1106 | −0.340 | 4.129 | −68.452 | 1.00 | 51.41 | RNA2 C |
| ATOM | 3943 | O4* | A | D | 1106 | −0.379 | 4.381 | −67.026 | 1.00 | 57.25 | RNA2 O |
| ATOM | 3944 | C3* | A | D | 1106 | 0.391 | 5.331 | −69.029 | 1.00 | 56.31 | RNA2 C |
| ATOM | 3945 | O3* | A | D | 1106 | 0.086 | 5.559 | −70.396 | 1.00 | 55.12 | RNA2 O |
| ATOM | 3946 | C2* | A | D | 1106 | −0.076 | 6.467 | −68.126 | 1.00 | 56.95 | RNA2 C |
| ATOM | 3947 | O2* | A | D | 1106 | −1.351 | 6.970 | −68.478 | 1.00 | 57.32 | RNA2 O |
| ATOM | 3948 | C1* | A | D | 1106 | −0.169 | 5.761 | −66.776 | 1.00 | 49.81 | RNA2 C |
| ATOM | 3949 | N9 | A | D | 1106 | 1.065 | 5.896 | −66.003 | 1.00 | 39.90 | RNA2 N |
| ATOM | 3950 | C8 | A | D | 1106 | 2.098 | 4.994 | −65.902 | 1.00 | 41.00 | RNA2 C |
| ATOM | 3951 | N7 | A | D | 1106 | 3.070 | 5.388 | −65.116 | 1.00 | 41.71 | RNA2 N |
| ATOM | 3952 | C5 | A | D | 1106 | 2.652 | 6.635 | −64.672 | 1.00 | 37.31 | RNA2 C |
| ATOM | 3953 | C6 | A | D | 1106 | 3.238 | 7.572 | −63.805 | 1.00 | 36.44 | RNA2 C |
| ATOM | 3954 | N6 | A | D | 1106 | 4.419 | 7.389 | −63.208 | 1.00 | 40.12 | RNA2 N |
| ATOM | 3955 | N1 | A | D | 1106 | 2.563 | 8.720 | −63.570 | 1.00 | 38.29 | RNA2 N |
| ATOM | 3956 | C2 | A | D | 1106 | 1.380 | 8.904 | −64.178 | 1.00 | 37.00 | RNA2 C |
| ATOM | 3957 | N3 | A | D | 1106 | 0.726 | 8.097 | −65.014 | 1.00 | 37.07 | RNA2 N |
| ATOM | 3958 | C4 | A | D | 1106 | 1.423 | 6.965 | −65.219 | 1.00 | 37.01 | RNA2 C |
| ATOM | 3959 | P | G | D | 1107 | 1.186 | 6.251 | −71.341 | 1.00 | 60.89 | RNA2 P |
| ATOM | 3960 | O1P | G | D | 1107 | 2.513 | 5.650 | −71.037 | 1.00 | 51.64 | RNA2 O |
| ATOM | 3961 | O2P | G | D | 1107 | 0.665 | 6.218 | −72.732 | 1.00 | 66.72 | RNA2 O |
| ATOM | 3962 | O5* | G | D | 1107 | 1.226 | 7.763 | −70.838 | 1.00 | 59.43 | RNA2 O |
| ATOM | 3963 | C5* | G | D | 1107 | 0.098 | 8.639 | −71.043 | 1.00 | 70.93 | RNA2 C |
| ATOM | 3964 | C4* | G | D | 1107 | 0.341 | 9.984 | −70.392 | 1.00 | 70.62 | RNA2 C |
| ATOM | 3965 | O4* | G | D | 1107 | 0.347 | 9.841 | −68.945 | 1.00 | 70.80 | RNA2 O |
| ATOM | 3966 | C3* | G | D | 1107 | 1.673 | 10.648 | −70.701 | 1.00 | 69.85 | RNA2 C |
| ATOM | 3967 | O3* | G | D | 1107 | 1.703 | 11.337 | −71.937 | 1.00 | 68.76 | RNA2 O |
| ATOM | 3968 | C2* | G | D | 1107 | 1.852 | 11.589 | −69.519 | 1.00 | 71.85 | RNA2 C |
| ATOM | 3969 | O2* | G | D | 1107 | 1.134 | 12.799 | −69.666 | 1.00 | 74.63 | RNA2 O |
| ATOM | 3970 | C1* | G | D | 1107 | 1.278 | 10.751 | −68.377 | 1.00 | 66.31 | RNA2 C |
| ATOM | 3971 | N9 | G | D | 1107 | 2.356 | 9.990 | −67.753 | 1.00 | 61.03 | RNA2 N |
| ATOM | 3972 | C8 | G | D | 1107 | 2.765 | 8.710 | −68.056 | 1.00 | 64.56 | RNA2 C |
| ATOM | 3973 | N7 | G | D | 1107 | 3.811 | 8.330 | −67.371 | 1.00 | 62.08 | RNA2 N |
| ATOM | 3974 | C5 | G | D | 1107 | 4.100 | 9.417 | −66.555 | 1.00 | 59.12 | RNA2 C |
| ATOM | 3975 | C6 | G | D | 1107 | 5.134 | 9.600 | −65.598 | 1.00 | 54.80 | RNA2 C |
| ATOM | 3976 | O6 | G | D | 1107 | 6.035 | 8.812 | −65.270 | 1.00 | 51.34 | RNA2 O |
| ATOM | 3977 | N1 | G | D | 1107 | 5.056 | 10.854 | −65.001 | 1.00 | 50.79 | RNA2 N |
| ATOM | 3978 | C2 | G | D | 1107 | 4.109 | 11.810 | −65.287 | 1.00 | 54.33 | RNA2 C |
| ATOM | 3979 | N2 | G | D | 1107 | 4.199 | 12.959 | −64.606 | 1.00 | 51.64 | RNA2 N |
| ATOM | 3980 | N3 | G | D | 1107 | 3.146 | 11.653 | −66.176 | 1.00 | 49.03 | RNA2 N |
| ATOM | 3981 | C4 | G | D | 1107 | 3.201 | 10.443 | −66.769 | 1.00 | 58.09 | RNA2 C |
| ATOM | 3982 | P | C | D | 1108 | 3.118 | 11.599 | −72.654 | 1.00 | 71.56 | RNA2 P |
| ATOM | 3983 | O1P | C | D | 1108 | 3.923 | 10.353 | −72.579 | 1.00 | 60.79 | RNA2 O |
| ATOM | 3984 | O2P | C | D | 1108 | 2.828 | 12.209 | −73.977 | 1.00 | 78.78 | RNA2 O |
| ATOM | 3985 | O5* | C | D | 1108 | 3.837 | 12.677 | −71.723 | 1.00 | 69.28 | RNA2 O |
| ATOM | 3986 | C5* | C | D | 1108 | 3.274 | 13.992 | −71.536 | 1.00 | 65.61 | RNA2 C |
| ATOM | 3987 | C4* | C | D | 1108 | 4.139 | 14.809 | −70.605 | 1.00 | 60.04 | RNA2 C |
| ATOM | 3988 | O4* | C | D | 1108 | 4.193 | 14.171 | −69.304 | 1.00 | 61.74 | RNA2 O |
| ATOM | 3989 | C3* | C | D | 1108 | 5.598 | 14.965 | −71.001 | 1.00 | 60.53 | RNA2 C |
| ATOM | 3990 | O3* | C | D | 1108 | 5.901 | 15.783 | −72.134 | 1.00 | 66.71 | RNA2 O |
| ATOM | 3991 | C2* | C | D | 1108 | 6.282 | 15.272 | −69.677 | 1.00 | 63.96 | RNA2 C |
| ATOM | 3992 | O2* | C | D | 1108 | 6.155 | 16.631 | −69.306 | 1.00 | 69.72 | RNA2 O |
| ATOM | 3993 | C1* | C | D | 1108 | 5.457 | 14.420 | −68.706 | 1.00 | 64.54 | RNA2 C |
| ATOM | 3994 | N1 | C | D | 1108 | 6.098 | 13.130 | −68.372 | 1.00 | 61.20 | RNA2 N |
| ATOM | 3995 | C2 | C | D | 1108 | 7.127 | 13.116 | −67.417 | 1.00 | 59.89 | RNA2 C |
| ATOM | 3996 | O2 | C | D | 1108 | 7.454 | 14.179 | −66.867 | 1.00 | 54.39 | RNA2 O |
| ATOM | 3997 | N3 | C | D | 1108 | 7.739 | 11.946 | −67.119 | 1.00 | 60.31 | RNA2 N |
| ATOM | 3998 | C4 | C | D | 1108 | 7.359 | 10.821 | −67.728 | 1.00 | 62.68 | RNA2 C |
| ATOM | 3999 | N4 | C | D | 1108 | 7.999 | 9.689 | −67.411 | 1.00 | 63.03 | RNA2 N |
| ATOM | 4000 | C5 | C | D | 1108 | 6.308 | 10.803 | −68.693 | 1.00 | 64.65 | RNA2 C |
| ATOM | 4001 | C6 | C | D | 1108 | 5.711 | 11.968 | −68.982 | 1.00 | 64.25 | RNA2 C |
| TER | 4002 | | C | D | 1108 | | | | | | |
| HETATM | 4003 | CD | CD | | 201 | 4.250 | −2.291 | −5.735 | 0.91 | 77.47 | CD |
| HETATM | 4004 | CD | CD | | 202 | 5.716 | 1.827 | 1.431 | 0.91 | 32.35 | CD |
| HETATM | 4005 | O | HOH | | 205 | 7.540 | −4.792 | −0.436 | 1.00 | 19.29 | O |

TABLE II-continued

| | | | | | | | | | |
|---|---|---|---|---|---|---|---|---|---|
| HETATM | 4006 | O | HOH | 209 | 8.097 | 9.026 | −9.315 | 1.00 | 27.99 O |
| HETATM | 4007 | MG | MG | 210 | 7.174 | 1.073 | −14.750 | 1.00 | 31.99 MG |
| HETATM | 4008 | CD | CD | 211 | 3.380 | 6.488 | −27.905 | 0.91 | 47.98 CD |
| HETATM | 4009 | O | HOH | 213 | −0.304 | 4.175 | −0.867 | 1.00 | 38.63 O |
| HETATM | 4010 | MG | MG | 214 | −17.505 | 21.323 | 11.148 | 1.00 | 36.28 MG |
| HETATM | 4011 | MG | MG | 215 | −1.702 | 7.910 | −11.196 | 1.00 | 23.07 MG |
| HETATM | 4012 | O | HOH | 216 | −3.510 | 9.209 | −16.056 | 1.00 | 43.93 O |
| HETATM | 4013 | O | HOH | 217 | −4.416 | −0.858 | −2.563 | 1.00 | 53.29 O |
| HETATM | 4014 | O | HOH | 218 | 6.288 | −5.327 | −3.385 | 1.00 | 23.44 O |
| HETATM | 4015 | O | HOH | 221 | −1.778 | 1.682 | −3.132 | 1.00 | 35.80 O |
| HETATM | 4016 | O | HOH | 222 | −6.849 | 10.117 | −5.442 | 1.00 | 24.81 O |
| HETATM | 4017 | MG | MG | 223 | 14.749 | −5.902 | 12.250 | 1.00 | 36.97 MG |
| HETATM | 4018 | MG | MG | 225 | 19.765 | −8.266 | 10.030 | 1.00 | 41.29 MG |
| HETATM | 4019 | MG | MG | 226 | 4.983 | 5.583 | −14.224 | 1.00 | 17.24 MG |
| HETATM | 4020 | HG | HG | 227 | 10.163 | 10.934 | −4.731 | 0.10 | 21.14 HG |
| HETATM | 4021 | MG | MG | 228 | 0.368 | −4.197 | 15.065 | 1.00 | 49.67 MG |
| HETATM | 4022 | HG | HG | 230 | −4.955 | 2.266 | −15.287 | 0.41 | 65.01 HG |
| HETATM | 4023 | O | HOH | 232 | 17.184 | −8.123 | 12.078 | 1.00 | 46.90 O |
| HETATM | 4024 | O | HOH | 233 | 5.132 | −9.156 | 11.493 | 1.00 | 39.77 O |
| HETATM | 4025 | O | HOH | 235 | −2.182 | 2.520 | −0.424 | 1.00 | 32.75 O |
| HETATM | 4026 | O | HOH | 236 | 3.337 | 3.950 | −2.832 | 1.00 | 22.74 O |
| HETATM | 4027 | O | HOH | 237 | −0.294 | 3.992 | −4.949 | 1.00 | 41.19 O |
| HETATM | 4028 | O | HOH | 238 | 3.987 | 7.706 | −7.271 | 1.00 | 22.33 O |
| HETATM | 4029 | O | HOH | 239 | −2.682 | 1.061 | −25.220 | 1.00 | 28.52 O |
| HETATM | 4030 | O | HOH | 241 | −0.901 | −1.716 | 11.637 | 1.00 | 34.24 O |
| HETATM | 4031 | O | HOH | 243 | 13.905 | −12.456 | 1.182 | 1.00 | 61.18 O |
| HETATM | 4032 | O | HOH | 244 | −6.595 | 6.151 | 4.226 | 1.00 | 33.67 O |
| HETATM | 4033 | O | HOH | 245 | −10.614 | 11.084 | 18.691 | 1.00 | 47.29 O |
| HETATM | 4034 | O | HOH | 246 | 2.153 | 6.645 | −5.263 | 1.00 | 42.17 O |
| HETATM | 4035 | O | HOH | 254 | 1.596 | 7.517 | −28.596 | 1.00 | 20.43 O |
| HETATM | 4036 | O | HOH | 255 | 5.496 | 5.982 | −27.129 | 1.00 | 15.56 O |
| HETATM | 4037 | O | HOH | 256 | 5.082 | 7.342 | −29.082 | 1.00 | 15.30 O |
| HETATM | 4038 | MG | MG | 257 | 4.272 | 8.284 | −11.053 | 1.00 | 18.63 MG |
| HETATM | 4039 | O | HOH | 258 | 5.759 | 9.095 | −9.332 | 1.00 | 22.95 O |
| HETATM | 4040 | O | HOH | 259 | 5.439 | 8.750 | −13.001 | 1.00 | 29.22 O |
| HETATM | 4041 | O | HOH | 260 | 3.112 | 6.893 | −9.834 | 1.00 | 15.63 O |
| HETATM | 4042 | O | HOH | 261 | 2.565 | 9.752 | −11.319 | 1.00 | 21.45 O |
| HETATM | 4043 | O | HOH | 262 | 2.003 | −1.889 | −6.293 | 1.00 | 39.08 O |
| HETATM | 4044 | O | HOH | 263 | 6.523 | −2.887 | −3.470 | 1.00 | 31.47 O |
| HETATM | 4045 | O | HOH | 264 | 5.691 | −4.152 | −6.413 | 1.00 | 49.36 O |
| HETATM | 4046 | O | HOH | 265 | 13.164 | −1.037 | −13.541 | 1.00 | 53.81 O |
| HETATM | 4047 | O | HOH | 266 | 1.658 | −4.440 | −6.534 | 1.00 | 54.55 O |
| HETATM | 4048 | O | HOH | 267 | 4.147 | −0.985 | −10.097 | 1.00 | 21.21 O |
| HETATM | 4049 | O | HOH | 268 | 7.729 | 0.998 | −17.041 | 1.00 | 32.76 O |
| HETATM | 4050 | O | HOH | 269 | 9.473 | 0.412 | −15.439 | 1.00 | 22.86 O |
| HETATM | 4051 | O | HOH | 270 | 5.281 | 1.436 | −15.928 | 1.00 | 30.01 O |
| HETATM | 4052 | O | HOH | 271 | 5.086 | −1.392 | −12.878 | 1.00 | 29.98 O |
| HETATM | 4053 | O | HOH | 272 | 5.284 | 18.973 | −15.526 | 1.00 | 29.56 O |
| HETATM | 4054 | MG | MG | 273 | 5.268 | 8.632 | 9.371 | 1.00 | 35.80 MG |
| HETATM | 4055 | O | HOH | 274 | 4.009 | 8.265 | 7.258 | 1.00 | 21.81 O |
| HETATM | 4056 | O | HOH | 275 | 6.536 | 8.905 | 7.475 | 1.00 | 34.86 O |
| HETATM | 4057 | O | HOH | 276 | 3.058 | 8.060 | 9.657 | 1.00 | 31.13 O |
| HETATM | 4058 | O | HOH | 277 | 5.081 | 6.362 | 8.463 | 1.00 | 31.02 O |
| HETATM | 4059 | O | HOH | 278 | 3.600 | 10.499 | 8.517 | 1.00 | 50.03 O |
| HETATM | 4060 | CD | CD | 302 | 0.011 | −4.071 | −53.380 | 0.91 | 31.52 CD |
| HETATM | 4061 | O | HOH | 305 | 1.845 | 2.702 | −51.597 | 1.00 | 14.19 O |
| HETATM | 4062 | CD | CD | 311 | 4.100 | −9.327 | −24.111 | 0.91 | 76.29 CD |
| HETATM | 4063 | O | HOH | 313 | −1.010 | −7.500 | −47.833 | 1.00 | 40.72 O |
| HETATM | 4064 | MG | MG | 318 | 1.219 | 3.097 | −48.942 | 1.00 | 17.48 MG |
| HETATM | 4065 | O | HOH | 322 | −10.157 | −13.890 | −44.431 | 1.00 | 41.81 O |
| HETATM | 4066 | MG | MG | 326 | 2.778 | −7.878 | −38.005 | 1.00 | 11.66 MG |
| HETATM | 4067 | O | HOH | 327 | 9.652 | −2.170 | −38.994 | 1.00 | 44.35 O |
| HETATM | 4068 | HG | HG | 332 | −7.089 | −5.545 | −35.006 | 0.60 | 82.38 HG |
| HETATM | 4069 | O | HOH | 333 | 1.493 | −12.458 | −57.479 | 1.00 | 39.19 O |
| HETATM | 4070 | O | HOH | 335 | −4.211 | 7.242 | −62.792 | 1.00 | 49.93 O |
| HETATM | 4071 | O | HOH | 336 | −7.759 | −5.212 | −49.585 | 1.00 | 35.75 O |
| HETATM | 4072 | O | HOH | 338 | −3.953 | −6.679 | −45.543 | 1.00 | 38.41 O |
| HETATM | 4073 | O | HOH | 339 | 0.508 | −10.010 | −44.801 | 1.00 | 28.38 O |
| HETATM | 4074 | O | HOH | 340 | −8.610 | 1.401 | −65.472 | 1.00 | 31.42 O |
| HETATM | 4075 | O | HOH | 343 | 5.058 | −10.891 | −43.391 | 1.00 | 29.07 O |
| HETATM | 4076 | O | HOH | 345 | 5.817 | −19.070 | −33.612 | 1.00 | 35.77 O |
| HETATM | 4077 | O | HOH | 346 | 8.758 | −14.281 | −46.244 | 1.00 | 40.41 O |
| HETATM | 4078 | HG | HG | 347 | 6.715 | −12.669 | −48.448 | 0.20 | 54.24 HG |
| HETATM | 4079 | O | HOH | 349 | 5.113 | −13.530 | −54.095 | 1.00 | 42.05 O |
| HETATM | 4080 | O | HOH | 352 | 6.195 | −6.263 | −57.438 | 1.00 | 39.69 O |
| HETATM | 4081 | O | HOH | 353 | 12.125 | 3.149 | −49.649 | 1.00 | 38.23 O |
| HETATM | 4082 | MG | MG | 354 | 11.145 | 8.122 | −61.981 | 1.00 | 29.67 MG |
| HETATM | 4083 | O | HOH | 355 | 10.792 | 7.517 | −64.576 | 1.00 | 68.09 O |
| HETATM | 4084 | O | HOH | 356 | 12.630 | 7.721 | −60.264 | 1.00 | 42.56 O |

TABLE II-continued

| | | | | | | | | | |
|---|---|---|---|---|---|---|---|---|---|
| HETATM | 4085 O | HOH | 357 | 13.374 | 7.731 | −62.491 | 1.00 | 44.36 | O |
| HETATM | 4086 O | HOH | 358 | 8.902 | 7.560 | −61.857 | 1.00 | 47.98 | O |
| HETATM | 4087 MG | MG | 360 | 6.237 | 6.431 | −66.914 | 1.00 | 28.74 | MG |
| HETATM | 4088 O | HOH | 361 | 6.408 | 4.325 | −65.550 | 1.00 | 56.01 | O |
| HETATM | 4089 O | HOH | 362 | 8.361 | 5.765 | −66.746 | 1.00 | 36.18 | O |
| HETATM | 4090 O | HOH | 363 | 4.653 | 5.030 | −68.186 | 1.00 | 40.11 | O |
| HETATM | 4091 O | HOH | 364 | 7.146 | 6.368 | −64.453 | 1.00 | 50.71 | O |
| HETATM | 4092 MG | MG | 365 | 4.856 | 8.795 | −57.034 | 1.00 | 57.29 | MG |
| HETATM | 4093 O | HOH | 367 | 5.981 | 7.693 | −58.709 | 1.00 | 45.32 | O |
| HETATM | 4094 O | HOH | 368 | 2.602 | 9.503 | −57.044 | 1.00 | 34.21 | O |
| HETATM | 4095 O | HOH | 369 | −3.740 | −7.741 | −49.878 | 1.00 | 34.52 | O |
| HETATM | 4096 O | HOH | 371 | −4.630 | −7.088 | −47.848 | 1.00 | 47.42 | O |
| HETATM | 4097 O | HOH | 372 | −1.660 | −6.106 | −49.542 | 1.00 | 29.15 | O |
| HETATM | 4098 O | HOH | 373 | −6.163 | −7.124 | −50.377 | 1.00 | 43.85 | O |
| HETATM | 4099 O | HOH | 374 | −4.330 | −5.161 | −49.766 | 1.00 | 36.71 | O |
| HETATM | 4100 MG | MG | 375 | −4.006 | −10.777 | −39.969 | 1.00 | 19.68 | MG |
| HETATM | 4101 O | HOH | 376 | −3.858 | −12.278 | −36.949 | 1.00 | 28.95 | O |
| HETATM | 4102 O | HOH | 377 | −2.097 | −12.249 | −40.683 | 1.00 | 38.24 | O |
| HETATM | 4103 O | HOH | 378 | −5.782 | −11.177 | −38.567 | 1.00 | 48.85 | O |
| HETATM | 4104 O | HOH | 379 | −3.396 | −9.585 | −37.760 | 1.00 | 53.51 | O |
| HETATM | 4105 MG | MG | 380 | 1.544 | −10.560 | −40.973 | 1.00 | 15.03 | MG |
| HETATM | 4106 O | HOH | 381 | 0.239 | −9.278 | −41.992 | 1.00 | 24.23 | O |
| HETATM | 4107 O | HOH | 382 | 3.079 | −11.151 | −39.552 | 1.00 | 29.52 | O |
| HETATM | 4108 O | HOH | 383 | 2.890 | −11.254 | −42.623 | 1.00 | 28.59 | O |
| HETATM | 4109 O | HOH | 384 | 0.497 | −12.218 | −40.320 | 1.00 | 24.46 | O |
| HETATM | 4110 MG | MG | 385 | 4.975 | −3.399 | −36.540 | 1.00 | 26.05 | MG |
| HETATM | 4111 O | HOH | 386 | 4.351 | −3.722 | −38.893 | 1.00 | 47.91 | O |
| HETATM | 4112 O | HOH | 387 | 6.538 | −3.279 | −34.525 | 1.00 | 52.58 | O |
| HETATM | 4113 O | HOH | 388 | 6.829 | −2.324 | −37.582 | 1.00 | 23.58 | O |
| HETATM | 4114 O | HOH | 389 | 2.776 | −4.208 | −36.379 | 1.00 | 47.45 | O |
| HETATM | 4115 CD | CD | 390 | −0.220 | −0.169 | −45.971 | 1.00 | 66.34 | CD |
| HETATM | 4116 O | HOH | 391 | 1.204 | 0.456 | −48.678 | 1.00 | 26.12 | O |
| HETATM | 4117 O | HOH | 392 | −2.039 | −0.298 | −44.457 | 1.00 | 74.79 | O |
| HETATM | 4118 O | HOH | 394 | −2.332 | −1.375 | −46.858 | 1.00 | 55.72 | O |
| HETATM | 4119 O | HOH | 395 | 0.735 | −1.415 | −41.666 | 1.00 | 23.21 | O |
| HETATM | 4120 O | HOH | 396 | −2.289 | 1.508 | −46.080 | 1.00 | 38.73 | O |
| HETATM | 4121 MG | MG | 397 | −1.117 | −10.966 | −60.412 | 1.00 | 36.18 | MG |
| HETATM | 4122 O | HOH | 399 | −2.144 | −9.538 | −58.861 | 1.00 | 29.70 | O |
| HETATM | 4123 O | HOH | 400 | 1.112 | −10.642 | −59.923 | 1.00 | 66.19 | O |
| HETATM | 4124 O | HOH | 401 | −3.291 | −10.503 | −60.904 | 1.00 | 35.31 | O |
| HETATM | 4125 O | HOH | 402 | −2.294 | −12.413 | −59.078 | 1.00 | 39.66 | O |
| HETATM | 4126 O | HOH | 403 | −1.467 | −8.797 | −61.459 | 1.00 | 53.05 | O |
| HETATM | 4127 O | HOH | 404 | −12.040 | −30.139 | −41.430 | 1.00 | 41.13 | O |
| HETATM | 4128 O | HOH | 405 | −2.445 | −24.982 | −35.646 | 1.00 | 41.49 | O |
| HETATM | 4129 O | HOH | 406 | −12.232 | −9.609 | −53.785 | 1.00 | 19.82 | O |
| HETATM | 4130 O | HOH | 407 | −10.736 | −14.577 | −49.559 | 1.00 | 27.37 | O |
| HETATM | 4131 O | HOH | 408 | −18.946 | −19.067 | −62.962 | 1.00 | 48.41 | O |
| HETATM | 4132 O | HOH | 409 | −19.414 | −10.463 | −60.502 | 1.00 | 52.79 | O |
| HETATM | 4133 O | HOH | 410 | −6.651 | −19.456 | −54.939 | 1.00 | 26.78 | O |
| HETATM | 4134 O | HOH | 411 | −2.899 | −18.491 | −49.891 | 1.00 | 31.34 | O |
| HETATM | 4135 O | HOH | 412 | −4.041 | −25.738 | −47.368 | 1.00 | 61.51 | O |
| HETATM | 4136 CD | CD | 413 | −13.027 | 8.492 | 10.933 | 0.10 | 33.43 | CD |
| HETATM | 4137 CD | CD | 414 | −11.592 | 5.003 | −2.412 | 0.10 | 14.13 | CD |
| HETATM | 4138 HG | HG | 415 | −23.456 | −2.491 | −20.626 | 0.10 | 35.19 | HG |
| HETATM | 4139 HG | HG | 416 | −17.183 | −2.624 | −19.816 | 0.10 | 45.02 | HG |
| HETATM | 4140 O | HOH | 418 | −0.113 | 29.557 | −9.189 | 1.00 | 36.18 | O |
| HETATM | 4141 O | HOH | 419 | −1.958 | 16.568 | 4.135 | 1.00 | 22.82 | O |
| HETATM | 4142 O | HOH | 420 | 0.874 | 15.995 | −1.216 | 1.00 | 36.22 | O |
| HETATM | 4143 O | HOH | 421 | −0.098 | 21.800 | −5.101 | 1.00 | 35.12 | O |
| HETATM | 4144 O | HOH | 422 | −1.412 | 23.130 | −2.906 | 1.00 | 36.67 | O |
| HETATM | 4145 O | HOH | 423 | −3.317 | 24.792 | 0.592 | 1.00 | 45.31 | O |
| HETATM | 4146 O | HOH | 424 | 0.019 | 9.295 | −10.598 | 1.00 | 36.37 | O |
| HETATM | 4147 O | HOH | 425 | −2.568 | 8.364 | −13.958 | 1.00 | 50.92 | O |
| HETATM | 4148 O | HOH | 426 | −2.689 | 18.373 | −24.066 | 1.00 | 34.21 | O |
| HETATM | 4149 O | HOH | 427 | 7.170 | 6.156 | −29.910 | 1.00 | 17.29 | O |
| HETATM | 4150 O | HOH | 428 | 8.929 | 4.171 | −22.749 | 1.00 | 41.67 | O |
| HETATM | 4151 O | HOH | 429 | 12.036 | 0.863 | −14.965 | 1.00 | 42.52 | O |
| HETATM | 4152 O | HOH | 431 | −1.202 | 8.279 | 12.504 | 1.00 | 41.33 | O |
| HETATM | 4153 O | HOH | 432 | 8.485 | 7.265 | 7.104 | 1.00 | 46.57 | O |
| HETATM | 4154 O | HOH | 434 | 4.018 | 10.172 | 4.758 | 1.00 | 37.32 | O |
| HETATM | 4155 O | HOH | 435 | 18.225 | −9.006 | −2.120 | 1.00 | 60.80 | O |
| HETATM | 4156 MG | MG | 437 | 11.760 | −10.915 | 4.311 | 1.00 | 47.79 | MG |
| HETATM | 4157 O | HOH | 438 | 12.113 | −10.561 | 1.951 | 1.00 | 58.11 | O |
| HETATM | 4158 O | HOH | 440 | 14.043 | −10.435 | 3.845 | 1.00 | 43.62 | O |
| HETATM | 4159 O | HOH | 441 | 9.524 | −10.398 | 4.381 | 1.00 | 41.20 | O |
| HETATM | 4160 O | HOH | 442 | 11.946 | −13.321 | 4.538 | 1.00 | 65.98 | O |
| HETATM | 4161 O | HOH | 443 | 12.227 | −8.461 | 4.164 | 1.00 | 61.70 | O |
| HETATM | 4162 O | HOH | 444 | 1.040 | 4.817 | −2.689 | 1.00 | 32.93 | O |
| HETATM | 4163 O | HOH | 445 | 4.226 | 0.914 | 2.202 | 1.00 | 3.57 | O |

TABLE II-continued

| HETATM | 4164 | O  | HOH | 446 | 6.340   | −0.071  | 1.151   | 1.00 | 19.50 | O  |
|--------|------|----|-----|-----|---------|---------|---------|------|-------|----|
| HETATM | 4165 | O  | HOH | 447 | 4.234   | 3.232   | 1.596   | 1.00 | 12.18 | O  |
| HETATM | 4166 | HG | HG  | 448 | −4.015  | −8.066  | −15.150 | 0.10 | 21.04 | HG |
| HETATM | 4167 | O  | HOH | 450 | −4.907  | −3.163  | −52.117 | 1.00 | 24.48 | O  |
| HETATM | 4168 | HG | HG  | 451 | −5.485  | 5.932   | −35.358 | 0.10 | 26.20 | HG |
| HETATM | 4169 | O  | HOH | 452 | −4.427  | 1.650   | −44.668 | 1.00 | 47.88 | O  |
| HETATM | 4170 | O  | HOH | 453 | −6.126  | −4.197  | −47.630 | 1.00 | 40.28 | O  |
| HETATM | 4171 | O  | HOH | 454 | −14.902 | −5.184  | −53.399 | 1.00 | 41.04 | O  |
| HETATM | 4172 | O  | HOH | 455 | 2.198   | −31.615 | −45.895 | 1.00 | 38.45 | O  |
| HETATM | 4173 | O  | HOH | 456 | −0.111  | −29.053 | −48.914 | 1.00 | 37.64 | O  |
| HETATM | 4174 | O  | HOH | 457 | 5.023   | −28.677 | −39.390 | 1.00 | 42.30 | O  |
| HETATM | 4175 | O  | HOH | 459 | −8.700  | −0.565  | −36.045 | 1.00 | 32.85 | O  |
| HETATM | 4176 | O  | HOH | 460 | −1.593  | −4.423  | −51.572 | 1.00 | 28.40 | O  |
| HETATM | 4177 | O  | HOH | 461 | −1.729  | −3.181  | −53.813 | 1.00 | 2.00  | O  |
| HETATM | 4178 | O  | HOH | 462 | −1.294  | −5.593  | −53.672 | 1.00 | 22.25 | O  |
| HETATM | 4179 | O  | HOH | 463 | 0.388   | −1.958  | −53.133 | 1.00 | 27.43 | O  |
| MASTER | 320  | 0  | 35  | 8   | 7       | 0       | 3       | 12   | 4175  | 4  0  32 |
| END    |      |    |     |     |         |         |         |      |       |    |

---

What is claimed is:

1. A method for identifying a potential modulator of ribosomal protein L11/GAR activity, comprising the steps of:
   a) providing the atomic co-ordinates of the L11 GTPase Activating Region (L11/GAR) in Table II, thereby defining a three-dimensional structure of the L11/GAR;
   b) using said three dimensional structure of the L11/GAR to design or select a potential modulator by computer modeling;
   c) providing said potential modulator; and
   d) physically contacting said potential modulator with L11/GAR to determine the ability of said potential modulator to modulate L11/GAR activity, wherein a modulator of L11/GAR activity is identified.

2. The method according to claim 1, wherein said potential modulator is designed de novo.

3. The method according to claim 1, wherein said potential modulator is designed from a known modulator.

4. The method according to claim 1, wherein said step of employing said three-dimensional structure to design or select said potential modulator comprises the steps of:
   a) identifying chemical entities or fragments with the potential to bind said L11/GAR; and
   b) assembling the identified chemical entities or fragments into a single molecule to provide the structure of said potential modulator.

5. The method according to claim 4, wherein said potential modulator is designed de novo.

6. The method according to claim 4, wherein said potential modulator is designed from a known modulator.

* * * * *